(12) United States Patent
Acton et al.

(10) Patent No.: US 7,780,963 B2
(45) Date of Patent: Aug. 24, 2010

(54) ANTI-ADDL ANTIBODIES AND USES THEREOF

(75) Inventors: Paul Acton, Quakertown, PA (US); Zhiqiang An, Ambler, PA (US); Andrew J. Bett, Lansdale, PA (US); Robert Breese, Quakertown, PA (US); Lei Chang, Westmont, IL (US); Elizabeth Chen Dodson, Souderton, PA (US); Gene Kinney, Collegeville, PA (US); William Klein, Winetka, IL (US); Mary P. Lambert, Glenview, IL (US); Xiaoping Liang, Collegeville, PA (US); Paul Shughrue, West Chester, PA (US); William R. Strohl, Bridgewater, NJ (US); Kirsten Viola, Chicago, IL (US)

(73) Assignees: Merck & Co., Inc., Rahway, NJ (US); Northwestern University, Evanston, IL (US)

( * ) Notice: Subject to any disclaimer, the term of this patent is extended or adjusted under 35 U.S.C. 154(b) by 969 days.

(21) Appl. No.: 11/256,332

(22) Filed: Oct. 21, 2005

(65) Prior Publication Data

US 2006/0228349 A1    Oct. 12, 2006

Related U.S. Application Data

(60) Provisional application No. 60/621,776, filed on Oct. 25, 2004, provisional application No. 60/652,538, filed on Feb. 14, 2005.

(51) Int. Cl.
*A61K 39/395* (2006.01)
*C07K 16/18* (2006.01)
*G01N 33/53* (2006.01)

(52) U.S. Cl. .................. 424/133.1; 530/387.3; 435/7.2; 424/141.1

(58) Field of Classification Search ........................ None
See application file for complete search history.

(56) References Cited

U.S. PATENT DOCUMENTS

| | | | | |
|---|---|---|---|---|
| 5,693,762 | A * | 12/1997 | Queen et al. ............ | 530/387.3 |
| 6,218,506 | B1 | 4/2001 | Krafft et al. .............. | 530/324 |
| 6,743,427 | B1 | 6/2004 | Schenk .................... | 424/130.1 |
| 6,750,324 | B1 | 6/2004 | Schenk et al. ........... | 530/387.1 |
| 6,761,888 | B1 | 7/2004 | Schenk .................... | 424/130.1 |
| 6,787,637 | B1 | 9/2004 | Schenk .................... | 530/387.1 |
| 6,797,492 | B2 | 9/2004 | Daugherty et al. ....... | 435/69.6 |
| 6,913,745 | B1 | 7/2005 | Schenk .................... | 424/130.1 |
| 2003/0068316 | A1 | 4/2003 | Klein et al. ............... | 424/130.1 |

FOREIGN PATENT DOCUMENTS

| | | |
|---|---|---|
| EP | 613007 A2 * | 8/1994 |
| WO | WO 97/11971 | 4/1997 |
| WO | WO 03/104437 | 12/2003 |
| WO | WO 2005/025516 | 3/2005 |

OTHER PUBLICATIONS

Barrow et al. Solution conformations and aggregational properties of synthetic amyloid beta-peptides of Alzheimer's disease. Analysis of circular dichroism spectra. J Mol Biol. Jun. 20, 1992;225(4):1075-93.*
Paul W. E. Fundamental Immunology, 3rd edition, 1993, pp. 292-295.*
Rudikoff et al. Single amino acid substitution altering antigen-binding specificity. Proc Natl Acad Sci U S A. Mar. 1982;79(6):1979-83.*
Diaz. Somatic immunoglobulin hypermutation. 1: Curr Opin Immunol. Apr. 2002;14(2):235-40.*
Chromy. Self-assembly of Abeta(1-42) into globular neurotoxins. Biochemistry. Nov. 11, 2003;42(44):12749-60.*
Guerette 1999 (Society for Neuroscience Abstracts vol. 25, Part 2, p. 2129 abstract 852.1).*
MacCallum et al. Journal of Molecular. Biology, 1996, vol. 262, pp. 732-745.*
Pascalis et al. Journal of Immunology, 2002, vol. 169, pp. 3076-3084.*
Casset et al. Biochemical and Biophysical Research Communications, 2003, vol. 307, pp. 198-205.*
Vajdos et al. Journal of Molecular biology, 2002, vol. 320, pp. 415-428.*
Holm et al. Molecular Immunology, 2007, vol. 44, pp. 1075-1084.*
Chen et al. Journal of Molecular Biology, 1999, vol. 293, pp. 865-881.*
Wu et al. Journal of Molecular Biology, 1999, vol. 294, pp. 151-162.*
Armour et al., "Recombinant human IgG molecules lacking Fcγ receptor I binding and monocyte triggering activities", Eur. J. Immuno. 1999 29:2613.
Birmingham, K. and Frantz, S., "Set back to Alzheimer vaccine studies", Nat. Med. 2002 8:199-200.
Bitan et al., "Neurotoxic protein oligomers-what you see is not always what you get", Amyloid 2005 12(2):88-95.
Canfield and Morrison, "The Binding Affinity of Human IgG for its High Affinity Fc Receptor Is Determined by Multiple Amino Acids in the $C_H2$ Domain and Is Modulated by the Hinge Region", J. Exp. Med. 1991 173:1483-1491.
Chang et al., "Femtomole Immunodetection of Synthetic and Endogenous Amyloid-β Oligomers and Its Application to Alzheimer's Disease Drug Candidate Screening", J. Molecular Neuroscience 2003 20:305-313.
Dodart et al., "Immunization reverses memory deficits without reducing brain Aβ burden in Alzheimer's disease model", Nat. Neurosci. 2002 5:452-457.
Gong et al., "Alzheimer's disease-affected brain:Presence of oligomeric Aβ ligands (ADDLs) suggests a molecular basis for reversible memory loss", Proc. Natl. Acad. Sci. USA 2003 100:10417-10422.

(Continued)

*Primary Examiner*—Daniel E. Kolker
*Assistant Examiner*—Gregory S Emch
(74) *Attorney, Agent, or Firm*—Licata & Tyrrell P.C.

(57) ABSTRACT

The present invention relates to antibodies that differentially recognize multi-dimensional conformations of Aβ-derived diffusible ligands, also known as ADDLs. The antibodies of the invention can distinguish between Alzheimer's Disease and control human brain extracts and are useful in methods of detecting ADDLs and diagnosing Alzheimer's Disease. The present antibodies also block binding of ADDLs to neurons, assembly of ADDLS, and tau phosphorylation and are there useful in methods for the preventing and treating diseases associated with soluble oligomers of amyloid β1-42.

14 Claims, 47 Drawing Sheets

OTHER PUBLICATIONS

Hardy et al., "The Amyloid Hypothesis of Alzheimer's Disease:Progress and Problems on the Road to Therapeutics", Science 2002 297:353-356.

Hock et al., "Antibodies against β-Amyloid Slow Cognitive Decline in Alzheimer's Disease", Neuron 2003 38:547-554.

Hougs et al., "The first constant-domain (CH1) exon of human *IGHG2* is polymorphic and in strong linkage disequilibrium with the CHW exon polymorphism encoding the G2m(n+) allotype in Caucasians", Immunogenetics 2001 52:242-248.

Ida et al., "Analysis of Heterogeneous βA4 Peptides in Human Cerebrospinal Fluid and blood by a Newly Developed Sensitive Western Blot Assay", J. Biol. Chem. 1996 271(37):22903-22914.

Kayed et al., "Common Structure of Soluble Amyloid Oligomers Implies Common Mechanism of Pathogenesis", Science 2003 300:486-489.

Klein, William L., "Aβ toxicity in Alzheimer's disease:globular oligomers (ADDLs) as new vaccine and drug targets", Neurochemistry International 2002 41:345-352.

Kotilnek et al., "Reversible Memory Loss in a Mouse Transgenic Model of Alzheimer's Disease", J. Neurosci 2002 22:6331-6335.

Lambert et al., "Vaccination with soluble Aβ oligomers generates toxicity-neutralizing antibodies", J. Neurochemistry 2001 79:595-605.

Lambert et al., "Diffusible, nonfibrillar ligands derived from Aβ$_{1-42}$ are potent central nervous system neurotoxins", Proc. Natl. Acad. Sci. USA 1998 95:6448-6453.

Lathe, R., "Synthetic Oligonucleotide Probes Deduced from Amino Acid Sequence Data-Theoretical and Practical Considerations", J. Mol. Biol. 1985 183:1-12.

Lu et al., "A second cytotoxic proteolytic peptide derived from amyloid β-protein precursor", Nat. Med. 2000 6:397-404.

Medgyesi et al., "Functional mapping of the FcγRll binding site on human IgG1 by synthetic peptides", Eur. J. Immunol. 2004 34:1127-1135.

Padlan, Eduardo A., "Anatomy of the Antibody Molecule", Molecular Immunology 1994 31(3):169-217.

Tao et al., "The Differential Ability of Human IgG1 and IgG4 to Activate Complement Is Determined by the COOH-terminal Sequence of the $C_H2$ Domain", J. Exp. Med. 1991 173:1025-1028.

Xu et al., "Residue at Position 331 in the IgG1 and IgG4 $C_H2$ Domains Contributes to Their Differential Ability to Bind and Activate Complement", J. Biol. Chem 1994 269:3469-3474.

Zuckier et al., "The Use of Severe Combined Immunodeficiency Mice to Study the Metabolism of Human Immunoglobulin G", Cancer Suppl. 1994 73:794-799.

\* cited by examiner

| Clone Name | Isotype | DENATURED SPECIES IDENTIFIED | | | Identified Native ADDLs | Peak 1/Peak 2 Ratio (ELISA) | Immunofluorescence |
|---|---|---|---|---|---|---|---|
| | | ADDLs | HMW ADDLs | Human Fibrils | | | |
| 2A10 | IgG1 | Trimer, tetramer | Yes | Yes | High/low MW | 20 | Hot spots on processes, cell body |
| 2B4 | IgG2b | Trimer, tetramer | Yes | Yes | High/low MW | 63 | Cell body |
| 2D6 | IgG1 | Tetramer | Yes | Yes | High/low MW | 19 | Cell body |
| 4C2 | IgG1 | No | Yes | Yes | High/low MW | 18 | Cell body |
| 4E2 | IgG1 | Tetramer | Yes | Yes | High/low MW | 22 | Cell body |
| 5F10 | IgG2a | Trimer, tetramer | Yes | | High/low MW | 18 | Processes, no hot spots |
| 5G12 | IgM | Trimer, tetramer | Yes | Yes | Only low MW | 5 | Cell body, processes |
| 6B7 | | No | Yes | Slight | | 15 | NR |
| 6B11 | | No | Yes | Slight | | 12 | Faint cell body |
| 11B4 | | Monomer, trimer, tetramer | Yes | | High/low MW | 15 | |
| 11B5 | IgG1 | Monomer, trimer, tetramer | Yes | | High/low MW | 22 | |
| 14A11 | | Monomer, trimer, tetramer | Yes | | High/low MW | 14 | |
| 15G6 | | Monomer, trimer, tetramer | Yes | | High/low MW | 16 | |
| 17G4 | | Monomer, trimer, tetramer | Yes | | High/low MW | 11 | |
| 20C2 | IgG1 | Monomer, trimer, tetramer | Yes | | High/low MW | 12 | |
| 3B7 | | Trimer, tetramer, 7-mer, 8-mer | No | No | No | -2 | |

FIG. 3

20C2 - HEAVY CHAIN VARIABLE REGION SEQUENCE
tgggcagacttaccattctcattcctgctgctgattgtccctgcatatg
tcttgtccCAAGTTACTCTAAAAGAGTCTGGCCCTGGGATATTGAAGCC
CTCACAGACCCTCAGTCTGACTTGTTCTCTCTCTGGGTTTTCACTGAGC
ACTTCTGGTATGGGTGTAGGCTGGTTTCGTCAGCCTTCAGGGAAGGGTC
TGGAGTGGCTGGCACACATTTGGTGGGATGATGATAAGTCCTATAATCC
ATCCCTGAAGAGCCGGCTCACAATCTCCAAGTATACCTCTAGAAACCAG
GTTTTCCTCACGATCACCAGTGTGGACACTGCAGATACTGCCACTTACT
ATTGTGCTCGAAGACAACTCGGACTAAGATCAATTGATGCTATGGACTA
CTGGGGTCAAGGAACCTCAGTCACCGTCTCCTCAGCCAAAACGACACCC
CCATCTGTCTATCCACTG (SEQ ID NO:1)

FIG. 6A

20C2 - LIGHT CHAIN VARIABLE REGION SEQUENCE
agattgcctgttaggctgttggtgctgatgttctggattcctgcttcca
ccagtGATGTTTTGATGACCCAAACTCCTCTCTCCCTGCCTGTCAGTCT
TGGAGATCAAGCCTCCATCTCTTGCAGATCTAGTCAGAGCATTCTACAT
AGTAATGGAAACACCTATTTAGAGTGGTACCTGCAGAAACCAGGCCAGT
CTCCAAAGCTCCTGATCTACAAAGTTTCCAACCGATTTTCTGGGGTCCC
AGACAGGTTCAGTGGCAGTGGATCAGGGACAGATTTCACACTCAAGATC
AGCAGAGTGGAGGCTGAGGATCTGGGAGTTTATTACTGTTTTCAAGGTT
CACTTGTTCCGCTCACGTTCGGTGCTGGGACCAAGCTGGAGCTGAAACG
GGCTGATGCTGCACCAACTGTATCCATCTTCCCACCATCCAGT
(SEQ ID NO:2)

FIG. 6B

5F10 - HEAVY CHAIN VARIABLE REGION SEQUENCE
tgggcagacttaccattctcattcctgctgctgattgtccctgcatatg
tcctttccCAGGTTACTCTGAAAGAGTCTGGCCCTGGGATATTGCAGCC
CTCCCAGACCCTCAGTCTGACTTGTTCTTTCTCTGGGTTTTCACTGAGC
ACTTCTGGTATGGGTGTGAGCTGGATTCGTCAGCCTTCAGGAAAGGGTC
TGGAGTGGCTGGCACACATTTACTGGGATGATGACAAGCGCTATAACCC
ATCCCTGAAGAGCCGGCTCACATTCTCCAAGGATTCCTCCAGAAACCAG
GTATTCCTCAAGATCACCAGTGTGGACACTGCAGATACTGCCACATACT
ACTGTGCTCGCTATGATGGTTACCCCTACTGGTACTTCGATGTCTGGGG
CGCAGGGACCACGGTCACCGTCTCCTCAGCCAAAACAACACCCCCATCG
GTCTATCCACTG (SEQ ID NO:3)

FIG. 6C

5F10 - LIGHT CHAIN VARIABLE REGION SEQUENCE
agattgcctgttaggctgttggtgctgatgttctggattcctgtttcca
gcagtGTTGTTCTGATGACCCAAACTCCACTCTCCCTGCCTGTCAGTCT
TGGAGATCAAGCCTCCATCTCTTGCAGATCTAGTCAGAGCCTTGTACAC
AGTAATGGAAACACCTATTTACATTGGTACCTGCAGAAGCCAGGCCAGT
CTCCAAAGCTCCTGATCTACAAAGTTTCCAACCGATTTTCTGGGGTCCC
AGACAGGTTCAGTGGCAGTGGATCAGGGACAGATTTCACACTCAAGATC
AGCAGAGTGGAGGCTGAGGATCTGGGAGTTTATTTCTGTTTTCAAAGTA
CACATGTTCCGCTCACGTTCGGTGCTGGGACCAAGCTGGAGCTGAAACG
GGCTGATGCTGCACCAACTGTATCCATCTTCCCACCATCCAGT
(SEQ ID NO:4)

FIG. 6D

2D6 - HEAVY CHAIN VARIABLE REGION SEQUENCE
tgggcagacttaccattctcattcctgctgctgattgtccctgcatatg
tcttgtccCAAGTTACTCTAAAAGAGTCTGGCCCTGGGATATTGAAGCC
CTCACAGACCCTCAGTCTGACTTGTTCTTTCTCTGGGTTTTCACTGAGC
ACTTCTGGTATGGGTGTAGGCTGGATTCGTCAGCCTTCAGGGAAGGGTC
TGGAGTGGCTGGCACACATTTGGTGGGATGATGATAAGTACTATAACCC
ATCCCTGAAGAGCCAGCTCACAATCTCCAAGGATACCTCCAGAAACCAG
GTATTCCTCAAGATCACCAGTGTGGACACTGCAGATACTGCCACTTACT
ACTGTGCTCGAAGATCCATTAGTACGGTAATACCTGAGGACTACTTTGA
CTACTGGGGCCAAGGCACCATTCTCACAGTCTCCTCAGCCAAAACGACA
CCCCCATCTGTCTATCCACTG (SEQ ID NO:5)

FIG. 6E

2D6 - LIGHT CHAIN VARIABLE REGION SEQUENCE
agattgcctgttaggctgttggtgctgatgttctggattcctgcttcca
ccagtGATGTTTTGATGACCCAAACTCCACTCTCCCTGACCGTCAGTCT
TGGAGATCAAGCCTCCATCTCTTGCAGATCTAGTCAGAGCATTGTGCAT
AGTAATGGAAACACCTATTTAGAATGGTACCTGCAGAAACCAGGCCAGT
CTCCAAAGCTCCTGATCTACAAAGTTTCCAACCGATTTTCTGGGGTCCC
AGACAGGTTCAGTGGCAGTGGATCAGGGACAGATTTCACACTCAAGATC
AGCAGAGTGGAGGCTGAGGATCTGGGAGTTTATTACTGCTTTCAAGGTT
CACATGTTCCGCTCACGTTCGGTGCTGGGACCAAGCTGGAGCTGAAACG
GGCTGATGCTGCACCAACTGTATCCATCTTCCCACCATCCAGT
(SEQ ID NO:6)

FIG. 6F

2B4 - HEAVY CHAIN VARIABLE REGION SEQUENCE
tgggcagacttaccattctcattcctgctgctgattgtccctgcatatg
tcctttccCAGGTTACTCTGAAAGAGTCTGGCCCTGGGATATTGCAGCC
CTCCCAGACCCTCAGTCTGACTTGTTCTTTCTCTGGGTTTTCACTGAGC
ACTTCTGGTATGGGTGTGAGCTGGATTCGTCAGCCTTCAGGAAAGGGTC
TGGAGTGGCTGGCACACATTTACTGGGATGATGACAAGCGCTATAACCC
ATCCCTGAAGAGCCGGCTCACAATCTCCAAGGATACCTCCAGAAACCAG
GTATTCCTCAAGATCACCAGTGTGGACACTGCAGATACTGCCACATACT
ACTGTGCTCGCTATGATGGTTACCCCTACTGGTACTTCGATGTCTGGGG
CGCAGGGACCACGGTCACCGTCTCCTCAGCCAAAACAACACCCCCATCA
GCTCATCCACTG (SEQ ID NO:7)

FIG. 6G

2B4 - LIGHT CHAIN VARIABLE REGION SEQUENCE
agattgcctgttaggctgttggtgctgatgttctggattcctgcttcca
gcagtGATGTTGTGATGACCCAAACTCCACTCTCCCTGCCTGTCAGTCT
TGGAGATCAAGCCTCCATCTCTTGCAGATCTAGTCAGAGCCTTGTACAC
AGTAATGGAAACACCTATTTACATTGGTACCTGCAGAAGCCAGGCCAGT
CTCCAAAGCTCCTGATCTACAAAGTTTCCAACCGATTTTTTGGGGTCCC
AGACAGGTTCAGTGGCAGTGGATCAGGACAGATTTCACACTCAAGATC
AGCAGAGTGGAGGCTGAGGATCTGGGAGTTTACTTCTGCTCTCAAACTA
CATATGTTCCGCTCACGTTCGGTGCTGGGACCAAGCTGGAGCTGAAACG
GGCTGATGCTGCACCAACTGTATCCATCTTCCCACCATCCAGT
(SEQ ID NO:8)

FIG. 6H

4E2 - HEAVY CHAIN VARIABLE REGION SEQUENCE
tgggcagacttaccattctcattcctgctgctgattgtccctgcatatg
tcttgtccCAAGTTACTCTAAAAGAGTCTGGCCCTGGGATATTGAAGCC
CTCACAGACCCTCAGTCTGACTTGTTCTTTCTCTGGGTTTTCACTGAGC
ACTTCTGGTATGGGTGTAGGCTGGATTCGTCAGCCTTCAGGGAAGGGTC
TGGAGTGGCTGGCACACATTTGGTGGGATGATGATAAGTACTATAACCC
ATCCCTGAAGAGCCAGCTCACAATCTCCAAGGATACCTCCAGAAACCAG
GTATTCCTCAAGATCACCAGTGTGGACACTGCAGATACTGCCACTTACT
ACTGTGCTCGAAGATCCATTAATTCGGTAGTACCTGAGGACTACTTTGA
CTACTGGGGCCAAGGCACCACTCTCACAGTCTCCTTAGCCAAAACGACA
CCCCCATCTGTCTATCCACTG (SEQ ID NO:9)

FIG. 6I

4E2 - LIGHT CHAIN VARIABLE REGION SEQUENCE
agattgcctgttaggctgttggtgctgatgttctggattcctgcttcca
gcagtGATGTTTTGATGACCCAAACTCCACTCTCCCTGCCTGTCAGTCT
TGGAGATCAAGCCTCCATCTCTTGCAGATCTAGTCAGAGCATTGTGCAT
AGTAATGGAAACACCTATTTAGAATGGTACCTGCAGAAACCAGGCCAGT
CTCCAAAGCTCCTGATCTACAAAGTTTCCAACCGATTTTCTGGGGTCCC
AGACAGGTTCAGTGGCAGTGGATCAGGGACAGATTTCACACTCAAGATC
AGCAGAGTGGAGGCTGAGGATCTGGGAGTTTATTATTGTTTTCAAGGTT
CACATGTTCCGCTCACGTTCGGTGCTGGGACCAAGCTGGAGCTGAAACG
GGCTGATGCTGCACCAACTGTATCCATCTTCCACCATCCAGT
(SEQ ID NO:10)

FIG. 6J

2H4 - HEAVY CHAIN VARIABLE REGION SEQUENCE
tgggactccaggcttcaatttagttttccttgtccttattttaaaaggt
gtccagtgtGATGTGCAGCTGGTGGAGTCTGGGGGAGGCTTAGTGCAGC
CTGGAGGGTCCCGGAAACTCTCCTGTGCAGCCTCTGGATTCACTTTCAG
TAGCTTTGGAATGCACTGGGTTCGTCAGGCTCCAGAGAAGGGGCTGGAG
TGGGTCGCATACATTCGTAGTGGCAGTAGTACCATCTACTATGCAGACA
CAGTGAAGGGCCGATTCACCATCTCCAGAGACAATCCCAAGAACACCCT
GTTCCTGCAAATGACCAGTCTAAGGTCTGAGGACACGGCCATGTATTAC
TGTACAAGAGGCGGGAATTACTACGGTAGTAGCCGGTTTGCTTACTGGG
GCCAAGGGACTCTGGTCACTGTCTCTGCAGCCAAAACAACAGCCCCCAT
CGGTCTATCCACTG (SEQ ID NO:11)

FIG. 6K

2H4 - LIGHT CHAIN VARIABLE REGION SEQUENCE
tgagggcccctgctcagttttttggattcttgttgctctggtttccagg
tatcaaatgtGACATCAAGATGACCCAGTCTCCATCTTCCATGTATGCA
TCTCTAGGAGAGAGTCACTATCACTTGCAAGGCGAGTCAGGACATTA
ATAGCTATTTAAGCTGGTTCCAGCAGAAACCAGGGAAATCTCCTAAGAC
CCTGATCTATCGTGCAAACAGATTCGTAGATGGGGTCCCATCAAGGTTC
AGTGGCAGTGGATCTGGGCAAGATTATTCTCTCACCATCAGCAGCCTGG
AGTATGAAGATATGGGAATTTATTTTTGTCTACAGTATGATGAGTTTCC
GCTCACGTTCGGTGCTGGGACCAAGCTGGTACTGAAACGGGCTGATGCT
GCACCAACTGTATCCATCTTCCACCATCCAGT (SEQ ID NO:12)

FIG. 6L

2A10 - HEAVY CHAIN VARIABLE REGION SEQUENCE
tgggcagacttaccattctcattcctgctgctgattgtccctgcatatg
tcttgtccCAAGTTACTCTAAAAGAGTCTGGCCCTGGGATATTGAAGCC
CTCACAGACCCTCAGTCTGACTTGTTCTTTCTCTGGGTTTTCACTGAGC
ACTTCTGGTATGGGTGTAGGCTGGATTCGTCAGCCTTCAGGGAAGGGTC
TGGAGTGGCTGGCACACATTTGGTGGGATGATGATAAGTACTATAACCC
ATCCCTGAAGAGCCAGCTCACAATCTCCAAGGATACCTCCAGAAACCAG
GTTTTCCTCAAGATCACCAGTGTGGACACTGCAGATACTGCCACTTACT
ACTGTGCTCGAAGATCCATTAGTACGTTGGTACCTGAGGACTACTTTGA
CTACTGGGGCCAAGGCACCACTCTCACAGTCTCCTCAGCCAAAACGACA
CCCCCATCTGTCTATCCACTG (SEQ ID NO:13)

FIG. 6M

2A10 - LIGHT CHAIN VARIABLE REGION SEQUENCE
tgaagattgcctgttaggctgttggtgctgatgttctggattcctgctt
ccagcagtGATGTTTTGATGACCCAAACTCCACTCTCCCTGCCTGTCAG
TCTTGGAGATCAAGCCTCCATCTCTTGCAGATCTAGTCAGAGCATTGTA
CATAGTAATGGAAACACCTATTTAGAATGGTACCTGCAGAAACCAGGCC
AGTCTCCAAAGCTCCTGATCTACAAAGTTTCCAACCGATTTTCTGGGGT
CCCAGACAGGTTCAGTGGCAGTGGATCAGGGACAGATTTCACACTCAAG
ATCAGCAGAGTGGAGGCTGAGGATCTGGGAGTTTATTATTGCTTTCAAG
GTTCACATGTTCCGCTCACGTTCGGTGCTGGGACCAAGCTGGAGCTGAA
ACGGGCTGATGCTGCACCAACTGTATCCATCTTCCCACCATCCAGT
(SEQ ID NO:14)

FIG. 6N

3B3 - HEAVY CHAIN VARIABLE REGION SEQUENCE
tgggactccaggcttcaatttagttttccttgtccttatttaaaaggt
gtccagtgtGATGTGCAGCTGGTGGAGTCTGGGGGAGGCTTAGTGCAGC
CTGGAGGGTCCCGGAAACTCTCCTGTGCAGCCTCTGGATTCACTTTCAG
TAGCTTTGGAATGCACTGGGTTCGTCAGGCTCCAGAGAAGGGGCTGGAG
TGGGTCGCATACATTAGTAGAGGCAGTAGCACCATCTACTATGCAGACA
CAGTGAAGGGCCGATTCACCATCTCCAGAGACAATCCCAAGAACACCCT
GTTCCTGCAAATGACCAGTCTAAGGTCTGAGGACACGGCCATGTATTAC
TGTGCAAGAGGGATTACGACGGCCTTGGACTACTGGGGTCAAGGAACCT
CAGTCACCGTCTCCTCAGCCAAAACGACACCCCCATCTGTCTATCCACT
G (SEQ ID NO:15)

FIG. 6O

3B3 - LIGHT CHAIN VARIABLE REGION SEQUENCE
tgaagattgcctgttaggctgttggtgctgatgttctggattcctgctt
ccagaagtGATGTTTTGATGACCCAAACTCCACTCTCCCTGCCTGTCAG
TCTTGGAGATCAAGCCTCCATCTCTTGCAGATCTAGTCAGAGCATTGTA
CATAGTAATGGAAACACCTATTTAGAATGGTACCTGCAGAAACCAGGCC
AGTCTCCAAAGCTCCTGATCTACAAAGCTTCCAACCGATTTTCTGGGGT
CCCAGACAGGTTCAGTGGCAGTGGATCAGGGACAGATTTCACACTCAAG
ATCAGCAGAGTGGAGGCTGAGGATCTGGGAGTTTATTACTGCTTTCAAG
GTTCACATGTTCCTCCGACGTTCGGTGGAGGCACCAAGCTGGAAATCAA
ACGGGCTGATGCTGCACCAACTGTATCCATCTTCCCACCATCCAGT
(SEQ ID NO:16)

FIG. 6P

1F6 - HEAVY CHAIN VARIABLE REGION SEQUENCE
tgggactccaggcttcaatttagttttccttgtccttatttaaaggt
gtccagtgtGATGTGCAGCTGGTGGAGTCTGGGGGAGGCTTAGTGCAGC
CTGGAGGGTCCCGGAAACTCTCCTGTGCAGCCTCTGGATTCACTTTCAG
TAGCTTTGGAATGCACTGGGTTCGTCAGGCTCCAGAGAAGGGGCTGGAG
TGGGTCGCATACATTAGTAGTGTCAGTAGTACCATCTACTATGCAGACA
CAGTGAAGGGCCGATTCACCATCTCCAGAGACAATCCCAAGAATACTCT
GTTCCTGCAAATGACCAGTCTAAGGTCTGAGGACACGGCCATGTATTAC
TGTGCAAGATCGGGCTACGGTAGTAGTTACGGGTATGGTATGGACTACT
GGGGTCAAGGAACCTTAGTCACCGTCTCCTCAGCCAAAACGACACCCCC
ATCTGTCTATCCACTG (SEQ ID NO:17)

FIG. 6Q

1F6 - LIGHT CHAIN VARIABLE REGION SEQUENCE
tgaagattgcctgttaggctgttggtgctgatgttctggattcctgctt
ccagcagtGATGTTTTGATGACCCAAACTCCACTCTCCCTGCCTGTCAG
TCTTGGAGATCAAGCCTCCATCTCTTGCAGATCTAGTCAGAGCATTGTA
CATAGTAATGGAAACACCTATTTAGAATGGTACCTGCAGAAACCAGGCC
AGTCTCCAAAGCTCCTGATCTACAAAGTTTCCAACCGATTTTCTGGGGT
CCCAGACAGGTTCAGTGGCAGTGGATCAGGGACAGATTTCACACTCAAG
ATCAGCAGAGTGGAGGCTGAGGATCTGGGAGTTTATTACTGCTTTCAAG
GTTCACATGTTCCGCTCACGTTCGGTGCTGGGACCAAGCTGGAGCTGAA
ACGGGCTGATGCTGCACCAACTGTATCCATCTTCCCACCATCCAGT
(SEQ ID NO:18)

FIG. 6R

1F4 - HEAVY CHAIN VARIABLE REGION SEQUENCE
tgggactccaggcttcaatttagttttccttgtccttatttttaaaaggt
gtccagtgtGATGTGCAGCTGGTGGAGTCTGGGGGAGGCTTAGTGCAGC
CTGGAGGGTCCCGGAAACTCTCCTGTGCAGCCTCTGGATTCACTTTCAG
TAGCTTTGGAATGCACTGGGTTCGTCAGGCTCCAGAGAAGGGGCTGGAG
TGGGTCGCATACATTAGTAGTGTCAGTAGTACCATCTACTATGCAGACA
CAGTGAAGGGCCGATTCACCATCTCCAGAGACAATCCCAAGAATACTCT
GTTCCTGCAAATGACCAGTCTAAGGTCTGAGGACACGGCCATGTATTAC
TGTGCAAGATCGGGCTACGGTAGTAGTTACGGGTATGGTATGGACTACT
GGGGTCAAGGAACCTTAGTCACCGTCTCCTCAGCCAAAACGACACCCCC
ATCTGTCTATCCACTG (SEQ ID NO:19)

FIG. 6S

1F4 - LIGHT CHAIN VARIABLE REGION SEQUENCE
tgaagattgcctgttaggctgttggtgctgatgttctggattcctgctt
ccagcagtGATGTTTTGATGACCCAAACTCCACTCTCCTGCCTGTCAG
TCTTGGAGATCAAGCCTCCATCTCTTGCAGATCTAGTCAGAGCATTGTA
CATAGTAATGGAAACACCTATTTAGAATGGTACCTGCAGAAACCAGGCC
AGTCTCCAAAGCTCCTGATCTACAAAGTTTCCAACCGATTTTCTGGGGT
CCCAGACAGGTTCAGTGGCAGTGGATCAGGGACAGATTTCACACTCAAG
ATCAGCAGAGTGGAGGCTGAGGATCTGGGAGTTTATTACTGCTTTCAAG
GTTCACATGTTCCGCTCACGTTCGGTGCTGGGACCAAGCTGGAGCTGAA
ACGGGCTGATGCTGCACCAACTGTATCCATCTTCCCACCATCCAGT
(SEQ ID NO:20)

FIG. 6T

2E12 - HEAVY CHAIN VARIABLE REGION SEQUENCE
tgggactccaggcttcaatttagttttccttgtccttatttttaaaaggt
gtccagtgtGATGTGCAGCTGGTGGAGTCTGGGGGAGGCTTAGTGCAGC
CTGGAGGGTCCCGGAAACTCTCCTGTGCAGCCTCTGGATTCACTTTCAG
TAGCTTTGGAATGCACTGGGTTCGTCAGGCTCCAGAGAAGGGGCTGGAG
TGGGTCGCATACATTAGTAGTGGCAGTTATACCATCTACTATGCAGACA
CAGTGAAGGGCCGATTCACCATCTCCAGAGACAATCCCAAGAACACCCT
GTTCCTGCAAATGACCAGTCTAAGGTCTGAGGACACGGCCATGTATTAC
TGTGCAAGATACGGTAATTACGGCTATTACTATGGTATGGACTACTGGG
GTCAAGGAACCTCAGTCACCGTCTCCTCAGCCAAAACGACACCCCATC
TGTCTATCCACTG (SEQ ID NO:21)

FIG. 6U

2E12 - LIGHT CHAIN VARIABLE REGION SEQUENCE
tgaagattgcctgttaggctgttggtgctgatgttctggattcctgctt
ccagcagtGATGTTGTGATGACCCAAACTCCACTCTCCCTGCCTGTCAG
TCTTGGAGATCAAGCCTCCATCTCTTGCAGATCTAGTCAGAGCCTTGTA
CACAGTAATGGAAACACCTATTTACATTGGTACCTGCAGAAGCCAGGCC
AGTCTCCAAAGCTCCTGATCTACAAAGTTTCCAACCGATTTTCTGGGGT
CCCAGACAGGTTCAGTGGCAGTGGATCAGGGACAGATTTCACACTCAAG
ATCAGCAGAGTGGAGGCTGAGGATCTGGGAGTTTATTTCTGCTCTCAAA
GTACACATGTTCCTCCGACGTTCGGTGGAGGCACCAAGCTGGAAATCAA
ACGGGCTGATGCTGCACCAACTGTATCCATCTTCCCACCATCCAGT
(SEQ ID NO:22)

FIG. 6V

4C2 - HEAVY CHAIN VARIABLE REGION SEQUENCE
tgggcagacttaccattctcattcctgctgctgattgtccctgcatatg
tcttgtccCAAGTTACTCTAAAAGAGTCTGGCCCTGGGATATTGAAGCC
CTCACAGACCCTCAGTCTGACTTGTTCTTTCTCTGGGTTTTCACTGAGC
ACTTCTGGTATGGGTGTAGGCTGGATTCGTCAGCCTTCAGGGAAGGGTC
TGGAGTGGCTGGCACACATTTGGTGGGATGATGATAAGTACTATAACCC
ATCCCTGAAGAGCCAGCTCACAATCTCCAAGGATACCTCCAGAAACCAG
GTATTCCTCAAGATCACCAGTGTGGACACTGCAGATACTGCCACTTACT
ACTGTGCTCGAAGATCCATTACTACGGTAGTACCTGAGGACTACTTTGC
CTACTGGGGCCAAGGCACCACTCTCACAGTCTCCTCAGCCAAAACAACA
GCCCCCATCTGTCTATCCACT (SEQ ID NO:23)

FIG. 6W

4C2 - LIGHT CHAIN VARIABLE REGION SEQUENCE
tgaagattgcctgttaggctgttggtgctgatgttctggattcctgctt
ccagcagtGATGTTTTGATGACCCAAAGTCCACTCTCCCTGCCTGTCAG
TCTTGGAGATCAAGCCTCCATCTCTTGCAGATCTAGTCAGAGCATTGTA
CATAGTAATGGAAACACCTATTTAGAATGGTATTTGCAGAAACCAGGCC
AGTCTCCAAAGCTCCTGATCTACAAAGTTTCCAACCGATTTTCTGGGGT
CCCAGACAGGTTCAGTGGCAGTGGATCAGGGACAGATTTCACACTCAAG
ATCAGCAGAGTGGAGGCTGAGGATCTGGGAGTTTATTACTGCTTTCAAG
GTTCACATGTTCCGCTCACGTTCGGTGCTGGGACCAAGCTGGAGCTGAA
AAGGGCTGATGCTGCACCAACTGTATCCATCTTCCCACCATCCAGT
(SEQ ID NO:24)

FIG. 6X

| ANTIBODY | Aβ EPITOPE | CDR1 | SEQ ID NO: |
|---|---|---|---|
| 2A10 | 3-8 | T S G M G V G | 25 |
| 4C2 | 3-8 | T S G M G V G | 25 |
| 2D6 | 3-8 | T S G M G V G | 25 |
| 4E2 | 3-8 | T S G M G V G | 25 |
| 20C2 | 3-8 | T S G M G V G | 25 |
| 2B4 | 3-8 | T S G M G V S | 26 |
| 5F10 | 3-8 | T S G M G V S | 26 |
| CONSENSUS | | T S G M G V X | 27 |
| 2H4 | 1-8 | S F G M H | 28 |
| 2E12 | 3-10 | S F G M H | 28 |
| 1F6 | 1-20* | S F G M H | 28 |
| 1F4 | 1-20* | S F G M H | 28 |
| 3B3 | 1-20* | S F G M H | 28 |
| CONSENSUS | | S F G M H | 28 |

FIG. 7A

| ANTIBODY | Aβ EPITOPE | CDR2 | SEQ ID NO: |
|---|---|---|---|
| 2A10 | 3-8 | H I W W D D D K Y Y N P S L K S | 29 |
| 4C2 | 3-8 | H I W W D D D K Y Y N P S L K S | 29 |
| 2D6 | 3-8 | H I W W D D D K Y Y N P S L K S | 29 |
| 4E2 | 3-8 | H I W W D D D K Y Y N P S L K S | 29 |
| 20C2 | 3-8 | H I W W D D D K S Y N P S L K S | 30 |
| 2B4 | 3-8 | H I Y W D D D K R Y N P S L K S | 31 |
| 5F10 | 3-8 | H I Y W D D D K R Y N P S L K S | 31 |
| CONSENSUS | | H I X W D D D K X Y N P S L K S | 32 |
| 2H4 | 1-8 | Y I R S G S S T I Y Y A D T V K G | 33 |
| 2E12 | 3-10 | Y I S S G S Y T I Y Y A D T V K G | 34 |
| 1F6 | 1-20* | Y I S S V S S T I Y Y A D T V K G | 35 |
| 1F4 | 1-20* | Y I S S V S S T I Y Y A D T V K G | 35 |
| 3B3 | 1-20* | Y I S R G S S T I Y Y A D T V K G | 36 |
| CONSENSUS | | Y I X X X S X T I Y Y A D T V K G | 37 |

FIG. 7B

| ANTIBODY | Aβ EPITOPE | CDR3 | SEQ ID NO: |
|---|---|---|---|
| 2A10 | 3-8 | R S I S T L V P E D Y F D Y | 38 |
| 4C2 | 3-8 | R S I T T V V P E D Y F A Y | 39 |
| 2D6 | 3-8 | R S I S T V I P E D Y F D Y | 40 |
| 4E2 | 3-8 | R S I N S V V P E D Y F D Y | 41 |
| CONSENSUS | | R S I X X X P E D Y F X Y | 42 |
| 20C2 | 3-8 | R Q L G L R S I D A M D Y | 43 |
| 2B4 | 3-8 | Y D G Y P Y W Y F D V | 44 |
| 5F10 | 3-8 | Y D G Y P Y W Y F D V | 44 |
| 2H4 | 1-8 | G G N Y Y G S S R F A Y | 45 |
| 2E12 | 3-10 | Y G N Y G Y Y Y G M D Y | 46 |
| 1F6 | 1-20* | S G Y G S S Y G Y G M D Y | 47 |
| 1F4 | 1-20* | S G Y G S S Y G Y G M D Y | 47 |
| 3B3 | 1-20* | G I T T A L D Y | 48 |

FIG. 7C

| ANTIBODY | Aβ EPITOPE | CDR1 | SEQ ID NO: |
|---|---|---|---|
| 2A10 | 3-8 | R S S Q S I V H S N G N T Y L E | 49 |
| 4C2 | 3-8 | R S S Q S I V H S N G N T Y L E | 49 |
| 2D6 | 3-8 | R S S Q S I V H S N G N T Y L E | 49 |
| 4E2 | 3-8 | R S S Q S I V H S N G N T Y L E | 49 |
| 20C2 | 3-8 | R S S Q S I L H S N G N T Y L E | 50 |
| 2B4 | 3-8 | R S S Q S L V H S N G N T Y L H | 51 |
| 5F10 | 3-8 | R S S Q S L V H S N G N T Y L H | 51 |
| 2E12 | 3-10 | R S S Q S L V H S N G N T Y L H | 51 |
| 1F6 | 1-20* | R S S Q S I V H S N G N T Y L E | 49 |
| 1F4 | 1-20* | R S S Q S I V H S N G N T Y L E | 49 |
| 3B3 | 1-20* | R S S Q S I V H S N G N T Y L E | 49 |
| CONSENSUS | | R S S Q S X X H S N G N T Y L X | 52 |
| 2H4 | 1-8 | K A S Q D I N S Y L S | 53 |

FIG. 7D

| ANTIBODY | Aβ EPITOPE | CDR2 | SEQ ID NO: |
|---|---|---|---|
| 2A10 | 3-8 | K V S N R F S | 54 |
| 4C2 | 3-8 | K V S N R F S | 54 |
| 2D6 | 3-8 | K V S N R F S | 54 |
| 4E2 | 3-8 | K V S N R F S | 54 |
| 20C2 | 3-8 | K V S N R F S | 54 |
| 2B4 | 3-8 | K V S N R F F | 55 |
| 5F10 | 1-8 | K V S N R F S | 54 |
| 2E12 | 3-10 | K V S N R F S | 54 |
| 1F6 | 1-20* | K V S N R F S | 54 |
| 1F4 | 1-20* | K V S N R F S | 54 |
| 3B3 | 1-20* | K A S N R F S | 56 |
| CONSENSUS | | K X S N R F X | 57 |
| 2H4 | 3-8 | R A N R F V D | 58 |

FIG. 7E

| ANTIBODY | Aβ EPITOPE | CDR3 | SEQ ID NO: |
|---|---|---|---|
| 2A10 | 3-8 | F Q G S H V P L T | 59 |
| 4C2 | 3-8 | F Q G S H V P L T | 59 |
| 2D6 | 3-8 | F Q G S H V P L T | 59 |
| 4E2 | 3-8 | F Q G S H V P L T | 59 |
| 20C2 | 3-8 | F Q G S L V P L T | 60 |
| 2B4 | 3-8 | S Q T T Y V P L T | 61 |
| 5F10 | 3-8 | F Q S T H V P L T | 62 |
| 2E12 | 3-10 | S Q S T H V P P T | 63 |
| 1F6 | 1-20* | F Q G S H V P L T | 59 |
| 1F4 | 1-20* | F Q G S H V P L T | 59 |
| 3B3 | 1-20* | F Q G S H V P P T | 64 |
| CONSENSUS | | X Q X X X V P X T | 65 |
| 2H4 | 1-8 | L Q Y D E F P L T | 66 |

FIG. 7F

```
                                  *  *** *       # *          #      #   #     #  #
 1  Mouse 20C2 HCVR       QVTLKESGPG ILKPSQTLSL TCSLSGFSLS TSGMGVGWFR QPSGKGLEWL
    AAW29123              QVTLKESGPA LVKPTQTLTL TCTFSGFSLS TSGMCVSWIR QPPGKALEWL
    VH2_3-1_2-70          QVTLKESGPA LVKPTQTLTL TCTFSGFSLS TSGMRVSWIR QPPGKALEWL
    Humanized 20C2 HCVRA  QVTLKESGPA LVKPTQTLTL TCTFSGFSLS TSGMGVGWIR QPPGKALEWL
    Humanized 20C2 HCVRB  QVTLKESGPA LVKPTQTLTL TCTLSGFSLS TSGMGVGWIR QPPGKALEWL
                                                    HCDR1
                                                                       #  #*
 51                       *                                                *
    Mouse 20C2 HCVR       AHIWWDDDKS YNPSLKSRLT ISKYTSRNQV FLTITSVDTA DTATYYCARR
    AAW29123              ALIDWDDDKY YSTSLKTRLT ISKDTSKNQV VLTMTNMDPV DTATYYCARI
    VH2_3-1_2-70          ARIDWDDDKF YSTSLKTRLT ISKDTSKNQV VLTMTNMDPV DTATYYCARI
    Humanized 20C2 HCVRA  AHIWWDDDKS YNPSLKSRLT ISKDTSKNQV VLTMTNMDPV DTATYYCARR
    Humanized 20C2 HCVRB  AHIWWDDDKS YNPSLKSRLT ISKDTSKNQV VLTMTNMDPV DTATYYCARR
                                 HCDR2

101                                            #  #
    Mouse 20C2 HCVR       QLG........ LRSIDAMDYW GQGTSVTVSS  (SEQ ID NO:67)
    AAW29123              FGDYDFWSGY YRSYYGMDVW  GQGTTVTVSS  (SEQ ID NO:68)
    VH2_3-1_2-70          FGDYDFWSGY YRSYYGMDVW  GQGTTVTVSS  (SEQ ID NO:69)
    Humanized 20C2 HCVRA  QLG........ LRSIDAMDYW GQGTTVTVSS  (SEQ ID NO:70)
    Humanized 20C2 HCVRB  QLG........ LRSIDAMDYW GQGTTVTVSS  (SEQ ID NO:71)
                                HCDR3
```

*FIG. 8A*

```
                              1*                                                    *#        # #
Mouse 20C2 LCVR               DVLMTQTPLS LPVSLGDQAS ISCRSSQSIL HSNGNTYLEW YLQKPGQSPK
BAC01733                      DVVMTQSPLS LPVTPGEPAS ISCRSSQSLL HSNGYNYLDW YLQKPGQSPQ
VKII_4-1-(1)A18               DIVMTQTPLS LSVTPGQPAS ISCKSSQSLL HSDGKTYLYW YLQKPGQSPQ
Humanized 20C2 LCVR           DVVMTQSPLS LPVTPGEPAS ISCRSSQSIL HSNGNTYLEW YLQKPGQSPQ
                                                              LCDR1

#  *   **   *                            #   # *#    *
Mouse 20C2 LCVR               LLIYKVSNRF SGVPDRFSGS GSGTDFTLKI SRVEAEDLGV YYCFQGSLVP
BAC01733                      LLIYLGSNRA SGVPDRFSGS GSGTDFTLKI SRVEAEDVGV YYCMQALQTP
VKII_4-1-(1)A18               LLIYEVSSRF SGVPDRFSGS GSGTDFTLKI SRVEAEDVGV YYCMQGIHLP
Humanized 20C2 LCVR           LLIYKVSNRF SGVPDRFSGS GSGTDFTLKI SRVEAEDVGV YYCFQGSLVP
                                  LCDR2                                          LCDR3

101
Mouse 20C2 LCVR               LTFGAGTKLE LKRAD      (SEQ ID NO:72)
BAC01733                      YTFGQGTKLE IKRTV      (SEQ ID NO:73)
VKII_4-1-(1)A18                                     (SEQ ID NO:74)
Humanized 20C2 LCVR           LTFGQGTKLE IKRTV      (SEQ ID NO:75)
```

FIG. 8B

```
                              #          #  #             *  #      #     # #
                    1                                            *
Mouse 26D6 HCVR     QVTLKESGPG IVQPSQTLSL TCSFSGFSLS TSGMGVSWIR QPSGKGLEWL
AAD53816            QVTLKESGPT LVKPTQTLTL TCTFSGFSLS TSGVGVGWIR QPPGKALEWL
VH2 3-1 2-70        QVTLKESGPA LVKPTQTLTL TCTFSGFSLS TSGMRVSWIR QPPGKALEWL
Humanized 26D6 HCVR QVTLKESGPT LVKPTQTLTL TCTFSGFSLS TSGMGVSWIR QPPGKALEWL
                                                    ‾‾‾‾‾
                                                    HCDR1

51   *   *                      *              # #*#
Mouse 26D6 HCVR     AHIYWDDDKQ YNPSLKSRLT ISKDTSRRKV FLEITSVDTA DTATYCVRR
AAD53816            ALIYWNDDKR YSPSLKSRLT ITKDTSKNQV VLTMTNMDPV DTATYYCAQS
VH2 3-1 2-70        ARIDWDDDKF YSTSLKTRLT ISKDTSKNQV VLTMTNMDPV DTATYYCARI
Humanized 26D6 HCVR AHIYWDDDKQ YNPSLKSRLT ITKDTSKNQV VLTMTNMDPV DTATYYCARR
                    ‾‾‾‾‾‾‾‾‾‾‾‾‾‾‾‾‾‾‾‾
                          HCDR2

101         #   #
Mouse 26D6 HCVR     ASSSRYDDQF DYWGQGTPLT VSS (SEQ ID NO:76)
AAD53816            IMATSTSDYF DYWGQGTLVP VSS (SEQ ID NO:77)
VH2 3-1 2-70                              VSS (SEQ ID NO:78)
Humanized 26D6 HCVR ASSSRYDDQF DYWGQGTLVP VSS (SEQ ID NO:79)
                    ‾‾‾‾‾‾‾‾‾‾‾‾‾‾‾‾‾
                         HCDR3
```

*FIG. 8C*

```
                       1*                                              *#       ##    #
Mouse 26D6 LCVR        DVIMIQTPLS LPVSLGDPAS ISCRASQSIV HSNGNTYLEW YLQKPGQSPK
BAC01733               DVVMTQSPLS LPVTPGEPAS ISCRSSQSLL HSNGYNYLDW  YLQKPGQSPQ
VKII 4-1-(1)A18        DIVMTQTPLS LSVTPGQPAS ISCKSSQSLL HSDGKTYLYW  YLQKPGQSPQ
Humanized 26D6 LCVR    DVVMTQSPLS LPVTPGEPAS ISCRASQSIV HSNGNTYLEW  YLQKPGQSPQ
                                                            LCDR1

#   *    **      *                                           #  #*#   *
Mouse 26D6 LCVR        LLIYRVSNRF SGVPDRFSGS GSGTDFTLRI SRVEAEDLGV YFCFQVTHVP
BAC01733               LLIYLGSNRA SGVPDRFSGS GSGTDFTLKI SRVEAEDVGV YYCMQALQTP
VKII 4-1-(1)A18        LLIYEVSSRF SGVPDRFSGS GSGTDFTLKI SRVEAEDVGV YYCMQGIHLP
Humanized 26D6 LCVR    LLIYRVSNRF SGVPDRFSGS GSGTDFTLKI SRVEAEDVGV YYCFQVTHVP
                            LCDR2                                              LCDR3

# #
Mouse 26D6 LCVR        LTFGAGTKLE LKRAD    (SEQ ID NO:80)
BAC01733               YTFGQGTKLE IKRTV    (SEQ ID NO:81)
VKII 4-1-(1)A18                            (SEQ ID NO:82)
Humanized 26D6 LCVR    LTFGQGTKLE IKRTV    (SEQ ID NO:83)
```

FIG. 8D

```
                     *    * **  *                      #*    #  #  #  #
Mouse 4E2 HCVR    QVTLKESGPG ILKPSQTLSL TCSFSGFSLS TSGMGVGWIR QPSGKGLEWL
AAW29123          QVTLKESGPA LVKPTQTLTL TCTFSGFSLS TSGMCVSWIR QPPGKALEWL
VH2 3-1 2-70      QVTLKESGPA LVKPTQTLTL TCTFSGFSLS TSGMRVSWIR QPPGKALEWL
Humanized 4E2 HCVR QVTLKESGPA LVKPTQTLTL TCTFSGFSLS TSGMGVGWIR QPPGKALEWL
                                                       HCDR1

*                                            #     #  *
Mouse 4E2 HCVR    AHIWWDDDKY YNPSLKSQLT ISKDTSRNQV FLKITSVDTA DTATYYCARR
AAW29123          ALIDWDDDKY YSTSLKTRLT ISKDTSKNQV VLTMTNMDPV DTATYYCARI
VH2 3-1 2-70      ARIDWDDDKF YSTSLKTRLT ISKDTSKNQV VLTMTNMDPV DTATYYCARI
Humanized 4E2 HCVR AHIWWDDDKY YNPSLKSQLT ISKDTSKNQV VLTMTNMDPV DTATYYCARR
                       HCDR2

Mouse 4E2 HCVR    SINSVVPEDY F......DYW GQGTTLTVSL  (SEQ ID NO:84)
AAW29123          FGDYDFWSGY YRSYYGMDVW GQGTTVTVSS  (SEQ ID NO:85)
VH2 3-1 2-70                                        (SEQ ID NO:86)
Humanized 4E2 HCVR SINSVVPEDY F......DYW GQGTTVTVSS (SEQ ID NO:87)
                       HCDR3
```

FIG. 8E

```
                       1*
Mouse 4E2 LCVR         DVLMTQTPLS LPVSLGDQAS ISCRSSQSIV HSNGNTYLEW YLQKPGQSPK
BAC01733               DVVMTQSPLS LPVTPGEPAS ISCRSSQSLL HSNGYNYLDW YLQKPGQSPQ
VKII 4-1-(1) A18       DIVMTQTPLS LSVTPGQPAS ISCKSSQSLL HSDGKTYLYW YLQKPGQSPQ
Humanized 4E2 LCVR     DVVMTQSPLS LPVTPGEPAS ISCRSSQSIV HSNGNTYLEW YLQKPGQSPQ
                                                        LCDR1

Mouse 4E2 LCVR         LLIYKVSNRF SGVPDRFSGS GSGTDFTLKI SRVEAEDLGV YYCFQGSHVP
BAC01733               LLIYLGSNRA SGVPDRFSGS GSGTDFTLKI SRVEAEDVGV YYCMQALQTP
VKII 4-1-(1) A18       LLIYEVSSRF SGVPDRFSGS GSGTDFTLKI SRVEAEDVGV YYCMQGIHLP
Humanized 4E2 LCVR     LLIYKVSNRF SGVPDRFSGS GSGTDFTLKI SRVEAEDVGV YYCFQGSHVP
                            LCDR2                                    LCDR3

Mouse 4E2 LCVR         LTFGAGTKLE LKRAD    (SEQ ID NO:88)
BAC01733               YTFGQGTKLE IKRTV    (SEQ ID NO:89)
VKII 4-1-(1) A18                           (SEQ ID NO:90)
Humanized 4E2 LCVR     LTFGQGTKLE IKRTV    (SEQ ID NO:91)
```

FIG. 8F

```
                          *  *  *       * #  #         *#  #  #          #  #
Mouse 3B3 HCVR    1 DVQLVESGGG LVQPGGSRKL SCAASGFTFS SFGMHWVRQA PEKGLEWVAY
BAC01520            EVQLVESGGG LVQPGGSLRL SCAASGFTFS SYWMSWVRQA PGKGLEWVAN
VH3 1-3 3-48        EVQLVESGGG LVQPGGSLRL SCAASGFTFS SYSMNWVRQA PGKGLEWVSY
Humanized 3B3 HCVR  EVQLVESGGG LVQPGGSLRL SCAASGFTFS SFGMHWVRQA PGKGLEWVAY
                                                     ‾‾‾‾‾‾‾‾‾‾‾‾‾‾‾
                                                          HCDR1

*              *                              #  #*#
Mouse 3B3 HCVR   51 ISRGSSTIYY ADTVKGRFTI SRDNPKNTLF LQMTSLRSED TAMYYCARGI
BAC01520            IKQDGSEKYY VDSVKGRFTI SRDNAKNSLY LQMNSLRAED TAVYYCARVR
VH3 1-3 3-48        ISSSSTIYY  ADSVKGRFTI SRDNAKNSLY LQMNSLRDED TAVYYCAR
Humanized 3B3 HCVR  ISRGSSTIYY ADTVKGRFTI SRDNAKNSLY LQMNSLRAED TAVYYCARGI
                        ‾‾‾‾‾‾‾‾‾‾‾‾‾‾‾‾‾                                ‾‾
                              HCDR2

Mouse 3B3 HCVR  101# TTALDYWGQG TSVTVSS  (SEQ ID NO:92)
BAC01520             RGSGDSWGQG TLVTVSS  (SEQ ID NO:93)
VH3 1-3 3-48                             (SEQ ID NO:94)
Humanized 3B3 HCVR   TTALDYWGQG TLVTVSS  (SEQ ID NO:95)
                     ‾‾‾‾‾‾‾‾
                      HCDR3
```

FIG. 8G

```
                          1*                                                         *     #  #   #
Mouse 3B3 LCVR            DVLMTQTPLS  LPVSLGDQAS  ISCRSSQSIV  HSNGNTYLEW  YLQKPGQSPK
BAC01733                  DVVMTQSPLS  LPVTPGEPAS  ISCRSSQSLL  HSNGNTYLDW  YLQKPGQSPQ
VKII 4-1-(1) A18          DIVMTQTPLS  LSVTPGQPAS  ISCKSSQSLL  HSDGKTYLYW  YLQKPGQSPQ
Humanized 3B3 LCVR        DVVMTQSPLS  LPVTPGEPAS  ISCRSSQSIV  HSNGNTYLEW  YLQKPGQSPQ
                                                  LCDR1

# *  * **                  *                               # *#  #
Mouse 3B3 LCVR            LLIYKASNRF  SGVPDRFSGS  GSGTDFTLKI  SRVEAEDLGV  YYCFQGSHVP
BAC01733                  LLIYLGSNRA  SGVPDRFSGS  GSGTDFTLKI  SRVEAEDVGV  YYCMQALQTP
VKII 4-1-(1) A18          LLIYEVSSRF  SGVPDRFSGS  GSGTDFTLKI  SRVEAEDVGV  YYCMQGIHLP
Humanized 3B3 LCVR        LLIYKASNRF  SGVPDRFSGS  GSGTDFTLKI  SRVEAEDVGV  YYCFQGSHVP
                                 LCDR2                                                   LCDR3

# #
Mouse 3B3 LCVR            PTFGGGTKLE  IKRAD         (SEQ ID NO:96)
BAC01733                  YTFGQGTKLE  IKRTV         (SEQ ID NO:97)
VKII 4-1-(1) A18                                    (SEQ ID NO:98)
Humanized 3B3 LCVR        PTFGQGTKLE  IKRTV         (SEQ ID NO:99)
```

FIG. 8H

```
                      1              *  *  **  *          *#   #  #       #   #
Mouse 2H4 HCVR        DVQLVESGGG LVQPGGSRKL SCAASGFTFS SFGMHWVRQA PEKGLEWVAY
AAL57837              EVQLVESGGG LVQPGGSLRL SCAASGFTFS SYAMSWVRQA PGKGLEWVSG
VH3 1-3 3-48          EVQLVESGGG LVQPGGSLRL SCAASGFTFS SYSMNWVRQA PGKGLEWVSY
Humanized 2H4 HCVR    EVQLVESGGG LVQPGGSLRL SCAASGFTFS SFGMHWVRQA PGKGLEWVAY
                                                         HCDR1

51          *                 *             # #*#
Mouse 2H4 HCVR        IRSGSSSTIYY ADTVKGRFTI SRDNPKNTLF LQMTSLRSED TAMYCTRGG
AAL57837              ISARGGSTYY  ADSVKGRFTI SRDNSKNTLY LQMNSLRAED TAVYYCAKDR
VH3 1-3 3-48          ISSSSSTIYY  ADSVKGRFTI SRDNAKNSLY LQMNSLRDED TAVYYCAR
Humanized 2H4 HCVR    IRSGSSSTIYY ADTVKGRFTI SRDNSKNTLY LQMNSLRAED TAVYYCARGG
                                                                         HCDR2

101   #        #
Mouse 2H4 HCVR        NYYGSSRFAY WGQGTLVTVS A   (SEQ ID NO:100)
AAL57837              GRIAAAHFDY WGQGTLVTVS S   (SEQ ID NO:101)
VH3 1-3 3-48                                    (SEQ ID NO:102)
Humanized 2H4 HCVR    NYYGSSRFAY WGQGTLVTVS S   (SEQ ID NO:103)
                        HCDR3
```

FIG. 8I

```
                     1*              *                  *          *#   # #            # #
Mouse 2H4 LCVR       DIKMTQSPSS MYASLGERVT ITCKASQDIN SYLSWFQQKP GKSPKTLIYR
BAC01676             DIQMTQSPSS LSASVGDRVT ITCRASQSIS SYLNWYQQKP GKAPKLLIYA
VKI 2-1-(1) L1       DIQMTQSPSS LSASVGDRVT ITCRASQGIS NYLAWFQQKP GKAPKSLIYA
Humanized 2H4 LCVR   DIQMTQSPSS LSASVGDRVT ITCKASQDIN SYLSWFQQKP GKAPKTLIYR
                                                      LCDR1

**           *                       *        # #*    *#
Mouse 2H4 LCVR       ANRFVDGVPS RFSGSGSGQD YSLTISSLEY EDMGIYFCLQ YDEFPLTFGA
BAC01676             ASSLQSGVPS RFSGSGSGTD FTLTISSLQP EDFATYYCQQ SYSTLLTFGG
VKI 2-1-(1) L1       ASSLQSGVPS RFSGSGSGTD FTLTISSLQP EDFATYCQQ  YNSYP
Humanized 2H4 LCVR   ANRFVDGVPS RFSGSGSGTD YTLTISSLQP EDFATYFCLQ YDEFPLTFGG
                       LCDR2                                          LCDR3

101
Mouse 2H4 LCVR       GTKLVLKRAD  (SEQ ID NO:104)
BAC01676             GTKVEIKRTV  (SEQ ID NO:105)
VKI 2-1-(1) L1                   (SEQ ID NO:106)
Humanized 2H4 LCVR   GTKVEIKRTV  (SEQ ID NO:107)
```

FIG. 8J

```
                      1                                              *         *#   #  #      #  #
Mouse 1F6 HCVR           DVQLVESGGG LVQPGGSRKL SCAASGFTFS SFGMHWVRQA PEKGLEWVAY
AAA17909                 EVQLVESGGG LVQPGGSLRL SCAASGFTFS SYAMSWVRQA PGKGLEWVSA
VH3 1-3 3-48             EVQLVESGGG LVQPGGSLRL SCAASGFTFS SYSMNWVRQA PGKGLEWVSY
Humanized 1F6 HCVR       EVQLVESGGG LVQPGGSLRL SCAASGFTFS SFGMHWVRQA PGKGLEWVAY
                                                                     HCDR1

51        *       * *** *                              *               #  #*  #
Mouse 1F6 HCVR           ISSVSSTIYY ADTVKGRFTI SRDNPKNTLF LQMTSLRSED TAMYYCARSG
AAA17909                 ISGSGGSTYY ADSVKGRFTI SRDNSKNTLY LQMNSLRAED TAVYYCAKCS
VH3 1-3 3-48             ISSSSSTIYY ADSVKGRFTI SRDNAKNSLY LQMNSLRDED TAVYYCAR
Humanized 1F6 HCVR       ISSVSSTIYY ADTVKGRFTI SRDNSKNTLY LQMNSLRAED TAVYYCARSG
                              HCDR2

101       #    #                   122
Mouse 1F6 HCVR           YGSSYGYGMD YWGQGTLVTV SS (SEQ ID NO:108)
AAA17909                 ELRYFDWSVD YWGQGTLVTV SS (SEQ ID NO:109)
VH3 1-3 3-48                                       (SEQ ID NO:110)
Humanized 1F6 HCVR       YGSSYGYGMD YWGQGTLVTV SS (SEQ ID NO:111)
                              HCDR3
```

FIG. 8K

```
                             1                                          *   ***  *                                  *  #  #       #  #         #  #
      Mouse 20C2 HCVR        QVTLKESGPG ILKPSQTLSL TCSLSGFSLS TSGMGVGWFR QPSGKGLEWL
             AAW29123        QVTLKESGPA LVKPTQTLTL TCTFSGFSLS TSGMCVSWIR QPPGKALEWL
          VH2 3-1 2-70       QVTLKESGPA LVKPTQTLTL TCTFSGFSLS TSGMRVSWIR QPPGKALEWL
Humanized 20C2 HCVR VenA     QVTLKESGPG ILKPSQTLSL TCTFSGFSLS TSGMGVGWFR QPPGKGLEWL
Humanized 20C2 HCVR VenB     QVTLKESGPG ILKPSQTLSL TCTFSGFSLS TSGMGVGWFR QPPGKGLEWL
                                                                        HCDR1
                             51          *                              *                                       #   #  #*
      Mouse 20C2 HCVR        AHIWWDDDKS YNPSLKSRLT ISKYTSRNQV FLTITSVDTA DTATYYCARR
             AAW29123        ALIDWDDDKY YSTSLKTRLT ISKDTSKNQV VLTMTNMDPV DTATYYCARI
          VH2 3-1 2-70       ARIDWDDDKF YSTSLKTRLT ISKDTSKNQV VLTMTNMDPV DTATYYCARI
Humanized 20C2 HCVR VenA     AHIWWDDDKS YNPSLKSRLT ISKDTSKNQV FLTITNMDPV DTATYYCARR
Humanized 20C2 HCVR VenB     AHIWWDDDKS YNPSLKSRLT ISKDTSKNQV VLTITNMDPV DTATYYCARR
                                  HCDR2                                                       
                             101                #   #
      Mouse 20C2 HCVR        QLG.......LRSIDAMDY WGQGTSVTVSS           (SEQ ID NO:112)
             AAW2912         FGDYDFWSGYYRSYYGMDV WGQGTTVTVSS            (SEQ ID NO:113)
          VH2 3-1 2-70                                                  (SEQ ID NO:114)
Humanized 20C2 HCVR VenA     QLG.......LRSIDAMDY WGQGTTVTVSS           (SEQ ID NO:115)
Humanized 20C2 HCVR VenB     QLG.......LRSIDAMDY WGQGTTVTVSS           (SEQ ID NO:116)
                                  HCDR3
```

FIG. 9A

```
                        1*                    *        *              *#          #  #   #
Mouse 20C2 LCVR    DVLMTQTPLS LPVSLGDQAS ISCRSSQSIL HSNGNTYLEW YLQKPGQSPK
         BAC01733  DVVMTQSPLS LPVTPGEPAS ISCRSSQSLL HSNGYNYLDW YLQKPGQSPQ
    VKII 4-1(1)A18 DIVMTQTPLS LSVTPGQPAS ISCKSSQSLL HSDGKTYLYW YLQKPGQSPQ
Humanized 20C2 LCVR Ven DVVMTQSPLS LPVSLGDPAS ISCRSSQSIL HSNGNTYLEW YLQKPGQSPQ
                                                       LCDR1

#   *  **                  *                              #  #*#
Mouse 20C2 LCVR    LLIYKVSNRF SGVPDRFSGS GSGTDFTLKI SRVEAEDLGV YYCFQGSLVP
         BAC01733  LLIYLGSNRA SGVPDRFSGS GSGTDFTLKI SRVEAEDVGV YYCMQALQTP
    VKII 4-1(1)A18 LLIYEVSSRF SGVPDRFSGS GSGTDFTLKI SRVEAEDVGV YYCMQGIHLP
Humanized 20C2 LCVR Ven LLIYKVSNRF SGVPDRFSGS GSGTDFTLKI SRVEAEDLGV YYCFQGSLVP
                          LCDR2                                          LCDR3

101
Mouse 20C2 LCVR    LTFGAGTKLE LKR  (SEQ ID NO:117)
         BAC01733  YTFGQGTKLE IKR  (SEQ ID NO:118)
    VKII 4-1(1)A18                 (SEQ ID NO:119)
Humanized 20C2 LCVR Ven LTFGAGTKLE LKR (SEQ ID NO:120)
```

FIG. 9B

```
                              *  *  *            #  *          #   #   #         #  #
                    1
Mouse 26D6 HCVR     QVTLKESGPG IVQPSQTLSL TCSFSGFSLS TSGMGVSWIR QPSGKGLEWL
AAD53816            QVTLKESGPT LVKPTQTLTL TCTFSGFSLS TSGVGVGWIR QPPGKALEWL
VH2 3-1 2-70        QVTLKESGPA LVKPTQTLTL TCTFSGFSLS TSGMRVSWIR QPPGKALEWL
Humanized 26D6 HCVRVen1  QVTLKESGPG IVQPSQTLSL TCSFSGFSLS TSGMGVSWIR QPSGKGLEWL
Humanized 26D6 HCVRVen2  QVTLKESGPT LVKPTQTLTL TCSFSGFSLS TSGMGVSWIR QPSGKGLEWL
Humanized 26D6 HCVRVen3  QVTLKESGPG LVKPTQTLSL TCSFSGFSLS TSGMGVSWIR QPSGKGLEWL
                                                            ‾‾‾‾‾‾‾‾‾‾
                                                              HCDR1

51       *                                     #   #  *  #
Mouse 26D6 HCVR     AHIYWDDDKQ YNPSLKSRLT ISKDTSRRKV FLEITSVDTA DTATYYCVRR
AAD53816            ALIYWNDDKR YSPSLKSRLT ITKDTSKNQV VLTMTNMDPV DTATYYCAQS
VH2 3-1 2-70        ARIDWDDDKF YSTSLKTRLT ISKDTSKNQV VLTMTNMDPV DTATYYCARI
Humanized 26D6 HCVRVen1  AHIYWDDDKQ YNPSLKSRLT ISKDTSKNQV FLTITSVDTV DTATYYCVRR
Humanized 26D6 HCVRVen2  AHIYWDDDKQ YNPSLKSRLT ISKDTSKNQV FLTITSVDPV DTATYYCVRR
Humanized 26D6 HCVRVen3  AHIYWDDDKQ YNPSLKSRLT ISKDTSKNQV VLTITSVDPV DTATYYCVRR
                        ‾‾‾‾‾‾‾‾‾‾                                          ‾
                          HCDR2

101       #          #
Mouse 26D6 HCVR     ASSSRYDDQF DYWGQGTPLT VSS  (SEQ ID NO:121)
AAD53816            IMATSTSDYF DYWGQGTLVP VSS  (SEQ ID NO:122)
VH2 3-1 2-70                                   (SEQ ID NO:123)
Humanized 26D6 HCVRVen1  ASSSRYDDQF DYWGQGTPLT VSS  (SEQ ID NO:124)
Humanized 26D6 HCVRVen2  ASSSRYDDQF DYWGQGTPLT VSS  (SEQ ID NO:125)
Humanized 26D6 HCVRVen3  ASSSRYDDQF DYWGQGTLLT VSS  (SEQ ID NO:126)
                        ‾‾‾‾‾‾‾‾‾‾
                          HCDR3
```

FIG. 9C

```
                                1*
Mouse 26D6 LCVR         DVLMIQTPLS LPVSLGDPAS ISCRASQSIV HSNGNTYLEW YLQKPGQSPK
         BAC01733       DVVMTQSPLS LPVTPGEPAS ISCRSSQSLL HSNGYNYLDW YLQKPGQSPQ
VKII 4-1-(1) A18        DIVMTQTPLS LSVTPGQPAS ISCKSSQSLL HSDGKTYLYW YLQKPGQSPQ
Humanized 26D6 LCVR Ven1 DVVMTQTPLS LPVSLGDPAS ISCRASQSIV HSNGNTYLEW YLQKPGQSPK
Humanized 26D6 LCVR Ven2 DVVMTQTPLS LPVSLGDPAS ISCRASQSIV HSNGNTYLEW YLQKPGQSPK
                                                    LCDR1

Mouse 26D6 LCVR         LLIYRVSNRF SGVPDRFSGS GSGTDFTLRI SRVEAEDLGV YFCFQVTHVP
         BAC01733       LLIYLGSNRA SGVPDRFSGS GSGTDFTLKI SRVEAEDVGV YYCMQALQTP
VKII 4-1-(1) A18        LLIYEVSSRF SGVPDRFSGS GSGTDFTLKI SRVEAEDVGV YYCMQGIHLP
Humanized 26D6 LCVR Ven1 LLIYRVSNRF SGVPDRFSGS GSGTDFTLKI SRVEAEDLGV YFCFQVTHVP
Humanized 26D6 LCVR Ven2 LLIYRVSNRF SGVPDRFSGS GSGTDFTLKI SRVEAEDVGV YFCFQVTHVP
                             LCDR2                                      LCDR3

Mouse 26D6 LCVR         LTFGAGTKLE LK (SEQ ID NO:127)
         BAC01733       YTFGQGTKLE IK (SEQ ID NO:128)
VKII 4-1-(1) A18                    (SEQ ID NO:129)
Humanized 26D6 LCVR Ven1 LTFGAGTKLE LK (SEQ ID NO:130)
Humanized 26D6 LCVR Ven2 LTFGGGTKLE LK (SEQ ID NO:131)
```

FIG. 9D

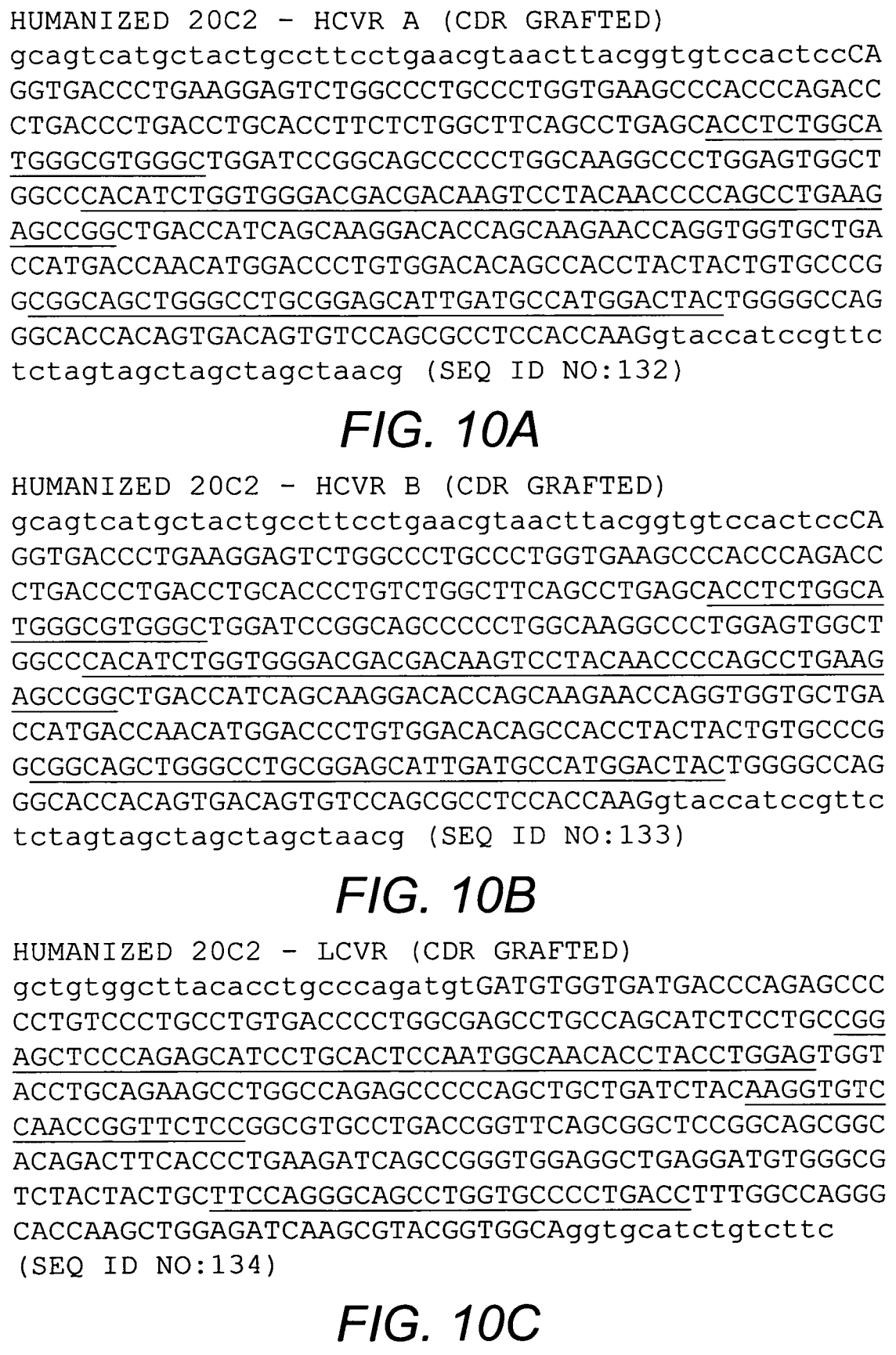

HUMANIZED 20C2 - HCVR A (CDR GRAFTED)
gcagtcatgctact

HUMANIZED 26D6 - HCVR (CDR GRAFTED)
gcagtcatgctactgccttcctgaacgtaacttacggtgtccactccCA
GGTGACCCTGAAAGAGTCTGGCCCCACCCTGGTGAAGCCCACCCAGACC
CTGACCCTGACCTGCACCTTCTCTGGCTTCTCCCTGAGCACCTCTGGCA
TGGGCGTGTCCTGGATCCGGCAGCCCCTGGCAAAGCCCTGGAGTGGCT
GGCCCACATCTACTGGGATGATGACAAGCAGTACAACCCCAGCCTGAAG
TCCCGGCTGACCATCACCAAGACACCTCCAAGAACCAGGTGGTGCTGA
CCATGACCAACATGGACCCTGTGGACACAGCCACCTACTACTGCGCCCG
GCGCGCCTCCTCCAGCCGGTATGATGACCAGTTTGACTACTGGGGCCAG
GGCACCCTGGTGCCTGTGTCCTCTGCCTCCACCAAGgtaccatccgttc
tctagtagctagctagctaacg   (SEQ ID NO:135)

FIG. 10D

HUMANIZED 26D6 - LCVR (CDR GRAFTED)
gctgtggcttacacctgcccagatgtGATGTGGTGATGACCCAGTCCCC
CCTGAGCCTGCCTGTGACCCCTGGCGAGCCTGCCTCCATCAGCTGCCGC
GCCTCCCAGAGCATTGTGCACTCCAATGGCAACACCTACCTGGAGTGGT
ACCTGCAGAAGCCTGGCCAGTCCCCCCAGCTGCTGATCTACCGCGTGAG
CAACCGGTTCTCTGGCGTGCCTGACCGGTTCTCTGGCTCTGGCTCTGGC
ACAGACTTCACCCTGAAGATCAGCCGCGTGGAAGCTGAAGATGTGGGCG
TGTACTACTGCTTCCAGGTGACCCATGTGCCCCTGACCTTTGGCCAGGG
CACCAAGCTGGAGATCAAGCGTACGGTGGCAggtgcatctgtcttc
(SEQ ID NO:136)

FIG. 10E

HUMANIZED 4E2 - HCVR (CDR GRAFTED)
gcagtcatgctactgccttcctgaacgtaacttacggtgtccactccCA
GGTGACCCTGAAGGAGTCTGGCCCTGCCCTGGTGAAGCCCACCCAGACC
CTGACCCTGACCTGCACCTTCTCTGGCTTCAGCCTGTCCACCAGCGGCA
TGGGCGTGGGCTGGATCCGGCAGCCCCTGGCAAGGCCCTGGAGTGGCT
GGCCCACATCTGGTGGGATGATGACAAGTACTACAACCCCTCCCTGAAG
AGCCAGCTGACCATCTCCAAGGACACCAGCAAGAACCAGGTGGTGCTGA
CCATGACCAACATGGACCCTGTGGACACAGCCACCTACTACTGTGCCCG
GCGGAGCATCAACTCTGTGGTGCCTGAGGACTACTTTGACTACTGGGGC
CAGGGCACCACCGTGACAGTGTCCAGCGCCTCCACCAAGgtaccatccg
ttctctagtagctagctagctaacg   (SEQ ID NO:137)

FIG. 10F

HUMANIZED 4E2 - LCVR (CDR GRAFTED)
gctgtggcttacacctgcccagatgtGATGTGGTGATGACCCAGAGCCC
CCTGTCCCTGCCTGTGACCCCTGGCGAGCCTGCCAGCATCTCCTGCCGG
AGCTCCCAGAGCATTGTGCACTCCAATGGCAACACCTACCTGGAGTGGT
ACCTGCAGAAGCCTGGCCAGAGCCCCCAGCTGCTGATCTACAAGGTGTC
CAACCGGTTCTCCGGCGTGCCTGACCGGTTCAGCGGCTCCGGCAGCGGC
ACAGACTTCACCCTGAAGATCAGCCGGGTGGAGGCTGAGGATGTGGGCG
TCTACTACTGCTTCCAGGGCAGCCATGTGCCCCTGACCTTTGGCCAGGG
CACCAAGCTGGAGATCAAGCGTACGGTGGCAggtgcatctgtcttc
(SEQ ID NO:138)

FIG. 10G

HUMANIZED 3B3 - HCVR (CDR GRAFTED)
gcagtcatgctactgccttcctgaacgtaacttacggtgtccactccGA
GGTGCAGCTGGTGGAGTCCGGCGGCGGCCTGGTGCAGCCTGGCGGCAGC
CTGCGGCTGAGCTGTGCTGCCTCTGGCTTCACCTTCAGCTCCTTTGGCA
TGCACTGGGTGCGGCAGGCCCCTGGCAAGGGCCTGGAGTGGGTGGCCTA
CATCAGCCGGGGCTCCAGCACCATCTACTATGCTGACACAGTGAAGGGC
CGGTTCACCATCAGCCGGGACAATGCCAAGAACTCCCTGTATCTGCAGA
TGAACAGCCTGCGGGCTGAGGACACAGCAGTGTACTACTGTGCCCGGGG
CATCACCACAGCCCTGGACTACTGGGGCCAGGGCACCCTGGTGACCGTG
TCCAGCGCCTCCACCAAGgtaccatccgttctctagtagctagctagct
aacg (SEQ ID NO:139)

FIG. 10H

HUMANIZED 3B3 - LCVR (CDR GRAFTED)
gctgtggcttacacctgcccagatgtGATGTGGTGATGACCCAGAGCCC
CCTGTCCCTGCCTGTGACCCCTGGCGAGCCTGCCAGCATCTCCTGCCGG
AGCTCCCAGAGCATCGTGCACTCCAATGGCAACACCTACCTGGAGTGGT
ACCTGCAGAAGCCTGGCCAGAGCCCCCAGCTGCTGATCTACAAGGCTTC
CAACCGGTTCTCCGGCGTGCCTGACCGGTTCAGCGGCTCCGGCAGCGGC
ACAGACTTCACCCTGAAGATCAGCCGGGTGGAGGCTGAGGATGTGGGCG
TCTACTACTGCTTCCAGGGCAGCCATGTGCCCCCCACCTTTGGCCAGGG
CACCAAGCTGGAGATCAAGCGTACGGTGGCAggtgcatctgtcttc
(SEQ ID NO:140)

FIG. 10I

HUMANIZED 2H4 - HCVR (CDR GRAFTED)
gcagtcatgctactgccttcctgaacgtaacttacggtgtccactccGA
GGTGCAGCTGGTGGAGTCCGGCGGCGGCCTGGTGCAGCCTGGCGGCTCC
CTGCGGCTGAGCTGTGCTGCCTCTGGCTTCACCTTCTCCAGCTTTGGCA
TGCACTGGGTGCGGCAGGCCCCTGGCAAGGGCCTGGAGTGGGTGGCCTA
CATCCGGTCTGGCTCCAGCACCATCTACTATGCTGACACAGTGAAGGGC
CGGTTCACCATCTCCCGGGACAACAGCAAGAACACCCTGTATCTGCAGA
TGAACTCCCTGCGGGCTGAGGACACAGCTGTGTACTACTGTGCCCGGGG
CGGCAACTACTATGGCTCCAGCCGGTTTGCCTACTGGGGCCAGGGCACC
CTGGTGACCGTGTCCAGCGCCTCCACCAAGgtaccatccgttctctagt
agctagctagctaacg    (SEQ ID NO:141)

FIG. 10J

HUMANIZED 2H4 - LCVR (CDR GRAFTED)
gctgtggcttacacctgcccagatgtGACATCCAGATGACCCAGTCCCC
CAGCTCCCTGTCTGCCTCTGTGGGCGACCGGGTGACCATCACATGCAAG
GCCTCCAGGACATCAACTCCTACCTGAGCTGGTTCCAGCAGAAGCCTG
GCAAGGCCCCCAAGACCCTGATCTACCGGGCCAACCGGTTTGTGGATGG
CGTGCCCTCCCGGTTCAGCGGCTCTGGCAGCGGCACAGACTACACCCTG
ACCATCTCCAGCCTGCAGCCTGAGGACTTTGCCACCTACTTCTGCCTGC
AGTATGATGAGTTCCCCCTGACCTTTGGCGGCGGCACCAAGGTGGAGAT
CAAGCGTACGGTGGCAggtgcatctgtcttc (SEQ ID NO:142)

FIG. 10K

HUMANIZED 1F6 - HCVR (CDR GRAFTED)
gcagtcatgctactgccttcctgaacgtaacttacggtgtccactccGA
GGTGCAGCTGGTGGAGTCCGGCGGCGGCCTGGTGCAGCCTGGCGGCTCC
CTGCGGCTGAGCTGTGCTGCCAGCGGCTTCACCTTCTCCAGCTTTGGCA
TGCACTGGGTGCGGCAGGCCCCTGGCAAGGGCCTGGAGTGGGTGGCCTA
CATCTCCTCTGTGAGCAGCACCATCTACTATGCCGACACCGTGAAGGGC
CGGTTCACCATCAGCCGGGACAACAGCAAGAACACCCTGTATCTGCAGA
TGAACTCCCTGCGGGCTGAGGACACCGCCGTGTACTACTGTGCCCGGTC
TGGCTATGGCTCCAGCTATGGCTATGGCATGGACTACTGGGGCCAGGGC
ACCCTGGTGACCGTGTCCAGCGCCTCCACCAAGgtaccatccgttctct
agtagctagctagctaacg (SEQ ID NO:143)

FIG. 10L

HUMANIZED 20C2 - HCVR VENA (VENEERED)
gcagtcatgctactgccttcctgaacgtaacttacggtgtccactccCA
GGTGACCCTGAAAGAGAGCGGCCCTGGCATCCTGAAGCCATCTCAGACC
CTGAGCCTGACCTGCACCTTCTCTGGCTTCAGCCTGTCC<u>ACCAGCGGCA
TGGGCGTGGGC</u>TGGTTCCGGCAGCCCCCTGGCAAAGGCCTGGAGTGGCT
GGCCC<u>ACATCTGGTGGGATGATGACAAGAGCTACAACCCATCCCTGAAG</u>
AGCCGGCTGACCATCTCCAAGACACCAGCAAGAACCAGGTGTTCCTGA
CCATCACCAACATGGACCCTGTGGACACAGCCACCTACTACTGTGCCCG
GCGGCAGCTGGGCCTGCGGTCC<u>ATCGATGCCATGGACTAC</u>TGGGGCCAG
GGCACCACAGTGACTGTGTCCAGCGCCTCCACCAAGgtaccatccgttc
tctagtagctagctagctaacg (SEQ ID NO:144)

*FIG. 10M*

HUMANIZED 20C2 - HCVR VENB (VENEERED)
gcagtcatgctactgccttcctgaacgtaacttacggtgtccactccCA
GGTGACCCTGAAAGAGAGCGGCCCTGGCATCCTGAAGCCATCTCAGACC
CTGAGCCTGACCTGCACCTTCTCTGGCTTCAGCCTGTCC<u>ACCAGCGGCA
TGGGCGTGGGC</u>TGGTTCCGGCAGCCCCCTGGCAAAGGCCTGGAGTGGCT
GGCCC<u>ACATCTGGTGGGATGATGACAAGAGCTACAACCCATCCCTGAAG</u>
AGCCGGCTGACCATCTCCAAGACACCAGCAAGAACCAGGTGGTGCTGA
CCATCACCAACATGGACCCTGTGGACACAGCCACCTACTACTGTGCCCG
GCGGCAGCTGGGCCTGCGGTCC<u>ATCGATGCCATGGACTAC</u>TGGGGCCAG
GGCACCACAGTGACTGTGTCCAGCGCCTCCACCAAGgtaccatccgttc
tctagtagctagctagctaacg (SEQ ID NO:145)

*FIG. 10N*

HUMANIZED 20C2 - LCVR (VENEERED)
gctgtggcttacacctgcccagatgtGATGTGGTGATGACCCAGAGCCC
CCTGTCCCTGCCTGTGAGCCTGGGCGACCCTGCCTCCATCAGCTGC<u>CGG
TCCAGCCAGTCCATCCTGCACAGCAATGGCAACACCTACCTGGAGTGGT</u>
ACCTGCAGAAGCCTGGCCAGTCCCCCAGCTGCTGATCTAC<u>AAAGTGAG
CAACCGGTTCTCT</u>GGCGTGCCTGACCGGTTCTCTGGCAGCGGCAGCGGC
ACAGACTTCACCCTGAAGATCTCCCGCGTGGAGGCTGAAGACCTGGGCG
TCTACTACTGC<u>TTCCAGGGCAGCCTGGTGCCCCTGACC</u>TTTGGCGCTGG
CACCAAGCTGGAGCTGAAGcggacggtggcaggtgcatctgtcttc
(SEQ ID NO:146)

*FIG. 10O*

HUMANIZED 26D6 - HCVR VEN1 (VENEERED)
actccgaggtgacgccgagtgacttgcctcactagacccCAGGTGACCC
TGAAAGAATCCGGCCCTGGCATTGTGCAGCCCAGCCAGACCCTGTCCCT
GACCTGCTCCTTCTCTGGCTTCAGCCTGTCCACCTCCGGCATGGGCGTG
AGCTGGATTCGGCAGCCCTCTGGCAAAGGCCTGGAGTGGCTGGCCCACA
TCTACTGGGATGATGACAAGCAGTACAACCCCAGCCTGAAGTCCCGGCT
GACCATCAGCAAAGACACCTCCAAGAACCAGGTCTTCCTGACCATCACC
TCTGTGGACACAGTGGACACAGCCACCTACTACTGTGTGAGACGCGCCA
GCTCCAGCCGGTATGATGACCAGTTTGACTACTGGGGCCAGGGCACCCC
CCTGACAGTCTCCAGCgcgaggtgacgccgagtgacttgcctctctagt
cgatgt (SEQ ID NO:147)

FIG. 10P

HUMANIZED 26D6 - HCVR VEN2 (VENEERED)
actccgaggtgacgccgagtgacttgcctcactagacccCAGGTGACCC
TGAAAGAATCCGGCCCTGGCCTGGTGAAGCCCACCCAGACCCTGTCCCT
GACCTGCTCCTTCTCTGGCTTCAGCCTGTCCACCTCCGGCATGGGCGTG
AGCTGGATTCGGCAGCCCTCTGGCAAAGGCCTGGAGTGGCTGGCCCACA
TCTACTGGGATGATGACAAGCAGTACAACCCCAGCCTGAAGTCCCGGCT
GACCATCAGCAAAGACACCTCCAAGAACCAGGTCTTCCTGACCATCACC
TCTGTGGACCCTGTGGACACAGCCACCTACTACTGTGTGAGACGCGCCA
GCTCCAGCCGGTATGATGACCAGTTTGACTACTGGGGCCAGGGCACCCC
CCTGACAGTCTCCAGCgcgaggtgacgccgagtgacttgcctctctagt
cgatgt (SEQ ID NO:148)

FIG. 10Q

HUMANIZED 26D6 - HCVR VEN3 (VENEERED)
actccgaggtgacgccgagtgacttgcctcactagacccCAGGTGACCC
TGAAAGAATCCGGCCCTGGCCTGGTGAAGCCCACCCAGACCCTGTCCCT
GACCTGCTCCTTCTCTGGCTTCAGCCTGTCCACCTCCGGCATGGGCGTG
AGCTGGATTCGGCAGCCCTCTGGCAAAGGCCTGGAGTGGCTGGCCCACA
TCTACTGGGATGATGACAAGCAGTACAACCCCAGCCTGAAGTCCCGGCT
GACCATCAGCAAAGACACCTCCAAGAACCAGGTCGTGCTGACCATCACC
TCTGTGGACCCTGTGGACACAGCCACCTACTACTGTGTGAGACGCGCCA
GCTCCAGCCGGTATGATGACCAGTTTGACTACTGGGGCCAGGGCACCCT
GCTGACAGTCTCCAGCgcgaggtgacgccgagtgacttgcctctctagt
cgatgt (SEQ ID NO:149)

FIG. 10R

HUMANIZED 26D6 - LCVR VEN1 (VENEERED)
gtcacctgcccagatgtGATGTGGTGATGACCCAGACCCCCCTGTCCCT
GCCTGTGAGCCTGGGCGACCCTGCCTCCATCAGCTGCCGCGCCTCCAG
AGCATTGTGCACAGCAATGGCAACACCTACCTGGAGTGGTACCTGCAAA
AGCCTGGCCAGTCCCCCAAGCTGCTGATCTACCGCGTGAGCAACCGGTT
CTCTGGCGTGCCTGACCGCTTCTCTGGCTCTGGCTCTGGCACAGACTTC
ACCCTGAAGATCAGCCGCGTGGAAGCTGAAGACCTGGGCGTCTACTTCT
GCTTCCAGGTGACCCATGTGCCCCTGACCTTTGGCGCTGGCACCAAACT
GGAACTGAAAcgtacggtggcaggtgat (SEQ ID NO:150)

FIG. 10S

HUMANIZED 26D6 - LCVR VEN2 (VENEERED)
gtcacctgcccagatgtGATGTGGTGATGACCCAGACCCCCCTGTCCCT
GCCTGTGAGCCTGGGCGACCCTGCCTCCATCAGCTGCCGCGCCTCCAG
AGCATTGTGCACAGCAATGGCAACACCTACCTGGAGTGGTACCTGCAAA
AGCCTGGCCAGTCCCCCAAGCTGCTGATCTACCGCGTGAGCAACCGGTT
CTCTGGCGTGCCTGACCGCTTCTCTGGCTCTGGCTCTGGCACAGACTTC
ACCCTGAAGATCAGCCGCGTGGAAGCTGAAGACGTGGGCGTCTACTTCT
GCTTCCAGGTGACCCATGTGCCCCTGACCTTTGGCGGCGGCACCAAACT
GGAACTGAAAcgtacggtggcaggtgat (SEQ ID NO:151)

FIG. 10T

HUMANIZED 20C2 - HCVRA IgG1 (CDR GRAFTED)
QVTLKESGPALVKPTQTLTLTCTFSGFSLSTSGMGVGWIRQPPGKALEW
LAHIWWDDDKSYNPSLKSRLTISKDTSKNQVVLTMTNMDPVDTATYYCA
RRQLGLRSIDAMDYWGQGTTVTVSSASTKGPSVFPLAPSSKSTSGGTAA
LGCLVKDYFPEPVTVSWNSGALTSGVHTFPAVLQSSGLYSLSSVVTVPS
SSLGTQTYICNVNHKPSNTKVDKRVEPKSCDKTHTCPPCPAPELLGGPS
VFLFPPKPKDTLMISRTPEVTCVVVDVSHEDPEVKFNWYVDGVEVHNAK
TKPREEQYNSTYRVVSVLTVLHQDWLNGKEYKCKVSNKALPAPIEKTIS
KAKGQPREPQVYTLPPSREEMTKNQVSLTCLVKGFYPSDIAVEWESNGQ
PENNYKTTPPVLDSDGSFFLYSKLTVDKSRWQQGNVFSCSVMHEALHNH
YTQKSLSLSPGK* (SEQ ID NO:152)

FIG. 11A

HUMANIZED 20C2 - HCVRB IgG1 (CDR GRAFTED)
QVTLKESGPALVKPTQTLTLTCTLSGFSLSTSGMGVGWIRQPPGKALEW
LAHIWWDDDKSYNPSLKSRLTISKDTSKNQVVLTMTNMDPVDTATYYCA
RRQLGLRSIDAMDYWGQGTTVTVSSASTKGPSVFPLAPSSKSTSGGTAA
LGCLVKDYFPEPVTVSWNSGALTSGVHTFPAVLQSSGLYSLSSVVTVPS
SSLGTQTYICNVNHKPSNTKVDKRVEPKSCDKTHTCPPCPAPELLGGPS
VFLFPPKPKDTLMISRTPEVTCVVVDVSHEDPEVKFNWYVDGVEVHNAK
TKPREEQYNSTYRVVSVLTVLHQDWLNGKEYKCKVSNKALPAPIEKTIS
KAKGQPREPQVYTLPPSREEMTKNQVSLTCLVKGFYPSDIAVEWESNGQ
PENNYKTTPPVLDSDGSFFLYSKLTVDKSRWQQGNVFSCSVMHEALHNH
YTQKSLSLSPGK* (SEQ ID NO:153)

FIG. 11B

HUMANIZED 20C2 - HCVRA IgG2M4 (CDR GRAFTED)
QVTLKESGPALVKPTQTLTLTCTFSGFSLSTSGMGVGWIRQPPGKALEW
LAHIWWDDDKSYNPSLKSRLTISKDTSKNQVVLTMTNMDPVDTATYYCA
RRQLGLRSIDAMDYWGQGTTVTVSSASTKGPSVFPLAPCSRSTSESTAA
LGCLVKDYFPEPVTVSWNSGALTSGVHTFPAVLQSSGLYSLSSVVTVTS
SNFGTQTYTCNVDHKPSNTKVDKTVERKCCVECPPCPAPPVAGPSVFLF
PPKPKDTLMISRTPEVTCVVVDVSQEDPEVQFNWYVDGVEVHNAKTKPR
EEQFNSTFRVVSVLTVLHQDWLNGKEYKCKVSNKGLPSSIEKTISKTKG
QPREPQVYTLPPSREEMTKNQVSLTCLVKGFYPSDIAVEWESNGQPENN
YKTTPPMLDSDGSFFLYSKLTVDKSRWQQGNVFSCSVMHEALHNHYTQK
SLSLSPGK* (SEQ ID NO:154)

FIG. 11C

HUMANIZED 20C2 HCVRB IgG2M4 (CDR GRAFTED)
QVTLKESGPALVKPTQTLTLTCTLSGFSLSTSGMGVGWIRQPPGKALEW
LAHIWWDDDKSYNPSLKSRLTISKDTSKNQVVLTMTNMDPVDTATYYCA
RRQLGLRSIDAMDYWGQGTTVTVSSASTKGPSVFPLAPCSRSTSESTAA
LGCLVKDYFPEPVTVSWNSGALTSGVHTFPAVLQSSGLYSLSSVVTVTS
SNFGTQTYTCNVDHKPSNTKVDKTVERKCCVECPPCPAPPVAGPSVFLF
PPKPKDTLMISRTPEVTCVVVDVSQEDPEVQFNWYVDGVEVHNAKTKPR
EEQFNSTFRVVSVLTVLHQDWLNGKEYKCKVSNKGLPSSIEKTISKTKG
QPREPQVYTLPPSREEMTKNQVSLTCLVKGFYPSDIAVEWESNGQPENN
YKTTPPMLDSDGSFFLYSKLTVDKSRWQQGNVFSCSVMHEALHNHYTQK
SLSLSPGK* (SEQ ID NO:155)

FIG. 11D

HUMANIZED 20C2 - LCVR Kappa (CDR GRAFTED)
DVVMTQSPLSLPVTPGEPASISCRSSQSILHSNGNTYLEWYLQKPGQSP
QLLIYKVSNRFSGVPDRFSGSGSGTDFTLKISRVEAEDVGVYYCFQGSL
VPLTFGQGTKLEIKRTVAAPSVFIFPPSDEQLKSGTASVVCLLNNFYPR
EAKVQWKVDNALQSGNSQESVTEQDSKDSTYSLSSTLTLSKADYEKHKV
YACEVTHQGLSSPVTKSFNRGEC* (SEQ ID NO:156)

FIG. 11E

HUMANIZED 26D6 - HCVR IgG1 (CDR GRAFTED)
QVTLKESGPTLVKPTQTLTLTCTFSGFSLSTSGMGVSWIRQPPGKALEW
LAHIYWDDDKQYNPSLKSRLTITKDTSKNQVVLTMTNMDPVDTATYYCA
RRASSSRYDDQFDYWGQGTLVPVSSASTKGPSVFPLAPSSKSTSGGTAA
LGCLVKDYFPEPVTVSWNSGALTSGVHTFPAVLQSSGLYSLSSVVTVPS
SSLGTQTYICNVNHKPSNTKVDKRVEPKSCDKTHTCPPCPAPELLGGPS
VFLFPPKPKDTLMISRTPEVTCVVVDVSHEDPEVKFNWYVDGVEVHNAK
TKPREEQYNSTYRVVSVLTVLHQDWLNGKEYKCKVSNKALPAPIEKTIS
KAKGQPREPQVYTLPPSREEMTKNQVSLTCLVKGFYPSDIAVEWESNGQ
PENNYKTTPPVLDSDGSFFLYSKLTVDKSRWQQGNVFSCSVMHEALHNH
YTQKSLSLSPGK* (SEQ ID NO:157)

FIG. 11F

HUMANIZED 26D6 - HCVR IgG2M4 (CDR GRAFTED)
QVTLKESGPTLVKPTQTLTLTCTFSGFSLSTSGMGVSWIRQPPGKALEW
LAHIYWDDDKQYNPSLKSRLTITKDTSKNQVVLTMTNMDPVDTATYYCA
RRASSSRYDDQFDYWGQGTLVPVSSASTKGPSVFPLAPCSRSTSESTAA
LGCLVKDYFPEPVTVSWNSGALTSGVHTFPAVLQSSGLYSLSSVVTVTS
SNFGTQTYTCNVDHKPSNTKVDKTVERKCCVECPPCPAPPVAGPSVFLF
PPKPKDTLMISRTPEVTCVVVDVSQEDPEVQFNWYVDGVEVHNAKTKPR
EEQFNSTFRVVSVLTVLHQDWLNGKEYKCKVSNKGLPSSIEKTISKTKG
QPREPQVYTLPPSREEMTKNQVSLTCLVKGFYPSDIAVEWESNGQPENN
YKTTPPMLDSDGSFFLYSKLTVDKSRWQQGNVFSCSVMHEALHNHYTQK
SLSLSPGK* (SEQ ID NO:158)

FIG. 11G

HUMANIZED 26D6 - LCVR Kappa (CDR GRAFTED)
DVVMTQSPLSLPVTPGEPASISCRASQSIVHSNGNTYLEWYLQKPGQSP
QLLIYRVSNRFSGVPDRFSGSGSGTDFTLKISRVEAEDVGVYYCFQVTH
VPLTFGQGTKLEIKRTVAAPSVFIFPPSDEQLKSGTASVVCLLNNFYPR
EAKVQWKVDNALQSGNSQESVTEQDSKDSTYSLSSTLTLSKADYEKHKV
YACEVTHQGLSSPVTKSFNRGEC* (SEQ ID NO:159)

FIG. 11H

HUMANIZED 4E2 - HCVR IgG1 (CDR GRAFTED)
QVTLKESGPALVKPTQTLTLTCTFSGFSLSTSGMGVGWIRQPPGKALEW
LAHIWWDDDKYYNPSLKSQLTISKDTSKNQVVLTMTNMDPVDTATYYCA
RRSINSVVPEDYFDYWGQGTTVTVSSASTKGPSVFPLAPSSKSTSGGTA
ALGCLVKDYFPEPVTVSWNSGALTSGVHTFPAVLQSSGLYSLSSVVTVP
SSSLGTQTYICNVNHKPSNTKVDKRVEPKSCDKTHTCPPCPAPELLGGP
SVFLFPPKPKDTLMISRTPEVTCVVVDVSHEDPEVKFNWYVDGVEVHNA
KTKPREEQYNSTYRVVSVLTVLHQDWLNGKEYKCKVSNKALPAPIEKTI
SKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHN
HYTQKSLSLSPGK* (SEQ ID NO:160)

FIG. 11I

HUMANIZED 4E2 - LCVR Kappa (CDR GRAFTED)
DVVMTQSPLSLPVTPGEPASISCRSSQSIVHSNGNTYLEWYLQKPGQSP
QLLIYKVSNRFSGVPDRFSGSGSGTDFTLKISRVEAEDVGVYYCFQGSH
VPLTFGQGTKLEIKRTVAAPSVFIFPPSDEQLKSGTASVVCLLNNFYPR
EAKVQWKVDNALQSGNSQESVTEQDSKDSTYSLSSTLTLSKADYEKHKV
YACEVTHQGLSSPVTKSFNRGEC* (SEQ ID NO:161)

FIG. 11J

HUMANIZED 3B3 - HCVR IgG1 (CDR GRAFTED)
EVQLVESGGGLVQPGGSLRLSCAASGFTFSSFGMHWVRQAPGKGLEWVA
YISRGSSTIYYADTVKGRFTISRDNAKNSLYLQMNSLRAEDTAVYYCAR
GITTALDYWGQGTLVTVSSASTKGPSVFPLAPSSKSTSGGTAALGCLVK
DYFPEPVTVSWNSGALTSGVHTFPAVLQSSGLYSLSSVVTVPSSSLGTQ
TYICNVNHKPSNTKVDKRVEPKSCDKTHTCPPCPAPELLGGPSVFLFPP
KPKDTLMISRTPEVTCVVVDVSHEDPEVKFNWYVDGVEVHNAKTKPREE
QYNSTYRVVSVLTVLHQDWLNGKEYKCKVSNKALPAPIEKTISKAKGQP
REPQVYTLPPSREEMTKNQVSLTCLVKGFYPSDIAVEWESNGQPENNYK
TTPPVLDSDGSFFLYSKLTVDKSRWQQGNVFSCSVMHEALHNHYTQKSL
SLSPGK* (SEQ ID NO:162)

FIG. 11K

HUMANIZED 3B3 LCVR Kappa (CDR GRAFTED)
DVVMTQSPLSLPVTPGEPASISCRSSQSIVHSNGNTYLEWYLQKPGQSP
QLLIYKASNRFSGVPDRFSGSGSGTDFTLKISRVEAEDVGVYYCFQGSH
VPPTFGQGTKLEIKRTVAAPSVFIFPPSDEQLKSGTASVVCLLNNFYPR
EAKVQWKVDNALQSGNSQESVTEQDSKDSTYSLSSTLTLSKADYEKHKV
YACEVTHQGLSSPVTKSFNRGEC* (SEQ ID NO:163)

FIG. 11L

HUMANIZED 2H4 HCVR IgG1 (CDR GRAFTED)
EVQLVESGGGLVQPGGSLRLSCAASGFTFSSFGMHWVRQAPGKGLEWVA
YIRSGSSTIYYADTVKGRFTISRDNSKNTLYLQMNSLRAEDTAVYYCAR
GGNYYGSSRFAYWGQGTLVTVSSASTKGPSVFPLAPSSKSTSGGTAALG
CLVKDYFPEPVTVSWNSGALTSGVHTFPAVLQSSGLYSLSSVVTVPSSS
LGTQTYICNVNHKPSNTKVDKRVEPKSCDKTHTCPPCPAPELLGGPSVF
LFPPKPKDTLMISRTPEVTCVVVDVSHEDPEVKFNWYVDGVEVHNAKTK
PREEQYNSTYRVVSVLTVLHQDWLNGKEYKCKVSNKALPAPIEKTISKA
KGQPREPQVYTLPPSREEMTKNQVSLTCLVKGFYPSDIAVEWESNGQPE
NNYKTTPPVLDSDGSFFLYSKLTVDKSRWQQGNVFSCSVMHEALHNHYT
QKSLSLSPGK* (SEQ ID NO:164)

FIG. 11M

HUMANIZED 2H4 LCVR Kappa (CDR GRAFTED)
DIQMTQSPSSLSASVGDRVTITCKASQDINSYLSWFQQKPGKAPKTLIY
RANRFVDGVPSRFSGSGSGTDYTLTISSLQPEDFATYFCLQYDEFPLTF
GGGTKVEIKRTVAAPSVFIFPPSDEQLKSGTASVVCLLNNFYPREAKVQ
WKVDNALQSGNSQESVTEQDSKDSTYSLSSTLTLSKADYEKHKVYACEV
THQGLSSPVTKSFNRGEC* (SEQ ID NO:165)

FIG. 11N

HUMANIZED 1F6 HCVR IgG1 (CDR GRAFTED)
EVQLVESGGGLVQPGGSLRLSCAASGFTFSSFGMHWVRQAPGKGLEWVA
YISSVSSTIYYADTVKGRFTISRDNSKNTLYLQMNSLRAEDTAVYYCAR
SGYGSSYGYGMDYWGQGTLVTVSSASTKGPSVFPLAPSSKSTSGGTAAL
GCLVKDYFPEPVTVSWNSGALTSGVHTFPAVLQSSGLYSLSSVVTVPSS
SLGTQTYICNVNHKPSNTKVDKRVEPKSCDKTHTCPPCPAPELLGGPSV
FLFPPKPKDTLMISRTPEVTCVVVDVSHEDPEVKFNWYVDGVEVHNAKT
KPREEQYNSTYRVVSVLTVLHQDWLNGKEYKCKVSNKALPAPIEKTISK
AKGQPREPQVYTLPPSREEMTKNQVSLTCLVKGFYPSDIAVEWESNGQP
ENNYKTTPPVLDSDGSFFLYSKLTVDKSRWQQGNVFSCSVMHEALHNHY
TQKSLSLSPGK* (SEQ ID NO:166)

FIG. 11O

HUMANIZED 20C2 HCVR VenA IgG1 (VENEERED)
QVTLKESGPGILKPSQTLSLTCTFSGFSLSTSGMGVGWFRQPPGKGLEW
LAHIWWDDDKSYNPSLKSRLTISKDTSKNQVFLTITNMDPVDTATYYCA
RRQLGLRSIDAMDYWGQGTTVTVSSASTKGPSVFPLAPSSKSTSGGTAA
LGCLVKDYFPEPVTVSWNSGALTSGVHTFPAVLQSSGLYSLSSVVTVPS
SSLGTQTYICNVNHKPSNTKVDKRVEPKSCDKTHTCPPCPAPELLGGPS
VFLFPPKPKDTLMISRTPEVTCVVVDVSHEDPEVKFNWYVDGVEVHNAK
TKPREEQYNSTYRVVSVLTVLHQDWLNGKEYKCKVSNKALPAPIEKTIS
KAKGQPREPQVYTLPPSREEMTKNQVSLTCLVKGFYPSDIAVEWESNGQ
PENNYKTTPPVLDSDGSFFLYSKLTVDKSRWQQGNVFSCSVMHEALHNH
YTQKSLSLSPGK* (SEQ ID NO:167)

FIG. 11P

HUMANIZED 20C2 HCVR VenB IgG1 (VENEERED)
QVTLKESGPGILKPSQTLSLTCTFSGFSLSTSGMGVGWFRQPPGKGLEW
LAHIWWDDDKSYNPSLKSRLISKDTSKNQVVLTITNMDPVDTATYYCAR
RQLGLRSIDAMDYWGQGTTVTVSSASTKGPSVFPLAPSSKSTSGGTAAL
GCLVKDYFPEPVTVSWNSGALTSGVHTFPAVLQSSGLYSLSSVVTVPSS
SLGTQTYICNVNHKPSNTKVDKRVEPKSCDKTHTCPPCPAPELLGGPSV
FLFPPKPKDTLMISRTPEVTCVVVDVSHEDPEVKFNWYVDGVEVHNAKT
KPREEQYNSTYRVVSVLTVLHQDWLNGKEYKCKVSNKALPAPIEKTISK
AKGQPREPQVYTLPPSREEMTKNQVSLTCLVKGFYPSDIAVEWESNGQP
ENNYKTTPPVLDSDGSFFLYSKLTVDKSRWQQGNVFSCSVMHEALHNHY
TQKSLSLSPGK* (SEQ ID NO:168)

*FIG. 11Q*

HUMANIZED 20C2 HCVR VenA IgG2M4 (VENEERED)
QVTLKESGPGILKPSQTLSLTCTFSGFSLSTSGMGVGWFRQPPGKGLEW
LAHIWWDDDKSYNPSLKSRLTISKDTSKNQVFLTITNMDPVDTATYYCA
RRQLGLRSIDAMDYWGQGTTVTVSSASTKGPSVFPLAPCSRSTSESTAA
LGCLVKDYFPEPVTVSWNSGALTSGVHTFPAVLQSSGLYSLSSVVTVTS
SNFGTQTYTCNVDHKPSNTKVDKTVERKCCVECPPCPAPPVAGPSVFLF
PPKPKDTLMISRTPEVTCVVVDVSQEDPEVQFNWYVDGVEVHNAKTKPR
EEQFNSTFRVVSVLTVLHQDWLNGKEYKCKVSNKGLPSSIEKTISKTKG
QPREPQVYTLPPSREEMTKNQVSLTCLVKGFYPSDIAVEWESNGQPENN
YKTTPPMLDSDGSFFLYSKLTVDKSRWQQGNVFSCSVMHEALHNHYTQK
SLSLSPGK * (SEQ ID NO:169)

*FIG. 11R*

HUMANIZED 20C2 HCVR VenB IgG2M4 (VENEERED)
QVTLKESGPGILKPSQTLSLTCTFSGFSLSTSGMGVGWFRQPPGKGLEW
LAHIWWDDDKSYNPSLKSRLTISKDTSKNQVVLTITNMDPVDTATYYCA
RRQLGLRSIDAMDYWGQGTTVTVSSASTKGPSVFPLAPCSRSTSESTAA
LGCLVKDYFPEPVTVSWNSGALTSGVHTFPAVLQSSGLYSLSSVVTVTS
SNFGTQTYTCNVDHKPSNTKVDKTVERKCCVECPPCPAPPVAGPSVFLF
PPKPKDTLMISRTPEVTCVVVDVSQEDPEVQFNWYVDGVEVHNAKTKPR
EEQFNSTFRVVSVLTVLHQDWLNGKEYKCKVSNKGLPSSIEKTISKTKG
QPREPQVYTLPPSREEMTKNQVSLTCLVKGFYPSDIAVEWESNGQPENN
YKTTPPMLDSDGSFFLYSKLTVDKSRWQQGNVFSCSVMHEALHNHYTQK
SLSLSPGK * (SEQ ID NO:170)

*FIG. 11S*

HUMANIZED 20C2 LCVR Kappa (VENEERED)
DVVMTQSPLSLPVSLGDPASISCRSSQSILHSNGNTYLEWYLQKPGQSP
QLLIYKVSNRFSGVPDRFSGSGSGTDFTLKISRVEAEDLGVYYCFQGSL
VPLTFGAGTKLELKRTVAAPSVFIFPPSDEQLKSGTASVVCLLNNFYPR
EAKVQWKVDNALQSGNSQESVTEQDSKDSTYSLSSTLTLSKADYEKHKV
YACEVTHQGLSSPVTKSFNRGEC* (SEQ ID NO:171)

FIG. 11T

HUMANIZED 26D6 HCVR Ven1 IgG1 (VENEERED)
QVTLKESGPGIVQPSQTLSLTCSFSGFSLSTSGMGVSWIRQPSGKGLEW
LAHIYWDDDKQYNPSLKSRLTISKDTSKNQVFLTITSVDTVDTATYYCV
RRASSSRYDDQFDYWGQGTPLTVSSASTKGPSVFPLAPSSKSTSGGTAA
LGCLVKDYFPEPVTVSWNSGALTSGVHTFPAVLQSSGLYSLSSVVTVPS
SSLGTQTYICNVNHKPSNTKVDKRVEPKSCDKTHTCPPCPAPELLGGPS
VFLFPPKPKDTLMISRTPEVTCVVVDVSHEDPEVKFNWYVDGVEVHNAK
TKPREEQYNSTYRVVSVLTVLHQDWLNGKEYKCKVSNKALPAPIEKTIS
KAKGQPREPQVYTLPPSREEMTKNQVSLTCLVKGFYPSDIAVEWESNGQ
PENNYKTTPPVLDSDGSFFLYSKLTVDKSRWQQGNVFSCSVMHEALHNH
YTQKSLSLSPGK * (SEQ ID NO:172)

FIG. 11U

HUMANIZED 26D6 HCVR Ven2 IgG1 (VENEERED)
QVTLKESGPGLVKPTQTLSLTCSFSGFSLSTSGMGVSWIRQPSGKGLEW
LAHIYWDDDKQYNPSLKSRLTISKDTSKNQVFLTITSVDPVDTATYYCV
RRASSSRYDDQFDYWGQGTPLTVSSASTKGPSVFPLAPSSKSTSGGTAA
LGCLVKDYFPEPVTVSWNSGALTSGVHTFPAVLQSSGLYSLSSVVTVPS
SSLGTQTYICNVNHKPSNTKVDKRVEPKSCDKTHTCPPCPAPELLGGPS
VFLFPPKPKDTLMISRTPEVTCVVVDVSHEDPEVKFNWYVDGVEVHNAK
TKPREEQYNSTYRVVSVLTVLHQDWLNGKEYKCKVSNKALPAPIEKTIS
KAKGQPREPQVYTLPPSREEMTKNQVSLTCLVKGFYPSDIAVEWESNGQ
PENNYKTTPPVLDSDGSFFLYSKLTVDKSRWQQGNVFSCSVMHEALHNH
YTQKSLSLSPGK* (SEQ ID NO:173)

FIG. 11V

HUMANIZED 26D6 HCVR Ven3 IgG1 (VENEERED)
QVTLKESGPGLVKPTQTLSLTCSFSGFSLSTSGMGVSWIRQPSGKGLEW
LAHIYWDDDKQYNPSLKSRLTISKDTSKNQVVLTITSVDPVDTATYYCV
RRASSSRYDDQFDYWGQGTLLTVSSASTKGPSVFPLAPSSKSTSGGTAA
LGCLVKDYFPEPVTVSWNSGALTSGVHTFPAVLQSSGLYSLSSVVTVPS
SSLGTQTYICNVNHKPSNTKVDKRVEPKSCDKTHTCPPCPAPELLGGPS
VFLFPPKPKDTLMISRTPEVTCVVVDVSHEDPEVKFNWYVDGVEVHNAK
TKPREEQYNSTYRVVSVLTVLHQDWLNGKEYKCKVSNKALPAPIEKTIS
KAKGQPREPQVYTLPPSREEMTKNQVSLTCLVKGFYPSDIAVEWESNGQ
PENNYKTTPPVLDSDGSFFLYSKLTVDKSRWQQGNVFSCSVMHEALHNH
YTQKSLSLSPGK* (SEQ ID NO:174)

FIG. 11W

HUMANIZED 26D6 LCVR Ven1 Kappa (VENEERED)
DVVMTQTPLSLPVSLGDPASISCRASQSIVHSNGNTYLEWYLQKPGQSP
KLLIYRVSNRFSGVPDRFSGSGSGTDFTLKISRVEAEDLGVYFCFQVTH
VPLTFGAGTKLELKRTVAAPSVFIFPPSDEQLKSGTASVVCLLNNFYPR
EAKVQWKVDNALQSGNSQESVTEQDSKDSTYSLSSTLTLSKADYEKHKV
YACEVTHQGLSSPVTKSFNRGEC* (SEQ ID NO:175)

FIG. 11X

HUMANIZED 26D6 LCVR Ven2 Kappa (VENEERED)
DVVMTQTPLSLPVSLGDPASISCRASQSIVHSNGNTYLEWYLQKPGQSP
KLLIYRVSNRFSGVPDRFSGSGSGTDFTLKISRVEAEDVGVYFCFQVTH
VPLTFGGGTKLELKRTVAAPSVFIFPPSDEQLKSGTASVVCLLNNFYPR
EAKVQWKVDNALQSGNSQESVTEQDSKDSTYSLSSTLTLSKADYEKHKV
YACEVTHQGLSSPVTKSFNRGEC* (SEQ ID NO:176)

FIG. 11Y

```
              |--- CH1 STARTS HERE          C144
IgG1    /// ASTK GPSVFPLAPS SKSTSGGTAA LGCLVKDYFP EPVTVSWNSG
IgG2    /// ASTK GPSVFPLAPC SRSTSESTAA LGCLVKDYFP EPVTVSWNSG
IgG4    /// ASTK GPSVFPLAPC SRSTSESTAA LGCLVKDYFP EPVTVSWNSG
IgG2M4  /// ASTK GPSVFPLAPC SRSTSESTAA LGCLVKDYFP EPVTVSWNSG
        (VH-C1 LINKER)
                                                    C200
IgG1    ALTSGVHTFP AVLQSSGLYS LSSVVTVPSS SLGTQTYICN VNHKPSNTKV
IgG2    ALTSGVHTFP AVLQSSGLYS LSSVVTVTSS NFGTQTYTCN VDHKPSNTKV
IgG4    ALTSGVHTFP AVLQSSGLYS LSSVVTVPSS SLGTKTYTCN VDHKPSNTKV
IgG2M4  ALTSGVHTFP AVLQSSGLYS LSSVVTVTSS NFGTQTYTCN VDHKPSNTKV

-HINGE REGION--||----CH2-> P238         M252      C261
IgG1    DKKAEPKSCD KTHTCPPCPA PELLGGPSVF LFPPKPKDTL MISRTPEVTC
IgG2    DKTVERKCC- --VECPPCPA PP-VAGPSVF LFPPKPKDTL MISRTPEVTC
IgG4    DKRVESKYGP ---PCPSCPA PEFLGGPSVF LFPPKPKDTL MISRTPEVTC
IgG2M4  DKTVERKCC- --VECPPCPA PP-VAGPSVF LFPPKPKDTL MISRTPEVTC
                            (LOWER HINGE)         FcRn-BIND

Q268                          N297*       L309
IgG1    VVVDVSHEDP EVKFNWYVDG VEVHNAKTKP REEQYNSTYR VVSVLTVLHQ
IgG2    VVVDVSHEDP EVQFNWYVDG VEVHNAKTKP REEQFNSTFR VVSVLTVVHQ
IgG4    VVVDVSQEDP EVQFNWYVDG VEVHNAKTKP REEQFNSTYR VVSVLTVLHQ
IgG2M4  VVVDVSQEDP EVQFNWYVDG VEVHNAKTKP REEQFNSTFR VVSVLTVLHQ
        B/C LOOP                         C'E LOOP    FcRn-BIND
                                P331
              C321        A330        |----CH3->
IgG1    DWLNGKEYKC KVSNKALPAPI EKTISKAKG QPREPQVYTL PPSRDELTKN
IgG2    DWLNGKEYKC KVSNKGLPAPI EKTISKTKG QPREPQVYTL PPSREEMTKN
IgG4    DWLNGKEYKC KVSNKGLPSSI EKTISKAKG QPREPQVYTL PPSQEEMTKN
IgG2M4  DWLNGKEYKC KVSNKGLPSSI EKTISKTKG QPREPQVYTL PPSREEMTKN
                  F/G LOOP

IgG1    QVSLTCLVKG FYPSDIAVEW ESNGQPENNY KTTPPVLDSD GSFFLYSKLT
IgG2    QVSLTCLVKG FYPSDIAVEW ESNGQPENNY KTTPPMLDSD GSFFLYSKLT
IgG4    QVSLTCLVKG FYPSDIAVEW ESNGQPENNY KTTPPVLDSD GSFFLYSRLT
IgG2M4  QVSLTCLVKG FYPSDIAVEW ESNGQPENNY KTTPPMLDSD GSFFLYSKLT

M428L H433
IgG1    VDKSRWQQGN VFSCSVMHEA LHNHYTQKSL SLSPGK* (SEQ ID NO:251)
IgG2    VDKSRWQQGN VFSCSVMHEA LHNHYTQKSL SLSPGK* (SEQ ID NO:252)
IgG4    VDKSRWQEGN VFSCSVMHEA LHNHYTQKSL SLSLGK* (SEQ ID NO:253)
IgG2M4  VDKSRWQQGN VFSCSVMHEA LHNHYTQKSL SLSPGK* (SEQ ID NO:254)
                             FcRn-BIND
```

FIG. 12 pFab3 20C2 HEAVY CHAIN
<u>MKKTAIAIAVALAGFATVAQAALE</u>QVTLKESGPALVKPTQTLTLTCTFS
<u>Omp SECRETION SIGNAL</u>            A20C2vH-hu

GFSLSTSGMGVGWIRQPPGKALEWLAHIWWDDDKSYNPSLKSRLTISKD
<u>       CDR1       </u>              <u>       CDR2       </u>

TSKNQVVLTMTNMDPVDTATYYCARRQLGLRSIDAMDYWGQGTTVTVSS
                         <u>      CDR3      </u>
<u>ASTKGPSVFPLAPSSKSTSGGTAALGCLVKDYFPEPVTVSWNSGALTSG</u>
<u>                         hCH1</u>

<u>VHTFPAVLQSSGLYSLSSVVTVPSSSLGTQTYICNVNHKPSNTKVDKRV</u>

<u>EPKSCDKTHTCPPCPTS</u>GHHHHHHGGEQKLISEEDLGG*PFVCEYQGQS
                  <u>HIS-TAG</u>   <u>MYC-TAG</u>    ◆Amb

SDLPQPPVNAGGGSGGGSGGGSEGGGSEGGGSEGGGSEGGGSGGGSGSG
  <u>pIII STUMP (aa 198-406)</u>

DFDYEKMANANKGAMTENADENALQSDAKGKLDSVATDYGAAIDGFIGD
VSGLANGNGATGDFAGSNSQMAQVGDGDNSPLMNNFRQYLPSLPQSVEC
RPYVFGAGKPYEFSIDCDKINLFRGVFAFLLYVATFMYVFSTFANILRN
KES* (SEQ ID NO:255)

FIG. 13A pFab3 20C2 LIGHT CHAIN
<u>MKYLLPTAAAGLLLLAAQPAMA</u>SRDVVMTQSPLSLPVTPGEPASISCRS
<u>Pel SECRETION SIGNAL</u>                20C2vL

SQSILHSNGNTYLEWYLQKPGQSPQLLIYKVSNRFSGVPDRFSGSGSGT
<u>       CDR1       </u>           <u>  CDR2  </u>

DFTLKISRVEAEDVGVYYCFQGSLVPLTFGQGTKLEIKRTVAAPSVFIF
                   <u>   CDR3    </u>

<u>PPSDEQLKSGTASVVCLLNNFYPREAKVQWKVDNALQSGNSQESVTEQD</u>
<u>SKDSTYSLSSTLTLSKADYEKHKVYACEVTHQGLSSPVTKSFNRGEC</u>
(SEQ ID NO:256)

FIG. 13B

Biotin-5'-ctatggcttctctagaGATGTGGTGATG (Primer 20C2LC3F; SEQ ID NO:261)
agctgctggtctgctgctggcgccagccggctatggcttctctagaGATGTGGTGATGGTGATGACCAGAGCCCCCCTGTCCCTGCCTGTGACCCCTGGCAGC
CTGCCAGCAGATCTCCTGCACTCCTGCACTCCAATGGCAACACCTACCTGAGTGGTACCTGGAGTACCTGGAGAAGCCTGGCAGAAGCCTGGCAGAGCCCCAGCTG
CTGATCTACAAGGTGTCCAACCGGTTCTCCGGCGTCCCTGACCGGTTCAGCGGCTCCGGGCTCCGGCAGCGGGCACAGACTTCACCCTGAAGATCAGCCGGGTGGAGGC
TGAGGATGTGGGC
                    F  Q  G  S  L  V  P  L  T  (SEQ ID NO:60)
           GTCTACTACTGCTTCCAGGGCAGCCTGGTGCCCCTGACCTTTGGCCAGGGCACCAAGCTGGAGATCAAGcgtacggtggctg
           GTCTACTACTGCTTCCAGGGCAGCCTGGTGCCCCTGACCTTTGGCCAGGGCACCAAGCTGGAGATCAAGcgtacggtggctg (SEQ ID NO:257)
                    X  X  X  X  X  V  P  L  T  (SEQ ID NO:321)

Biotin-5'-cagccaccgtacgCTTGATCTCCAGCTTGGTGCCCTGGCCAAAGGTCAGGGCACMNNMNNMNNMNNGCAGTAGTAGAC 82
                                                                                    (Primer 20C2LC3-1; SEQ ID NO:259)
                    F  Q  G  S  L  V  P  L  T  (SEQ ID NO:60)
           GTCTACTACTGCTTCCAGGGCAGCCTGGTGCCCCTGACCTTTGGCCAGGGCACCAAGCTGGAGATCAAGcgtacggtggctg (SEQ ID NO:320)
           GTCTACTACTGCTTCCAGGGCAGCNNKNNKNNKNNKTTTGGCCAGGGCACCAAGCTGGAGATCAAGcgtacggtggctg (SEQ ID NO:258)
                    F  Q  G  S  X  X  X  X  X  (SEQ ID NO:322)

Biotin-5'-cagccaccgtacgCTTGATCTCCAGCTTGGTGCCCTGGCCAAAMNNMNNMNNMNNNGCTGCCCTGGAAGCAGTAGTAGAC 82
                                                                                    (Primer 20C2LC3-2; SEQ ID NO:260)

FIG. 14

SEQUENCE LISTING

<160> NUMBER OF SEQ ID NOS: 323

<210> SEQ ID NO 1
<211> LENGTH: 459
<212> TYPE: DNA
<213> ORGANISM: Mus musculus

<400> SEQUENCE: 1

```
tgggcagact taccattctc attcctgctg ctgattgtcc ctgcatatgt cttgtcccaa      60
gttactctaa aagagtctgg ccctgggata ttgaagccct cacagaccct cagtctgact     120
tgttctctct ctgggttttc actgagcact tctggtatgg gtgtaggctg gtttcgtcag     180
ccttcaggga agggtctgga gtggctggca cacatttggt gggatgatga taagtcctat     240
aatccatccc tgaagagccg gctcacaatc tccaagtata cctctagaaa ccaggttttc     300
ctcacgatca ccagtgtgga cactgcagat actgccactt actattgtgc tcgaagacaa     360
ctcggactaa gatcaattga tgctatggac tactggggtc aaggaacctc agtcaccgtc     420
tcctcagcca aaacgacacc cccatctgtc tatccactg                            459
```

<210> SEQ ID NO 2
<211> LENGTH: 435
<212> TYPE: DNA
<213> ORGANISM: Mus musculus

<400> SEQUENCE: 2

```
agattgcctg ttaggctgtt ggtgctgatg ttctggattc ctgcttccac cagtgatgtt      60
ttgatgaccc aaactcctct ctccctgcct gtcagtcttg gagatcaagc ctccatctct     120
tgcagatcta gtcagagcat tctacatagt aatggaaaca cctatttaga gtggtacctg     180
cagaaaccag gccagtctcc aaagctcctg atctacaaag tttccaaccg attttctggg     240
gtcccagaca ggttcagtgg cagtggatca gggacagatt tcacactcaa gatcagcaga     300
gtggaggctg aggatctggg agtttattac tgttttcaag gttcacttgt tccgctcacg     360
```

```
ttcggtgctg ggaccaagct ggagctgaaa cgggctgatg ctgcaccaac tgtatccatc    420
ttcccaccat ccagt                                                     435

<210> SEQ ID NO 3
<211> LENGTH: 453
<212> TYPE: DNA
<213> ORGANISM: Mus musculus

<400> SEQUENCE: 3
tgggcagact taccattctc attcctgctg ctgattgtcc ctgcatatgt cctttcccag     60
gttactctga aagagtctgg ccctgggata ttgcagccct cccagaccct cagtctgact    120
tgttctttct ctgggttttc actgagcact tctggtatgg gtgtgagctg gattcgtcag    180
ccttcaggaa agggtctgga gtggctggca cacatttact gggatgatga caagcgctat    240
aacccatccc tgaagagccg gctcacattc tccaaggatt cctccagaaa ccaggtattc    300
ctcaagatca ccagtgtgga cactgcagat actgccacat actactgtgc tcgctatgat    360
ggttacccct actggtactt cgatgtctgg ggcgcaggga ccacggtcac cgtctcctca    420
gccaaaacaa cacccccatc ggtctatcca ctg                                 453

<210> SEQ ID NO 4
<211> LENGTH: 435
<212> TYPE: DNA
<213> ORGANISM: Mus musculus

<400> SEQUENCE: 4
agattgcctg ttaggctgtt ggtgctgatg ttctggattc ctgtttccag cagtgttgtt     60
ctgatgaccc aaactccact ctccctgcct gtcagtcttg agatcaagc ctccatctct    120 tgcagatcta gtcagagcct tgtacacagt aatggaaaca cctatttaca ttggtacctg    180
cagaagccag gccagtctcc aaagctcctg atctacaaag tttccaaccg attttctggg    240
gtcccagaca ggttcagtgg cagtggatca gggacagatt tcacactcaa gatcagcaga    300
gtggaggctg aggatctggg agtttatttc tgttttcaaa gtacacatgt tccgctcacg    360
ttcggtgctg ggaccaagct ggagctgaaa cgggctgatg ctgcaccaac tgtatccatc    420
ttcccaccat ccagt                                                     435

<210> SEQ ID NO 5
<211> LENGTH: 462
<212> TYPE: DNA
<213> ORGANISM: Mus musculus

<400> SEQUENCE: 5
tgggcagact taccattctc attcctgctg ctgattgtcc ctgcatatgt cttgtcccaa     60
gttactctaa aagagtctgg ccctgggata ttgaagccct cacagaccct cagtctgact    120
tgttctttct ctgggttttc actgagcact tctggtatgg gtgtaggctg gattcgtcag    180
ccttcaggga agggtctgga gtggctggca cacatttggt gggatgatga taagtactat    240
aacccatccc tgaagagcca gctcacaatc tccaaggata cctccagaaa ccaggtattc    300
ctcaagatca ccagtgtgga cactgcagat actgccactt actactgtgc tcgaagatcc    360
attagtacgg taatacctga ggactacttt gactactggg gccaaggcac cattctcaca    420
gtctcctcag ccaaaacgac accccatct gtctatccac tg                        462

<210> SEQ ID NO 6
<211> LENGTH: 435
```

```
<212> TYPE: DNA
<213> ORGANISM: Mus musculus

<400> SEQUENCE: 6
agattgcctg ttaggctgtt ggtgctgatg ttctggattc ctgcttccac cagtgatgtt      60
ttgatgaccc aaactccact ctccctgacc gtcagtcttg agatcaagc ctccatctct      120 tgcagatcta gtcagagcat tgtgcatagt aatggaaaca cctatttaga atggtacctg      180
cagaaaccag gccagtctcc aaagctcctg atctacaaag tttccaaccg attttctggg      240
gtcccagaca ggttcagtgg cagtggatca gggacagatt tcacactcaa gatcagcaga      300
gtggaggctg aggatctggg agtttattac tgctttcaag gttcacatgt tccgctcacg      360
ttcggtgctg ggaccaagct ggagctgaaa cgggctgatg ctgcaccaac tgtatccatc      420
ttcccaccat ccagt                                                      435

<210> SEQ ID NO 7
<211> LENGTH: 453
<212> TYPE: DNA
<213> ORGANISM: Mus musculus

<400> SEQUENCE: 7
tgggcagact taccattctc attcctgctg ctgattgtcc ctgcatatgt cctttcccag      60
gttactctga aagagtctgg ccctgggata ttgcagccct cccagaccct cagtctgact      120
tgttctttct ctgggttttc actgagcact tctggtatgg gtgtgagctg gattcgtcag      180
ccttcaggaa agggtctgga gtggctggca cacatttact gggatgatga caagcgctat      240
aacccatccc tgaagagccg gctcacaatc tccaaggata cctccagaaa ccaggtattc      300
ctcaagatca ccagtgtgga cactgcagat actgccacat actactgtgc tcgctatgat      360
ggttacccct actggtactt cgatgtctgg ggcgcaggga ccacggtcac cgtctcctca      420
gccaaaacaa caccccatc agctcatcca ctg                                    453

<210> SEQ ID NO 8
<211> LENGTH: 435
<212> TYPE: DNA
<213> ORGANISM: Mus musculus

<400> SEQUENCE: 8
agattgcctg ttaggctgtt ggtgctgatg ttctggattc ctgcttccag cagtgatgtt      60
gtgatgaccc aaactccact ctccctgcct gtcagtcttg agatcaagc ctccatctct      120 tgcagatcta gtcagagcct tgtacacagt aatggaaaca cctatttaca ttggtacctg      180
cagaagccag gccagtctcc aaagctcctg atctacaaag tttccaaccg atttttgggg      240
gtcccagaca ggttcagtgg cagtggatca gggacagatt tcacactcaa gatcagcaga      300
gtggaggctg aggatctggg agtttacttc tgctctcaaa ctacatatgt tccgctcacg      360
ttcggtgctg ggaccaagct ggagctgaaa cgggctgatg ctgcaccaac tgtatccatc      420
ttcccaccat ccagt                                                      435

<210> SEQ ID NO 9
<211> LENGTH: 462
<212> TYPE: DNA
<213> ORGANISM: Mus musculus

<400> SEQUENCE: 9
tgggcagact taccattctc attcctgctg ctgattgtcc ctgcatatgt cttgtcccaa      60
```

-continued

| | |
|---|---|
| gttactctaa aagagtctgg ccctgggata ttgaagccct cacagaccct cagtctgact | 120 |
| tgttctttct ctgggttttc actgagcact tctggtatgg gtgtaggctg gattcgtcag | 180 |
| ccttcaggga agggtctgga gtggctggca cacatttggt gggatgatga taagtactat | 240 |
| aacccatccc tgaagagcca gctcacaatc tccaaggata cctccagaaa ccaggtattc | 300 |
| ctcaagatca ccagtgtgga cactgcagat actgccactt actactgtgc tcgaagatcc | 360 |
| attaattcgg tagtacctga ggactacttt gactactggg gccaaggcac cactctcaca | 420 |
| gtctccttag ccaaaacgac accccatct gtctatccac tg | 462 |

<210> SEQ ID NO 10
<211> LENGTH: 435
<212> TYPE: DNA
<213> ORGANISM: Mus musculus

<400> SEQUENCE: 10

| | |
|---|---|
| agattgcctg ttaggctgtt ggtgctgatg ttctggattc ctgcttccag cagtgatgtt | 60 |
| ttgatgaccc aaactccact ctccctgcct gtcagtcttg agatcaagc ctccatctct | 120 |
| tgcagatcta gtcagagcat tgtgcatagt aatggaaaca cctatttaga atggtacctg | 180 |
| cagaaaccag gccagtctcc aaagctcctg atctacaaag tttccaaccg attttctggg | 240 |
| gtcccagaca ggttcagtgg cagtggatca gggacagatt tcacactcaa gatcagcaga | 300 |
| gtggaggctg aggatctggg agtttattat tgttttcaag gttcacatgt tccgctcacg | 360 |
| ttcggtgctg ggaccaagct ggagctgaaa cgggctgatg ctgcaccaac tgtatccatc | 420 |
| ttcccaccat ccagt | 435 |

<210> SEQ ID NO 11
<211> LENGTH: 455
<212> TYPE: DNA
<213> ORGANISM: Mus musculus

<400> SEQUENCE: 11

| | |
|---|---|
| tgggactcca ggcttcaatt tagttttcct tgtccttatt ttaaaaggtg tccagtgtga | 60 |
| tgtgcagctg gtggagtctg ggggaggctt agtgcagcct ggagggtccc ggaaactctc | 120 |
| ctgtgcagcc tctggattca ctttcagtag ctttggaatg cactgggttc gtcaggctcc | 180 |
| agagaagggg ctggagtggg tcgcatacat tcgtagtggc agtagtacca tctactatgc | 240 |
| agacacagtg aagggccgat tcaccatctc cagagacaat cccaagaaca ccctgttcct | 300 |
| gcaaatgacc agtctaaggt ctgaggacac ggccatgtat tactgtacaa gaggcgggaa | 360 |
| ttactacggt agtagccggt ttgcttactg gggccaaggg actctggtca ctgtctctgc | 420 |
| agccaaaaca acagccccca tcggtctatc cactg | 455 |

<210> SEQ ID NO 12
<211> LENGTH: 425
<212> TYPE: DNA
<213> ORGANISM: Mus musculus

<400> SEQUENCE: 12

| | |
|---|---|
| tgagggcccc tgctcagttt tttggattct tgttgctctg gtttccaggt atcaaatgtg | 60 |
| acatcaagat gacccagtct ccatcttcca tgtatgcatc tctaggagag agagtcacta | 120 |
| tcacttgcaa ggcgagtcag gacattaata ctatttaag ctggttccag cagaaaccag | 180 |
| ggaaatctcc taagaccctg atctatcgtg caaacagatt cgtagatggg gtcccatcaa | 240 |
| ggttcagtgg cagtggatct gggcaagatt attctctcac catcagcagc ctggagtatg | 300 |

```
aagatatggg aatttatttt tgtctacagt atgatgagtt ccgctcacg ttcggtgctg      360 ggaccaagct ggtactgaaa cgggctgatg ctgcaccaac tgtatccatc ttcccaccat     420
ccagt                                                                  425
```

```
<210> SEQ ID NO 13
<211> LENGTH: 462
<212> TYPE: DNA
<213> ORGANISM: Mus musculus

<400> SEQUENCE: 13
tgggcagact taccattctc attcctgctg ctgattgtcc ctgcatatgt cttgtcccaa      60
gttactctaa aagagtctgg ccctgggata ttgaagccct cacagaccct cagtctgact     120
tgttctttct ctgggttttc actgagcact tctggtatgg gtgtaggctg gattcgtcag     180
ccttcaggga agggtctgga gtggctggca cacatttggt gggatgatga taagtactat     240
aacccatccc tgaagagcca gctcacaatc tccaaggata cctccagaaa ccaggttttc     300
ctcaagatca ccagtgtgga cactgcagat actgccactt actactgtgc tcgaagatcc     360
attagtacgt tggtacctga ggactacttt gactactggg gccaaggcac cactctcaca     420
gtctcctcag ccaaaacgac accccatct gtctatccac tg                        462
```

```
<210> SEQ ID NO 14
<211> LENGTH: 438
<212> TYPE: DNA
<213> ORGANISM: Mus musculus

<400> SEQUENCE: 14
tgaagattgc ctgttaggct gttggtgctg atgttctgga ttcctgcttc cagcagtgat      60
gttttgatga cccaaactcc actctccctg cctgtcagtc ttggagatca agcctccatc     120
tcttgcagat ctagtcagag cattgtacat agtaatggaa acacctattt agaatggtac     180
ctgcagaaac caggccagtc tccaaagctc ctgatctaca agtttccaa ccgattttct      240 ggggtcccag acaggttcag tggcagtgga tcagggacag atttcacact caagatcagc     300
agagtggagg ctgaggatct gggagtttat tattgctttc aaggttcaca tgttccgctc     360
acgttcggtg ctgggaccaa gctggagctg aaacgggctg atgctgcacc aactgtatcc     420
atcttcccac catccagt                                                   438
```

```
<210> SEQ ID NO 15
<211> LENGTH: 442
<212> TYPE: DNA
<213> ORGANISM: Mus musculus

<400> SEQUENCE: 15
tgggactcca ggcttcaatt tagttttcct tgtccttatt ttaaaggtg tccagtgtga       60 tgtgcagctg gtggagtctg ggggaggctt agtgcagcct ggagggtccc ggaaactctc     120
ctgtgcagcc tctggattca ctttcagtag ctttggaatg cactgggttc gtcaggctcc     180
agagaagggg ctggagtggg tcgcatacat tagtagaggc agtagcacca tctactatgc     240
agacacagtg aagggccgat tcaccatctc cagagacaat cccaagaaca ccctgttcct     300
gcaaatgacc agtctaaggt ctgaggacac ggccatgtat tactgtgcaa gagggattac     360
gacggccttg gactactggg gtcaaggaac ctcagtcacc gtctcctcag ccaaaacgac     420 accccatct gtctatccac tg                                              442
```

<210> SEQ ID NO 16
<211> LENGTH: 438
<212> TYPE: DNA
<213> ORGANISM: Mus musculus

<400> SEQUENCE: 16

```
tgaagattgc ctgttaggct gttggtgctg atgttctgga ttcctgcttc cagaagtgat      60
gttttgatga cccaaactcc actctccctg cctgtcagtc ttggagatca agcctccatc     120
tcttgcagat ctagtcagag cattgtacat agtaatggaa acacctattt agaatggtac     180
ctgcagaaac caggccagtc tccaaagctc ctgatctaca aagcttccaa ccgattttct     240
ggggtcccag acaggttcag tggcagtgga tcagggacag atttcacact caagatcagc     300
agagtggagg ctgaggatct gggagtttat tactgctttc aaggttcaca tgttcctccg     360
acgttcggtg gaggcaccaa gctggaaatc aaacgggctg atgctgcacc aactgtatcc     420
atcttcccac catccagt                                                    438
```

<210> SEQ ID NO 17
<211> LENGTH: 457
<212> TYPE: DNA
<213> ORGANISM: Mus musculus

<400> SEQUENCE: 17

```
tgggactcca ggcttcaatt tagttttcct tgtccttatt ttaaaaggtg tccagtgtga      60
tgtgcagctg gtggagtctg ggggaggctt agtgcagcct ggagggtccc ggaaactctc     120
ctgtgcagcc tctggattca ctttcagtag ctttggaatg cactgggttc gtcaggctcc     180
agagaagggg ctggagtggg tcgcatacat tagtagtgtc agtagtacca tctactatgc     240
agacacagtg aagggccgat tcaccatctc cagagacaat cccaagaata ctctgttcct     300
gcaaatgacc agtctaaggt ctgaggacac ggccatgtat tactgtgcaa gatcgggcta     360
cggtagtagt tacgggtatg gtatggacta ctggggtcaa ggaaccttag tcaccgtctc     420
ctcagccaaa acgacacccc catctgtcta tccactg                               457
```

<210> SEQ ID NO 18
<211> LENGTH: 438
<212> TYPE: DNA
<213> ORGANISM: Mus musculus

<400> SEQUENCE: 18

```
tgaagattgc ctgttaggct gttggtgctg atgttctgga ttcctgcttc cagcagtgat      60
gttttgatga cccaaactcc actctccctg cctgtcagtc ttggagatca agcctccatc     120
tcttgcagat ctagtcagag cattgtacat agtaatggaa acacctattt agaatggtac     180
ctgcagaaac caggccagtc tccaaagctc ctgatctaca agtttccaa ccgattttct     240
ggggtcccag acaggttcag tggcagtgga tcagggacag atttcacact caagatcagc     300
agagtggagg ctgaggatct gggagtttat tactgctttc aaggttcaca tgttccgctc     360
acgttcggtg ctgggaccaa gctggagctg aaacgggctg atgctgcacc aactgtatcc     420
atcttcccac catccagt                                                    438
```

<210> SEQ ID NO 19
<211> LENGTH: 457
<212> TYPE: DNA
<213> ORGANISM: Mus musculus

<400> SEQUENCE: 19

```
tgggactcca ggcttcaatt tagttttcct tgtccttatt ttaaaaggtg tccagtgtga      60
tgtgcagctg gtggagtctg ggggaggctt agtgcagcct ggagggtccc ggaaactctc     120
ctgtgcagcc tctggattca cttttcagtag ctttggaatg cactgggttc gtcaggctcc    180
agagaagggg ctggagtggg tcgcatacat tagtagtgtc agtagtacca tctactatgc     240
agacacagtg aagggccgat tcaccatctc cagagacaat cccaagaata ctctgttcct     300
gcaaatgacc agtctaaggt ctgaggacac ggccatgtat tactgtgcaa gatcgggcta     360
cggtagtagt tacgggtatg gtatggacta ctggggtcaa ggaaccttag tcaccgtctc     420
ctcagccaaa acgacacccc catctgtcta tccactg                              457

<210> SEQ ID NO 20
<211> LENGTH: 438
<212> TYPE: DNA
<213> ORGANISM: Mus musculus

<400> SEQUENCE: 20
tgaagattgc ctgttaggct gttggtgctg atgttctgga ttcctgcttc cagcagtgat      60
gttttgatga cccaaactcc actctccctg cctgtcagtc ttggagatca agcctccatc     120
tcttgcagat ctagtcagag cattgtacat agtaatggaa acacctattt agaatggtac     180
ctgcagaaac caggccagtc tccaaagctc ctgatctaca agtttccaa ccgatttttct    240 ggggtcccag acaggttcag tggcagtgga tcagggacag atttcacact caagatcagc     300
agagtggagg ctgaggatct gggagtttat tactgctttc aaggttcaca tgttccgctc     360
acgttcggtg ctgggaccaa gctggagctg aaacgggctg atgctgcacc aactgtatcc     420
atcttcccac catccagt                                                   438

<210> SEQ ID NO 21
<211> LENGTH: 454
<212> TYPE: DNA
<213> ORGANISM: Mus musculus

<400> SEQUENCE: 21
tgggactcca ggcttcaatt tagttttcct tgtccttatt ttaaaaggtg tccagtgtga      60
tgtgcagctg gtggagtctg ggggaggctt agtgcagcct ggagggtccc ggaaactctc     120
ctgtgcagcc tctggattca cttttcagtag ctttggaatg cactgggttc gtcaggctcc    180
agagaagggg ctggagtggg tcgcatacat tagtagtggc agttatacca tctactatgc     240
agacacagtg aagggccgat tcaccatctc cagagacaat cccaagaaca ccctgttcct     300
gcaaatgacc agtctaaggt ctgaggacac ggccatgtat tactgtgcaa gatacggtaa     360
ttacggctat tactatggta tggactactg gggtcaagga acctcagtca ccgtctcctc     420
agccaaaacg acacccccat ctgtctatcc actg                                 454

<210> SEQ ID NO 22
<211> LENGTH: 438
<212> TYPE: DNA
<213> ORGANISM: Mus musculus

<400> SEQUENCE: 22
tgaagattgc ctgttaggct gttggtgctg atgttctgga ttcctgcttc cagcagtgat      60
gttgtgatga cccaaactcc actctccctg cctgtcagtc ttggagatca agcctccatc     120
tcttgcagat ctagtcagag ccttgtacac agtaatggaa acacctattt acattggtac     180
```

-continued

```
ctgcagaagc caggccagtc tccaaagctc ctgatctaca aagtttccaa ccgattttct    240
ggggtcccag acaggttcag tggcagtgga tcagggacag atttcacact caagatcagc    300
agagtggagg ctgaggatct gggagtttat ttctgctctc aaagtacaca tgttcctccg    360
acgttcggtg gaggcaccaa gctggaaatc aaacgggctg atgctgcacc aactgtatcc    420
atcttcccac catccagt                                                  438
```

<210> SEQ ID NO 23
<211> LENGTH: 462
<212> TYPE: DNA
<213> ORGANISM: Mus musculus

<400> SEQUENCE: 23

```
tgggcagact taccattctc attcctgctg ctgattgtcc ctgcatatgt cttgtcccaa     60
gttactctaa aagagtctgg ccctgggata ttgaagccct cacagaccct cagtctgact    120
tgttctttct ctgggttttc actgagcact tctggtatgg gtgtaggctg gattcgtcag    180
ccttcaggga agggtctgga gtggctggca cacatttggt gggatgatga taagtactat    240
aacccatccc tgaagagcca gctcacaatc tccaaggata cctccagaaa ccaggtattc    300
ctcaagatca ccagtgtgga cactgcagat actgccactt actactgtgc tcgaagatcc    360
attactacgg tagtacctga ggactacttt gcctactggg gccaaggcac cactctcaca    420
gtctcctcag ccaaaacaac agcccccatc tgtctatcca ct                       462
```

<210> SEQ ID NO 24
<211> LENGTH: 438
<212> TYPE: DNA
<213> ORGANISM: Mus musculus

<400> SEQUENCE: 24

```
tgaagattgc ctgttaggct gttggtgctg atgttctgga ttcctgcttc cagcagtgat     60
gttttgatga cccaaagtcc actctccctg cctgtcagtc ttggagatca agcctccatc    120
tcttgcagat ctagtcagag cattgtacat agtaatggaa acacctattt agaatggtat    180
ttgcagaaac caggccagtc tccaaagctc ctgatctaca agtttccaa ccgattttct     240 ggggtcccag acaggttcag tggcagtgga tcagggacag atttcacact caagatcagc    300
agagtggagg ctgaggatct gggagtttat tactgctttc aaggttcaca tgttccgctc    360
acgttcggtg ctgggaccaa gctggagctg aaaagggctg atgctgcacc aactgtatcc    420
atcttcccac catccagt                                                  438
```

<210> SEQ ID NO 25
<211> LENGTH: 7
<212> TYPE: PRT
<213> ORGANISM: Artificial Sequence
<220> FEATURE:
<223> OTHER INFORMATION: Heavy chain CDR1

<400> SEQUENCE: 25

Thr Ser Gly Met Gly Val Gly
1               5

<210> SEQ ID NO 26
<211> LENGTH: 7
<212> TYPE: PRT
<213> ORGANISM: Artificial Sequence
<220> FEATURE:
<223> OTHER INFORMATION: Heavy chain CDR1

-continued

```
<400> SEQUENCE: 26

Thr Ser Gly Met Gly Val Ser
1               5

<210> SEQ ID NO 27
<211> LENGTH: 7
<212> TYPE: PRT
<213> ORGANISM: Artificial Sequence
<220> FEATURE:
<223> OTHER INFORMATION: Concensus heavy chain CDR1
<220> FEATURE:
<221> NAME/KEY: MISC_FEATURE
<222> LOCATION: (7)..(7)
<223> OTHER INFORMATION: Xaa denotes an amino acid with no side chain or
      a small side chain

<400> SEQUENCE: 27

Thr Ser Gly Met Gly Val Xaa
1               5

<210> SEQ ID NO 28
<211> LENGTH: 5
<212> TYPE: PRT
<213> ORGANISM: Artificial Sequence
<220> FEATURE:
<223> OTHER INFORMATION: Consensus heavy chain CDR1

<400> SEQUENCE: 28

Ser Phe Gly Met His
1               5

<210> SEQ ID NO 29
<211> LENGTH: 16
<212> TYPE: PRT
<213> ORGANISM: Artificial Sequence
<220> FEATURE:
<223> OTHER INFORMATION: Heavy chain CDR2

<400> SEQUENCE: 29

His Ile Trp Trp Asp Asp Asp Lys Tyr Tyr Asn Pro Ser Leu Lys Ser
1               5                   10                  15

<210> SEQ ID NO 30
<211> LENGTH: 16
<212> TYPE: PRT
<213> ORGANISM: Artificial Sequence
<220> FEATURE:
<223> OTHER INFORMATION: Heavy chain CDR2

<400> SEQUENCE: 30

His Ile Trp Trp Asp Asp Asp Lys Ser Tyr Asn Pro Ser Leu Lys Ser
1               5                   10                  15

<210> SEQ ID NO 31
<211> LENGTH: 16
<212> TYPE: PRT
<213> ORGANISM: Artificial Sequence
<220> FEATURE:
<223> OTHER INFORMATION: Heavy chain CDR2

<400> SEQUENCE: 31

His Ile Tyr Trp Asp Asp Asp Lys Arg Tyr Asn Pro Ser Leu Lys Ser
1               5                   10                  15

<210> SEQ ID NO 32
<211> LENGTH: 16
<212> TYPE: PRT
```

```
<213> ORGANISM: Artificial Sequence
<220> FEATURE:
<223> OTHER INFORMATION: Consensus heavy chain CDR2
<220> FEATURE:
<221> NAME/KEY: MISC_FEATURE
<222> LOCATION: (3)..(3)
<223> OTHER INFORMATION: Xaa denotes an amino acid with an aromatic side
      chain group
<220> FEATURE:
<221> NAME/KEY: MISC_FEATURE
<222> LOCATION: (9)..(9)
<223> OTHER INFORMATION: Xaa denotes Ser, Arg or Tyr

<400> SEQUENCE: 32

His Ile Xaa Trp Asp Asp Asp Lys Xaa Tyr Asn Pro Ser Leu Lys Ser
1               5                   10                  15

<210> SEQ ID NO 33
<211> LENGTH: 17
<212> TYPE: PRT
<213> ORGANISM: Artificial Sequence
<220> FEATURE:
<223> OTHER INFORMATION: Heavy chain CDR2

<400> SEQUENCE: 33

Tyr Ile Arg Ser Gly Ser Ser Thr Ile Tyr Tyr Ala Asp Thr Val Lys
1               5                   10                  15

Gly

<210> SEQ ID NO 34
<211> LENGTH: 17
<212> TYPE: PRT
<213> ORGANISM: Artificial Sequence
<220> FEATURE:
<223> OTHER INFORMATION: Heavy chain CDR2

<400> SEQUENCE: 34

Tyr Ile Ser Ser Gly Ser Tyr Thr Ile Tyr Tyr Ala Asp Thr Val Lys
1               5                   10                  15

Gly

<210> SEQ ID NO 35
<211> LENGTH: 17
<212> TYPE: PRT
<213> ORGANISM: Artificial Sequence
<220> FEATURE:
<223> OTHER INFORMATION: Heavy chain CDR2

<400> SEQUENCE: 35

Tyr Ile Ser Ser Val Ser Ser Thr Ile Tyr Tyr Ala Asp Thr Val Lys
1               5                   10                  15

Gly

<210> SEQ ID NO 36
<211> LENGTH: 17
<212> TYPE: PRT
<213> ORGANISM: Artificial Sequence
<220> FEATURE:
<223> OTHER INFORMATION: Heavy chain CDR2

<400> SEQUENCE: 36

Tyr Ile Ser Arg Gly Ser Ser Thr Ile Tyr Tyr Ala Asp Thr Val Lys
1               5                   10                  15

Gly
```

```
<210> SEQ ID NO 37
<211> LENGTH: 17
<212> TYPE: PRT
<213> ORGANISM: Artificial Sequence
<220> FEATURE:
<223> OTHER INFORMATION: Consensus heavy chain CDR2
<220> FEATURE:
<221> NAME/KEY: MISC_FEATURE
<222> LOCATION: (3)..(4)
<223> OTHER INFORMATION: Xaa denotes amino acids with a polar side chain
      group
<220> FEATURE:
<221> NAME/KEY: MISC_FEATURE
<222> LOCATION: (5)..(5)
<223> OTHER INFORMATION: Xaa denotes Gly or Val
<220> FEATURE:
<221> NAME/KEY: MISC_FEATURE
<222> LOCATION: (7)..(7)
<223> OTHER INFORMATION: Xaa denotes an amino acid with a polar and
      uncharged side group

<400> SEQUENCE: 37

Tyr Ile Xaa Xaa Xaa Ser Xaa Thr Ile Tyr Tyr Ala Asp Thr Val Lys
1               5                   10                  15
Gly

<210> SEQ ID NO 38
<211> LENGTH: 14
<212> TYPE: PRT
<213> ORGANISM: Artificial Sequence
<220> FEATURE:
<223> OTHER INFORMATION: Heavy chain CDR3

<400> SEQUENCE: 38

Arg Ser Ile Ser Thr Leu Val Pro Glu Asp Tyr Phe Asp Tyr
1               5                   10

<210> SEQ ID NO 39
<211> LENGTH: 14
<212> TYPE: PRT
<213> ORGANISM: Artificial Sequence
<220> FEATURE:
<223> OTHER INFORMATION: Heavy chain CDR3

<400> SEQUENCE: 39

Arg Ser Ile Thr Thr Val Val Pro Glu Asp Tyr Phe Ala Tyr
1               5                   10

<210> SEQ ID NO 40
<211> LENGTH: 14
<212> TYPE: PRT
<213> ORGANISM: Artificial Sequence
<220> FEATURE:
<223> OTHER INFORMATION: Heavy chain CDR3

<400> SEQUENCE: 40

Arg Ser Ile Ser Thr Val Ile Pro Glu Asp Tyr Phe Asp Tyr
1               5                   10

<210> SEQ ID NO 41
<211> LENGTH: 14
<212> TYPE: PRT
<213> ORGANISM: Artificial Sequence
<220> FEATURE:
<223> OTHER INFORMATION: Heavy chain CDR3

<400> SEQUENCE: 41

Arg Ser Ile Asn Ser Val Val Pro Glu Asp Tyr Phe Asp Tyr
1               5                   10
```

```
<210> SEQ ID NO 42
<211> LENGTH: 14
<212> TYPE: PRT
<213> ORGANISM: Artificial Sequence
<220> FEATURE:
<223> OTHER INFORMATION: Consensus heavy chain CDR3
<220> FEATURE:
<221> NAME/KEY: MISC_FEATURE
<222> LOCATION: (4)..(4)
<223> OTHER INFORMATION: Xaa denotes an amino acid with a polar and
      uncharged side group
<220> FEATURE:
<221> NAME/KEY: MISC_FEATURE
<222> LOCATION: (5)..(5)
<223> OTHER INFORMATION: Xaa denotes an amino acid with hyroxyl side
      chain group
<220> FEATURE:
<221> NAME/KEY: MISC_FEATURE
<222> LOCATION: (6)..(7)
<223> OTHER INFORMATION: Xaa denotes an amino acid with an aliphatic
      side chain group
<220> FEATURE:
<221> NAME/KEY: MISC_FEATURE
<222> LOCATION: (13)..(13)
<223> OTHER INFORMATION: Xaa denotes Asp or Ala

<400> SEQUENCE: 42

Arg Ser Ile Xaa Xaa Xaa Xaa Pro Glu Asp Tyr Phe Xaa Tyr
1               5                   10

<210> SEQ ID NO 43
<211> LENGTH: 13
<212> TYPE: PRT
<213> ORGANISM: Artificial Sequence
<220> FEATURE:
<223> OTHER INFORMATION: Heavy chain CDR3

<400> SEQUENCE: 43

Arg Gln Leu Gly Leu Arg Ser Ile Asp Ala Met Asp Tyr
1               5                   10

<210> SEQ ID NO 44
<211> LENGTH: 11
<212> TYPE: PRT
<213> ORGANISM: Artificial Sequence
<220> FEATURE:
<223> OTHER INFORMATION: Heavy chain CDR3

<400> SEQUENCE: 44

Tyr Asp Gly Tyr Pro Tyr Trp Tyr Phe Asp Val
1               5                   10

<210> SEQ ID NO 45
<211> LENGTH: 12
<212> TYPE: PRT
<213> ORGANISM: Artificial Sequence
<220> FEATURE:
<223> OTHER INFORMATION: Heavy chain CDR3

<400> SEQUENCE: 45

Gly Gly Asn Tyr Tyr Gly Ser Ser Arg Phe Ala Tyr
1               5                   10

<210> SEQ ID NO 46
<211> LENGTH: 12
<212> TYPE: PRT
<213> ORGANISM: Artificial Sequence
<220> FEATURE:
<223> OTHER INFORMATION: Heavy chain CDR3
```

```
<400> SEQUENCE: 46

Tyr Gly Asn Tyr Gly Tyr Tyr Tyr Gly Met Asp Tyr
1               5                   10

<210> SEQ ID NO 47
<211> LENGTH: 13
<212> TYPE: PRT
<213> ORGANISM: Artificial Sequence
<220> FEATURE:
<223> OTHER INFORMATION: Heavy chain CDR3

<400> SEQUENCE: 47

Ser Gly Tyr Gly Ser Ser Tyr Gly Tyr Gly Met Asp Tyr
1               5                   10

<210> SEQ ID NO 48
<211> LENGTH: 8
<212> TYPE: PRT
<213> ORGANISM: Artificial Sequence
<220> FEATURE:
<223> OTHER INFORMATION: Heavy chain CDR3

<400> SEQUENCE: 48

Gly Ile Thr Thr Ala Leu Asp Tyr
1               5

<210> SEQ ID NO 49
<211> LENGTH: 16
<212> TYPE: PRT
<213> ORGANISM: Artificial Sequence
<220> FEATURE:
<223> OTHER INFORMATION: Light chain CDR1

<400> SEQUENCE: 49

Arg Ser Ser Gln Ser Ile Val His Ser Asn Gly Asn Thr Tyr Leu Glu
1               5                   10                  15

<210> SEQ ID NO 50
<211> LENGTH: 16
<212> TYPE: PRT
<213> ORGANISM: Artificial Sequence
<220> FEATURE:
<223> OTHER INFORMATION: Light chain CDR1

<400> SEQUENCE: 50

Arg Ser Ser Gln Ser Ile Leu His Ser Asn Gly Asn Thr Tyr Leu Glu
1               5                   10                  15

<210> SEQ ID NO 51
<211> LENGTH: 16
<212> TYPE: PRT
<213> ORGANISM: Artificial Sequence
<220> FEATURE:
<223> OTHER INFORMATION: Light chain CDR1

<400> SEQUENCE: 51

Arg Ser Ser Gln Ser Leu Val His Ser Asn Gly Asn Thr Tyr Leu His
1               5                   10                  15

<210> SEQ ID NO 52
<211> LENGTH: 16
<212> TYPE: PRT
<213> ORGANISM: Artificial Sequence
<220> FEATURE:
<223> OTHER INFORMATION: Consensus light chain CDR1
<220> FEATURE:
```

```
<221> NAME/KEY: MISC_FEATURE
<222> LOCATION: (6)..(7)
<223> OTHER INFORMATION: Xaa denotes an amino acid with an aliphatic
      side chain group
<220> FEATURE:
<221> NAME/KEY: MISC_FEATURE
<222> LOCATION: (16)..(16)
<223> OTHER INFORMATION: Xaa denotes an amino acid with a charged side
      chain group

<400> SEQUENCE: 52

Arg Ser Ser Gln Ser Xaa Xaa His Ser Asn Gly Asn Thr Tyr Leu Xaa
1               5                   10                  15

<210> SEQ ID NO 53
<211> LENGTH: 11
<212> TYPE: PRT
<213> ORGANISM: Artificial Sequence
<220> FEATURE:
<223> OTHER INFORMATION: Light chain CDR1

<400> SEQUENCE: 53

Lys Ala Ser Gln Asp Ile Asn Ser Tyr Leu Ser
1               5                   10

<210> SEQ ID NO 54
<211> LENGTH: 7
<212> TYPE: PRT
<213> ORGANISM: Artificial Sequence
<220> FEATURE:
<223> OTHER INFORMATION: Light chain CDR2

<400> SEQUENCE: 54

Lys Val Ser Asn Arg Phe Ser
1               5

<210> SEQ ID NO 55
<211> LENGTH: 7
<212> TYPE: PRT
<213> ORGANISM: Artificial Sequence
<220> FEATURE:
<223> OTHER INFORMATION: Light chain CDR2

<400> SEQUENCE: 55

Lys Val Ser Asn Arg Phe Phe
1               5

<210> SEQ ID NO 56
<211> LENGTH: 7
<212> TYPE: PRT
<213> ORGANISM: Artificial Sequence
<220> FEATURE:
<223> OTHER INFORMATION: Light chain CDR2

<400> SEQUENCE: 56

Lys Ala Ser Asn Arg Phe Ser
1               5

<210> SEQ ID NO 57
<211> LENGTH: 7
<212> TYPE: PRT
<213> ORGANISM: Artificial Sequence
<220> FEATURE:
<223> OTHER INFORMATION: Consensus light chain CDR2
<220> FEATURE:
<221> NAME/KEY: MISC_FEATURE
<222> LOCATION: (2)..(2)
<223> OTHER INFORMATION: Xaa denotes an amino acid with an aliphatic
      side chain group
```

```
<220> FEATURE:
<221> NAME/KEY: MISC_FEATURE
<222> LOCATION: (7)..(7)
<223> OTHER INFORMATION: Xaa denotes Ser or Phe

<400> SEQUENCE: 57

Lys Xaa Ser Asn Arg Phe Xaa
1               5

<210> SEQ ID NO 58
<211> LENGTH: 7
<212> TYPE: PRT
<213> ORGANISM: Artificial Sequence
<220> FEATURE:
<223> OTHER INFORMATION: Light chain CDR2

<400> SEQUENCE: 58

Arg Ala Asn Arg Phe Val Asp
1               5

<210> SEQ ID NO 59
<211> LENGTH: 9
<212> TYPE: PRT
<213> ORGANISM: Artificial Sequence
<220> FEATURE:
<223> OTHER INFORMATION: Light chain CDR3

<400> SEQUENCE: 59

Phe Gln Gly Ser His Val Pro Leu Thr
1               5

<210> SEQ ID NO 60
<211> LENGTH: 9
<212> TYPE: PRT
<213> ORGANISM: Artificial Sequence
<220> FEATURE:
<223> OTHER INFORMATION: Light chain CDR3

<400> SEQUENCE: 60

Phe Gln Gly Ser Leu Val Pro Leu Thr
1               5

<210> SEQ ID NO 61
<211> LENGTH: 9
<212> TYPE: PRT
<213> ORGANISM: Artificial Sequence
<220> FEATURE:
<223> OTHER INFORMATION: Light chain CDR3

<400> SEQUENCE: 61

Ser Gln Thr Thr Tyr Val Pro Leu Thr
1               5

<210> SEQ ID NO 62
<211> LENGTH: 9
<212> TYPE: PRT
<213> ORGANISM: Artificial Sequence
<220> FEATURE:
<223> OTHER INFORMATION: Light chain CDR3

<400> SEQUENCE: 62

Phe Gln Ser Thr His Val Pro Leu Thr
1               5

<210> SEQ ID NO 63
<211> LENGTH: 9
<212> TYPE: PRT
```

```
<213> ORGANISM: Artificial Sequence
<220> FEATURE:
<223> OTHER INFORMATION: Light chain CDR3

<400> SEQUENCE: 63

Ser Gln Ser Thr His Val Pro Pro Thr
1               5

<210> SEQ ID NO 64
<211> LENGTH: 9
<212> TYPE: PRT
<213> ORGANISM: Artificial Sequence
<220> FEATURE:
<223> OTHER INFORMATION: Light chain CDR3

<400> SEQUENCE: 64

Phe Gln Gly Ser His Val Pro Pro Thr
1               5

<210> SEQ ID NO 65
<211> LENGTH: 9
<212> TYPE: PRT
<213> ORGANISM: Artificial Sequence
<220> FEATURE:
<223> OTHER INFORMATION: Consensus light chain CDR3
<220> FEATURE:
<221> NAME/KEY: MISC_FEATURE
<222> LOCATION: (1)..(1)
<223> OTHER INFORMATION: Xaa denotes Ser or Phe
<220> FEATURE:
<221> NAME/KEY: MISC_FEATURE
<222> LOCATION: (3)..(3)
<223> OTHER INFORMATION: Xaa denotes an amino acid with no side chain or
      hyroxyl side chain group
<220> FEATURE:
<221> NAME/KEY: MISC_FEATURE
<222> LOCATION: (4)..(4)
<223> OTHER INFORMATION: Xaa denotes an amino acid with a hyroxyl side
      chain group
<220> FEATURE:
<221> NAME/KEY: MISC_FEATURE
<222> LOCATION: (5)..(5)
<223> OTHER INFORMATION: Xaa denotes His, Tyr or Leu
<220> FEATURE:
<221> NAME/KEY: MISC_FEATURE
<222> LOCATION: (8)..(8)
<223> OTHER INFORMATION: Xaa denotes an amino acid with an aliphatic
      side chain group

<400> SEQUENCE: 65

Xaa Gln Xaa Xaa Xaa Val Pro Xaa Thr
1               5

<210> SEQ ID NO 66
<211> LENGTH: 9
<212> TYPE: PRT
<213> ORGANISM: Artificial Sequence
<220> FEATURE:
<223> OTHER INFORMATION: Light chain CDR3

<400> SEQUENCE: 66

Leu Gln Tyr Asp Glu Phe Pro Leu Thr
1               5

<210> SEQ ID NO 67
<211> LENGTH: 123
<212> TYPE: PRT
<213> ORGANISM: Mus musculus

<400> SEQUENCE: 67
```

```
Gln Val Thr Leu Lys Glu Ser Gly Pro Gly Ile Leu Lys Pro Ser Gln
  1               5                  10                  15

Thr Leu Ser Leu Thr Cys Ser Leu Ser Gly Phe Ser Leu Ser Thr Ser
             20                  25                  30

Gly Met Gly Val Gly Trp Phe Arg Gln Pro Ser Gly Lys Gly Leu Glu
         35                  40                  45

Trp Leu Ala His Ile Trp Trp Asp Asp Lys Ser Tyr Asn Pro Ser
 50                  55                  60

Leu Lys Ser Arg Leu Thr Ile Ser Lys Tyr Thr Ser Arg Asn Gln Val
 65                  70                  75                  80

Phe Leu Thr Ile Thr Ser Val Asp Thr Ala Asp Ala Thr Tyr Tyr
                 85                  90                  95

Cys Ala Arg Arg Gln Leu Gly Leu Arg Ser Ile Asp Ala Met Asp Tyr
            100                 105                 110

Trp Gly Gln Gly Thr Ser Val Thr Val Ser Ser
            115                 120

<210> SEQ ID NO 68
<211> LENGTH: 130
<212> TYPE: PRT
<213> ORGANISM: Homo sapiens

<400> SEQUENCE: 68

Gln Val Thr Leu Lys Glu Ser Gly Pro Ala Leu Val Lys Pro Thr Gln
  1               5                  10                  15

Thr Leu Thr Leu Thr Cys Thr Phe Ser Gly Phe Ser Leu Ser Thr Ser
             20                  25                  30

Gly Met Cys Val Ser Trp Ile Arg Gln Pro Pro Gly Lys Ala Leu Glu
         35                  40                  45

Trp Leu Ala Leu Ile Asp Trp Asp Asp Lys Tyr Tyr Ser Thr Ser
 50                  55                  60

Leu Lys Thr Arg Leu Thr Ile Ser Lys Asp Thr Ser Lys Asn Gln Val
 65                  70                  75                  80

Val Leu Thr Met Thr Asn Met Asp Pro Val Asp Thr Ala Thr Tyr Tyr
                 85                  90                  95

Cys Ala Arg Ile Phe Gly Asp Tyr Asp Phe Trp Ser Gly Tyr Tyr Arg
            100                 105                 110

Ser Tyr Tyr Gly Met Asp Val Trp Gly Gln Gly Thr Thr Val Thr Val
            115                 120                 125

Ser Ser
    130

<210> SEQ ID NO 69
<211> LENGTH: 100
<212> TYPE: PRT
<213> ORGANISM: Homo sapiens

<400> SEQUENCE: 69

Gln Val Thr Leu Lys Glu Ser Gly Pro Ala Leu Val Lys Pro Thr Gln
  1               5                  10                  15

Thr Leu Thr Leu Thr Cys Thr Phe Ser Gly Phe Ser Leu Ser Thr Ser
             20                  25                  30

Gly Met Arg Val Ser Trp Ile Arg Gln Pro Pro Gly Lys Ala Leu Glu
         35                  40                  45

Trp Leu Ala Arg Ile Asp Trp Asp Asp Lys Phe Tyr Ser Thr Ser
 50                  55                  60
```

```
Leu Lys Thr Arg Leu Thr Ile Ser Lys Asp Thr Ser Lys Asn Gln Val
 65                  70                  75                  80

Val Leu Thr Met Thr Asn Met Asp Pro Val Asp Thr Ala Thr Tyr Tyr
                 85                  90                  95

Cys Ala Arg Ile
            100

<210> SEQ ID NO 70
<211> LENGTH: 123
<212> TYPE: PRT
<213> ORGANISM: Artificial Sequence
<220> FEATURE:
<223> OTHER INFORMATION: Humanized heavy chain variable region

<400> SEQUENCE: 70

Gln Val Thr Leu Lys Glu Ser Gly Pro Ala Leu Val Lys Pro Thr Gln
  1               5                  10                  15

Thr Leu Thr Leu Thr Cys Thr Phe Ser Gly Phe Ser Leu Ser Thr Ser
                 20                  25                  30

Gly Met Gly Val Gly Trp Ile Arg Gln Pro Pro Gly Lys Ala Leu Glu
             35                  40                  45

Trp Leu Ala His Ile Trp Trp Asp Asp Lys Ser Tyr Asn Pro Ser
 50                  55                  60

Leu Lys Ser Arg Leu Thr Ile Ser Lys Asp Thr Ser Lys Asn Gln Val
 65                  70                  75                  80

Val Leu Thr Met Thr Asn Met Asp Pro Val Asp Thr Ala Thr Tyr Tyr
                 85                  90                  95

Cys Ala Arg Arg Gln Leu Gly Leu Arg Ser Ile Asp Ala Met Asp Tyr
            100                 105                 110

Trp Gly Gln Gly Thr Thr Val Thr Val Ser Ser
            115                 120

<210> SEQ ID NO 71
<211> LENGTH: 123
<212> TYPE: PRT
<213> ORGANISM: Artificial Sequence
<220> FEATURE:
<223> OTHER INFORMATION: Humanized heavy chain variable region

<400> SEQUENCE: 71

Gln Val Thr Leu Lys Glu Ser Gly Pro Ala Leu Val Lys Pro Thr Gln
  1               5                  10                  15

Thr Leu Thr Leu Thr Cys Thr Leu Ser Gly Phe Ser Leu Ser Thr Ser
                 20                  25                  30

Gly Met Gly Val Gly Trp Ile Arg Gln Pro Pro Gly Lys Ala Leu Glu
             35                  40                  45

Trp Leu Ala His Ile Trp Trp Asp Asp Lys Ser Tyr Asn Pro Ser
 50                  55                  60

Leu Lys Ser Arg Leu Thr Ile Ser Lys Asp Thr Ser Lys Asn Gln Val
 65                  70                  75                  80

Val Leu Thr Met Thr Asn Met Asp Pro Val Asp Thr Ala Thr Tyr Tyr
                 85                  90                  95

Cys Ala Arg Arg Gln Leu Gly Leu Arg Ser Ile Asp Ala Met Asp Tyr
            100                 105                 110

Trp Gly Gln Gly Thr Thr Val Thr Val Ser Ser
            115                 120

<210> SEQ ID NO 72
```

<211> LENGTH: 115
<212> TYPE: PRT
<213> ORGANISM: Mus musculus

<400> SEQUENCE: 72

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Leu His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser Leu Val Pro Leu Thr Phe Gly Ala Gly Thr Lys Leu Glu Leu Lys
            100                 105                 110

Arg Ala Asp
        115

<210> SEQ ID NO 73
<211> LENGTH: 115
<212> TYPE: PRT
<213> ORGANISM: Homo sapiens

<400> SEQUENCE: 73

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Tyr Thr Phe Gly Gln Gly Thr Lys Leu Glu Ile Lys
            100                 105                 110

Arg Thr Val
        115

<210> SEQ ID NO 74
<211> LENGTH: 100
<212> TYPE: PRT
<213> ORGANISM: Homo sapiens

<400> SEQUENCE: 74

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu His Ser
            20                  25                  30

Asp Gly Lys Thr Tyr Leu Tyr Trp Tyr Leu Gln Lys Pro Gly Gln Ser
        35                  40                  45

```
Pro Gln Leu Leu Ile Tyr Glu Val Ser Ser Arg Phe Ser Gly Val Pro
    50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Gly
                 85                  90                  95

Ile His Leu Pro
            100

<210> SEQ ID NO 75
<211> LENGTH: 115
<212> TYPE: PRT
<213> ORGANISM: Artificial Sequence
<220> FEATURE:
<223> OTHER INFORMATION: Humanized light chain variable region

<400> SEQUENCE: 75

Asp Val Val Met Thr Gln Ser Pro Leu Ser Leu Pro Val Thr Pro Gly
 1               5                  10                  15

Glu Pro Ala Ser Ile Ser Cys Arg Ser Ser Gln Ser Ile Leu His Ser
                 20                  25                  30

Asn Gly Asn Thr Tyr Leu Glu Trp Tyr Leu Gln Lys Pro Gly Gln Ser
             35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Phe Gln Gly
                 85                  90                  95

Ser Leu Val Pro Leu Thr Phe Gly Gln Gly Thr Lys Leu Glu Ile Lys
            100                 105                 110

Arg Thr Val
        115

<210> SEQ ID NO 76
<211> LENGTH: 123
<212> TYPE: PRT
<213> ORGANISM: Mus musculus

<400> SEQUENCE: 76

Gln Val Thr Leu Lys Glu Ser Gly Pro Gly Ile Val Gln Pro Ser Gln
 1               5                  10                  15

Thr Leu Ser Leu Thr Cys Ser Phe Ser Gly Phe Ser Leu Ser Thr Ser
                 20                  25                  30

Gly Met Gly Val Ser Trp Ile Arg Gln Pro Ser Gly Lys Gly Leu Glu
             35                  40                  45

Trp Leu Ala His Ile Tyr Trp Asp Asp Asp Lys Gln Tyr Asn Pro Ser
    50                  55                  60

Leu Lys Ser Arg Leu Thr Ile Ser Lys Asp Thr Ser Arg Arg Lys Val
 65                  70                  75                  80

Phe Leu Glu Ile Thr Ser Val Asp Thr Ala Asp Thr Ala Thr Tyr Tyr
                 85                  90                  95

Cys Val Arg Arg Ala Ser Ser Ser Arg Tyr Asp Asp Gln Phe Asp Tyr
            100                 105                 110

Trp Gly Gln Gly Thr Pro Leu Thr Val Ser Ser
        115                 120
```

```
<210> SEQ ID NO 77
<211> LENGTH: 123
<212> TYPE: PRT
<213> ORGANISM: Homo sapiens

<400> SEQUENCE: 77

Gln Val Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Ser Thr Ser
                20                  25                  30

Gly Val Gly Val Gly Trp Ile Arg Gln Pro Pro Gly Lys Ala Leu Glu
            35                  40                  45

Trp Leu Ala Leu Ile Tyr Trp Asn Asp Asp Lys Arg Tyr Ser Pro Ser
50                  55                  60

Leu Lys Ser Arg Leu Thr Ile Thr Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Gln Ser Ile Met Ala Thr Ser Thr Ser Asp Tyr Phe Asp Tyr
            100                 105                 110

Trp Gly Gln Gly Thr Leu Val Pro Val Ser Ser
        115                 120

<210> SEQ ID NO 78
<211> LENGTH: 100
<212> TYPE: PRT
<213> ORGANISM: Homo sapiens

<400> SEQUENCE: 78

Gln Val Thr Leu Lys Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ser
                20                  25                  30

Gly Met Arg Val Ser Trp Ile Arg Gln Pro Pro Gly Lys Ala Leu Glu
            35                  40                  45

Trp Leu Ala Arg Ile Asp Trp Asp Asp Lys Phe Tyr Ser Thr Ser
50                  55                  60

Leu Lys Thr Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Ile
            100

<210> SEQ ID NO 79
<211> LENGTH: 123
<212> TYPE: PRT
<213> ORGANISM: Artificial Sequence
<220> FEATURE:
<223> OTHER INFORMATION: Humanized heavy chain variable region

<400> SEQUENCE: 79

Gln Val Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Ser Thr Ser
                20                  25                  30

Gly Met Gly Val Ser Trp Ile Arg Gln Pro Pro Gly Lys Ala Leu Glu
            35                  40                  45
```

Trp Leu Ala His Ile Tyr Trp Asp Asp Lys Gln Tyr Asn Pro Ser
    50                  55                  60

Leu Lys Ser Arg Leu Thr Ile Thr Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Arg Ala Ser Ser Ser Arg Tyr Asp Asp Gln Phe Asp Tyr
            100                 105                 110

Trp Gly Gln Gly Thr Leu Val Pro Val Ser Ser
            115                 120

<210> SEQ ID NO 80
<211> LENGTH: 115
<212> TYPE: PRT
<213> ORGANISM: Mus musculus

<400> SEQUENCE: 80

Asp Val Leu Met Ile Gln Thr Pro Leu Ser Leu Pro Val Ser Leu Gly
1               5                   10                  15

Asp Pro Ala Ser Ile Ser Cys Arg Ala Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Arg Val Ser Asn Arg Phe Ser Gly Val Pro
    50                  55                  60

Asp Arg Phe Ser Gly Ser Gly Ser Gly Thr Asp Phe Thr Leu Arg Ile
65                  70                  75                  80

Ser Arg Val Glu Ala Glu Asp Leu Gly Val Tyr Phe Cys Phe Gln Val
                85                  90                  95

Thr His Val Pro Leu Thr Phe Gly Ala Gly Thr Lys Leu Glu Leu Lys
            100                 105                 110

Arg Ala Asp
        115

<210> SEQ ID NO 81
<211> LENGTH: 115
<212> TYPE: PRT
<213> ORGANISM: Homo sapiens

<400> SEQUENCE: 81

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Tyr Thr Phe Gly Gln Gly Thr Lys Leu Glu Ile Lys
            100                 105                 110

Arg Thr Val
        115

<210> SEQ ID NO 82
<211> LENGTH: 100
<212> TYPE: PRT
<213> ORGANISM: Homo sapiens

<400> SEQUENCE: 82

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu His Ser
            20                  25                  30

Asp Gly Lys Thr Tyr Leu Tyr Trp Tyr Leu Gln Lys Pro Gly Gln Ser
        35                  40                  45

Pro Gln Leu Leu Ile Tyr Glu Val Ser Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Ile His Leu Pro
            100

<210> SEQ ID NO 83
<211> LENGTH: 115
<212> TYPE: PRT
<213> ORGANISM: Artificial Sequence
<220> FEATURE:
<223> OTHER INFORMATION: Humanized light chain variable region

<400> SEQUENCE: 83

Asp Val Val Met Thr Gln Ser Pro Leu Ser Leu Pro Val Thr Pro Gly
1               5                   10                  15

Glu Pro Ala Ser Ile Ser Cys Arg Ala Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Gln Leu Leu Ile Tyr Arg Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Val
                85                  90                  95

Thr His Val Pro Leu Thr Phe Gly Gln Gly Thr Lys Leu Glu Ile Lys
            100                 105                 110

Arg Thr Val
        115

<210> SEQ ID NO 84
<211> LENGTH: 124
<212> TYPE: PRT
<213> ORGANISM: Mus musculus

<400> SEQUENCE: 84

Gln Val Thr Leu Lys Glu Ser Gly Pro Gly Ile Leu Lys Pro Ser Gln
1               5                   10                  15

Thr Leu Ser Leu Thr Cys Ser Phe Ser Gly Phe Ser Leu Ser Thr Ser
            20                  25                  30

Gly Met Gly Val Gly Trp Ile Arg Gln Pro Ser Gly Lys Gly Leu Glu
        35                  40                  45

```
Trp Leu Ala His Ile Trp Asp Asp Asp Lys Tyr Tyr Asn Pro Ser
        50                  55                  60
Leu Lys Ser Gln Leu Thr Ile Ser Lys Asp Thr Ser Arg Asn Gln Val
 65                  70                  75                  80
Phe Leu Lys Ile Thr Ser Val Asp Thr Ala Asp Thr Ala Thr Tyr Tyr
                 85                  90                  95
Cys Ala Arg Arg Ser Ile Asn Ser Val Val Pro Glu Tyr Phe Asp
            100                 105                 110
Tyr Trp Gly Gln Gly Thr Thr Leu Thr Val Ser Leu
            115                 120
```

<210> SEQ ID NO 85
<211> LENGTH: 130
<212> TYPE: PRT
<213> ORGANISM: Homo sapiens

<400> SEQUENCE: 85

```
Gln Val Thr Leu Lys Glu Ser Gly Pro Ala Leu Val Lys Pro Thr Gln
 1                5                  10                  15
Thr Leu Thr Leu Thr Cys Thr Phe Ser Gly Phe Ser Leu Ser Thr Ser
                 20                  25                  30
Gly Met Cys Val Ser Trp Ile Arg Gln Pro Pro Gly Lys Ala Leu Glu
             35                  40                  45
Trp Leu Ala Leu Ile Asp Trp Asp Asp Asp Lys Tyr Tyr Ser Thr Ser
        50                  55                  60
Leu Lys Thr Arg Leu Thr Ile Ser Lys Asp Thr Ser Lys Asn Gln Val
 65                  70                  75                  80
Val Leu Thr Met Thr Asn Met Asp Pro Val Asp Thr Ala Thr Tyr Tyr
                 85                  90                  95
Cys Ala Arg Ile Phe Gly Asp Tyr Asp Phe Trp Ser Gly Tyr Tyr Arg
            100                 105                 110
Ser Tyr Tyr Gly Met Asp Val Trp Gly Gln Gly Thr Thr Val Thr Val
            115                 120                 125
Ser Ser
    130
```

<210> SEQ ID NO 86
<211> LENGTH: 100
<212> TYPE: PRT
<213> ORGANISM: Homo sapiens

<400> SEQUENCE: 86

```
Gln Val Thr Leu Lys Glu Ser Gly Pro Ala Leu Val Lys Pro Thr Gln
 1                5                  10                  15
Thr Leu Thr Leu Thr Cys Thr Phe Ser Gly Phe Ser Leu Ser Thr Ser
                 20                  25                  30
Gly Met Arg Val Ser Trp Ile Arg Gln Pro Pro Gly Lys Ala Leu Glu
             35                  40                  45
Trp Leu Ala Arg Ile Asp Trp Asp Asp Asp Lys Phe Tyr Ser Thr Ser
        50                  55                  60
Leu Lys Thr Arg Leu Thr Ile Ser Lys Asp Thr Ser Lys Asn Gln Val
 65                  70                  75                  80
Val Leu Thr Met Thr Asn Met Asp Pro Val Asp Thr Ala Thr Tyr Tyr
                 85                  90                  95
Cys Ala Arg Ile
            100
```

```
<210> SEQ ID NO 87
<211> LENGTH: 124
<212> TYPE: PRT
<213> ORGANISM: Artificial Sequence
<220> FEATURE:
<223> OTHER INFORMATION: Humanized heavy chain variable region

<400> SEQUENCE: 87

Gln Val Thr Leu Lys Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Met Gly Val Gly Trp Ile Arg Gln Pro Pro Gly Lys Ala Leu Glu
        35                  40                  45

Trp Leu Ala His Ile Trp Trp Asp Asp Lys Tyr Tyr Asn Pro Ser
    50                  55                  60

Leu Lys Ser Gln Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Arg Ser Ile Asn Ser Val Val Pro Glu Asp Tyr Phe Asp
            100                 105                 110

Tyr Trp Gly Gln Gly Thr Thr Val Thr Val Ser Ser
            115                 120

<210> SEQ ID NO 88
<211> LENGTH: 115
<212> TYPE: PRT
<213> ORGANISM: Mus musculus

<400> SEQUENCE: 88

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Leu Thr Phe Gly Ala Gly Thr Lys Leu Glu Leu Lys
            100                 105                 110

Arg Ala Asp
        115

<210> SEQ ID NO 89
<211> LENGTH: 115
<212> TYPE: PRT
<213> ORGANISM: Homo sapiens

<400> SEQUENCE: 89

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
```

```
                    20                  25                  30
Asn Gly Tyr Asn Tyr Leu Asp Trp Tyr Leu Gln Lys Pro Gly Gln Ser
                35                  40                  45
Pro Gln Leu Leu Ile Tyr Leu Gly Ser Asn Arg Ala Ser Gly Val Pro
            50                  55                  60
Asp Arg Phe Ser Gly Ser Gly Ser Gly Thr Asp Phe Thr Leu Lys Ile
65                  70                  75                  80
Ser Arg Val Glu Ala Glu Asp Val Gly Val Tyr Tyr Cys Met Gln Ala
                85                  90                  95
Leu Gln Thr Pro Tyr Thr Phe Gly Gln Gly Thr Lys Leu Glu Ile Lys
            100                 105                 110
Arg Thr Val
        115

<210> SEQ ID NO 90
<211> LENGTH: 100
<212> TYPE: PRT
<213> ORGANISM: Homo sapiens

<400> SEQUENCE: 90

Asp Ile Val Met Thr Gln Thr Pro Leu Ser Leu Ser Val Thr Pro Gly
1               5                   10                  15
Gln Pro Ala Ser Ile Ser Cys Lys Ser Ser Gln Ser Leu Leu His Ser
            20                  25                  30
Asp Gly Lys Thr Tyr Leu Tyr Trp Tyr Leu Gln Lys Pro Gly Gln Ser
                35                  40                  45
Pro Gln Leu Leu Ile Tyr Glu Val Ser Ser Arg Phe Ser Gly Val Pro
            50                  55                  60
Asp Arg Phe Ser Gly Ser Gly Ser Gly Thr Asp Phe Thr Leu Lys Ile
65                  70                  75                  80
Ser Arg Val Glu Ala Glu Asp Val Gly Val Tyr Tyr Cys Met Gln Gly
                85                  90                  95
Ile His Leu Pro
            100

<210> SEQ ID NO 91
<211> LENGTH: 115
<212> TYPE: PRT
<213> ORGANISM: Artificial Sequence
<220> FEATURE:
<223> OTHER INFORMATION: Humanized light chain variable region

<400> SEQUENCE: 91

Asp Val Val Met Thr Gln Ser Pro Leu Ser Leu Pro Val Thr Pro Gly
1               5                   10                  15
Glu Pro Ala Ser Ile Ser Cys Arg Ser Ser Gln Ser Ile Val His Ser
            20                  25                  30
Asn Gly Asn Thr Tyr Leu Glu Trp Tyr Leu Gln Lys Pro Gly Gln Ser
                35                  40                  45
Pro Gln Leu Leu Ile Tyr Lys Val Ser Asn Arg Phe Ser Gly Val Pro
            50                  55                  60
Asp Arg Phe Ser Gly Ser Gly Ser Gly Thr Asp Phe Thr Leu Lys Ile
65                  70                  75                  80
Ser Arg Val Glu Ala Glu Asp Val Gly Val Tyr Tyr Cys Phe Gln Gly
                85                  90                  95
Ser His Val Pro Leu Thr Phe Gly Gln Gly Thr Lys Leu Glu Ile Lys
            100                 105                 110
```

Arg Thr Val
        115

<210> SEQ ID NO 92
<211> LENGTH: 117
<212> TYPE: PRT
<213> ORGANISM: Mus musculus

<400> SEQUENCE: 92

Asp Val Gln Leu Val Glu Ser Gly Gly Gly Leu Val Gln Pro Gly Gly
1               5                   10                  15

Ser Arg Lys Leu Ser Cys Ala Ala Ser Gly Phe Thr Phe Ser Ser Phe
            20                  25                  30

Gly Met His Trp Val Arg Gln Ala Pro Glu Lys Gly Leu Glu Trp Val
        35                  40                  45

Ala Tyr Ile Ser Arg Gly Ser Ser Thr Ile Tyr Tyr Ala Asp Thr Val
    50                  55                  60

Lys Gly Arg Phe Thr Ile Ser Arg Asp Asn Pro Lys Asn Thr Leu Phe
65                  70                  75                  80

Leu Gln Met Thr Ser Leu Arg Ser Glu Asp Thr Ala Met Tyr Tyr Cys
                85                  90                  95

Ala Arg Gly Ile Thr Thr Ala Leu Asp Tyr Trp Gly Gln Gly Thr Ser
            100                 105                 110

Val Thr Val Ser Ser
        115

<210> SEQ ID NO 93
<211> LENGTH: 117
<212> TYPE: PRT
<213> ORGANISM: Homo sapiens

<400> SEQUENCE: 93

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Val Arg Arg Gly Ser Gly Asp Ser Trp Gly Gln Gly Thr Leu
            100                 105                 110

Val Thr Val Ser Ser
        115

<210> SEQ ID NO 94
<211> LENGTH: 98
<212> TYPE: PRT
<213> ORGANISM: Homo sapiens

<400> SEQUENCE: 94

Glu Val Gln Leu Val Glu Ser Gly Gly Gly Leu Val Gln Pro Gly Gly
1               5                   10                  15

```
Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
            35                  40                  45

Ser Tyr Ile Ser Ser Ser Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                   70                  75                  80

Leu Gln Met Asn Ser Leu Arg Asp Glu Asp Thr Ala Val Tyr Tyr Cys
                85                  90                  95

Ala Arg
```

<210> SEQ ID NO 95
<211> LENGTH: 117
<212> TYPE: PRT
<213> ORGANISM: Artificial Sequence
<220> FEATURE:
<223> OTHER INFORMATION: Humanized heavy chain variable region

<400> SEQUENCE: 95

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Gly Met His Trp Val Arg Gln Ala Pro Gly Lys Gly Leu Glu Trp Val
            35                  40                  45

Ala Tyr Ile Ser Arg Gly Ser Ser Thr Ile Tyr Tyr Ala Asp Thr Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Ile Thr Thr Ala Leu Asp Tyr Trp Gly Gln Gly Thr Leu
            100                 105                 110

Val Thr Val Ser Ser
        115
```

<210> SEQ ID NO 96
<211> LENGTH: 115
<212> TYPE: PRT
<213> ORGANISM: Mus musculus

<400> SEQUENCE: 96

```
Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
            35                  40                  45

Pro Lys Leu Leu Ile Tyr Lys Ala Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Pro Thr Phe Gly Gly Gly Thr Lys Leu Glu Ile Lys
            100                 105                 110
```

```
Arg Ala Asp
        115

<210> SEQ ID NO 97
<211> LENGTH: 115
<212> TYPE: PRT
<213> ORGANISM: Homo sapiens

<400> SEQUENCE: 97

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Tyr Thr Phe Gly Gln Gly Thr Lys Leu Glu Ile Lys
            100                 105                 110

Arg Thr Val
        115

<210> SEQ ID NO 98
<211> LENGTH: 100
<212> TYPE: PRT
<213> ORGANISM: Homo sapiens

<400> SEQUENCE: 98

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu His Ser
            20                  25                  30

Asp Gly Lys Thr Tyr Leu Tyr Trp Tyr Leu Gln Lys Pro Gly Gln Ser
        35                  40                  45

Pro Gln Leu Leu Ile Tyr Glu Val Ser Ser Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Ile His Leu Pro
        100

<210> SEQ ID NO 99
<211> LENGTH: 115
<212> TYPE: PRT
<213> ORGANISM: Artificial Sequence
<220> FEATURE:
<223> OTHER INFORMATION: Humanized light chain variable region

<400> SEQUENCE: 99

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Ile Val His Ser
```

-continued

```
                    20                  25                  30
Asn Gly Asn Thr Tyr Leu Glu Trp Tyr Leu Gln Lys Pro Gly Gln Ser
            35                  40                  45
Pro Gln Leu Leu Ile Tyr Lys Ala Ser Asn Arg Phe Ser Gly Val Pro
    50                  55                  60
Asp Arg Phe Ser Gly Ser Gly Ser Gly Thr Asp Phe Thr Leu Lys Ile
65                  70                  75                  80
Ser Arg Val Glu Ala Glu Asp Val Gly Val Tyr Tyr Cys Phe Gln Gly
                85                  90                  95
Ser His Val Pro Pro Thr Phe Gly Gln Gly Thr Lys Leu Glu Ile Lys
            100                 105                 110
Arg Thr Val
        115

<210> SEQ ID NO 100
<211> LENGTH: 121
<212> TYPE: PRT
<213> ORGANISM: Mus musculus

<400> SEQUENCE: 100

Asp Val Gln Leu Val Glu Ser Gly Gly Gly Leu Val Gln Pro Gly Gly
1               5                   10                  15
Ser Arg Lys Leu Ser Cys Ala Ala Ser Gly Phe Thr Phe Ser Ser Phe
            20                  25                  30
Gly Met His Trp Val Arg Gln Ala Pro Glu Lys Gly Leu Glu Trp Val
        35                  40                  45
Ala Tyr Ile Arg Ser Gly Ser Ser Thr Ile Tyr Tyr Ala Asp Thr Val
    50                  55                  60
Lys Gly Arg Phe Thr Ile Ser Arg Asp Asn Pro Lys Asn Thr Leu Phe
65                  70                  75                  80
Leu Gln Met Thr Ser Leu Arg Ser Glu Asp Thr Ala Met Tyr Tyr Cys
                85                  90                  95
Thr Arg Gly Gly Asn Tyr Tyr Gly Ser Ser Arg Phe Ala Tyr Trp Gly
            100                 105                 110
Gln Gly Thr Leu Val Thr Val Ser Ala
        115                 120

<210> SEQ ID NO 101
<211> LENGTH: 121
<212> TYPE: PRT
<213> ORGANISM: Homo sapiens

<400> SEQUENCE: 101

Glu Val Gln Leu Val Glu Ser Gly Gly Gly Leu Val Gln Pro Gly Gly
1               5                   10                  15
Ser Leu Arg Leu Ser Cys Ala Ala Ser Gly Phe Thr Phe Ser Ser Tyr
            20                  25                  30
Ala Met Ser Trp Val Arg Gln Ala Pro Gly Lys Gly Leu Glu Trp Val
        35                  40                  45
Ser Gly Ile Ser Ala Arg Gly Ser Thr Tyr Tyr Ala Asp Ser Val
    50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Lys Asp Arg Gly Arg Ile Ala Ala Ala His Phe Asp Tyr Trp Gly
```

```
                    100                 105                 110

Gln Gly Thr Leu Val Thr Val Ser Ser
        115                 120

<210> SEQ ID NO 102
<211> LENGTH: 98
<212> TYPE: PRT
<213> ORGANISM: Homo sapiens

<400> SEQUENCE: 102

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Tyr Ile Ser Ser Ser Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Asp Glu Asp Thr Ala Val Tyr Tyr Cys
                85                  90                  95

Ala Arg

<210> SEQ ID NO 103
<211> LENGTH: 121
<212> TYPE: PRT
<213> ORGANISM: Artificial Sequence
<220> FEATURE:
<223> OTHER INFORMATION: Humanized heavy chain variable region

<400> SEQUENCE: 103

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Gly Met His Trp Val Arg Gln Ala Pro Gly Lys Gly Leu Glu Trp Val
        35                  40                  45

Ala Tyr Ile Arg Ser Gly Ser Thr Ile Tyr Tyr Ala Asp Thr Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Asn Tyr Tyr Gly Ser Ser Arg Phe Ala Tyr Trp Gly
            100                 105                 110

Gln Gly Thr Leu Val Thr Val Ser Ser
        115                 120

<210> SEQ ID NO 104
<211> LENGTH: 110
<212> TYPE: PRT
<213> ORGANISM: Mus musculus

<400> SEQUENCE: 104

Asp Ile Lys Met Thr Gln Ser Pro Ser Ser Met Tyr Ala Ser Leu Gly
1               5                   10                  15

Glu Arg Val Thr Ile Thr Cys Lys Ala Ser Gln Asp Ile Asn Ser Tyr
```

-continued

```
                20                  25                  30

Leu Ser Trp Phe Gln Gln Lys Pro Gly Lys Ser Pro Lys Thr Leu Ile
            35                  40                  45

Tyr Arg Ala Asn Arg Phe Val Asp Gly Val Pro Ser Arg Phe Ser Gly
 50                  55                  60

Ser Gly Ser Gly Gln Asp Tyr Ser Leu Thr Ile Ser Ser Leu Glu Tyr
 65                  70                  75                  80

Glu Asp Met Gly Ile Tyr Phe Cys Leu Gln Tyr Asp Glu Phe Pro Leu
                 85                  90                  95

Thr Phe Gly Ala Gly Thr Lys Leu Val Leu Lys Arg Ala Asp
                100                 105                 110

<210> SEQ ID NO 105
<211> LENGTH: 110
<212> TYPE: PRT
<213> ORGANISM: Homo sapiens

<400> SEQUENCE: 105

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Ser Ile Ser Ser Tyr
                20                  25                  30

Leu Asn Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Ser Thr Leu Leu
                 85                  90                  95

Thr Phe Gly Gly Gly Thr Lys Val Glu Ile Lys Arg Thr Val
                100                 105                 110

<210> SEQ ID NO 106
<211> LENGTH: 95
<212> TYPE: PRT
<213> ORGANISM: Homo sapiens

<400> SEQUENCE: 106

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Gly Ile Ser Asn Tyr
                20                  25                  30

Leu Ala Trp Phe Gln Gln Lys Pro Gly Lys Ala Pro Lys Ser Leu Ile
            35                  40                  45

Tyr Ala Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Asn Ser Tyr Pro
                 85                  90                  95

<210> SEQ ID NO 107
<211> LENGTH: 110
<212> TYPE: PRT
<213> ORGANISM: Artificial Sequence
<220> FEATURE:
<223> OTHER INFORMATION: Humanized light chain variable region
```

<400> SEQUENCE: 107

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Asn Ser Tyr
            20                  25                  30

Leu Ser Trp Phe Gln Gln Lys Pro Gly Lys Ala Pro Lys Thr Leu Ile
        35                  40                  45

Tyr Arg Ala Asn Arg Phe Val Asp Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Phe Cys Leu Gln Tyr Asp Glu Phe Pro Leu
                85                  90                  95

Thr Phe Gly Gly Gly Thr Lys Val Glu Ile Lys Arg Thr Val
            100                 105                 110

<210> SEQ ID NO 108
<211> LENGTH: 122
<212> TYPE: PRT
<213> ORGANISM: Mus musculus

<400> SEQUENCE: 108

Asp Val Gln Leu Val Glu Ser Gly Gly Gly Leu Val Gln Pro Gly Gly
1               5                   10                  15

Ser Arg Lys Leu Ser Cys Ala Ala Ser Gly Phe Thr Phe Ser Ser Phe
            20                  25                  30

Gly Met His Trp Val Arg Gln Ala Pro Glu Lys Gly Leu Glu Trp Val
        35                  40                  45

Ala Tyr Ile Ser Ser Val Ser Ser Thr Ile Tyr Tyr Ala Asp Thr Val
    50                  55                  60

Lys Gly Arg Phe Thr Ile Ser Arg Asp Asn Pro Lys Asn Thr Leu Phe
65                  70                  75                  80

Leu Gln Met Thr Ser Leu Arg Ser Glu Asp Thr Ala Met Tyr Tyr Cys
                85                  90                  95

Ala Arg Ser Gly Tyr Gly Ser Ser Tyr Gly Tyr Gly Met Asp Tyr Trp
            100                 105                 110

Gly Gln Gly Thr Leu Val Thr Val Ser Ser
        115                 120

<210> SEQ ID NO 109
<211> LENGTH: 122
<212> TYPE: PRT
<213> ORGANISM: Homo sapiens

<400> SEQUENCE: 109

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

```
Leu Gln Met Asn Ser Leu Arg Ala Glu Asp Thr Ala Val Tyr Tyr Cys
                85                  90                  95

Ala Lys Cys Ser Glu Leu Arg Tyr Phe Asp Trp Ser Val Asp Tyr Trp
            100                 105                 110

Gly Gln Gly Thr Leu Val Thr Val Ser Ser
        115                 120

<210> SEQ ID NO 110
<211> LENGTH: 98
<212> TYPE: PRT
<213> ORGANISM: Homo sapiens

<400> SEQUENCE: 110

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Tyr Ile Ser Ser Ser Ser Ser Thr Ile Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Asp Glu Asp Thr Ala Val Tyr Tyr Cys
                85                  90                  95

Ala Arg

<210> SEQ ID NO 111
<211> LENGTH: 122
<212> TYPE: PRT
<213> ORGANISM: Artificial Sequence
<220> FEATURE:
<223> OTHER INFORMATION: Humanized heavy chain variable region

<400> SEQUENCE: 111

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Gly Met His Trp Val Arg Gln Ala Pro Gly Lys Gly Leu Glu Trp Val
        35                  40                  45

Ala Tyr Ile Ser Ser Val Ser Ser Thr Ile Tyr Tyr Ala Asp Thr Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Gly Tyr Gly Ser Ser Tyr Gly Tyr Gly Met Asp Tyr Trp
            100                 105                 110

Gly Gln Gly Thr Leu Val Thr Val Ser Ser
        115                 120

<210> SEQ ID NO 112
<211> LENGTH: 123
<212> TYPE: PRT
<213> ORGANISM: Mus musculus

<400> SEQUENCE: 112
```

```
Gln Val Thr Leu Lys Glu Ser Gly Pro Gly Ile Leu Lys Pro Ser Gln
1               5                   10                  15

Thr Leu Ser Leu Thr Cys Ser Leu Ser Gly Phe Ser Leu Ser Thr Ser
            20                  25                  30

Gly Met Gly Val Gly Trp Phe Arg Gln Pro Ser Gly Lys Gly Leu Glu
        35                  40                  45

Trp Leu Ala His Ile Trp Trp Asp Asp Lys Ser Tyr Asn Pro Ser
50                  55                  60

Leu Lys Ser Arg Leu Thr Ile Ser Lys Tyr Thr Ser Arg Asn Gln Val
65                  70                  75                  80

Phe Leu Thr Ile Thr Ser Val Asp Thr Ala Asp Thr Ala Thr Tyr Tyr
                85                  90                  95

Cys Ala Arg Arg Gln Leu Gly Leu Arg Ser Ile Asp Ala Met Asp Tyr
            100                 105                 110

Trp Gly Gln Gly Thr Ser Val Thr Val Ser Ser
        115                 120
```

<210> SEQ ID NO 113
<211> LENGTH: 130
<212> TYPE: PRT
<213> ORGANISM: Homo sapiens

<400> SEQUENCE: 113

```
Gln Val Thr Leu Lys Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Met Cys Val Ser Trp Ile Arg Gln Pro Pro Gly Lys Ala Leu Glu
        35                  40                  45

Trp Leu Ala Leu Ile Asp Trp Asp Asp Lys Tyr Tyr Ser Thr Ser
50                  55                  60

Leu Lys Thr Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Ile Phe Gly Asp Tyr Asp Phe Trp Ser Gly Tyr Tyr Arg
            100                 105                 110

Ser Tyr Tyr Gly Met Asp Val Trp Gly Gln Gly Thr Thr Val Thr Val
            115                 120                 125

Ser Ser
    130
```

<210> SEQ ID NO 114
<211> LENGTH: 100
<212> TYPE: PRT
<213> ORGANISM: Homo sapiens

<400> SEQUENCE: 114

```
Gln Val Thr Leu Lys Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Met Arg Val Ser Trp Ile Arg Gln Pro Pro Gly Lys Ala Leu Glu
        35                  40                  45

Trp Leu Ala Arg Ile Asp Trp Asp Asp Lys Phe Tyr Ser Thr Ser
50                  55                  60
```

Leu Lys Thr Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
            85                  90                  95

Cys Ala Arg Ile
            100

<210> SEQ ID NO 115
<211> LENGTH: 123
<212> TYPE: PRT
<213> ORGANISM: Artificial Sequence
<220> FEATURE:
<223> OTHER INFORMATION: Humanized heavy chain variable region

<400> SEQUENCE: 115

Gln Val Thr Leu Lys Glu Ser Gly Pro Gly Ile Leu Lys Pro Ser Gln
1               5                   10                  15

Thr Leu Ser Leu Thr Cys Thr Phe Ser Gly Phe Ser Leu Ser Thr Ser
            20                  25                  30

Gly Met Gly Val Gly Trp Phe Arg Gln Pro Pro Gly Lys Gly Leu Glu
        35                  40                  45

Trp Leu Ala His Ile Trp Trp Asp Asp Asp Lys Ser Tyr Asn Pro Ser
    50                  55                  60

Leu Lys Ser Arg Leu Thr Ile Ser Lys Asp Thr Ser Lys Asn Gln Val
65                  70                  75                  80

Phe Leu Thr Ile Thr Asn Met Asp Pro Val Asp Thr Ala Thr Tyr Tyr
            85                  90                  95

Cys Ala Arg Arg Gln Leu Gly Leu Arg Ser Ile Asp Ala Met Asp Tyr
            100                 105                 110

Trp Gly Gln Gly Thr Thr Val Thr Val Ser Ser
        115                 120

<210> SEQ ID NO 116
<211> LENGTH: 123
<212> TYPE: PRT
<213> ORGANISM: Artificial Sequence
<220> FEATURE:
<223> OTHER INFORMATION: Humanized heavy chain variable region

<400> SEQUENCE: 116

Gln Val Thr Leu Lys Glu Ser Gly Pro Gly Ile Leu Lys Pro Ser Gln
1               5                   10                  15

Thr Leu Ser Leu Thr Cys Thr Phe Ser Gly Phe Ser Leu Ser Thr Ser
            20                  25                  30

Gly Met Gly Val Gly Trp Phe Arg Gln Pro Pro Gly Lys Gly Leu Glu
        35                  40                  45

Trp Leu Ala His Ile Trp Trp Asp Asp Asp Lys Ser Tyr Asn Pro Ser
    50                  55                  60

Leu Lys Ser Arg Leu Thr Ile Ser Lys Asp Thr Ser Lys Asn Gln Val
65                  70                  75                  80

Val Leu Thr Ile Thr Asn Met Asp Pro Val Asp Thr Ala Thr Tyr Tyr
            85                  90                  95

Cys Ala Arg Arg Gln Leu Gly Leu Arg Ser Ile Asp Ala Met Asp Tyr
            100                 105                 110

Trp Gly Gln Gly Thr Thr Val Thr Val Ser Ser
        115                 120

<210> SEQ ID NO 117

-continued

```
<211> LENGTH: 113
<212> TYPE: PRT
<213> ORGANISM: Mus musculus

<400> SEQUENCE: 117

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Leu His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser Leu Val Pro Leu Thr Phe Gly Ala Gly Thr Lys Leu Glu Leu Lys
            100                 105                 110

Arg

<210> SEQ ID NO 118
<211> LENGTH: 113
<212> TYPE: PRT
<213> ORGANISM: Homo sapiens

<400> SEQUENCE: 118

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Tyr Thr Phe Gly Gln Gly Thr Lys Leu Glu Ile Lys
            100                 105                 110

Arg

<210> SEQ ID NO 119
<211> LENGTH: 100
<212> TYPE: PRT
<213> ORGANISM: Homo sapiens

<400> SEQUENCE: 119

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu His Ser
            20                  25                  30

Asp Gly Lys Thr Tyr Leu Tyr Trp Tyr Leu Gln Lys Pro Gly Gln Ser
        35                  40                  45

Pro Gln Leu Leu Ile Tyr Glu Val Ser Ser Arg Phe Ser Gly Val Pro
    50                  55                  60
```

```
Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Ile His Leu Pro
            100

<210> SEQ ID NO 120
<211> LENGTH: 113
<212> TYPE: PRT
<213> ORGANISM: Artificial Sequence
<220> FEATURE:
<223> OTHER INFORMATION: Humanized light chain variable region

<400> SEQUENCE: 120

Asp Val Val Met Thr Gln Ser Pro Leu Ser Leu Pro Val Ser Leu Gly
1               5                   10                  15

Asp Pro Ala Ser Ile Ser Cys Arg Ser Ser Gln Ser Ile Leu His Ser
            20                  25                  30

Asn Gly Asn Thr Tyr Leu Glu Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser Leu Val Pro Leu Thr Phe Gly Ala Gly Thr Lys Leu Glu Leu Lys
            100                 105                 110

Arg

<210> SEQ ID NO 121
<211> LENGTH: 123
<212> TYPE: PRT
<213> ORGANISM: Mus musculus

<400> SEQUENCE: 121

Gln Val Thr Leu Lys Glu Ser Gly Pro Gly Ile Val Gln Pro Ser Gln
1               5                   10                  15

Thr Leu Ser Leu Thr Cys Ser Phe Ser Gly Phe Ser Leu Ser Thr Ser
            20                  25                  30

Gly Met Gly Val Ser Trp Ile Arg Gln Pro Ser Gly Lys Gly Leu Glu
        35                  40                  45

Trp Leu Ala His Ile Tyr Trp Asp Asp Lys Gln Tyr Asn Pro Ser
    50                  55                  60

Leu Lys Ser Arg Leu Thr Ile Ser Lys Asp Thr Ser Arg Arg Lys Val
65                  70                  75                  80

Phe Leu Glu Ile Thr Ser Val Asp Thr Ala Asp Thr Ala Thr Tyr Tyr
                85                  90                  95

Cys Val Arg Arg Ala Ser Ser Arg Tyr Asp Asp Gln Phe Asp Tyr
            100                 105                 110

Trp Gly Gln Gly Thr Pro Leu Thr Val Ser Ser
        115                 120

<210> SEQ ID NO 122
<211> LENGTH: 123
<212> TYPE: PRT
```

<213> ORGANISM: Homo sapiens

<400> SEQUENCE: 122

```
Gln Val Thr Leu Lys Glu Ser Gly Pro Thr Leu Val Lys Pro Thr Gln
1               5                   10                  15
Thr Leu Thr Leu Thr Cys Thr Phe Ser Gly Phe Ser Leu Ser Thr Ser
            20                  25                  30
Gly Val Gly Val Gly Trp Ile Arg Gln Pro Pro Gly Lys Ala Leu Glu
        35                  40                  45
Trp Leu Ala Leu Ile Tyr Trp Asn Asp Asp Lys Arg Tyr Ser Pro Ser
    50                  55                  60
Leu Lys Ser Arg Leu Thr Ile Thr Lys Asp Thr Ser Lys Asn Gln Val
65                  70                  75                  80
Val Leu Thr Met Thr Asn Met Asp Pro Val Asp Thr Ala Thr Tyr Tyr
                85                  90                  95
Cys Ala Gln Ser Ile Met Ala Thr Ser Thr Ser Asp Tyr Phe Asp Tyr
            100                 105                 110
Trp Gly Gln Gly Thr Leu Val Pro Val Ser Ser
        115                 120
```

<210> SEQ ID NO 123
<211> LENGTH: 100
<212> TYPE: PRT
<213> ORGANISM: Homo sapiens

<400> SEQUENCE: 123

```
Gln Val Thr Leu Lys Glu Ser Gly Pro Ala Leu Val Lys Pro Thr Gln
1               5                   10                  15
Thr Leu Thr Leu Thr Cys Thr Phe Ser Gly Phe Ser Leu Ser Thr Ser
            20                  25                  30
Gly Met Arg Val Ser Trp Ile Arg Gln Pro Pro Gly Lys Ala Leu Glu
        35                  40                  45
Trp Leu Ala Arg Ile Asp Trp Asp Asp Asp Lys Phe Tyr Ser Thr Ser
    50                  55                  60
Leu Lys Thr Arg Leu Thr Ile Ser Lys Asp Thr Ser Lys Asn Gln Val
65                  70                  75                  80
Val Leu Thr Met Thr Asn Met Asp Pro Val Asp Thr Ala Thr Tyr Tyr
                85                  90                  95
Cys Ala Arg Ile
            100
```

<210> SEQ ID NO 124
<211> LENGTH: 123
<212> TYPE: PRT
<213> ORGANISM: Artificial Sequence
<220> FEATURE:
<223> OTHER INFORMATION: Humanized heavy chain variable region

<400> SEQUENCE: 124

```
Gln Val Thr Leu Lys Glu Ser Gly Pro Gly Ile Val Gln Pro Ser Gln
1               5                   10                  15
Thr Leu Ser Leu Thr Cys Ser Phe Ser Gly Phe Ser Leu Ser Thr Ser
            20                  25                  30
Gly Met Gly Val Ser Trp Ile Arg Gln Pro Ser Gly Lys Gly Leu Glu
        35                  40                  45
Trp Leu Ala His Ile Tyr Trp Asp Asp Asp Lys Gln Tyr Asn Pro Ser
    50                  55                  60
```

```
Leu Lys Ser Arg Leu Thr Ile Ser Lys Asp Thr Ser Lys Asn Gln Val
 65                  70                  75                  80

Phe Leu Thr Ile Thr Ser Val Asp Thr Val Asp Thr Ala Thr Tyr Tyr
                 85                  90                  95

Cys Val Arg Arg Ala Ser Ser Arg Tyr Asp Asp Gln Phe Asp Tyr
            100                 105                 110

Trp Gly Gln Gly Thr Pro Leu Thr Val Ser Ser
        115                 120

<210> SEQ ID NO 125
<211> LENGTH: 123
<212> TYPE: PRT
<213> ORGANISM: Artificial Sequence
<220> FEATURE:
<223> OTHER INFORMATION: Humanized heavy chain variable region

<400> SEQUENCE: 125

Gln Val Thr Leu Lys Glu Ser Gly Pro Gly Leu Val Lys Pro Thr Gln
 1               5                  10                  15

Thr Leu Ser Leu Thr Cys Ser Phe Ser Gly Phe Ser Leu Ser Thr Ser
                 20                  25                  30

Gly Met Gly Val Ser Trp Ile Arg Gln Pro Ser Gly Lys Gly Leu Glu
             35                  40                  45

Trp Leu Ala His Ile Tyr Trp Asp Asp Lys Gln Tyr Asn Pro Ser
 50                  55                  60

Leu Lys Ser Arg Leu Thr Ile Ser Lys Asp Thr Ser Lys Asn Gln Val
 65                  70                  75                  80

Phe Leu Thr Ile Thr Ser Val Asp Pro Val Asp Thr Ala Thr Tyr Tyr
                 85                  90                  95

Cys Val Arg Arg Ala Ser Ser Arg Tyr Asp Asp Gln Phe Asp Tyr
            100                 105                 110

Trp Gly Gln Gly Thr Pro Leu Thr Val Ser Ser
        115                 120

<210> SEQ ID NO 126
<211> LENGTH: 123
<212> TYPE: PRT
<213> ORGANISM: Artificial Sequence
<220> FEATURE:
<223> OTHER INFORMATION: Humanized heavy chain variable region

<400> SEQUENCE: 126

Gln Val Thr Leu Lys Glu Ser Gly Pro Gly Leu Val Lys Pro Thr Gln
 1               5                  10                  15

Thr Leu Ser Leu Thr Cys Ser Phe Ser Gly Phe Ser Leu Ser Thr Ser
                 20                  25                  30

Gly Met Gly Val Ser Trp Ile Arg Gln Pro Ser Gly Lys Gly Leu Glu
             35                  40                  45

Trp Leu Ala His Ile Tyr Trp Asp Asp Lys Gln Tyr Asn Pro Ser
 50                  55                  60

Leu Lys Ser Arg Leu Thr Ile Ser Lys Asp Thr Ser Lys Asn Gln Val
 65                  70                  75                  80

Val Leu Thr Ile Thr Ser Val Asp Pro Val Asp Thr Ala Thr Tyr Tyr
                 85                  90                  95

Cys Val Arg Arg Ala Ser Ser Arg Tyr Asp Asp Gln Phe Asp Tyr
            100                 105                 110

Trp Gly Gln Gly Thr Leu Leu Thr Val Ser Ser
        115                 120
```

<210> SEQ ID NO 127
<211> LENGTH: 112
<212> TYPE: PRT
<213> ORGANISM: Mus musculus

<400> SEQUENCE: 127

Asp Val Leu Met Ile Gln Thr Pro Leu Ser Leu Pro Val Ser Leu Gly
1               5                   10                  15

Asp Pro Ala Ser Ile Ser Cys Arg Ala Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Arg Val Ser Asn Arg Phe Ser Gly Val Pro
    50                  55                  60

Asp Arg Phe Ser Gly Ser Gly Ser Gly Thr Asp Phe Thr Leu Arg Ile
65                  70                  75                  80

Ser Arg Val Glu Ala Glu Asp Leu Gly Val Tyr Phe Cys Phe Gln Val
                85                  90                  95

Thr His Val Pro Leu Thr Phe Gly Ala Gly Thr Lys Leu Glu Leu Lys
            100                 105                 110

<210> SEQ ID NO 128
<211> LENGTH: 112
<212> TYPE: PRT
<213> ORGANISM: Homo sapiens

<400> SEQUENCE: 128

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Tyr Thr Phe Gly Gln Gly Thr Lys Leu Glu Ile Lys
            100                 105                 110

<210> SEQ ID NO 129
<211> LENGTH: 100
<212> TYPE: PRT
<213> ORGANISM: Homo sapiens

<400> SEQUENCE: 129

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu His Ser
            20                  25                  30

Asp Gly Lys Thr Tyr Leu Tyr Trp Tyr Leu Gln Lys Pro Gly Gln Ser
        35                  40                  45

Pro Gln Leu Leu Ile Tyr Glu Val Ser Ser Arg Phe Ser Gly Val Pro
    50                  55                  60

```
Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Gly
                 85                  90                  95

Ile His Leu Pro
            100

<210> SEQ ID NO 130
<211> LENGTH: 112
<212> TYPE: PRT
<213> ORGANISM: Artificial Sequence
<220> FEATURE:
<223> OTHER INFORMATION: Humanized light chain variable region

<400> SEQUENCE: 130

Asp Val Val Met Thr Gln Thr Pro Leu Ser Leu Pro Val Ser Leu Gly
  1               5                  10                  15

Asp Pro Ala Ser Ile Ser Cys Arg Ala Ser Gln Ser Ile Val His Ser
                 20                  25                  30

Asn Gly Asn Thr Tyr Leu Glu Trp Tyr Leu Gln Lys Pro Gly Gln Ser
             35                  40                  45

Pro Lys Leu Leu Ile Tyr Arg Val Ser Asn Arg Phe Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Leu Gly Val Tyr Phe Cys Phe Gln Val
                 85                  90                  95

Thr His Val Pro Leu Thr Phe Gly Ala Gly Thr Lys Leu Glu Leu Lys
            100                 105                 110

<210> SEQ ID NO 131
<211> LENGTH: 112
<212> TYPE: PRT
<213> ORGANISM: Artificial Sequence
<220> FEATURE:
<223> OTHER INFORMATION: Humanized light chain variable region

<400> SEQUENCE: 131

Asp Val Val Met Thr Gln Thr Pro Leu Ser Leu Pro Val Ser Leu Gly
  1               5                  10                  15

Asp Pro Ala Ser Ile Ser Cys Arg Ala Ser Gln Ser Ile Val His Ser
                 20                  25                  30

Asn Gly Asn Thr Tyr Leu Glu Trp Tyr Leu Gln Lys Pro Gly Gln Ser
             35                  40                  45

Pro Lys Leu Leu Ile Tyr Arg Val Ser Asn Arg Phe Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Phe Cys Phe Gln Val
                 85                  90                  95

Thr His Val Pro Leu Thr Phe Gly Gly Gly Thr Lys Leu Glu Leu Lys
            100                 105                 110

<210> SEQ ID NO 132
<211> LENGTH: 463
<212> TYPE: DNA
<213> ORGANISM: Artificial Sequence
<220> FEATURE:
<223> OTHER INFORMATION: Humanized heavy chain variable region
```

<400> SEQUENCE: 132

```
gcagtcatgc tactgccttc ctgaacgtaa cttacggtgt ccactcccag gtgaccctga      60
aggagtctgg ccctgccctg gtgaagccca cccagaccct gaccctgacc tgcaccttct     120
ctggcttcag cctgagcacc tctggcatgg gcgtgggctg gatccggcag ccccctggca     180
aggccctgga gtggctggcc cacatctggt gggacgacga caagtcctac aaccccagcc     240
tgaagagccg gctgaccatc agcaaggaca ccagcaagaa ccaggtggtg ctgaccatga     300
ccaacatgga ccctgtggac acagccacct actactgtgc ccggcggcag ctgggcctgc     360
ggagcattga tgccatggac tactggggcc agggcaccac agtgacagtg tccagcgcct     420
ccaccaaggt accatccgtt ctctagtagc tagctagcta acg                       463
```

<210> SEQ ID NO 133
<211> LENGTH: 463
<212> TYPE: DNA
<213> ORGANISM: Artificial Sequence
<220> FEATURE:
<223> OTHER INFORMATION: Humanized heavy chain variable region

<400> SEQUENCE: 133

```
gcagtcatgc tactgccttc ctgaacgtaa cttacggtgt ccactcccag gtgaccctga      60
aggagtctgg ccctgccctg gtgaagccca cccagaccct gaccctgacc tgcaccctgt     120
ctggcttcag cctgagcacc tctggcatgg gcgtgggctg gatccggcag ccccctggca     180
aggccctgga gtggctggcc cacatctggt gggacgacga caagtcctac aaccccagcc     240
tgaagagccg gctgaccatc agcaaggaca ccagcaagaa ccaggtggtg ctgaccatga     300
ccaacatgga ccctgtggac acagccacct actactgtgc ccggcggcag ctgggcctgc     360
ggagcattga tgccatggac tactggggcc agggcaccac agtgacagtg tccagcgcct     420
ccaccaaggt accatccgtt ctctagtagc tagctagcta acg                       463
```

<210> SEQ ID NO 134
<211> LENGTH: 389
<212> TYPE: DNA
<213> ORGANISM: Artificial Sequence
<220> FEATURE:
<223> OTHER INFORMATION: Humanized light chain variable region

<400> SEQUENCE: 134

```
gctgtggctt acacctgccc agatgtgatg tggtgatgac ccagagcccc ctgtccctgc      60
ctgtgacccc tggcgagcct gccagcatct cctgccggag ctcccagagc atcctgcact     120
ccaatggcaa cacctacctg gagtggtacc tgcagaagcc tggccagagc ccccagctgc     180
tgatctacaa ggtgtccaac cggttctccg gcgtgcctga ccggttcagc ggctccggca     240
gcggcacaga cttcacccTG aagatcagcc gggtggaggc tgaggatgtg ggcgtctact     300
actgcttcca gggcagcctg gtgccCctga ccttTggcca gggcaccaag ctggagatca     360
agcgtacggt ggcaggtgca tctgtcttc                                       389
```

<210> SEQ ID NO 135
<211> LENGTH: 463
<212> TYPE: DNA
<213> ORGANISM: Artificial Sequence
<220> FEATURE:
<223> OTHER INFORMATION: Humanized heavy chain variable region

<400> SEQUENCE: 135

```
gcagtcatgc tactgccttc ctgaacgtaa cttacggtgt ccactcccag gtgaccctga      60
```

```
aagagtctgg ccccaccctg gtgaagccca cccagaccct gaccctgacc tgcaccttct    120
ctggcttctc cctgagcacc tctggcatgg gcgtgtcctg gatccggcag cccctggca     180 aagccctgga gtggctggcc cacatctact gggatgatga caagcagtac aaccccagcc    240
tgaagtcccg gctgaccatc accaaagaca cctccaagaa ccaggtggtg ctgaccatga    300
ccaacatgga ccctgtggac acagccacct actactgcgc ccggcgcgcc tcctccagcc    360
ggtatgatga ccagtttgac tactggggcc agggcaccct ggtgcctgtg tcctctgcct    420
ccaccaaggt accatccgtt ctctagtagc tagctagcta acg                      463
```

<210> SEQ ID NO 136
<211> LENGTH: 389
<212> TYPE: DNA
<213> ORGANISM: Artificial Sequence
<220> FEATURE:
<223> OTHER INFORMATION: Humanized light chain variable region

<400> SEQUENCE: 136

```
gctgtggctt acacctgccc agatgtgatg tggtgatgac ccagtccccc ctgagcctgc     60
ctgtgacccc tggcgagcct gcctccatca gctgccgcgc ctcccagagc attgtgcact    120
ccaatggcaa cacctacctg gagtggtacc tgcagaagcc tggccagtcc cccagctgc     180 tgatctaccg cgtgagcaac cggttctctg gcgtgcctga ccggttctct ggctctggct    240
ctggcacaga cttcaccctg aagatcagcc gcgtggaagc tgaagatgtg ggcgtgtact    300
actgcttcca ggtgacccat gtgcccctga cctttggcca gggcaccaag ctggagatca    360
agcgtacggt ggcaggtgca tctgtcttc                                      389
```

<210> SEQ ID NO 137
<211> LENGTH: 466
<212> TYPE: DNA
<213> ORGANISM: Artificial Sequence
<220> FEATURE:
<223> OTHER INFORMATION: Humanized heavy chain variable region

<400> SEQUENCE: 137

```
gcagtcatgc tactgccttc ctgaacgtaa cttacggtgt ccactcccag gtgaccctga     60
aggagtctgg ccctgccctg gtgaagccca cccagaccct gaccctgacc tgcaccttct    120
ctggcttcag cctgtccacc agcggcatgg gcgtgggctg gatccggcag cccctggca     180 aggccctgga gtggctggcc cacatctggt gggatgatga caagtactac aaccccctcc    240
tgaagagcca gctgaccatc tccaaggaca ccagcaagaa ccaggtggtg ctgaccatga    300
ccaacatgga ccctgtggac acagccacct actactgtgc ccggcggagc atcaactctg    360
tggtgcctga ggactacttt gactactggg gccagggcac caccgtgaca gtgtccagcg    420
cctccaccaa ggtaccatcc gttctctagt agctagctag ctaacg                   466
```

<210> SEQ ID NO 138
<211> LENGTH: 389
<212> TYPE: DNA
<213> ORGANISM: Artificial Sequence
<220> FEATURE:
<223> OTHER INFORMATION: Humanized light chain variable region

<400> SEQUENCE: 138

```
gctgtggctt acacctgccc agatgtgatg tggtgatgac ccagagcccc ctgtccctgc     60
ctgtgacccc tggcgagcct gccagcatct cctgccggag ctcccagagc attgtgcact    120
```

```
ccaatggcaa cacctacctg gagtggtacc tgcagaagcc tggccagagc ccccagctgc      180
tgatctacaa ggtgtccaac cggttctccg gcgtgcctga ccggttcagc ggctccggca      240
gcggcacaga cttcaccctg aagatcagcc gggtggaggc tgaggatgtg ggcgtctact      300
actgcttcca gggcagccat gtgcccctga cctttggcca gggcaccaag ctggagatca      360
agcgtacggt ggcaggtgca tctgtcttc                                        389
```

<210> SEQ ID NO 139
<211> LENGTH: 445
<212> TYPE: DNA
<213> ORGANISM: Artificial Sequence
<220> FEATURE:
<223> OTHER INFORMATION: Humanized heavy chain variable region

<400> SEQUENCE: 139

```
gcagtcatgc tactgccttc ctgaacgtaa cttacggtgt ccactccgag gtgcagctgg       60
tggagtccgg cggcggcctg gtgcagcctg gcggcagcct gcggctgagc tgtgctgcct      120
ctggcttcac cttcagctcc tttggcatgc actgggtgcg gcaggcccct ggcaagggcc      180
tggagtgggt ggcctacatc agccgggggct ccagcaccat ctactatgct gacacagtga      240
agggccggtt caccatcagc cggacaatgc caagaactc cctgtatctg cagatgaaca      300
gcctgcgggt gaggacaca gcagtgtact actgtgcccg gggcatcacc acagccctgg      360
actactgggg ccagggcacc ctggtgaccg tgtccagcgc ctccaccaag gtaccatccg      420
ttctctagta gctagctagc taacg                                            445
```

<210> SEQ ID NO 140
<211> LENGTH: 389
<212> TYPE: DNA
<213> ORGANISM: Artificial Sequence
<220> FEATURE:
<223> OTHER INFORMATION: Humanized light chain variable region

<400> SEQUENCE: 140

```
gctgtggctt acacctgccc agatgtgatg tggtgatgac ccagagcccc ctgtccctgc       60
ctgtgacccc tggcgagcct gccagcatct cctgccggag ctcccagagc atcgtgcact      120
ccaatggcaa cacctacctg gagtggtacc tgcagaagcc tggccagagc ccccagctgc      180
tgatctacaa ggcttccaac cggttctccg gcgtgcctga ccggttcagc ggctccggca      240
gcggcacaga cttcaccctg aagatcagcc gggtggaggc tgaggatgtg ggcgtctact      300
actgcttcca gggcagccat gtgccccca cctttggcca gggcaccaag ctggagatca      360
agcgtacggt ggcaggtgca tctgtcttc                                        389
```

<210> SEQ ID NO 141
<211> LENGTH: 457
<212> TYPE: DNA
<213> ORGANISM: Artificial Sequence
<220> FEATURE:
<223> OTHER INFORMATION: Humanized heavy chain variable region

<400> SEQUENCE: 141

```
gcagtcatgc tactgccttc ctgaacgtaa cttacggtgt ccactccgag gtgcagctgg       60
tggagtccgg cggcggcctg gtgcagcctg gcggctccct gcggctgagc tgtgctgcct      120
ctggcttcac cttctccagc tttggcatgc actgggtgcg gcaggcccct ggcaagggcc      180
tggagtgggt ggcctacatc cggtctggct ccagcaccat ctactatgct gacacagtga      240
agggccggtt caccatctcc cggacaacag caagaacac cctgtatctg cagatgaact      300
```

```
cctgcgggc tgaggacaca gctgtgtact actgtgcccg ggcggcaac tactatggct      360 ccagccggtt tgcctactgg ggccagggca ccctggtgac cgtgtccagc gcctccacca    420
aggtaccatc cgttctctag tagctagcta gctaacg                             457
```

```
<210> SEQ ID NO 142
<211> LENGTH: 374
<212> TYPE: DNA
<213> ORGANISM: Artificial Sequence
<220> FEATURE:
<223> OTHER INFORMATION: Humanized light chain variable region

<400> SEQUENCE: 142
gctgtggctt acacctgccc agatgtgaca tccagatgac ccagtccccc agctccctgt     60
ctgcctctgt gggcgaccgg gtgaccatca catgcaaggc ctcccaggac atcaactcct    120
acctgagctg gttccagcag aagcctggca aggcccccaa gaccctgatc taccgggcca    180
accggtttgt ggatggcgtg ccctcccggt tcagcggctc tggcagcggc acagactaca    240
ccctgaccat ctccagcctg cagcctgagg actttgccac ctacttctgc ctgcagtatg    300
atgagttccc cctgaccttt ggcggcggca ccaaggtgga gatcaagcgt acggtggcag    360
gtgcatctgt cttc                                                      374
```

```
<210> SEQ ID NO 143
<211> LENGTH: 460
<212> TYPE: DNA
<213> ORGANISM: Artificial Sequence
<220> FEATURE:
<223> OTHER INFORMATION: Humanized heavy chain variable region

<400> SEQUENCE: 143
gcagtcatgc tactgccttc ctgaacgtaa cttacggtgt ccactccgag gtgcagctgg     60
tggagtccgg cggcggcctg gtgcagcctg gcggctccct gcggctgagc tgtgctgcca    120
gcggcttcac cttctccagc tttggcatgc actgggtgcg gcaggcccct ggcaagggcc    180
tggagtgggt ggcctacatc tcctctgtga gcagcaccat ctactatgcc gacaccgtga    240
agggccggtt caccatcagc cgggacaaca gcaagaacac cctgtatctg cagatgaact    300
ccctgcgggc tgaggacacc gccgtgtact actgtgcccg gtctggctat ggctccagct    360
atggctatgg catggactac tggggccagg gcaccctggt gaccgtgtcc agcgcctcca    420
ccaaggtacc atccgttctc tagtagctag ctagctaacg                          460
```

```
<210> SEQ ID NO 144
<211> LENGTH: 463
<212> TYPE: DNA
<213> ORGANISM: Artificial Sequence
<220> FEATURE:
<223> OTHER INFORMATION: Humanized heavy chain variable region

<400> SEQUENCE: 144
gcagtcatgc tactgccttc ctgaacgtaa cttacggtgt ccactcccag gtgaccctga     60 agagagcgg ccctggcatc ctgaagccat ctcagaccct gagcctgacc tgcaccttct    120
ctggcttcag cctgtccacc agcggcatgg gcgtgggctg gttccggcag ccccctggca    180
aaggcctgga gtggctggcc cacatctggt gggatgatga caagagctac aacccatccc    240
tgaagagccg gctgaccatc tccaaagaca ccagcaagaa ccaggtgttc ctgaccatca    300
ccaacatgga ccctgtggac acagccacct actactgtgc ccggcggcag ctgggcctgc    360
```

```
ggtccatcga tgccatggac tactggggcc agggcaccac agtgactgtg tccagcgcct    420
ccaccaaggt accatccgtt ctctagtagc tagctagcta acg                      463

<210> SEQ ID NO 145
<211> LENGTH: 463
<212> TYPE: DNA
<213> ORGANISM: Artificial Sequence
<220> FEATURE:
<223> OTHER INFORMATION: Humanized heavy chain variable region

<400> SEQUENCE: 145
gcagtcatgc tactgccttc ctgaacgtaa cttacggtgt ccactcccag gtgaccctga     60
aagagagcgg ccctggcatc ctgaagccat ctcagaccct gagcctgacc tgcaccttct    120
ctggcttcag cctgtccacc agcggcatgg gcgtgggctg gttccggcag ccccctggca    180
aaggcctgga gtggctggcc cacatctggt gggatgatga caagagctac aacccatccc    240
tgaagagccg gctgaccatc tccaaagaca ccagcaagaa ccaggtggtg ctgaccatca    300
ccaacatgga ccctgtggac acagccacct actactgtgc ccggcggcag ctgggcctgc    360
ggtccatcga tgccatggac tactggggcc agggcaccac agtgactgtg tccagcgcct    420
ccaccaaggt accatccgtt ctctagtagc tagctagcta acg                      463

<210> SEQ ID NO 146
<211> LENGTH: 389
<212> TYPE: DNA
<213> ORGANISM: Artificial Sequence
<220> FEATURE:
<223> OTHER INFORMATION: Humanized light chain variable region

<400> SEQUENCE: 146
gctgtggctt acacctgccc agatgtgatg tggtgatgac ccagagcccc ctgtccctgc     60
ctgtgagcct gggcgaccct gcctccatca gctgccggtc cagccagtcc atcctgcaca    120
gcaatggcaa cacctacctg gagtggtacc tgcagaagcc tggccagtcc ccccagctgc    180
tgatctacaa agtgagcaac cggttctctg gcgtgcctga ccggttctct ggcagcggca    240
gcggcacaga cttcaccctg aagatctccc gcgtggaggc tgaagacctg ggcgtctact    300
actgcttcca gggcagcctg gtgccccctga ccttttggcgc tggcaccaag ctggagctga    360
agcggacggt ggcaggtgca tctgtcttc                                      389

<210> SEQ ID NO 147
<211> LENGTH: 447
<212> TYPE: DNA
<213> ORGANISM: Artificial Sequence
<220> FEATURE:
<223> OTHER INFORMATION: Humanized heavy chain variable region

<400> SEQUENCE: 147
actccgaggt gacgccgagt gacttgcctc actagacccc aggtgaccct gaaagaatcc     60
ggccctggca ttgtgcagcc cagccagacc ctgtccctga cctgctcctt ctctggcttc    120
agcctgtcca cctccggcat gggcgtgagc tggattcggc agccctctgg caaaggcctg    180
gagtggctgg cccacatcta ctgggatgat gacaagcagt acaacccag cctgaagtcc    240 cggctgacca tcagcaaaga cacctccaag aaccaggtct cctgaccat cacctctgtg    300 gacacagtgg acacagccac ctactactgt gtgagacgcg ccagctccag ccggtatgat    360
gaccagtttg actactgggg ccagggcacc cccctgacag tctccagcgc gaggtgacgc    420
cgagtgactt gcctctctag tcgatgt                                        447
```

<210> SEQ ID NO 148
<211> LENGTH: 447
<212> TYPE: DNA
<213> ORGANISM: Artificial Sequence
<220> FEATURE:
<223> OTHER INFORMATION: Humanized heavy chain variable region

<400> SEQUENCE: 148

```
actccgaggt gacgccgagt gacttgcctc actagacccc aggtgaccct gaaagaatcc      60
ggccctggcc tggtgaagcc cacccagacc ctgtccctga cctgctcctt ctctggcttc     120
agcctgtcca cctccggcat gggcgtgagc tggattcggc agccctctgg caaaggcctg     180
gagtggctgg cccacatcta ctgggatgat gacaagcagt acaacccag cctgaagtcc      240
cggctgacca tcagcaaaga cacctccaag aaccaggtct tcctgaccat cacctctgtg     300
gaccctgtgg acacagccac ctactactgt gtgagacgcg ccagctccag ccggtatgat     360
gaccagtttg actactgggg ccagggcacc cccctgacag tctccagcgc gaggtgacgc     420
cgagtgactt gcctctctag tcgatgt                                         447
```

<210> SEQ ID NO 149
<211> LENGTH: 447
<212> TYPE: DNA
<213> ORGANISM: Artificial Sequence
<220> FEATURE:
<223> OTHER INFORMATION: Humanized heavy chain variable region

<400> SEQUENCE: 149

```
actccgaggt gacgccgagt gacttgcctc actagacccc aggtgaccct gaaagaatcc      60
ggccctggcc tggtgaagcc cacccagacc ctgtccctga cctgctcctt ctctggcttc     120
agcctgtcca cctccggcat gggcgtgagc tggattcggc agccctctgg caaaggcctg     180
gagtggctgg cccacatcta ctgggatgat gacaagcagt acaacccag cctgaagtcc      240
cggctgacca tcagcaaaga cacctccaag aaccaggtcg tgctgaccat cacctctgtg     300
gaccctgtgg acacagccac ctactactgt gtgagacgcg ccagctccag ccggtatgat     360
gaccagtttg actactgggg ccagggcacc ctgctgacag tctccagcgc gaggtgacgc     420
cgagtgactt gcctctctag tcgatgt                                         447
```

<210> SEQ ID NO 150
<211> LENGTH: 371
<212> TYPE: DNA
<213> ORGANISM: Artificial Sequence
<220> FEATURE:
<223> OTHER INFORMATION: Humanized light chain variable region

<400> SEQUENCE: 150

```
gtcacctgcc cagatgtgat gtggtgatga cccagacccc cctgtccctg cctgtgagcc      60
tgggcgaccc tgcctccatc agctgccgcg cctcccagag cattgtgcac agcaatggca     120
acacctacct ggagtggtac ctgcaaaaagc ctggccagtc ccccaagctg ctgatctacc     180
gcgtgagcaa ccggttctct ggcgtgcctg accgcttctc tggctctggc tctggcacag     240
acttcaccct gaagatcagc cgcgtggaag ctgaagacct gggcgtctac ttctgcttcc     300
aggtgaccca tgtgcccctg acctttggcg ctggcaccaa actggaactg aaacgtacgg     360
tggcaggtga t                                                          371
```

<210> SEQ ID NO 151

```
<211> LENGTH: 371
<212> TYPE: DNA
<213> ORGANISM: Artificial Sequence
<220> FEATURE:
<223> OTHER INFORMATION: Humanized light chain variable region

<400> SEQUENCE: 151
gtcacctgcc cagatgtgat gtggtgatga cccagacccc cctgtccctg cctgtgagcc      60
tgggcgaccc tgcctccatc agctgccgcg cctcccagag cattgtgcac agcaatggca     120
acacctacct ggagtggtac ctgcaaaagc ctggccagtc ccccaagctg ctgatctacc     180
gcgtgagcaa ccggttctct ggcgtgcctg accgcttctc tggctctggc tctggcacag     240
acttcaccct gaagatcagc cgcgtggaag ctgaagacgt gggcgtctac ttctgcttcc     300
aggtgaccca tgtgccctg  accttggcg gcggcaccaa actggaactg aaacgtacgg     360
tggcaggtga t                                                          371

<210> SEQ ID NO 152
<211> LENGTH: 453
<212> TYPE: PRT
<213> ORGANISM: Artificial Sequence
<220> FEATURE:
<223> OTHER INFORMATION: Humanized IgG1 heavy chain variable region

<400> SEQUENCE: 152

Gln Val Thr Leu Lys Glu Ser Gly Pro Ala Leu Val Lys Pro Thr Gln
 1               5                  10                  15

Thr Leu Thr Leu Thr Cys Thr Phe Ser Gly Phe Ser Leu Ser Thr Ser
                20                  25                  30

Gly Met Gly Val Gly Trp Ile Arg Gln Pro Pro Gly Lys Ala Leu Glu
            35                  40                  45

Trp Leu Ala His Ile Trp Trp Asp Asp Lys Ser Tyr Asn Pro Ser
        50                  55                  60

Leu Lys Ser Arg Leu Thr Ile Ser Lys Asp Thr Ser Lys Asn Gln Val
 65                  70                  75                  80

Val Leu Thr Met Thr Asn Met Asp Pro Val Asp Thr Ala Thr Tyr Tyr
                 85                  90                  95

Cys Ala Arg Arg Gln Leu Gly Leu Arg Ser Ile Asp Ala Met Asp Tyr
            100                 105                 110

Trp Gly Gln Gly Thr Thr Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Arg Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255
```

```
Leu Met Ile Ser Arg Thr Pro Glu Val Thr Cys Val Val Asp Val
            260                 265                 270

Ser His Glu Asp Pro Glu Val Lys Phe Asn Trp Tyr Val Asp Gly Val
            275                 280                 285

Glu Val His Asn Ala Lys Thr Lys Pro Arg Glu Glu Gln Tyr Asn Ser
            290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
                340                 345                 350

Gln Val Tyr Thr Leu Pro Pro Ser Arg Glu Glu Met Thr Lys Asn Gln
            355                 360                 365

Val Ser Leu Thr Cys Leu Val Lys Gly Phe Tyr Pro Ser Asp Ile Ala
            370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
                420                 425                 430

Val Met His Glu Ala Leu His Asn His Tyr Thr Gln Lys Ser Leu Ser
                435                 440                 445

Leu Ser Pro Gly Lys
    450

<210> SEQ ID NO 153
<211> LENGTH: 453
<212> TYPE: PRT
<213> ORGANISM: Artificial Sequence
<220> FEATURE:
<223> OTHER INFORMATION: Humanized IgG1 heavy chain variable region

<400> SEQUENCE: 153

Gln Val Thr Leu Lys Glu Ser Gly Pro Ala Leu Val Lys Pro Thr Gln
1               5                   10                  15

Thr Leu Thr Leu Thr Cys Thr Leu Ser Gly Phe Ser Leu Ser Thr Ser
            20                  25                  30

Gly Met Gly Val Gly Trp Ile Arg Gln Pro Pro Gly Lys Ala Leu Glu
            35                  40                  45

Trp Leu Ala His Ile Trp Trp Asp Asp Lys Ser Tyr Asn Pro Ser
    50                  55                  60

Leu Lys Ser Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Arg Gln Leu Gly Leu Arg Ser Ile Asp Ala Met Asp Tyr
                100                 105                 110

Trp Gly Gln Gly Thr Thr Val Thr Val Ser Ser Ala Ser Thr Lys Gly
            115                 120                 125

Pro Ser Val Phe Pro Leu Ala Pro Ser Ser Lys Ser Thr Ser Gly Gly
            130                 135                 140

Thr Ala Ala Leu Gly Cys Leu Val Lys Asp Tyr Phe Pro Glu Pro Val
145                 150                 155                 160
```

```
Thr Val Ser Trp Asn Ser Gly Ala Leu Thr Ser Gly Val His Thr Phe
            165                 170                 175

Pro Ala Val Leu Gln Ser Ser Gly Leu Tyr Ser Leu Ser Ser Val Val
        180                 185                 190

Thr Val Pro Ser Ser Ser Leu Gly Thr Gln Thr Tyr Ile Cys Asn Val
    195                 200                 205

Asn His Lys Pro Ser Asn Thr Lys Val Asp Lys Arg Val Glu Pro Lys
210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
    450

<210> SEQ ID NO 154
<211> LENGTH: 449
<212> TYPE: PRT
<213> ORGANISM: Artificial Sequence
<220> FEATURE:
<223> OTHER INFORMATION: Humanized IgG2M4 heavy chain variable region

<400> SEQUENCE: 154

Gln Val Thr Leu Lys Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Met Gly Val Gly Trp Ile Arg Gln Pro Pro Gly Lys Ala Leu Glu
        35                  40                  45

Trp Leu Ala His Ile Trp Trp Asp Asp Asp Lys Ser Tyr Asn Pro Ser
    50                  55                  60
```

```
Leu Lys Ser Arg Leu Thr Ile Ser Lys Asp Thr Ser Lys Asn Gln Val
 65                  70                  75                  80

Val Leu Thr Met Thr Asn Met Asp Pro Val Asp Thr Ala Thr Tyr Tyr
                 85                  90                  95

Cys Ala Arg Arg Gln Leu Gly Leu Arg Ser Ile Asp Ala Met Asp Tyr
            100                 105                 110

Trp Gly Gln Gly Thr Thr Val Thr Val Ser Ser Ala Ser Thr Lys Gly
        115                 120                 125

Pro Ser Val Phe Pro Leu Ala Pro Cys Ser Arg Ser Thr Ser Glu Ser
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Thr Ser Ser Asn Phe Gly Thr Gln Thr Tyr Thr Cys Asn Val
        195                 200                 205

Asp His Lys Pro Ser Asn Thr Lys Val Asp Lys Thr Val Glu Arg Lys
    210                 215                 220

Cys Cys Val Glu Cys Pro Pro Cys Pro Ala Pro Pro Val Ala Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Gln Glu Asp
            260                 265                 270

Pro Glu Val Gln Phe Asn Trp Tyr Val Asp Gly Val Glu Val His Asn
        275                 280                 285

Ala Lys Thr Lys Pro Arg Glu Glu Gln Phe Asn Ser Thr Phe Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
                325                 330                 335

Thr Ile Ser Lys Thr Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Met Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 155
<211> LENGTH: 449
<212> TYPE: PRT
```

<213> ORGANISM: Artificial Sequence
<220> FEATURE:
<223> OTHER INFORMATION: Humanized IgG2M4 heavy chain variable region

<400> SEQUENCE: 155

```
Gln Val Thr Leu Lys Glu Ser Gly Pro Ala Leu Val Lys Pro Thr Gln
 1               5                   10                  15

Thr Leu Thr Leu Thr Cys Thr Leu Ser Gly Phe Ser Leu Ser Thr Ser
             20                  25                  30

Gly Met Gly Val Gly Trp Ile Arg Gln Pro Pro Gly Lys Ala Leu Glu
         35                  40                  45

Trp Leu Ala His Ile Trp Trp Asp Asp Lys Ser Tyr Asn Pro Ser
50                  55                  60

Leu Lys Ser Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                 85                  90                  95

Cys Ala Arg Arg Gln Leu Gly Leu Arg Ser Ile Asp Ala Met Asp Tyr
            100                 105                 110

Trp Gly Gln Gly Thr Thr Val Thr Val Ser Ser Ala Ser Thr Lys Gly
        115                 120                 125

Pro Ser Val Phe Pro Leu Ala Pro Cys Ser Arg Ser Thr Ser Glu Ser
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Thr Ser Ser Asn Phe Gly Thr Gln Thr Tyr Thr Cys Asn Val
        195                 200                 205

Asp His Lys Pro Ser Asn Thr Lys Val Asp Lys Thr Val Glu Arg Lys
    210                 215                 220

Cys Cys Val Glu Cys Pro Pro Cys Pro Ala Pro Pro Val Ala Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Gln Glu Asp
            260                 265                 270

Pro Glu Val Gln Phe Asn Trp Tyr Val Asp Gly Val Glu Val His Asn
        275                 280                 285

Ala Lys Thr Lys Pro Arg Glu Glu Gln Phe Asn Ser Thr Phe Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
                325                 330                 335

Thr Ile Ser Lys Thr Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Met Leu
```

```
                385                 390                 395                 400
Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 156
<211> LENGTH: 219
<212> TYPE: PRT
<213> ORGANISM: Artificial Sequence
<220> FEATURE:
<223> OTHER INFORMATION: Humanized kappa light chain variable region

<400> SEQUENCE: 156

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Ile Leu His Ser
            20                  25                  30

Asn Gly Asn Thr Tyr Leu Glu Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser Leu Val Pro Leu Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Ser Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 157
<211> LENGTH: 453
<212> TYPE: PRT
<213> ORGANISM: Artificial Sequence
<220> FEATURE:
<223> OTHER INFORMATION: Humanized IgG1 heavy chain variable region

<400> SEQUENCE: 157

Gln Val Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Ser Thr Ser
```

-continued

```
                 20                  25                  30
Gly Met Gly Val Ser Trp Ile Arg Gln Pro Pro Gly Lys Ala Leu Glu
             35                  40                  45

Trp Leu Ala His Ile Tyr Trp Asp Asp Lys Gln Tyr Asn Pro Ser
 50                  55                  60

Leu Lys Ser Arg Leu Thr Ile Thr Lys Asp Thr Ser Lys Asn Gln Val
 65                  70                  75                  80

Val Leu Thr Met Thr Asn Met Asp Pro Val Asp Thr Ala Thr Tyr Tyr
                 85                  90                  95

Cys Ala Arg Arg Ala Ser Ser Ser Arg Tyr Asp Asp Gln Phe Asp Tyr
                100                 105                 110

Trp Gly Gln Gly Thr Leu Val Pro Val Ser Ser Ala Ser Thr Lys Gly
                115                 120                 125

Pro Ser Val Phe Pro Leu Ala Pro Ser Ser Lys Ser Thr Ser Gly Gly
                130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
                180                 185                 190

Thr Val Pro Ser Ser Ser Leu Gly Thr Gln Thr Tyr Ile Cys Asn Val
                195                 200                 205

Asn His Lys Pro Ser Asn Thr Lys Val Asp Lys Arg Val Glu Pro Lys
                210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
                260                 265                 270

Ser His Glu Asp Pro Glu Val Lys Phe Asn Trp Tyr Val Asp Gly Val
                275                 280                 285

Glu Val His Asn Ala Lys Thr Lys Pro Arg Glu Glu Gln Tyr Asn Ser
                290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
                340                 345                 350

Gln Val Tyr Thr Leu Pro Pro Ser Arg Glu Glu Met Thr Lys Asn Gln
                355                 360                 365

Val Ser Leu Thr Cys Leu Val Lys Gly Phe Tyr Pro Ser Asp Ile Ala
                370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
                420                 425                 430

Val Met His Glu Ala Leu His Asn His Tyr Thr Gln Lys Ser Leu Ser
                435                 440                 445
```

```
Leu Ser Pro Gly Lys
    450

<210> SEQ ID NO 158
<211> LENGTH: 449
<212> TYPE: PRT
<213> ORGANISM: Artificial Sequence
<220> FEATURE:
<223> OTHER INFORMATION: Humanized IgG2M4 heavy chain variable region

<400> SEQUENCE: 158

Gln Val Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Met Gly Val Ser Trp Ile Arg Gln Pro Pro Gly Lys Ala Leu Glu
        35                  40                  45

Trp Leu Ala His Ile Tyr Trp Asp Asp Lys Gln Tyr Asn Pro Ser
    50                  55                  60

Leu Lys Ser Arg Leu Thr Ile Thr Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Arg Ala Ser Ser Arg Tyr Asp Asp Gln Phe Asp Tyr
            100                 105                 110

Trp Gly Gln Gly Thr Leu Val Pro Val Ser Ser Ala Ser Thr Lys Gly
        115                 120                 125

Pro Ser Val Phe Pro Leu Ala Pro Cys Ser Arg Ser Thr Ser Glu Ser
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Thr Ser Ser Asn Phe Gly Thr Gln Thr Tyr Thr Cys Asn Val
        195                 200                 205

Asp His Lys Pro Ser Asn Thr Lys Val Asp Lys Thr Val Glu Arg Lys
    210                 215                 220

Cys Cys Val Glu Cys Pro Pro Cys Pro Ala Pro Val Ala Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Gln Glu Asp
            260                 265                 270

Pro Glu Val Gln Phe Asn Trp Tyr Val Asp Gly Val Glu Val His Asn
        275                 280                 285

Ala Lys Thr Lys Pro Arg Glu Glu Gln Phe Asn Ser Thr Phe Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
                325                 330                 335

Thr Ile Ser Lys Thr Lys Gly Gln Pro Arg Glu Pro Gln Val Tyr Thr
            340                 345                 350
```

-continued

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Met Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 159
<211> LENGTH: 219
<212> TYPE: PRT
<213> ORGANISM: Artificial Sequence
<220> FEATURE:
<223> OTHER INFORMATION: Humanized kappa light chain variable region

<400> SEQUENCE: 159

Asp Val Val Met Thr Gln Ser Pro Leu Ser Leu Pro Val Thr Pro Gly
1               5                   10                  15

Glu Pro Ala Ser Ile Ser Cys Arg Ala Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Gln Leu Leu Ile Tyr Arg Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Val
                85                  90                  95

Thr His Val Pro Leu Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 160
<211> LENGTH: 454
<212> TYPE: PRT
<213> ORGANISM: Artificial Sequence
<220> FEATURE:

<223> OTHER INFORMATION: Humanized IgG1 heavy chain variable region

<400> SEQUENCE: 160

```
Gln Val Thr Leu Lys Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Met Gly Val Gly Trp Ile Arg Gln Pro Pro Gly Lys Ala Leu Glu
        35                  40                  45

Trp Leu Ala His Ile Trp Trp Asp Asp Lys Tyr Tyr Asn Pro Ser
    50                  55                  60

Leu Lys Ser Gln Leu Thr Ile Ser Lys Asp Thr Ser Lys Asn Gln Val
65              70                  75                  80

Val Leu Thr Met Thr Asn Met Asp Pro Val Asp Thr Ala Thr Tyr Tyr
                85                  90                  95

Cys Ala Arg Arg Ser Ile Asn Ser Val Val Pro Glu Asp Tyr Phe Asp
            100                 105                 110

Tyr Trp Gly Gln Gly Thr Thr Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Arg Val Glu Pro
    210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Asn
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
            340                 345                 350

Pro Gln Val Tyr Thr Leu Pro Pro Ser Arg Glu Glu Met Thr Lys Asn
        355                 360                 365

Gln Val Ser Leu Thr Cys Leu Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400
```

-continued

```
Thr Pro Pro Val Leu Asp Ser Asp Gly Ser Phe Phe Leu Tyr Ser Lys
            405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
            435                 440                 445

Ser Leu Ser Pro Gly Lys
            450

<210> SEQ ID NO 161
<211> LENGTH: 219
<212> TYPE: PRT
<213> ORGANISM: Artificial Sequence
<220> FEATURE:
<223> OTHER INFORMATION: Humanized kappa light chain variable region

<400> SEQUENCE: 161

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Leu Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 162
<211> LENGTH: 447
<212> TYPE: PRT
<213> ORGANISM: Artificial Sequence
<220> FEATURE:
<223> OTHER INFORMATION: Humanized IgG1 heavy chain variable region

<400> SEQUENCE: 162

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30
```

-continued

```
Gly Met His Trp Val Arg Gln Ala Pro Gly Lys Gly Leu Glu Trp Val
         35                  40                  45

Ala Tyr Ile Ser Arg Gly Ser Ser Thr Ile Tyr Tyr Ala Asp Thr Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
             85                  90                  95

Ala Arg Gly Ile Thr Thr Ala Leu Asp Tyr Trp Gly Gln Gly Thr Leu
             100                 105                 110

Val Thr Val Ser Ser Ala Ser Thr Lys Gly Pro Ser Val Phe Pro Leu
         115                 120                 125

Ala Pro Ser Ser Lys Ser Thr Ser Gly Gly Thr Ala Ala Leu Gly Cys
 130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
             165                 170                 175

Ser Gly Leu Tyr Ser Leu Ser Ser Val Val Thr Val Pro Ser Ser Ser
             180                 185                 190

Leu Gly Thr Gln Thr Tyr Ile Cys Asn Val Asn His Lys Pro Ser Asn
         195                 200                 205

Thr Lys Val Asp Lys Arg Val Glu Pro Lys Ser Cys Asp Lys Thr His
 210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
             245                 250                 255

Pro Glu Val Thr Cys Val Val Val Asp Val Ser His Glu Asp Pro Glu
             260                 265                 270

Val Lys Phe Asn Trp Tyr Val Asp Gly Val Glu Val His Asn Ala Lys
         275                 280                 285

Thr Lys Pro Arg Glu Glu Gln Tyr Asn Ser Thr Tyr Arg Val Val Ser
 290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
             325                 330                 335

Ser Lys Ala Lys Gly Gln Pro Arg Glu Pro Gln Val Tyr Thr Leu Pro
             340                 345                 350

Pro Ser Arg Glu Glu Met Thr Lys Asn Gln Val Ser Leu Thr Cys Leu
         355                 360                 365

Val Lys Gly Phe Tyr Pro Ser Asp Ile Ala Val Glu Trp Glu Ser Asn
 370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
             405                 410                 415

Trp Gln Gln Gly Asn Val Phe Ser Cys Ser Val Met His Glu Ala Leu
             420                 425                 430

His Asn His Tyr Thr Gln Lys Ser Leu Ser Leu Ser Pro Gly Lys
         435                 440                 445
```

```
<210> SEQ ID NO 163
<211> LENGTH: 219
<212> TYPE: PRT
<213> ORGANISM: Artificial Sequence
<220> FEATURE:
<223> OTHER INFORMATION: Humanized kappa light chain variable region

<400> SEQUENCE: 163

Asp Val Val Met Thr Gln Ser Pro Leu Ser Leu Pro Val Thr Pro Gly
1               5                   10                  15

Glu Pro Ala Ser Ile Ser Cys Arg Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Gln Leu Leu Ile Tyr Lys Ala Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Pro Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 164
<211> LENGTH: 451
<212> TYPE: PRT
<213> ORGANISM: Artificial Sequence
<220> FEATURE:
<223> OTHER INFORMATION: Humanized IgG1 heavy chain variable region

<400> SEQUENCE: 164

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Gly Met His Trp Val Arg Gln Ala Pro Gly Lys Gly Leu Glu Trp Val
        35                  40                  45

Ala Tyr Ile Arg Ser Gly Ser Ser Thr Ile Tyr Tyr Ala Asp Thr Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95
```

```
Ala Arg Gly Gly Asn Tyr Tyr Gly Ser Ser Arg Phe Ala Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 165
<211> LENGTH: 214
<212> TYPE: PRT
<213> ORGANISM: Artificial Sequence
<220> FEATURE:
<223> OTHER INFORMATION: Humanized kappa light chain variable region

<400> SEQUENCE: 165
```

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Asn Ser Tyr
            20                  25                  30

Leu Ser Trp Phe Gln Gln Lys Pro Gly Lys Ala Pro Lys Thr Leu Ile
        35                  40                  45

Tyr Arg Ala Asn Arg Phe Val Asp Gly Val Pro Ser Arg Phe Ser Gly
50                  55                  60

Ser Gly Ser Gly Thr Asp Tyr Thr Leu Thr Ile Ser Ser Leu Gln Pro
65                  70                  75                  80

Glu Asp Phe Ala Thr Tyr Phe Cys Leu Gln Tyr Asp Glu Phe Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
        210

<210> SEQ ID NO 166
<211> LENGTH: 452
<212> TYPE: PRT
<213> ORGANISM: Artificial Sequence
<220> FEATURE:
<223> OTHER INFORMATION: Humanized IgG1 heavy chain variable region

<400> SEQUENCE: 166

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Gly Met His Trp Val Arg Gln Ala Pro Gly Lys Gly Leu Glu Trp Val
        35                  40                  45

Ala Tyr Ile Ser Ser Val Ser Ser Thr Ile Tyr Tyr Ala Asp Thr Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Gly Tyr Gly Ser Ser Tyr Gly Tyr Gly Met Asp Tyr Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
130                 135                 140
```

```
Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
            165                 170                 175

Ala Val Leu Gln Ser Ser Gly Leu Tyr Ser Leu Ser Ser Val Val Thr
        180                 185                 190

Val Pro Ser Ser Ser Leu Gly Thr Gln Thr Tyr Ile Cys Asn Val Asn
    195                 200                 205

His Lys Pro Ser Asn Thr Lys Val Asp Lys Arg Val Glu Pro Lys Ser
210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
            245                 250                 255

Met Ile Ser Arg Thr Pro Glu Val Thr Cys Val Val Val Asp Val Ser
        260                 265                 270

His Glu Asp Pro Glu Val Lys Phe Asn Trp Tyr Val Asp Gly Val Glu
    275                 280                 285

Val His Asn Ala Lys Thr Lys Pro Arg Glu Glu Gln Tyr Asn Ser Thr
290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
            325                 330                 335

Ile Glu Lys Thr Ile Ser Lys Ala Lys Gly Gln Pro Arg Glu Pro Gln
        340                 345                 350

Val Tyr Thr Leu Pro Pro Ser Arg Glu Glu Met Thr Lys Asn Gln Val
    355                 360                 365

Ser Leu Thr Cys Leu Val Lys Gly Phe Tyr Pro Ser Asp Ile Ala Val
370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
            405                 410                 415

Val Asp Lys Ser Arg Trp Gln Gln Gly Asn Val Phe Ser Cys Ser Val
        420                 425                 430

Met His Glu Ala Leu His Asn His Tyr Thr Gln Lys Ser Leu Ser Leu
    435                 440                 445

Ser Pro Gly Lys
    450

<210> SEQ ID NO 167
<211> LENGTH: 453
<212> TYPE: PRT
<213> ORGANISM: Artificial Sequence
<220> FEATURE:
<223> OTHER INFORMATION: Humanized IgG1 heavy chain variable region

<400> SEQUENCE: 167

Gln Val Thr Leu Lys Glu Ser Gly Pro Gly Ile Leu Lys Pro Ser Gln
1               5                   10                  15

Thr Leu Ser Leu Thr Cys Thr Phe Ser Gly Phe Ser Leu Ser Thr Ser
            20                  25                  30

Gly Met Gly Val Gly Trp Phe Arg Gln Pro Pro Gly Lys Gly Leu Glu
        35                  40                  45
```

```
Trp Leu Ala His Ile Trp Trp Asp Asp Lys Ser Tyr Asn Pro Ser
    50                  55                  60

Leu Lys Ser Arg Leu Thr Ile Ser Lys Asp Thr Ser Lys Asn Gln Val
65                  70                  75                  80

Phe Leu Thr Ile Thr Asn Met Asp Pro Val Asp Thr Ala Thr Tyr Tyr
                85                  90                  95

Cys Ala Arg Arg Gln Leu Gly Leu Arg Ser Ile Asp Ala Met Asp Tyr
            100                 105                 110

Trp Gly Gln Gly Thr Thr Val Thr Val Ser Ser Ala Ser Thr Lys Gly
            115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Arg Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
        355                 360                 365

Val Ser Leu Thr Cys Leu Val Lys Gly Phe Tyr Pro Ser Asp Ile Ala
370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
    450
```

-continued

```
<210> SEQ ID NO 168
<211> LENGTH: 452
<212> TYPE: PRT
<213> ORGANISM: Artificial Sequence
<220> FEATURE:
<223> OTHER INFORMATION: Humanized IgG1 heavy chain variable region

<400> SEQUENCE: 168
```

| | | | | | | | | | | | | | | |
|---|---|---|---|---|---|---|---|---|---|---|---|---|---|---|
| Gln | Val | Thr | Leu | Lys | Glu | Ser | Gly | Pro | Gly | Ile | Leu | Lys | Pro | Ser | Gln |
| 1 | | | | 5 | | | | | 10 | | | | | 15 | |
| Thr | Leu | Ser | Leu | Thr | Cys | Thr | Phe | Ser | Gly | Phe | Ser | Leu | Ser | Thr | Ser |
| | | | 20 | | | | | 25 | | | | | 30 | | |
| Gly | Met | Gly | Val | Gly | Trp | Phe | Arg | Gln | Pro | Pro | Gly | Lys | Gly | Leu | Glu |
| | | 35 | | | | | 40 | | | | | 45 | | | |
| Trp | Leu | Ala | His | Ile | Trp | Trp | Asp | Asp | Lys | Ser | Tyr | Asn | Pro | Ser |
| | 50 | | | | | 55 | | | | | 60 | | | | |
| Leu | Lys | Ser | Arg | Leu | Ile | Ser | Lys | Asp | Thr | Ser | Lys | Asn | Gln | Val | Val |
| 65 | | | | | 70 | | | | | 75 | | | | | 80 |
| Leu | Thr | Ile | Thr | Asn | Met | Asp | Pro | Val | Asp | Thr | Ala | Thr | Tyr | Tyr | Cys |
| | | | | 85 | | | | | 90 | | | | | 95 | |
| Ala | Arg | Arg | Gln | Leu | Gly | Leu | Arg | Ser | Ile | Asp | Ala | Met | Asp | Tyr | Trp |
| | | | 100 | | | | | 105 | | | | | 110 | | |
| Gly | Gln | Gly | Thr | Thr | Val | Thr | Val | Ser | Ser | Ala | Ser | Thr | Lys | Gly | Pro |
| | | 115 | | | | | 120 | | | | | 125 | | | |
| Ser | Val | Phe | Pro | Leu | Ala | Pro | Ser | Ser | Lys | Ser | Thr | Ser | Gly | Gly | Thr |
| | 130 | | | | | 135 | | | | | 140 | | | | |
| Ala | Ala | Leu | Gly | Cys | Leu | Val | Lys | Asp | Tyr | Phe | Pro | Glu | Pro | Val | Thr |
| 145 | | | | | 150 | | | | | 155 | | | | | 160 |
| Val | Ser | Trp | Asn | Ser | Gly | Ala | Leu | Thr | Ser | Gly | Val | His | Thr | Phe | Pro |
| | | | | 165 | | | | | 170 | | | | | 175 | |
| Ala | Val | Leu | Gln | Ser | Ser | Gly | Leu | Tyr | Ser | Leu | Ser | Ser | Val | Val | Thr |
| | | | 180 | | | | | 185 | | | | | 190 | | |
| Val | Pro | Ser | Ser | Ser | Leu | Gly | Thr | Gln | Thr | Tyr | Ile | Cys | Asn | Val | Asn |
| | | 195 | | | | | 200 | | | | | 205 | | | |
| His | Lys | Pro | Ser | Asn | Thr | Lys | Val | Asp | Lys | Arg | Val | Glu | Pro | Lys | Ser |
| | 210 | | | | | 215 | | | | | 220 | | | | |
| Cys | Asp | Lys | Thr | His | Thr | Cys | Pro | Pro | Cys | Pro | Ala | Pro | Glu | Leu | Leu |
| 225 | | | | | 230 | | | | | 235 | | | | | 240 |
| Gly | Gly | Pro | Ser | Val | Phe | Leu | Phe | Pro | Pro | Lys | Pro | Lys | Asp | Thr | Leu |
| | | | | 245 | | | | | 250 | | | | | 255 | |
| Met | Ile | Ser | Arg | Thr | Pro | Glu | Val | Thr | Cys | Val | Val | Val | Asp | Val | Ser |
| | | | 260 | | | | | 265 | | | | | 270 | | |
| His | Glu | Asp | Pro | Glu | Val | Lys | Phe | Asn | Trp | Tyr | Val | Asp | Gly | Val | Glu |
| | | 275 | | | | | 280 | | | | | 285 | | | |
| Val | His | Asn | Ala | Lys | Thr | Lys | Pro | Arg | Glu | Glu | Gln | Tyr | Asn | Ser | Thr |
| | 290 | | | | | 295 | | | | | 300 | | | | |
| Tyr | Arg | Val | Val | Ser | Val | Leu | Thr | Val | Leu | His | Gln | Asp | Trp | Leu | Asn |
| 305 | | | | | 310 | | | | | 315 | | | | | 320 |
| Gly | Lys | Glu | Tyr | Lys | Cys | Lys | Val | Ser | Asn | Lys | Ala | Leu | Pro | Ala | Pro |
| | | | | 325 | | | | | 330 | | | | | 335 | |
| Ile | Glu | Lys | Thr | Ile | Ser | Lys | Ala | Lys | Gly | Gln | Pro | Arg | Glu | Pro | Gln |
| | | | 340 | | | | | 345 | | | | | 350 | | |
| Val | Tyr | Thr | Leu | Pro | Pro | Ser | Arg | Glu | Glu | Met | Thr | Lys | Asn | Gln | Val |
| | | 355 | | | | | 360 | | | | | 365 | | | |

```
Ser Leu Thr Cys Leu Val Lys Gly Phe Tyr Pro Ser Asp Ile Ala Val
        370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly Lys
    450

<210> SEQ ID NO 169
<211> LENGTH: 449
<212> TYPE: PRT
<213> ORGANISM: Artificial Sequence
<220> FEATURE:
<223> OTHER INFORMATION: Humanized IgG2M4 heavy chain variable region

<400> SEQUENCE: 169

Gln Val Thr Leu Lys Glu Ser Gly Pro Gly Ile Leu Lys Pro Ser Gln
1               5                   10                  15

Thr Leu Ser Leu Thr Cys Thr Phe Ser Gly Phe Ser Leu Ser Thr Ser
            20                  25                  30

Gly Met Gly Val Gly Trp Phe Arg Gln Pro Pro Gly Lys Gly Leu Glu
        35                  40                  45

Trp Leu Ala His Ile Trp Trp Asp Asp Lys Ser Tyr Asn Pro Ser
50                  55                  60

Leu Lys Ser Arg Leu Thr Ile Ser Lys Asp Thr Ser Lys Asn Gln Val
65                  70                  75                  80

Phe Leu Thr Ile Thr Asn Met Asp Pro Val Asp Thr Ala Thr Tyr Tyr
                85                  90                  95

Cys Ala Arg Arg Gln Leu Gly Leu Arg Ser Ile Asp Ala Met Asp Tyr
            100                 105                 110

Trp Gly Gln Gly Thr Thr Val Thr Val Ser Ser Ala Ser Thr Lys Gly
        115                 120                 125

Pro Ser Val Phe Pro Leu Ala Pro Cys Ser Arg Ser Thr Ser Glu Ser
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Thr Ser Ser Asn Phe Gly Thr Gln Thr Tyr Thr Cys Asn Val
        195                 200                 205

Asp His Lys Pro Ser Asn Thr Lys Val Asp Lys Thr Val Glu Arg Lys
    210                 215                 220

Cys Cys Val Glu Cys Pro Pro Cys Pro Ala Pro Pro Val Ala Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Gln Glu Asp
            260                 265                 270
```

-continued

```
Pro Glu Val Gln Phe Asn Trp Tyr Val Asp Gly Val Glu Val His Asn
        275                 280                 285

Ala Lys Thr Lys Pro Arg Glu Glu Gln Phe Asn Ser Thr Phe Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
                325                 330                 335

Thr Ile Ser Lys Thr Lys Gly Gln Pro Arg Glu Pro Gln Val Tyr Thr
                340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Met Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
        435                 440                 445

Lys
```

<210> SEQ ID NO 170
<211> LENGTH: 449
<212> TYPE: PRT
<213> ORGANISM: Artificial Sequence
<220> FEATURE:
<223> OTHER INFORMATION: Humanized IgG2M4 heavy chain variable region

<400> SEQUENCE: 170

```
Gln Val Thr Leu Lys Glu Ser Gly Pro Gly Ile Leu Lys Pro Ser Gln
1               5                   10                  15

Thr Leu Ser Leu Thr Cys Thr Phe Ser Gly Phe Ser Leu Ser Thr Ser
            20                  25                  30

Gly Met Gly Val Gly Trp Phe Arg Gln Pro Pro Gly Lys Gly Leu Glu
        35                  40                  45

Trp Leu Ala His Ile Trp Trp Asp Asp Lys Ser Tyr Asn Pro Ser
50                  55                  60

Leu Lys Ser Arg Leu Thr Ile Ser Lys Asp Thr Ser Lys Asn Gln Val
65                  70                  75                  80

Val Leu Thr Ile Thr Asn Met Asp Pro Val Asp Thr Ala Thr Tyr Tyr
                85                  90                  95

Cys Ala Arg Arg Gln Leu Gly Leu Arg Ser Ile Asp Ala Met Asp Tyr
                100                 105                 110

Trp Gly Gln Gly Thr Thr Val Thr Val Ser Ser Ala Ser Thr Lys Gly
        115                 120                 125

Pro Ser Val Phe Pro Leu Ala Pro Cys Ser Arg Ser Thr Ser Glu Ser
130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
```

-continued

```
            180                 185                 190
Thr Val Thr Ser Ser Asn Phe Gly Thr Gln Thr Tyr Thr Cys Asn Val
            195                 200                 205
Asp His Lys Pro Ser Asn Thr Lys Val Asp Lys Thr Val Glu Arg Lys
210                 215                 220
Cys Cys Val Glu Cys Pro Pro Cys Pro Ala Pro Val Ala Gly Pro
225                 230                 235                 240
Ser Val Phe Leu Phe Pro Pro Lys Pro Lys Asp Thr Leu Met Ile Ser
                245                 250                 255
Arg Thr Pro Glu Val Thr Cys Val Val Val Asp Val Ser Gln Glu Asp
            260                 265                 270
Pro Glu Val Gln Phe Asn Trp Tyr Val Asp Gly Val Glu Val His Asn
            275                 280                 285
Ala Lys Thr Lys Pro Arg Glu Glu Gln Phe Asn Ser Thr Phe Arg Val
            290                 295                 300
Val Ser Val Leu Thr Val Leu His Gln Asp Trp Leu Asn Gly Lys Glu
305                 310                 315                 320
Tyr Lys Cys Lys Val Ser Asn Lys Gly Leu Pro Ser Ser Ile Glu Lys
                325                 330                 335
Thr Ile Ser Lys Thr Lys Gly Gln Pro Arg Glu Pro Gln Val Tyr Thr
            340                 345                 350
Leu Pro Pro Ser Arg Glu Glu Met Thr Lys Asn Gln Val Ser Leu Thr
            355                 360                 365
Cys Leu Val Lys Gly Phe Tyr Pro Ser Asp Ile Ala Val Glu Trp Glu
370                 375                 380
Ser Asn Gly Gln Pro Glu Asn Asn Tyr Lys Thr Thr Pro Pro Met Leu
385                 390                 395                 400
Asp Ser Asp Gly Ser Phe Phe Leu Tyr Ser Lys Leu Thr Val Asp Lys
                405                 410                 415
Ser Arg Trp Gln Gln Gly Asn Val Phe Ser Cys Ser Val Met His Glu
            420                 425                 430
Ala Leu His Asn His Tyr Thr Gln Lys Ser Leu Ser Leu Ser Pro Gly
            435                 440                 445
Lys

<210> SEQ ID NO 171
<211> LENGTH: 219
<212> TYPE: PRT
<213> ORGANISM: Artificial Sequence
<220> FEATURE:
<223> OTHER INFORMATION: Humanized kappa light chain variable region

<400> SEQUENCE: 171

Asp Val Val Met Thr Gln Ser Pro Leu Ser Leu Pro Val Ser Leu Gly
1               5                   10                  15
Asp Pro Ala Ser Ile Ser Cys Arg Ser Ser Gln Ser Ile Leu His Ser
            20                  25                  30
Asn Gly Asn Thr Tyr Leu Glu Trp Tyr Leu Gln Lys Pro Gly Gln Ser
        35                  40                  45
Pro Gln Leu Leu Ile Tyr Lys Val Ser Asn Arg Phe Ser Gly Val Pro
    50                  55                  60
Asp Arg Phe Ser Gly Ser Gly Ser Gly Thr Asp Phe Thr Leu Lys Ile
65                  70                  75                  80
Ser Arg Val Glu Ala Glu Asp Leu Gly Val Tyr Tyr Cys Phe Gln Gly
                85                  90                  95
```

-continued

Ser Leu Val Pro Leu Thr Phe Gly Ala Gly Thr Lys Leu Glu Leu Lys
                100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
        130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 172
<211> LENGTH: 453
<212> TYPE: PRT
<213> ORGANISM: Artificial Sequence
<220> FEATURE:
<223> OTHER INFORMATION: Humanized IgG1 heavy chain variable region

<400> SEQUENCE: 172

Gln Val Thr Leu Lys Glu Ser Gly Pro Gly Ile Val Gln Pro Ser Gln
1               5                   10                  15

Thr Leu Ser Leu Thr Cys Ser Phe Ser Gly Phe Ser Leu Ser Thr Ser
            20                  25                  30

Gly Met Gly Val Ser Trp Ile Arg Gln Pro Ser Gly Lys Gly Leu Glu
        35                  40                  45

Trp Leu Ala His Ile Tyr Trp Asp Asp Lys Gln Tyr Asn Pro Ser
50                  55                  60

Leu Lys Ser Arg Leu Thr Ile Ser Lys Asp Thr Ser Lys Asn Gln Val
65                  70                  75                  80

Phe Leu Thr Ile Thr Ser Val Asp Thr Val Asp Thr Ala Thr Tyr Tyr
                85                  90                  95

Cys Val Arg Arg Ala Ser Ser Arg Tyr Asp Asp Gln Phe Asp Tyr
            100                 105                 110

Trp Gly Gln Gly Thr Pro Leu Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Arg Val Glu Pro Lys
    210                 215                 220

Ser Cys Asp Lys Thr His Thr Cys Pro Pro Cys Pro Ala Pro Glu Leu
225                 230                 235                 240

```
Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
                260                 265                 270

Ser His Glu Asp Pro Glu Val Lys Phe Asn Trp Tyr Val Asp Gly Val
                275                 280                 285

Glu Val His Asn Ala Lys Thr Lys Pro Arg Glu Glu Gln Tyr Asn Ser
            290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
                340                 345                 350

Gln Val Tyr Thr Leu Pro Pro Ser Arg Glu Glu Met Thr Lys Asn Gln
                355                 360                 365

Val Ser Leu Thr Cys Leu Val Lys Gly Phe Tyr Pro Ser Asp Ile Ala
            370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
                420                 425                 430

Val Met His Glu Ala Leu His Asn His Tyr Thr Gln Lys Ser Leu Ser
            435                 440                 445

Leu Ser Pro Gly Lys
    450

<210> SEQ ID NO 173
<211> LENGTH: 453
<212> TYPE: PRT
<213> ORGANISM: Artificial Sequence
<220> FEATURE:
<223> OTHER INFORMATION: Humanized IgG1 heavy chain variable region

<400> SEQUENCE: 173

Gln Val Thr Leu Lys Glu Ser Gly Pro Gly Leu Val Lys Pro Thr Gln
1               5                   10                  15

Thr Leu Ser Leu Thr Cys Ser Phe Ser Gly Phe Ser Leu Ser Thr Ser
                20                  25                  30

Gly Met Gly Val Ser Trp Ile Arg Gln Pro Ser Gly Lys Gly Leu Glu
            35                  40                  45

Trp Leu Ala His Ile Tyr Trp Asp Asp Lys Gln Tyr Asn Pro Ser
    50                  55                  60

Leu Lys Ser Arg Leu Thr Ile Ser Lys Asp Thr Ser Lys Asn Gln Val
65                  70                  75                  80

Phe Leu Thr Ile Thr Ser Val Asp Pro Val Asp Thr Ala Thr Tyr Tyr
                85                  90                  95

Cys Val Arg Arg Ala Ser Ser Ser Arg Tyr Asp Asp Gln Phe Asp Tyr
                100                 105                 110

Trp Gly Gln Gly Thr Pro Leu Thr Val Ser Ser Ala Ser Thr Lys Gly
            115                 120                 125

Pro Ser Val Phe Pro Leu Ala Pro Ser Ser Lys Ser Thr Ser Gly Gly
        130                 135                 140
```

```
Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
            165                 170                 175

Pro Ala Val Leu Gln Ser Ser Gly Leu Tyr Ser Leu Ser Ser Val Val
        180                 185                 190

Thr Val Pro Ser Ser Ser Leu Gly Thr Gln Thr Tyr Ile Cys Asn Val
    195                 200                 205

Asn His Lys Pro Ser Asn Thr Lys Val Asp Lys Arg Val Glu Pro Lys
210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
    450

<210> SEQ ID NO 174
<211> LENGTH: 453
<212> TYPE: PRT
<213> ORGANISM: Artificial Sequence
<220> FEATURE:
<223> OTHER INFORMATION: Humanized IgG1 heavy chain variable region

<400> SEQUENCE: 174

Gln Val Thr Leu Lys Glu Ser Gly Pro Gly Leu Val Lys Pro Thr Gln
1               5                   10                  15

Thr Leu Ser Leu Thr Cys Ser Phe Ser Gly Phe Ser Leu Ser Thr Ser
            20                  25                  30

Gly Met Gly Val Ser Trp Ile Arg Gln Pro Ser Gly Lys Gly Leu Glu
        35                  40                  45
```

```
Trp Leu Ala His Ile Tyr Trp Asp Asp Lys Gln Tyr Asn Pro Ser
    50                  55                  60

Leu Lys Ser Arg Leu Thr Ile Ser Lys Asp Thr Ser Lys Asn Gln Val
65                  70                  75                  80

Val Leu Thr Ile Thr Ser Val Asp Pro Val Asp Thr Ala Thr Tyr Tyr
                85                  90                  95

Cys Val Arg Arg Ala Ser Ser Arg Tyr Asp Asp Gln Phe Asp Tyr
                100                 105                 110

Trp Gly Gln Gly Thr Leu Leu Thr Val Ser Ser Ala Ser Thr Lys Gly
                115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
                180                 185                 190

Thr Val Pro Ser Ser Ser Leu Gly Thr Gln Thr Tyr Ile Cys Asn Val
                195                 200                 205

Asn His Lys Pro Ser Asn Thr Lys Val Asp Lys Arg Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
                260                 265                 270

Ser His Glu Asp Pro Glu Val Lys Phe Asn Trp Tyr Val Asp Gly Val
    275                 280                 285

Glu Val His Asn Ala Lys Thr Lys Pro Arg Glu Glu Gln Tyr Asn Ser
290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
                340                 345                 350

Gln Val Tyr Thr Leu Pro Pro Ser Arg Glu Glu Met Thr Lys Asn Gln
                355                 360                 365

Val Ser Leu Thr Cys Leu Val Lys Gly Phe Tyr Pro Ser Asp Ile Ala
370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
                420                 425                 430

Val Met His Glu Ala Leu His Asn His Tyr Thr Gln Lys Ser Leu Ser
                435                 440                 445

Leu Ser Pro Gly Lys
    450
```

-continued

```
<210> SEQ ID NO 175
<211> LENGTH: 219
<212> TYPE: PRT
<213> ORGANISM: Artificial Sequence
<220> FEATURE:
<223> OTHER INFORMATION: Humanized kappa light chain variable region

<400> SEQUENCE: 175
```

Asp Val Val Met Thr Gln Thr Pro Leu Ser Leu Pro Val Ser Leu Gly
1               5                   10                  15

Asp Pro Ala Ser Ile Ser Cys Arg Ala Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Arg Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Phe Gln Val
                85                  90                  95

Thr His Val Pro Leu Thr Phe Gly Ala Gly Thr Lys Leu Glu Leu Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

```
<210> SEQ ID NO 176
<211> LENGTH: 219
<212> TYPE: PRT
<213> ORGANISM: Artificial Sequence
<220> FEATURE:
<223> OTHER INFORMATION: Humanized kappa light chain variable region

<400> SEQUENCE: 176
```

Asp Val Val Met Thr Gln Thr Pro Leu Ser Leu Pro Val Ser Leu Gly
1               5                   10                  15

Asp Pro Ala Ser Ile Ser Cys Arg Ala Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Arg Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Phe Cys Phe Gln Val
                85                  90                  95

Thr His Val Pro Leu Thr Phe Gly Gly Gly Thr Lys Leu Glu Leu Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 177
<211> LENGTH: 6
<212> TYPE: PRT
<213> ORGANISM: Artificial Sequence
<220> FEATURE:
<223> OTHER INFORMATION: Synthetic peptide

<400> SEQUENCE: 177

Glu Phe Arg His Asp Ser
1               5

<210> SEQ ID NO 178
<211> LENGTH: 8
<212> TYPE: PRT
<213> ORGANISM: Artificial Sequence
<220> FEATURE:
<223> OTHER INFORMATION: Synthetic peptide

<400> SEQUENCE: 178

Asp Ala Glu Phe Arg His Asp Ser
1               5

<210> SEQ ID NO 179
<211> LENGTH: 8
<212> TYPE: PRT
<213> ORGANISM: Artificial Sequence
<220> FEATURE:
<223> OTHER INFORMATION: Synthetic peptide

<400> SEQUENCE: 179

Glu Phe Arg His Asp Ser Gly Tyr
1               5

<210> SEQ ID NO 180
<211> LENGTH: 42
<212> TYPE: PRT
<213> ORGANISM: Homo sapiens

<400> SEQUENCE: 180

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val Ile Ala

```
                35                  40

<210> SEQ ID NO 181
<211> LENGTH: 7
<212> TYPE: PRT
<213> ORGANISM: Artificial Sequence
<220> FEATURE:
<223> OTHER INFORMATION: Synthetic peptide

<400> SEQUENCE: 181

Asp Ala Glu Phe Arg His Asp
1               5

<210> SEQ ID NO 182
<211> LENGTH: 9
<212> TYPE: PRT
<213> ORGANISM: Artificial Sequence
<220> FEATURE:
<223> OTHER INFORMATION: Synthetic peptide

<400> SEQUENCE: 182

Asp Ala Glu Phe Arg His Asp Ser Gly
1               5

<210> SEQ ID NO 183
<211> LENGTH: 10
<212> TYPE: PRT
<213> ORGANISM: Artificial Sequence
<220> FEATURE:
<223> OTHER INFORMATION: Synthetic peptide

<400> SEQUENCE: 183

Asp Ala Glu Phe Arg His Asp Ser Gly Tyr
1               5                   10

<210> SEQ ID NO 184
<211> LENGTH: 10
<212> TYPE: PRT
<213> ORGANISM: Artificial Sequence
<220> FEATURE:
<223> OTHER INFORMATION: Synthetic peptide

<400> SEQUENCE: 184

Ala Glu Phe Arg His Asp Ser Gly Tyr Glu
1               5                   10

<210> SEQ ID NO 185
<211> LENGTH: 10
<212> TYPE: PRT
<213> ORGANISM: Artificial Sequence
<220> FEATURE:
<223> OTHER INFORMATION: Synthetic peptide

<400> SEQUENCE: 185

Glu Phe Arg His Asp Ser Gly Tyr Glu Val
1               5                   10

<210> SEQ ID NO 186
<211> LENGTH: 10
<212> TYPE: PRT
<213> ORGANISM: Artificial Sequence
<220> FEATURE:
<223> OTHER INFORMATION: Synthetic peptide

<400> SEQUENCE: 186

Phe Arg His Asp Ser Gly Tyr Glu Val His
1               5                   10
```

<210> SEQ ID NO 187
<211> LENGTH: 10
<212> TYPE: PRT
<213> ORGANISM: Artificial Sequence
<220> FEATURE:
<223> OTHER INFORMATION: Synthetic peptide

<400> SEQUENCE: 187

Arg His Asp Ser Gly Tyr Glu Val His His
1               5                   10

<210> SEQ ID NO 188
<211> LENGTH: 10
<212> TYPE: PRT
<213> ORGANISM: Artificial Sequence
<220> FEATURE:
<223> OTHER INFORMATION: Synthetic peptide

<400> SEQUENCE: 188

His Asp Ser Gly Tyr Glu Val His His Gln
1               5                   10

<210> SEQ ID NO 189
<211> LENGTH: 10
<212> TYPE: PRT
<213> ORGANISM: Artificial Sequence
<220> FEATURE:
<223> OTHER INFORMATION: Synthetic peptide

<400> SEQUENCE: 189

Asp Ser Gly Tyr Glu Val His His Gln Lys
1               5                   10

<210> SEQ ID NO 190
<211> LENGTH: 10
<212> TYPE: PRT
<213> ORGANISM: Artificial Sequence
<220> FEATURE:
<223> OTHER INFORMATION: Synthetic peptide

<400> SEQUENCE: 190

Ser Gly Tyr Glu Val His His Gln Lys Leu
1               5                   10

<210> SEQ ID NO 191
<211> LENGTH: 10
<212> TYPE: PRT
<213> ORGANISM: Artificial Sequence
<220> FEATURE:
<223> OTHER INFORMATION: Synthetic peptide

<400> SEQUENCE: 191

Gly Tyr Glu Val His His Gln Lys Leu Val
1               5                   10

<210> SEQ ID NO 192
<211> LENGTH: 10
<212> TYPE: PRT
<213> ORGANISM: Artificial Sequence
<220> FEATURE:
<223> OTHER INFORMATION: Synthetic peptide

<400> SEQUENCE: 192

Tyr Glu Val His His Gln Lys Leu Val Phe
1               5                   10

```
<210> SEQ ID NO 193
<211> LENGTH: 10
<212> TYPE: PRT
<213> ORGANISM: Artificial Sequence
<220> FEATURE:
<223> OTHER INFORMATION: Synthetic peptide

<400> SEQUENCE: 193

Glu Val His His Gln Lys Leu Val Phe Phe
1               5                   10

<210> SEQ ID NO 194
<211> LENGTH: 10
<212> TYPE: PRT
<213> ORGANISM: Artificial Sequence
<220> FEATURE:
<223> OTHER INFORMATION: Synthetic peptide

<400> SEQUENCE: 194

Val His His Gln Lys Leu Val Phe Phe Ala
1               5                   10

<210> SEQ ID NO 195
<211> LENGTH: 10
<212> TYPE: PRT
<213> ORGANISM: Artificial Sequence
<220> FEATURE:
<223> OTHER INFORMATION: Synthetic peptide

<400> SEQUENCE: 195

His His Gln Lys Leu Val Phe Phe Ala Glu
1               5                   10

<210> SEQ ID NO 196
<211> LENGTH: 10
<212> TYPE: PRT
<213> ORGANISM: Artificial Sequence
<220> FEATURE:
<223> OTHER INFORMATION: Synthetic peptide

<400> SEQUENCE: 196

His Gln Lys Leu Val Phe Phe Ala Glu Asp
1               5                   10

<210> SEQ ID NO 197
<211> LENGTH: 10
<212> TYPE: PRT
<213> ORGANISM: Artificial Sequence
<220> FEATURE:
<223> OTHER INFORMATION: Synthetic peptide

<400> SEQUENCE: 197

Gln Lys Leu Val Phe Phe Ala Glu Asp Val
1               5                   10

<210> SEQ ID NO 198
<211> LENGTH: 10
<212> TYPE: PRT
<213> ORGANISM: Artificial Sequence
<220> FEATURE:
<223> OTHER INFORMATION: Synthetic peptide

<400> SEQUENCE: 198

Lys Leu Val Phe Phe Ala Glu Asp Val Gly
1               5                   10
```

```
<210> SEQ ID NO 199
<211> LENGTH: 10
<212> TYPE: PRT
<213> ORGANISM: Artificial Sequence
<220> FEATURE:
<223> OTHER INFORMATION: Synthetic peptide

<400> SEQUENCE: 199

Leu Val Phe Phe Ala Glu Asp Val Gly Ser
1               5                   10

<210> SEQ ID NO 200
<211> LENGTH: 10
<212> TYPE: PRT
<213> ORGANISM: Artificial Sequence
<220> FEATURE:
<223> OTHER INFORMATION: Synthetic peptide

<400> SEQUENCE: 200

Val Phe Phe Ala Glu Asp Val Gly Ser Asn
1               5                   10

<210> SEQ ID NO 201
<211> LENGTH: 10
<212> TYPE: PRT
<213> ORGANISM: Artificial Sequence
<220> FEATURE:
<223> OTHER INFORMATION: Synthetic peptide

<400> SEQUENCE: 201

Phe Phe Ala Glu Asp Val Gly Ser Asn Lys
1               5                   10

<210> SEQ ID NO 202
<211> LENGTH: 10
<212> TYPE: PRT
<213> ORGANISM: Artificial Sequence
<220> FEATURE:
<223> OTHER INFORMATION: Synthetic peptide

<400> SEQUENCE: 202

Phe Ala Glu Asp Val Gly Ser Asn Lys Gly
1               5                   10

<210> SEQ ID NO 203
<211> LENGTH: 10
<212> TYPE: PRT
<213> ORGANISM: Artificial Sequence
<220> FEATURE:
<223> OTHER INFORMATION: Synthetic peptide

<400> SEQUENCE: 203

Ala Glu Asp Val Gly Ser Asn Lys Gly Ala
1               5                   10

<210> SEQ ID NO 204
<211> LENGTH: 10
<212> TYPE: PRT
<213> ORGANISM: Artificial Sequence
<220> FEATURE:
<223> OTHER INFORMATION: Synthetic peptide

<400> SEQUENCE: 204

Glu Asp Val Gly Ser Asn Lys Gly Ala Ile
1               5                   10

<210> SEQ ID NO 205
```

```
<211> LENGTH: 10
<212> TYPE: PRT
<213> ORGANISM: Artificial Sequence
<220> FEATURE:
<223> OTHER INFORMATION: Synthetic peptide

<400> SEQUENCE: 205

Asp Val Gly Ser Asn Lys Gly Ala Ile Ile
1               5                   10

<210> SEQ ID NO 206
<211> LENGTH: 10
<212> TYPE: PRT
<213> ORGANISM: Artificial Sequence
<220> FEATURE:
<223> OTHER INFORMATION: Synthetic peptide

<400> SEQUENCE: 206

Val Gly Ser Asn Lys Gly Ala Ile Ile Gly
1               5                   10

<210> SEQ ID NO 207
<211> LENGTH: 10
<212> TYPE: PRT
<213> ORGANISM: Artificial Sequence
<220> FEATURE:
<223> OTHER INFORMATION: Synthetic peptide

<400> SEQUENCE: 207

Gly Ser Asn Lys Gly Ala Ile Ile Gly Leu
1               5                   10

<210> SEQ ID NO 208
<211> LENGTH: 10
<212> TYPE: PRT
<213> ORGANISM: Artificial Sequence
<220> FEATURE:
<223> OTHER INFORMATION: Synthetic peptide

<400> SEQUENCE: 208

Ser Asn Lys Gly Ala Ile Ile Gly Leu Met
1               5                   10

<210> SEQ ID NO 209
<211> LENGTH: 10
<212> TYPE: PRT
<213> ORGANISM: Artificial Sequence
<220> FEATURE:
<223> OTHER INFORMATION: Synthetic peptide

<400> SEQUENCE: 209

Asn Lys Gly Ala Ile Ile Gly Leu Met Val
1               5                   10

<210> SEQ ID NO 210
<211> LENGTH: 10
<212> TYPE: PRT
<213> ORGANISM: Artificial Sequence
<220> FEATURE:
<223> OTHER INFORMATION: Synthetic peptide

<400> SEQUENCE: 210

Lys Gly Ala Ile Ile Gly Leu Met Val Gly
1               5                   10

<210> SEQ ID NO 211
<211> LENGTH: 10
```

-continued

<212> TYPE: PRT
<213> ORGANISM: Artificial Sequence
<220> FEATURE:
<223> OTHER INFORMATION: Synthetic peptide

<400> SEQUENCE: 211

Gly Ala Ile Ile Gly Leu Met Val Gly Gly
1               5                   10

<210> SEQ ID NO 212
<211> LENGTH: 10
<212> TYPE: PRT
<213> ORGANISM: Artificial Sequence
<220> FEATURE:
<223> OTHER INFORMATION: Synthetic peptide

<400> SEQUENCE: 212

Ala Ile Ile Gly Leu Met Val Gly Gly Val
1               5                   10

<210> SEQ ID NO 213
<211> LENGTH: 10
<212> TYPE: PRT
<213> ORGANISM: Artificial Sequence
<220> FEATURE:
<223> OTHER INFORMATION: Synthetic peptide

<400> SEQUENCE: 213

Ile Ile Gly Leu Met Val Gly Gly Val Val
1               5                   10

<210> SEQ ID NO 214
<211> LENGTH: 10
<212> TYPE: PRT
<213> ORGANISM: Artificial Sequence
<220> FEATURE:
<223> OTHER INFORMATION: Synthetic peptide

<400> SEQUENCE: 214

Ile Gly Leu Met Val Gly Gly Val Val Ile
1               5                   10

<210> SEQ ID NO 215
<211> LENGTH: 10
<212> TYPE: PRT
<213> ORGANISM: Artificial Sequence
<220> FEATURE:
<223> OTHER INFORMATION: Synthetic peptide

<400> SEQUENCE: 215

Gly Leu Met Val Gly Gly Val Val Ile Ala
1               5                   10

<210> SEQ ID NO 216
<211> LENGTH: 14
<212> TYPE: PRT
<213> ORGANISM: Artificial Sequence
<220> FEATURE:
<223> OTHER INFORMATION: Synthetic peptide

<400> SEQUENCE: 216

His His Val Glu Tyr Gly Ser Asp His Arg Phe Glu Ala Asp
1               5                   10

<210> SEQ ID NO 217
<211> LENGTH: 14
<212> TYPE: PRT

<213> ORGANISM: Artificial Sequence
<220> FEATURE:
<223> OTHER INFORMATION: Synthetic peptide

<400> SEQUENCE: 217

```
Lys Asn Ser Gly Val Asp Glu Ala Phe Phe Val Leu Lys Gln
1               5                   10
```

<210> SEQ ID NO 218
<211> LENGTH: 16
<212> TYPE: PRT
<213> ORGANISM: Artificial Sequence
<220> FEATURE:
<223> OTHER INFORMATION: Synthetic peptide

<400> SEQUENCE: 218

```
Ala Ile Val Val Gly Gly Val Met Leu Gly Ile Ile Ala Gly Lys Lys
1               5                   10                  15
```

<210> SEQ ID NO 219
<211> LENGTH: 7
<212> TYPE: PRT
<213> ORGANISM: Artificial Sequence
<220> FEATURE:
<223> OTHER INFORMATION: Synthetic peptide

<400> SEQUENCE: 219

```
Arg His Asp Ser Gly Tyr Glu
1               5
```

<210> SEQ ID NO 220
<211> LENGTH: 6
<212> TYPE: PRT
<213> ORGANISM: Artificial Sequence
<220> FEATURE:
<223> OTHER INFORMATION: Synthetic peptide

<400> SEQUENCE: 220

```
Glu Phe Arg His Asp Ser
1               5
```

<210> SEQ ID NO 221
<211> LENGTH: 11
<212> TYPE: PRT
<213> ORGANISM: Artificial Sequence
<220> FEATURE:
<223> OTHER INFORMATION: Synthetic peptide

<400> SEQUENCE: 221

```
Glu Val His His Gln Lys Leu Val Phe Phe Ala
1               5                   10
```

<210> SEQ ID NO 222
<211> LENGTH: 8
<212> TYPE: PRT
<213> ORGANISM: Artificial Sequence
<220> FEATURE:
<223> OTHER INFORMATION: Synthetic peptide

<400> SEQUENCE: 222

```
Glu Phe Arg His Asp Ser Gly Tyr
1               5
```

<210> SEQ ID NO 223
<211> LENGTH: 40
<212> TYPE: DNA
<213> ORGANISM: Artificial Sequence

```
<220> FEATURE:
<223> OTHER INFORMATION: Synthetic oligonucleotide

<400> SEQUENCE: 223
gatctctaga tgaagattgc ctgttaggct gttggtgctg                          40

<210> SEQ ID NO 224
<211> LENGTH: 39
<212> TYPE: DNA
<213> ORGANISM: Artificial Sequence
<220> FEATURE:
<223> OTHER INFORMATION: Synthetic oligonucleotide

<400> SEQUENCE: 224
gatctctaga tggagwcaga cacactcctg ytatgggtg                           39

<210> SEQ ID NO 225
<211> LENGTH: 39
<212> TYPE: DNA
<213> ORGANISM: Artificial Sequence
<220> FEATURE:
<223> OTHER INFORMATION: Synthetic oligonucleotide

<400> SEQUENCE: 225
gatctctaga tgagtgtgct cactcaggtc ctggsgttg                           39

<210> SEQ ID NO 226
<211> LENGTH: 42
<212> TYPE: DNA
<213> ORGANISM: Artificial Sequence
<220> FEATURE:
<223> OTHER INFORMATION: Synthetic oligonucleotide

<400> SEQUENCE: 226
gatctctaga tgaggrcccc tgctcagwtt yttggmwtct tg                       42

<210> SEQ ID NO 227
<211> LENGTH: 39
<212> TYPE: DNA
<213> ORGANISM: Artificial Sequence
<220> FEATURE:
<223> OTHER INFORMATION: Synthetic oligonucleotide

<400> SEQUENCE: 227
gatctctaga tggatttwca ggtgcagatt wtcagcttc                           39

<210> SEQ ID NO 228
<211> LENGTH: 38
<212> TYPE: DNA
<213> ORGANISM: Artificial Sequence
<220> FEATURE:
<223> OTHER INFORMATION: Synthetic oligonucleotide

<400> SEQUENCE: 228
gatctctaga tgaggtkcyy tgytsaycty ctctgrgg                            38

<210> SEQ ID NO 229
<211> LENGTH: 41
<212> TYPE: DNA
<213> ORGANISM: Artificial Sequence
<220> FEATURE:
<223> OTHER INFORMATION: Synthetic oligonucleotide

<400> SEQUENCE: 229
gatctctaga tgggcwtcaa agatggagtc acakwyycwg g                        41
```

<210> SEQ ID NO 230
<211> LENGTH: 39
<212> TYPE: DNA
<213> ORGANISM: Artificial Sequence
<220> FEATURE:
<223> OTHER INFORMATION: Synthetic oligonucleotide

<400> SEQUENCE: 230
gatctctaga tgtggggayc tktttycmmt ttttcaatg                39

<210> SEQ ID NO 231
<211> LENGTH: 34
<212> TYPE: DNA
<213> ORGANISM: Artificial Sequence
<220> FEATURE:
<223> OTHER INFORMATION: Synthetic oligonucleotide

<400> SEQUENCE: 231
gatctctaga tggtrtccwc asctcagttc cttg                34

<210> SEQ ID NO 232
<211> LENGTH: 36
<212> TYPE: DNA
<213> ORGANISM: Artificial Sequence
<220> FEATURE:
<223> OTHER INFORMATION: Synthetic oligonucleotide

<400> SEQUENCE: 232
gatctctaga tgtatatatg tttgttgtct atttct                36

<210> SEQ ID NO 233
<211> LENGTH: 37
<212> TYPE: DNA
<213> ORGANISM: Artificial Sequence
<220> FEATURE:
<223> OTHER INFORMATION: Synthetic oligonucleotide

<400> SEQUENCE: 233
gatctctaga tggaagcccc agctcagctt ctcttcc                37

<210> SEQ ID NO 234
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 234
gatcgagctc actggatggt gggaagatgg                30

<210> SEQ ID NO 235
<211> LENGTH: 36
<212> TYPE: DNA
<213> ORGANISM: Artificial Sequence
<220> FEATURE:
<223> OTHER INFORMATION: Synthetic oligonucleotide

<400> SEQUENCE: 235
gatctctaga tgaaatgcag ctggggcats ttcttc                36

<210> SEQ ID NO 236
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 236
gatctctaga tgggatggag ctrtatcats ytctt         35

<210> SEQ ID NO 237
<211> LENGTH: 36
<212> TYPE: DNA
<213> ORGANISM: Artificial Sequence
<220> FEATURE:
<223> OTHER INFORMATION: Synthetic oligonucleotide

<400> SEQUENCE: 237
gatctctaga tgaagwtgtg gttaaactgg gttttt        36

<210> SEQ ID NO 238
<211> LENGTH: 34
<212> TYPE: DNA
<213> ORGANISM: Artificial Sequence
<220> FEATURE:
<223> OTHER INFORMATION: Synthetic oligonucleotide

<400> SEQUENCE: 238
gatctctaga tgractttgg gytcagcttg rttt          34

<210> SEQ ID NO 239
<211> LENGTH: 41
<212> TYPE: DNA
<213> ORGANISM: Artificial Sequence
<220> FEATURE:
<223> OTHER INFORMATION: Synthetic oligonucleotide

<400> SEQUENCE: 239
gatctctaga tgggactcca ggcttcaatt tagttttcct t   41

<210> SEQ ID NO 240
<211> LENGTH: 38
<212> TYPE: DNA
<213> ORGANISM: Artificial Sequence
<220> FEATURE:
<223> OTHER INFORMATION: Synthetic oligonucleotide

<400> SEQUENCE: 240
gatctctaga tggcttgtcy ttrgsgctrc tcttctgc      38

<210> SEQ ID NO 241
<211> LENGTH: 36
<212> TYPE: DNA
<213> ORGANISM: Artificial Sequence
<220> FEATURE:
<223> OTHER INFORMATION: Synthetic oligonucleotide

<400> SEQUENCE: 241
gatctctaga tggratggag ckggrgtctt tmtctt        36

<210> SEQ ID NO 242
<211> LENGTH: 32
<212> TYPE: DNA
<213> ORGANISM: Artificial Sequence
<220> FEATURE:
<223> OTHER INFORMATION: Synthetic oligonucleotide

<400> SEQUENCE: 242
gatctctaga tgagagtgct gattcttttg tg            32

<210> SEQ ID NO 243

```
<211> LENGTH: 40
<212> TYPE: DNA
<213> ORGANISM: Artificial Sequence
<220> FEATURE:
<223> OTHER INFORMATION: Synthetic oligonucleotide

<400> SEQUENCE: 243
gatctctaga tggmttgggt gtggamcttg cttattcctg                              40

<210> SEQ ID NO 244
<211> LENGTH: 37
<212> TYPE: DNA
<213> ORGANISM: Artificial Sequence
<220> FEATURE:
<223> OTHER INFORMATION: Synthetic oligonucleotide

<400> SEQUENCE: 244
gatctctaga tgggcagact taccattctc attcctg                                 37

<210> SEQ ID NO 245
<211> LENGTH: 37
<212> TYPE: DNA
<213> ORGANISM: Artificial Sequence
<220> FEATURE:
<223> OTHER INFORMATION: Synthetic oligonucleotide

<400> SEQUENCE: 245
gatctctaga tggatttttgg gctgattttt tttattg                                37

<210> SEQ ID NO 246
<211> LENGTH: 36
<212> TYPE: DNA
<213> ORGANISM: Artificial Sequence
<220> FEATURE:
<223> OTHER INFORMATION: Synthetic oligonucleotide

<400> SEQUENCE: 246
gatctctaga tgatggtgtt aagtcttctg tacctg                                  36

<210> SEQ ID NO 247
<211> LENGTH: 32
<212> TYPE: DNA
<213> ORGANISM: Artificial Sequence
<220> FEATURE:
<223> OTHER INFORMATION: Synthetic oligonucleotide

<400> SEQUENCE: 247
gcatcgagct ccagtggata gacagatggg gg                                      32

<210> SEQ ID NO 248
<211> LENGTH: 32
<212> TYPE: DNA
<213> ORGANISM: Artificial Sequence
<220> FEATURE:
<223> OTHER INFORMATION: Synthetic oligonucleotide

<400> SEQUENCE: 248
gcatcgagct ccagtggata gaccgatggg gg                                      32

<210> SEQ ID NO 249
<211> LENGTH: 32
<212> TYPE: DNA
<213> ORGANISM: Artificial Sequence
<220> FEATURE:
<223> OTHER INFORMATION: Synthetic oligonucleotide

<400> SEQUENCE: 249
```

```
gcatcgagct ccagtggatg agctgatggg gg                              32
```

<210> SEQ ID NO 250
<211> LENGTH: 32
<212> TYPE: DNA
<213> ORGANISM: Artificial Sequence
<220> FEATURE:
<223> OTHER INFORMATION: Synthetic oligonucleotide

<400> SEQUENCE: 250

```
gcatcgagct ccaagggata gacagatggg gc                              32
```

<210> SEQ ID NO 251
<211> LENGTH: 330
<212> TYPE: PRT
<213> ORGANISM: Homo sapiens

<400> SEQUENCE: 251

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Ala Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300
```

```
Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 252
<211> LENGTH: 326
<212> TYPE: PRT
<213> ORGANISM: Homo sapiens

<400> SEQUENCE: 252

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Thr Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
                325
```

-continued

<210> SEQ ID NO 253
<211> LENGTH: 327
<212> TYPE: PRT
<213> ORGANISM: Homo sapiens

<400> SEQUENCE: 253

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Met Leu Asp Ser Asp Gly Ser Phe Phe Leu Tyr Ser
        275                 280                 285

Lys Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 254
<211> LENGTH: 326
<212> TYPE: PRT
<213> ORGANISM: Artificial Sequence
<220> FEATURE:
<223> OTHER INFORMATION: Synthetic immunoglobulin constant region

<400> SEQUENCE: 254

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Thr Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
            115                 120                 125

Thr Leu Met Ile Ser Arg Thr Pro Glu Val Thr Cys Val Val Val Asp
130                 135                 140

Val Ser Gln Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Leu His Gln Asp Trp
            180                 185                 190

Leu Asn Gly Lys Glu Tyr Lys Cys Lys Val Ser Asn Lys Gly Leu Pro
            195                 200                 205

Ser Ser Ile Glu Lys Thr Ile Ser Lys Thr Lys Gly Gln Pro Arg Glu
            210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
            275                 280                 285

Leu Thr Val Asp Lys Ser Arg Trp Gln Gln Gly Asn Val Phe Ser Cys
            290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 255
<211> LENGTH: 492
<212> TYPE: PRT
<213> ORGANISM: Artificial Sequence
<220> FEATURE:
<223> OTHER INFORMATION: Synthetic protein

<400> SEQUENCE: 255

Met Lys Lys Thr Ala Ile Ala Ile Ala Val Ala Leu Ala Gly Phe Ala
1               5                   10                  15

Thr Val Ala Gln Ala Ala Leu Glu Gln Val Thr Leu Lys Glu Ser Gly
            20                  25                  30
```

-continued

```
Pro Ala Leu Val Lys Pro Thr Gln Thr Leu Thr Leu Thr Cys Thr Phe
             35                  40                  45

Ser Gly Phe Ser Leu Ser Thr Ser Gly Met Gly Val Gly Trp Ile Arg
         50                  55                  60

Gln Pro Pro Gly Lys Ala Leu Glu Trp Leu Ala His Ile Trp Trp Asp
 65                  70                  75                  80

Asp Asp Lys Ser Tyr Asn Pro Ser Leu Lys Ser Arg Leu Thr Ile Ser
                 85                  90                  95

Lys Asp Thr Ser Lys Asn Gln Val Val Leu Thr Met Thr Asn Met Asp
            100                 105                 110

Pro Val Asp Thr Ala Thr Tyr Tyr Cys Ala Arg Arg Gln Leu Gly Leu
        115                 120                 125

Arg Ser Ile Asp Ala Met Asp Tyr Trp Gly Gln Gly Thr Thr Val Thr
    130                 135                 140

Val Ser Ser Ala Ser Thr Lys Gly Pro Ser Val Phe Pro Leu Ala Pro
145                 150                 155                 160

Ser Ser Lys Ser Thr Ser Gly Gly Thr Ala Ala Leu Gly Cys Leu Val
                165                 170                 175

Lys Asp Tyr Phe Pro Glu Pro Val Thr Val Ser Trp Asn Ser Gly Ala
            180                 185                 190

Leu Thr Ser Gly Val His Thr Phe Pro Ala Val Leu Gln Ser Ser Gly
        195                 200                 205

Leu Tyr Ser Leu Ser Ser Val Val Thr Val Pro Ser Ser Ser Leu Gly
    210                 215                 220

Thr Gln Thr Tyr Ile Cys Asn Val Asn His Lys Pro Ser Asn Thr Lys
225                 230                 235                 240

Val Asp Lys Arg Val Glu Pro Lys Ser Cys Asp Lys Thr His Thr Cys
                245                 250                 255

Pro Pro Cys Pro Thr Ser Gly His His His His His Gly Gly Glu
            260                 265                 270

Gln Lys Leu Ile Ser Glu Glu Asp Leu Gly Gly Pro Phe Val Cys Glu
        275                 280                 285

Tyr Gln Gly Gln Ser Ser Asp Leu Pro Gln Pro Pro Val Asn Ala Gly
    290                 295                 300

Gly Gly Ser Gly Gly Gly Ser Gly Gly Gly Ser Glu Gly Gly Gly Ser
305                 310                 315                 320

Glu Gly Gly Gly Ser Glu Gly Gly Gly Ser Glu Gly Gly Gly Ser Gly
                325                 330                 335

Gly Gly Ser Gly Ser Gly Asp Phe Asp Tyr Glu Lys Met Ala Asn Ala
            340                 345                 350

Asn Lys Gly Ala Met Thr Glu Asn Ala Asp Glu Asn Ala Leu Gln Ser
        355                 360                 365

Asp Ala Lys Gly Lys Leu Asp Ser Val Ala Thr Asp Tyr Gly Ala Ala
    370                 375                 380

Ile Asp Gly Phe Ile Gly Asp Val Ser Gly Leu Ala Asn Gly Asn Gly
385                 390                 395                 400

Ala Thr Gly Asp Phe Ala Gly Ser Asn Ser Gln Met Ala Gln Val Gly
                405                 410                 415

Asp Gly Asp Asn Ser Pro Leu Met Asn Asn Phe Arg Gln Tyr Leu Pro
            420                 425                 430

Ser Leu Pro Gln Ser Val Glu Cys Arg Pro Tyr Val Phe Gly Ala Gly
        435                 440                 445
```

```
Lys Pro Tyr Glu Phe Ser Ile Asp Cys Asp Lys Ile Asn Leu Phe Arg
            450                 455                 460

Gly Val Phe Ala Phe Leu Leu Tyr Val Ala Thr Phe Met Tyr Val Phe
465                 470                 475                 480

Ser Thr Phe Ala Asn Ile Leu Arg Asn Lys Glu Ser
                485                 490

<210> SEQ ID NO 256
<211> LENGTH: 243
<212> TYPE: PRT
<213> ORGANISM: Artificial Sequence
<220> FEATURE:
<223> OTHER INFORMATION: Synthetic protein

<400> SEQUENCE: 256

Met Lys Tyr Leu Leu Pro Thr Ala Ala Ala Gly Leu Leu Leu Leu Ala
1               5                   10                  15

Ala Gln Pro Ala Met Ala Ser Arg Asp Val Val Met Thr Gln Ser Pro
            20                  25                  30

Leu Ser Leu Pro Val Thr Pro Gly Glu Pro Ala Ser Ile Ser Cys Arg
        35                  40                  45

Ser Ser Gln Ser Ile Leu His Ser Asn Gly Asn Thr Tyr Leu Glu Trp
    50                  55                  60

Tyr Leu Gln Lys Pro Gly Gln Ser Pro Gln Leu Leu Ile Tyr Lys Val
65                  70                  75                  80

Ser Asn Arg Phe Ser Gly Val Pro Asp Arg Phe Ser Gly Ser Gly Ser
                85                  90                  95

Gly Thr Asp Phe Thr Leu Lys Ile Ser Arg Val Glu Ala Glu Asp Val
            100                 105                 110

Gly Val Tyr Tyr Cys Phe Gln Gly Ser Leu Val Pro Leu Thr Phe Gly
        115                 120                 125

Gln Gly Thr Lys Leu Glu Ile Lys Arg Thr Val Ala Ala Pro Ser Val
    130                 135                 140

Phe Ile Phe Pro Pro Ser Asp Glu Gln Leu Lys Ser Gly Thr Ala Ser
145                 150                 155                 160

Val Val Cys Leu Leu Asn Asn Phe Tyr Pro Arg Glu Ala Lys Val Gln
                165                 170                 175

Trp Lys Val Asp Asn Ala Leu Gln Ser Gly Asn Ser Gln Glu Ser Val
            180                 185                 190

Thr Glu Gln Asp Ser Lys Asp Ser Thr Tyr Ser Leu Ser Ser Thr Leu
        195                 200                 205

Thr Leu Ser Lys Ala Asp Tyr Glu Lys His Lys Val Tyr Ala Cys Glu
    210                 215                 220

Val Thr His Gln Gly Leu Ser Ser Pro Val Thr Lys Ser Phe Asn Arg
225                 230                 235                 240

Gly Glu Cys

<210> SEQ ID NO 257
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(5)
<223> OTHER INFORMATION: Xaa denotes any amino acid residue

<400> SEQUENCE: 257
```

Xaa Xaa Xaa Xaa Xaa Val Pro Leu Thr
1               5

<210> SEQ ID NO 258
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (5)..(9)
<223> OTHER INFORMATION: Xaa denotes any amino acid residue

<400> SEQUENCE: 258

Phe Gln Gly Ser Xaa Xaa Xaa Xaa Xaa
1               5

<210> SEQ ID NO 259
<211> LENGTH: 82
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (57)..(58)
<223> OTHER INFORMATION: n denotes any nucleotide
<220> FEATURE:
<221> NAME/KEY: misc_feature
<222> LOCATION: (60)..(61)
<223> OTHER INFORMATION: n denotes any nucleotide
<220> FEATURE:
<221> NAME/KEY: misc_feature
<222> LOCATION: (63)..(64)
<223> OTHER INFORMATION: n denotes any nucleotide
<220> FEATURE:
<221> NAME/KEY: misc_feature
<222> LOCATION: (66)..(67)
<223> OTHER INFORMATION: n denotes any nucleotide
<220> FEATURE:
<221> NAME/KEY: misc_feature
<222> LOCATION: (69)..(70)
<223> OTHER INFORMATION: n denotes any nucleotide

<400> SEQUENCE: 259
cagccaccgt acgcttgatc tccagcttgg tgccctggcc aaaggtcagg ggcacmnnmn    60
nmnnmnnmnn gcagtagtag ac                                            82

<210> SEQ ID NO 260
<211> LENGTH: 82
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (45)..(46)
<223> OTHER INFORMATION: n denotes any nucleotide
<220> FEATURE:
<221> NAME/KEY: misc_feature
<222> LOCATION: (48)..(49)
<223> OTHER INFORMATION: n denotes any nucleotide
<220> FEATURE:
<221> NAME/KEY: misc_feature
<222> LOCATION: (51)..(52)
<223> OTHER INFORMATION: n denotes any nucleotide
<220> FEATURE:
<221> NAME/KEY: misc_feature
<222> LOCATION: (54)..(55)
<223> OTHER INFORMATION: n denotes any nucleotide
<220> FEATURE:

```
<221> NAME/KEY: misc_feature
<222> LOCATION: (57)..(58)
<223> OTHER INFORMATION: n denotes any nucleotide

<400> SEQUENCE: 260
cagccaccgt acgcttgatc tccagcttgg tgccctggcc aaamnmnmnm nnmnnmnngc    60
tgccctggaa gcagtagtag ac                                            82

<210> SEQ ID NO 261
<211> LENGTH: 26
<212> TYPE: DNA
<213> ORGANISM: Artificial Sequence
<220> FEATURE:
<223> OTHER INFORMATION: Synthetic primer

<400> SEQUENCE: 261
ctatggcttc tagagatgtg gtgatg                                        26

<210> SEQ ID NO 262
<211> LENGTH: 9
<212> TYPE: PRT
<213> ORGANISM: Artificial Sequence
<220> FEATURE:
<223> OTHER INFORMATION: Synthetic peptide

<400> SEQUENCE: 262

Ala Asp Thr Thr His Val Pro Leu Thr
1               5

<210> SEQ ID NO 263
<211> LENGTH: 9
<212> TYPE: PRT
<213> ORGANISM: Artificial Sequence
<220> FEATURE:
<223> OTHER INFORMATION: Synthetic peptide

<400> SEQUENCE: 263

Ala His Ser Thr Phe Val Pro Leu Thr
1               5

<210> SEQ ID NO 264
<211> LENGTH: 9
<212> TYPE: PRT
<213> ORGANISM: Artificial Sequence
<220> FEATURE:
<223> OTHER INFORMATION: Synthetic peptide

<400> SEQUENCE: 264

Ala Gln Ala Ser Phe Val Pro Leu Thr
1               5

<210> SEQ ID NO 265
<211> LENGTH: 9
<212> TYPE: PRT
<213> ORGANISM: Artificial Sequence
<220> FEATURE:
<223> OTHER INFORMATION: Synthetic peptide

<400> SEQUENCE: 265

Ala Gln Ala Thr Lys Val Pro Leu Thr
1               5

<210> SEQ ID NO 266
<211> LENGTH: 9
<212> TYPE: PRT
<213> ORGANISM: Artificial Sequence
```

```
<220> FEATURE:
<223> OTHER INFORMATION: Synthetic peptide

<400> SEQUENCE: 266

Ala Gln Ser Ser Lys Val Pro Leu Thr
1               5

<210> SEQ ID NO 267
<211> LENGTH: 9
<212> TYPE: PRT
<213> ORGANISM: Artificial Sequence
<220> FEATURE:
<223> OTHER INFORMATION: Synthetic peptide

<400> SEQUENCE: 267

Ala Gln Ser Thr Leu Val Pro Leu Thr
1               5

<210> SEQ ID NO 268
<211> LENGTH: 9
<212> TYPE: PRT
<213> ORGANISM: Artificial Sequence
<220> FEATURE:
<223> OTHER INFORMATION: Synthetic peptide

<400> SEQUENCE: 268

Phe Ala Ala Ser Ser Val Pro Leu Thr
1               5

<210> SEQ ID NO 269
<211> LENGTH: 9
<212> TYPE: PRT
<213> ORGANISM: Artificial Sequence
<220> FEATURE:
<223> OTHER INFORMATION: Synthetic peptide

<400> SEQUENCE: 269

Phe Glu Ser Thr Tyr Val Pro Leu Thr
1               5

<210> SEQ ID NO 270
<211> LENGTH: 9
<212> TYPE: PRT
<213> ORGANISM: Artificial Sequence
<220> FEATURE:
<223> OTHER INFORMATION: Synthetic peptide

<400> SEQUENCE: 270

Phe Glu Ser Ser Arg Val Pro Leu Thr
1               5

<210> SEQ ID NO 271
<211> LENGTH: 9
<212> TYPE: PRT
<213> ORGANISM: Artificial Sequence
<220> FEATURE:
<223> OTHER INFORMATION: Synthetic peptide

<400> SEQUENCE: 271

Phe Asn Ala Thr Trp Val Pro Leu Thr
1               5

<210> SEQ ID NO 272
<211> LENGTH: 9
<212> TYPE: PRT
<213> ORGANISM: Artificial Sequence
<220> FEATURE:
```

<223> OTHER INFORMATION: Synthetic peptide

<400> SEQUENCE: 272

Phe Gln Ala Ser Arg Val Pro Leu Thr
1               5

<210> SEQ ID NO 273
<211> LENGTH: 9
<212> TYPE: PRT
<213> ORGANISM: Artificial Sequence
<220> FEATURE:
<223> OTHER INFORMATION: Synthetic peptide

<400> SEQUENCE: 273

Phe Gln Ala Thr Arg Val Pro Leu Thr
1               5

<210> SEQ ID NO 274
<211> LENGTH: 9
<212> TYPE: PRT
<213> ORGANISM: Artificial Sequence
<220> FEATURE:
<223> OTHER INFORMATION: Synthetic peptide

<400> SEQUENCE: 274

Phe Gln Gly Ser Phe Ile Gly Leu Ser
1               5

<210> SEQ ID NO 275
<211> LENGTH: 9
<212> TYPE: PRT
<213> ORGANISM: Artificial Sequence
<220> FEATURE:
<223> OTHER INFORMATION: Synthetic peptide

<400> SEQUENCE: 275

Phe Gln Gly Ser Phe Ile Pro Gly Thr
1               5

<210> SEQ ID NO 276
<211> LENGTH: 9
<212> TYPE: PRT
<213> ORGANISM: Artificial Sequence
<220> FEATURE:
<223> OTHER INFORMATION: Synthetic peptide

<400> SEQUENCE: 276

Phe Gln Gly Ser Phe Leu Pro Pro Ser
1               5

<210> SEQ ID NO 277
<211> LENGTH: 9
<212> TYPE: PRT
<213> ORGANISM: Artificial Sequence
<220> FEATURE:
<223> OTHER INFORMATION: Synthetic peptide

<400> SEQUENCE: 277

Phe Gln Gly Ser Phe Leu Pro Gln Leu
1               5

<210> SEQ ID NO 278
<211> LENGTH: 9
<212> TYPE: PRT
<213> ORGANISM: Artificial Sequence
<220> FEATURE:
<223> OTHER INFORMATION: Synthetic peptide

```
<400> SEQUENCE: 278

Phe Gln Gly Ser Leu Phe Pro Pro Val
1               5

<210> SEQ ID NO 279
<211> LENGTH: 9
<212> TYPE: PRT
<213> ORGANISM: Artificial Sequence
<220> FEATURE:
<223> OTHER INFORMATION: Synthetic peptide

<400> SEQUENCE: 279

Phe Gln Gly Ser Leu Phe Ser Pro Ser
1               5

<210> SEQ ID NO 280
<211> LENGTH: 9
<212> TYPE: PRT
<213> ORGANISM: Artificial Sequence
<220> FEATURE:
<223> OTHER INFORMATION: Synthetic peptide

<400> SEQUENCE: 280

Phe Gln Gly Ser Arg Ile Pro Ile Ser
1               5

<210> SEQ ID NO 281
<211> LENGTH: 9
<212> TYPE: PRT
<213> ORGANISM: Artificial Sequence
<220> FEATURE:
<223> OTHER INFORMATION: Synthetic peptide

<400> SEQUENCE: 281

Phe Gln Gly Ser Arg Leu Pro Val Ser
1               5

<210> SEQ ID NO 282
<211> LENGTH: 9
<212> TYPE: PRT
<213> ORGANISM: Artificial Sequence
<220> FEATURE:
<223> OTHER INFORMATION: Synthetic peptide

<400> SEQUENCE: 282

Phe Gln Gly Ser Arg Val Pro Leu Val
1               5

<210> SEQ ID NO 283
<211> LENGTH: 9
<212> TYPE: PRT
<213> ORGANISM: Artificial Sequence
<220> FEATURE:
<223> OTHER INFORMATION: Synthetic peptide

<400> SEQUENCE: 283

Phe Gln Ser Ser Phe Val Pro Leu Thr
1               5

<210> SEQ ID NO 284
<211> LENGTH: 9
<212> TYPE: PRT
<213> ORGANISM: Artificial Sequence
<220> FEATURE:
<223> OTHER INFORMATION: Synthetic peptide
```

```
<400> SEQUENCE: 284

Phe Gln Ser Ser Arg Val Pro Leu Thr
 1               5

<210> SEQ ID NO 285
<211> LENGTH: 9
<212> TYPE: PRT
<213> ORGANISM: Artificial Sequence
<220> FEATURE:
<223> OTHER INFORMATION: Synthetic peptide

<400> SEQUENCE: 285

Gly Gln Thr Thr Leu Val Pro Leu Thr
 1               5

<210> SEQ ID NO 286
<211> LENGTH: 9
<212> TYPE: PRT
<213> ORGANISM: Artificial Sequence
<220> FEATURE:
<223> OTHER INFORMATION: Synthetic peptide

<400> SEQUENCE: 286

His Glu Ser Thr Leu Val Pro Leu Thr
 1               5

<210> SEQ ID NO 287
<211> LENGTH: 9
<212> TYPE: PRT
<213> ORGANISM: Artificial Sequence
<220> FEATURE:
<223> OTHER INFORMATION: Synthetic peptide

<400> SEQUENCE: 287

His Gln Ser Ser Lys Val Pro Leu Thr
 1               5

<210> SEQ ID NO 288
<211> LENGTH: 9
<212> TYPE: PRT
<213> ORGANISM: Artificial Sequence
<220> FEATURE:
<223> OTHER INFORMATION: Synthetic peptide

<400> SEQUENCE: 288

Ile Gln Thr Ser Leu Val Pro Leu Thr
 1               5

<210> SEQ ID NO 289
<211> LENGTH: 9
<212> TYPE: PRT
<213> ORGANISM: Artificial Sequence
<220> FEATURE:
<223> OTHER INFORMATION: Synthetic peptide

<400> SEQUENCE: 289

Ile Gln Ala Ala Leu Val Pro Leu Thr
 1               5

<210> SEQ ID NO 290
<211> LENGTH: 9
<212> TYPE: PRT
<213> ORGANISM: Artificial Sequence
<220> FEATURE:
<223> OTHER INFORMATION: Synthetic peptide

<400> SEQUENCE: 290
```

```
Leu Gln Ser Ser Phe Val Pro Leu Thr
1               5

<210> SEQ ID NO 291
<211> LENGTH: 9
<212> TYPE: PRT
<213> ORGANISM: Artificial Sequence
<220> FEATURE:
<223> OTHER INFORMATION: Synthetic peptide

<400> SEQUENCE: 291

Leu Glu Thr Ser Arg Val Pro Leu Thr
1               5

<210> SEQ ID NO 292
<211> LENGTH: 9
<212> TYPE: PRT
<213> ORGANISM: Artificial Sequence
<220> FEATURE:
<223> OTHER INFORMATION: Synthetic peptide

<400> SEQUENCE: 292

Leu Ala Ser Ser His Val Pro Leu Thr
1               5

<210> SEQ ID NO 293
<211> LENGTH: 9
<212> TYPE: PRT
<213> ORGANISM: Artificial Sequence
<220> FEATURE:
<223> OTHER INFORMATION: Synthetic peptide

<400> SEQUENCE: 293

Leu Asn Ser Thr Thr Val Pro Leu Thr
1               5

<210> SEQ ID NO 294
<211> LENGTH: 9
<212> TYPE: PRT
<213> ORGANISM: Artificial Sequence
<220> FEATURE:
<223> OTHER INFORMATION: Synthetic peptide

<400> SEQUENCE: 294

Leu Gln Ser Lys Ser Val Pro Leu Thr
1               5

<210> SEQ ID NO 295
<211> LENGTH: 9
<212> TYPE: PRT
<213> ORGANISM: Artificial Sequence
<220> FEATURE:
<223> OTHER INFORMATION: Synthetic peptide

<400> SEQUENCE: 295

Leu Gln Ser Val Arg Val Pro Leu Thr
1               5

<210> SEQ ID NO 296
<211> LENGTH: 9
<212> TYPE: PRT
<213> ORGANISM: Artificial Sequence
<220> FEATURE:
<223> OTHER INFORMATION: Synthetic peptide

<400> SEQUENCE: 296
```

```
Leu Gln Ser Ser Leu Val Pro Leu Thr
1               5

<210> SEQ ID NO 297
<211> LENGTH: 9
<212> TYPE: PRT
<213> ORGANISM: Artificial Sequence
<220> FEATURE:
<223> OTHER INFORMATION: Synthetic peptide

<400> SEQUENCE: 297

Leu Gln Thr Gly Arg Val Pro Leu Thr
1               5

<210> SEQ ID NO 298
<211> LENGTH: 9
<212> TYPE: PRT
<213> ORGANISM: Artificial Sequence
<220> FEATURE:
<223> OTHER INFORMATION: Synthetic peptide

<400> SEQUENCE: 298

Leu Gln Thr Ser Phe Val Pro Leu Thr
1               5

<210> SEQ ID NO 299
<211> LENGTH: 9
<212> TYPE: PRT
<213> ORGANISM: Artificial Sequence
<220> FEATURE:
<223> OTHER INFORMATION: Synthetic peptide

<400> SEQUENCE: 299

Leu Gln Thr Ser Asn Val Pro Leu Thr
1               5

<210> SEQ ID NO 300
<211> LENGTH: 9
<212> TYPE: PRT
<213> ORGANISM: Artificial Sequence
<220> FEATURE:
<223> OTHER INFORMATION: Synthetic peptide

<400> SEQUENCE: 300

Leu Gln Thr Thr Arg Val Pro Leu Thr
1               5

<210> SEQ ID NO 301
<211> LENGTH: 9
<212> TYPE: PRT
<213> ORGANISM: Artificial Sequence
<220> FEATURE:
<223> OTHER INFORMATION: Synthetic peptide

<400> SEQUENCE: 301

Leu Ser Ser Thr Phe Val Pro Leu Thr
1               5

<210> SEQ ID NO 302
<211> LENGTH: 9
<212> TYPE: PRT
<213> ORGANISM: Artificial Sequence
<220> FEATURE:
<223> OTHER INFORMATION: Synthetic peptide

<400> SEQUENCE: 302

Leu Ser Ser Thr His Val Pro Leu Thr
```

-continued

```
1               5

<210> SEQ ID NO 303
<211> LENGTH: 9
<212> TYPE: PRT
<213> ORGANISM: Artificial Sequence
<220> FEATURE:
<223> OTHER INFORMATION: Synthetic peptide

<400> SEQUENCE: 303

Leu Thr Ser Ser Ala Val Pro Leu Thr
1               5

<210> SEQ ID NO 304
<211> LENGTH: 9
<212> TYPE: PRT
<213> ORGANISM: Artificial Sequence
<220> FEATURE:
<223> OTHER INFORMATION: Synthetic peptide

<400> SEQUENCE: 304

Leu Val Ser Ser Leu Val Pro Leu Thr
1               5

<210> SEQ ID NO 305
<211> LENGTH: 9
<212> TYPE: PRT
<213> ORGANISM: Artificial Sequence
<220> FEATURE:
<223> OTHER INFORMATION: Synthetic peptide

<400> SEQUENCE: 305

Met Glu Thr Ala Asn Val Pro Leu Thr
1               5

<210> SEQ ID NO 306
<211> LENGTH: 9
<212> TYPE: PRT
<213> ORGANISM: Artificial Sequence
<220> FEATURE:
<223> OTHER INFORMATION: Synthetic peptide

<400> SEQUENCE: 306

Met Gln Ser Ser Phe Val Pro Leu Thr
1               5

<210> SEQ ID NO 307
<211> LENGTH: 9
<212> TYPE: PRT
<213> ORGANISM: Artificial Sequence
<220> FEATURE:
<223> OTHER INFORMATION: Synthetic peptide

<400> SEQUENCE: 307

Met Gln Ser Ser Leu Val Pro Leu Thr
1               5

<210> SEQ ID NO 308
<211> LENGTH: 9
<212> TYPE: PRT
<213> ORGANISM: Artificial Sequence
<220> FEATURE:
<223> OTHER INFORMATION: Synthetic peptide

<400> SEQUENCE: 308

Met Gln Thr Ser Lys Val Pro Leu Thr
1               5
```

```
<210> SEQ ID NO 309
<211> LENGTH: 9
<212> TYPE: PRT
<213> ORGANISM: Artificial Sequence
<220> FEATURE:
<223> OTHER INFORMATION: Synthetic peptide

<400> SEQUENCE: 309

Ser Gln Ala Arg Met Val Pro Leu Thr
1               5

<210> SEQ ID NO 310
<211> LENGTH: 9
<212> TYPE: PRT
<213> ORGANISM: Artificial Sequence
<220> FEATURE:
<223> OTHER INFORMATION: Synthetic peptide

<400> SEQUENCE: 310

Ser Gln Ala Ser Arg Val Pro Leu Thr
1               5

<210> SEQ ID NO 311
<211> LENGTH: 9
<212> TYPE: PRT
<213> ORGANISM: Artificial Sequence
<220> FEATURE:
<223> OTHER INFORMATION: Synthetic peptide

<400> SEQUENCE: 311

Thr Gln Ser Thr Gln Val Pro Leu Thr
1               5

<210> SEQ ID NO 312
<211> LENGTH: 9
<212> TYPE: PRT
<213> ORGANISM: Artificial Sequence
<220> FEATURE:
<223> OTHER INFORMATION: Synthetic peptide

<400> SEQUENCE: 312

Val Cys Ala Thr Phe Val Pro Leu Thr
1               5

<210> SEQ ID NO 313
<211> LENGTH: 9
<212> TYPE: PRT
<213> ORGANISM: Artificial Sequence
<220> FEATURE:
<223> OTHER INFORMATION: Synthetic peptide

<400> SEQUENCE: 313

Val Gln Ser Ser Ala Val Pro Leu Thr
1               5

<210> SEQ ID NO 314
<211> LENGTH: 9
<212> TYPE: PRT
<213> ORGANISM: Artificial Sequence
<220> FEATURE:
<223> OTHER INFORMATION: Synthetic peptide

<400> SEQUENCE: 314

Val Gln Thr Ser Leu Val Pro Leu Thr
1               5
```

<210> SEQ ID NO 315
<211> LENGTH: 9
<212> TYPE: PRT
<213> ORGANISM: Artificial Sequence
<220> FEATURE:
<223> OTHER INFORMATION: Synthetic peptide

<400> SEQUENCE: 315

Val Gln Thr Ser Val Val Pro Leu Thr
1               5

<210> SEQ ID NO 316
<211> LENGTH: 9
<212> TYPE: PRT
<213> ORGANISM: Artificial Sequence
<220> FEATURE:
<223> OTHER INFORMATION: Synthetic peptide

<400> SEQUENCE: 316

Val Gln Thr Thr Ala Val Pro Leu Thr
1               5

<210> SEQ ID NO 317
<211> LENGTH: 9
<212> TYPE: PRT
<213> ORGANISM: Artificial Sequence
<220> FEATURE:
<223> OTHER INFORMATION: Synthetic peptide

<400> SEQUENCE: 317

Leu Gln Thr Ala Arg Val Pro Leu Thr
1               5

<210> SEQ ID NO 318
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa denotes Phe or Leu
<220> FEATURE:
<221> NAME/KEY: MISC_FEATURE
<222> LOCATION: (3)..(3)
<223> OTHER INFORMATION: Xaa denotes Ala or Thr

<400> SEQUENCE: 318

Xaa Gln Xaa Thr Arg Val Pro Leu Thr
1               5

<210> SEQ ID NO 319
<211> LENGTH: 9
<212> TYPE: PRT
<213> ORGANISM: Artificial Sequence
<220> FEATURE:
<223> OTHER INFORMATION: Synthetic peptide

<400> SEQUENCE: 319

Phe Gln Gly Ser Leu Leu Pro Leu Ser
1               5

<210> SEQ ID NO 320
<211> LENGTH: 398
<212> TYPE: DNA
<213> ORGANISM: Artificial Sequence
<220> FEATURE:

<223> OTHER INFORMATION: Synthetic nucleic acid

<400> SEQUENCE: 320

```
agctgctggt ctgctgctgc tggcggccca gccggctatg gcttctagag atgtggtgat    60
gacccagagc ccctgtccc tgcctgtgac ccctggcgag cctgccagca tctcctgccg    120
gagctcccag agcatcctgc actccaatgg caacacctac ctggagtggt acctgcagaa   180
gcctggccag agccccagc tgctgatcta caaggtgtcc aaccggttct ccggcgtgcc    240
tgaccggttc agcggctccg gcagcggcac agacttcacc ctgaagatca gccgggtgga   300
ggctgaggat gtgggcgtct actactgctt ccagggcagc ctggtgcccc tgacctttgg   360
ccagggcacc aagctggaga tcaagcgtac ggtggctg                            398
```

<210> SEQ ID NO 321
<211> LENGTH: 398
<212> TYPE: DNA
<213> ORGANISM: Artificial Sequence
<220> FEATURE:
<223> OTHER INFORMATION: Synthetic nucleic acid
<220> FEATURE:
<221> NAME/KEY: misc_feature
<222> LOCATION: (329)..(330)
<223> OTHER INFORMATION: n denotes any nucleotide
<220> FEATURE:
<221> NAME/KEY: misc_feature
<222> LOCATION: (332)..(333)
<223> OTHER INFORMATION: n denotes any nucleotide
<220> FEATURE:
<221> NAME/KEY: misc_feature
<222> LOCATION: (335)..(336)
<223> OTHER INFORMATION: n denotes any nucleotide
<220> FEATURE:
<221> NAME/KEY: misc_feature
<222> LOCATION: (338)..(339)
<223> OTHER INFORMATION: n denotes any nucleotide
<220> FEATURE:
<221> NAME/KEY: misc_feature
<222> LOCATION: (341)..(342)
<223> OTHER INFORMATION: n denotes any nucleotide

<400> SEQUENCE: 321

```
agctgctggt ctgctgctgc tggcggccca gccggctatg gcttctagag atgtggtgat    60
gacccagagc ccctgtccc tgcctgtgac ccctggcgag cctgccagca tctcctgccg    120
gagctcccag agcatcctgc actccaatgg caacacctac ctggagtggt acctgcagaa   180
gcctggccag agccccagc tgctgatcta caaggtgtcc aaccggttct ccggcgtgcc    240
tgaccggttc agcggctccg gcagcggcac agacttcacc ctgaagatca gccgggtgga   300
ggctgaggat gtgggcgtct actactgcnn knnknnknnk nnkgtgcccc tgacctttgg   360
ccagggcacc aagctggaga tcaagcgtac ggtggctg                            398
```

<210> SEQ ID NO 322
<211> LENGTH: 398
<212> TYPE: DNA
<213> ORGANISM: Artificial Sequence
<220> FEATURE:
<223> OTHER INFORMATION: Synthetic nucleic acid
<220> FEATURE:
<221> NAME/KEY: misc_feature
<222> LOCATION: (341)..(342)
<223> OTHER INFORMATION: n denotes any nucleotide
<220> FEATURE:
<221> NAME/KEY: misc_feature
<222> LOCATION: (344)..(345)
<223> OTHER INFORMATION: n denotes any nucleotide
<220> FEATURE:
<221> NAME/KEY: misc_feature

```
<222> LOCATION: (347)..(348)
<223> OTHER INFORMATION: n denotes any nucleotide
<220> FEATURE:
<221> NAME/KEY: misc_feature
<222> LOCATION: (350)..(351)
<223> OTHER INFORMATION: n denotes any nucleotide
<220> FEATURE:
<221> NAME/KEY: misc_feature
<222> LOCATION: (353)..(354)
<223> OTHER INFORMATION: n denotes any nucleotide

<400> SEQUENCE: 322
agctgctggt ctgctgctgc tggcggccca gccggctatg gcttctagag atgtggtgat      60
gacccagagc cccctgtccc tgcctgtgac ccctggcgag cctgccagca tctcctgccg     120
gagctcccag agcatcctgc actccaatgg caacacctac ctggagtggt acctgcagaa     180
gcctggccag agcccccagc tgctgatcta caaggtgtcc aaccggttct ccggcgtgcc     240
tgaccggttc agcggctccg gcagcggcac agacttcacc ctgaagatca gccggtgga     300 ggctgaggat gtgggcgtct actactgctt ccagggcagc nnknnknnkn nknnktttgg     360
ccagggcacc aagctggaga tcaagcgtac ggtggctg                             398

<210> SEQ ID NO 323
<211> LENGTH: 115
<212> TYPE: PRT
<213> ORGANISM: Artificial Sequence
<220> FEATURE:
<223> OTHER INFORMATION: Humanized and affinity matured light chain
      variable region

<400> SEQUENCE: 323

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Ile Leu His Ser
            20                  25                  30

Asn Gly Asn Thr Tyr Leu Glu Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Leu Gln Thr
                85                  90                  95

Thr Arg Val Pro Leu Thr Phe Gly Gln Gly Thr Lys Leu Glu Ile Lys
            100                 105                 110

Arg Thr Val
        115
```

ANTI-ADDL ANTIBODIES AND USES THEREOF

INTRODUCTION

This application claims the benefit of priority from U.S. provisional patent application Ser. Nos. 60/621,776, filed Oct. 25, 2004, and 60/652,538, filed Feb. 14, 2005, whose contents are incorporated herein by reference in their entireties.

This invention was made in the course of research sponsored, in part, by the National Institutes of Health (Grant Nos. NIH RO1-AG18877 and NIH RO1-AG22547). The U.S. government may have certain rights in this invention.

DESCRIPTION OF THE COMPACT DISC-RECORDABLE (CD-R)

CD-R 1 is identified as MRK2US CD-R 1 and contains Copy 1 of the Sequence Listing MRK2US.seq.txt prepared in Patent 3.3 and formatted in plain ASCII text. This file was recorded on Oct. 21, 2005 and is 238 KB.

CD-R 1 (duplicate) is an exact copy of CD-R 1 and contains Copy 2 of the Sequence Listing MRK2US.seq.txt prepared in Patent 3.3 and formatted in plain ASCII text. This file was recorded on Oct. 21, 2005 and is 238 KB.

The contents of the Sequence Listing named above, which is being submitted in duplicate on two (2) compact discs CD-R 1 and CD-R 1 (duplicate) in accordance with 37 C.F.R. 1.52(e) (4), is incorporated by reference herein in its entirety.

BACKGROUND OF THE INVENTION

Alzheimer's Disease is a progressive and degenerative dementia (Terry, et al. (1991) *Ann. Neurol.* 30:572-580; Coyle (1987) In: *Encyclopedia of Neuroscience*, Adelman (ed.), Birkhäuser, Boston-Basel-Stuttgart, pp 29-31,). In its early stages, Alzheimer's Disease manifests primarily as a profound inability to form new memories (Selkoe (2002) *Science* 298:789-791), reportedly due to neurotoxins derived from amyloid beta (Aβ). Aβ is an amphipathic peptide whose abundance is increased by mutations and risk factors linked to Alzheimer's Disease. Fibrils formed from Aβ constitute the core of amyloid plaques, which are hallmarks of an Alzheimer's Disease brain. Analogous fibrils generated in vitro are lethal to cultured brain neurons. These findings indicate that memory loss is a consequence of neuron death caused by fibrillar Aβ.

Despite strong experimental support for fibrillar Aβ and memory loss, a poor correlation exists between dementia and amyloid plaque burden (Katzman (1988) *Ann. Neurol.* 23:138-144). Moreover, transgenic hAPP mice (Dodart, et al. (2002) *Nat. Neurosci.* 5:452-457; Kotilinek, et al. (2002) *J. Neurosci.* 22:6331-6335), which develop age-dependent amyloid plaques and, most importantly, age-dependent memory dysfunction, show that within 24 hours of vaccination with monoclonal antibodies against Aβ memory loss can be reversed with no change in plaque levels. Such findings are not consistent with a mechanism for memory loss dependent on neuron death caused by amyloid fibrils.

Additional neurologically active molecules formed by Aβ self-assembly have been suggested. These molecules include soluble Aβ oligomers, also referred to as Aβ-derived diffusible ligands or ADDLs. Oligomers are metastable and form at low concentrations of Aβ1-42 (Lambert, et al. (1998) *Proc. Natl. Acad. Sci. USA* 95:6448-6453). Aβ oligomers rapidly inhibit long-term potentiation (LTP), a classic experimental paradigm for memory and synaptic plasticity. As such, memory loss stems from synapse failure, prior to neuron death and synapse failure by Aβ oligomers, not fibrils (Hardy & Selkoe (2002) *Science* 297:353-356). Soluble oligomers have been found in brain tissue and are strikingly elevated in Alzheimer's Disease (Kayed, et al. (2003) *Science* 300:486-489; Gong, et al. (2003) *Proc. Natl. Acad. Sci. USA* 100:10417-10422) and in hAPP transgenic mice Alzheimer's Disease models (Kotilinek, et al. (2002) *J. Neurosci.* 22:6331-6335; Chang, et al. (2003) *J. Mol. Neurosci.* 20:305-313).

A variety of Alzheimer's Disease treatment options have been suggested. Vaccine clinical trials have revealed that persons mounting a vigorous immune response to the vaccine exhibit cognitive benefit (Hock, et al. (2003) *Neuron* 38:547-554); however, frequency of CNS inflammation caused early termination of part of the trial (Birmingham & Frantz (2002) *Nat. Med.* 8: 199-200). As an alternative to a vaccine, therapeutic antibodies that target ADDLs without binding monomers or fibrils have been suggested (Klein (2002) *Neurochem. Int.* 41:345-352). ADDLs are highly antigenic, generating oligomer-selective polyclonal antibodies in rabbits at concentration of ~50 μg/mL (Lambert, et al. (2001) *J. Neurochem.* 79:595-605). Results from transgenic mice models also suggest that antibodies can be successful in reversing memory decline (Dodart, et al. (2002) *Nat. Neurosci.* 5:452-457). Accordingly, there is a need in the art for ADDL-selective therapeutic antibodies for the prevention and treatment of Alzheimer's Disease. The present invention meets this need.

SUMMARY OF THE INVENTION

The present invention is an isolated antibody, or fragment thereof, capable of differentially recognizing a multi-dimensional conformation of one or more Aβ-derived diffusible ligands. In particular embodiments, the antibody of the present invention is in admixture with a pharmaceutically acceptable carrier. In other embodiments, the antibody of the present invention is in a kit.

Methods for preventing binding of Aβ-derived diffusible ligands to a neuron, inhibiting assembly of Aβ-derived diffusible ligands, and blocking the phosphorylation of tau protein at Ser202/Thr205 employing an antibody or antibody fragment which binds a multi-dimensional conformation of one or more Aβ-derived diffusible ligands are also provided.

The present invention further embraces a method for prophylactically or therapeutically treating a disease associated with Aβ-derived diffusible ligands using an antibody of the instant invention. Administration of an antibody of the invention can prevent binding of Aβ-derived diffusible ligands to a neuron thereby preventing or treating the disease associated with Aβ-derived diffusible ligands.

The present invention is also a method for identifying a therapeutic agent that prevents the binding of Aβ-derived diffusible ligands to a neuron. This method of the invention involves contacting a neuron with Aβ-derived diffusible ligands in the presence of an agent and using an antibody of the present invention to determine binding of the Aβ-derived diffusible ligands to the neuron in the presence of the agent.

The present invention also embraces a method for detecting Aβ-derived diffusible ligands in a sample and a method for diagnosing a disease associated with Aβ-derived diffusible ligands. Such methods involve contacting a sample with an antibody of the instant invention so that the Aβ-derived diffusible ligands can be detected and a disease associated with Aβ-derived diffusible ligands can be diagnosed.

BRIEF DESCRIPTION OF THE DRAWINGS

FIG. 3 shows a summary of binding characteristics of antibodies capable of differentially recognizing multidimensional conformations of ADDLs.

FIG. 6 shows the nucleic acid sequences for the heavy and light chain variable regions, respectively, for murine anti-ADDL antibodies, 20C2 (FIGS. 6A and 6B), 5F10 (FIGS. 6C and 6D), 2D6 (FIGS. 6E and 6F), 2B4 (FIGS. 6G and 6H), 4E2 (FIGS. 6I and 6J), 2H4 (FIGS. 6K and 6L), 2A10 (FIGS. 6M and 6N), 3B3 (FIGS. 6O and 6P), 1F6 (FIGS. 6Q and 6R), 1F4 (FIGS. 6S and 6T), 2E12 (FIGS. 6U and 6V) and 4C2 (FIGS. 6W and 6X). Lower case letters indicate the antibody leader sequences and uppercase letters indicate antibody variable region sequences. The nucleotides coding for the complementary determining regions (CDRs) are underlined.

FIG. 7 shows comparisons of CDR1 (FIG. 7A), CDR2 (FIG. 7B), CDR3 (FIG. 7C) sequences for the heavy chain variable regions and CDR1 (FIG. 7D), CDR2 (FIG. 7E), CDR3 (FIG. 7F) sequences for the light chain variable regions for the mouse anti-ADDL antibodies.

FIG. 8 shows the amino acid sequences for the heavy and light chain variable regions, respectively, for humanized anti-ADDL antibodies 20C2 (FIGS. 8A and 8B), 26D6 (FIGS. 8C and 8D), 4E2 (FIGS. 8E and 8F), 3B3 (FIGS. 8G and 8H), 2H4 (FIGS. 8I and 8J) and 1F6 (FIG. 8K) created by CDR grafting. Sequences are presented as comparisons between the mouse sequence, the most homologous human sequence obtained from the NCBI protein database, the most homologous human genomic sequence and the humanized sequence. Amino acids in the mouse, human and human genomic sequences that differ from the humanized sequences are in bold. CDRs are underlined. Residues important for the maintenance of CDR loop conformation are indicated with an *. Conserved residues found at the VL/VH interface are indicated with a #. Potential glycosylation sites are indicated by italic. For the 20C2 heavy chain two humanized sequences were generated (HCVRA and HCVRB) that differ by one amino acid at position 24. In 20C2 HCVRA the human amino acid was used and in 20C2 HCVRB the mouse amino acid was used. No light chain was designed for 1F6 because it has the same sequence as that of the light chain for 4E2.

FIG. 9 shows the amino acid sequences for the heavy and light chain variable regions, respectively, for humanized anti-ADDL antibodies 20C2 (FIGS. 9A and 9B) and 26D6 (FIGS. 9C and 9D) created by veneering. Sequences are presented as comparisons between the mouse sequence, the most homologous human sequence obtained from the NCBI protein database, the most homologous human genomic sequence and the humanized sequence. Amino Acids in the mouse, human and human genomic sequences that differ from the humanized sequences are bold. CDRs are underlined. Residues important for the maintenance of CDR loop conformation are indicated with an asterisk. Conserved residues found at the VL/VH interface are indicated with a pound symbol. Potential glycosylation sites are indicated by italic. For the 20C2 heavy chain, two humanized sequences were generated (HCVRVenA and HCVRVenB) that differ by one amino acid at position 81. In 20C2 HCVRVenA, the mouse amino acid was used and in 20C2 HCVRVenB, the human amino acid was used. For the 26D6 heavy chain, three humanized sequences were designed based on veneering (HCVR Ven1, Ven 2 and Ven3) that differ at amino acids 11, 23, 15, 81, 89 and 118. In HCVR Ven1, the mouse amino acid was used at all positions. In Ven2, the mouse amino acid was used for residues 81 and 118 and the human amino acid for residues 11, 13, 15, and 89. In Ven3, the human amino acids were used at all positions. For the 26D6 light chain, two veneered humanized sequences were designed (LCVR Ven1 and Ven2) that differ at amino acids 88 and 105. In LCVR Ven1, the mouse amino acid was used at both positions and in Ven2, the human amino acid was used.

FIG. 10 shows nucleic acid sequences for the heavy and light chain variable regions (HCVRs and LCVRs, respectively) for humanized anti-ADDL antibodies. CDR grafted HCVRs and LCVRs for 20C2, 2D6, 4E2, 3B3, 2H4, and IF6, are respectively presented in FIG. 10A to FIG. 10L. Veneered HCVRs (VenA and VenB) and the LCVR for 20C2 are presented in FIG. 10M to FIG. 10O, whereas the veneered HCVRs (Ven1, Ven2, Ven3) and LCVRs (Ven1, Ven2) for 26D6 are presented in FIG. 10P to FIG. 10T. Uppercase indicates antibody variable region sequences. CDRs are underlined. Variable region sequences were cloned into full heavy and light chain antibody expression vectors.

FIG. 11 shows the amino acid sequences for the full IgG1 and IgG2m4 humanized heavy chains and humanized Kappa light chains for anti-ADDL antibodies. FIG. 11A, CDR grafted 20C2 HCVRA IgG1; FIG. 11B, CDR grafted 20C2 HCVRB IgG1; FIG. 11C, CDR grafted 20C2 HCVRA IgG2m4; FIG. 11D, CDR grafted 20C2 HCVRB IgG2m4; FIG. 11E, CDR grafted 20C2 LCVR Kappa; FIG. 11F, CDR grafted 26D6 HCVR IgG1; FIG. 11G, CDR grafted 26D6 HCVR IgG2m4; FIG. 11H, CDR grafted 26D6 LCVR Kappa; FIG. 11, CDR grafted 4E2 HCVR IgG1; FIG. 11J, CDR grafted 4E2 LCVR Kappa; FIG. 11K, CDR grafted 3B3 HCVR IgG1; FIG. 11L, CDR grafted 3B3 LCVR Kappa; FIG. 11M, CDR grafted 2H4 HCVR IgG1; FIG. 11N, CDR grafted 2H4 LCVR Kappa; FIG. 11O, CDR grafted 1F6 HCVR IgG1; FIG. 11P, veneered 20C2 HCVR VenA IgG1; FIG. 11Q, veneered 20C2 HCVR VenB IgG1; FIG. 11R, veneered 20C2 HCVR VenB IgG2m4; FIG. 11S, veneered 20C2 LCVR Kappa; FIG. 11T, veneered 26D6 HCVR Ven1 Ig; FIG. 11U, veneered 26D6 HCVR Ven1 IgG1; FIG. 11V, 26D6 HCVR Ven2 IgG1; FIG. 11W, veneered 26D6 HCVR Ven3; FIG. 11X, veneered 26D6 LCVR Ven1 Kappa; and FIG. 11Y, veneered 26D6 LCVR Ven2 Kappa. Underlining indicates variable region sequences and amino acids corresponding to the CDRs are double-underlined. The remaining amino acid sequences are constant region sequences.

FIG. 12 shows a comparison of the amino acid sequence of human antibody constant regions and the sequence of IgG2m4. The asterisk indicates a glycosylation site at Asn297. Regions of FcRn binding are indicated. Sequences in which IgG2m4 is different from IgG2 are underlined.

FIG. 13 shows the annotated amino acid sequence for heavy (FIG. 13A) and light (FIG. 13B) chains of 20C2 humanized antibody in Fab phage-display vector pFab3d.

FIG. 14 depicts the design and primers employed in preparing two LC-CDR3 libraries, namely LC3-1 and LC3-2, for generating an affinity matured 20C2 light chain CDR3. Restriction endonuclease recognition sites used for cloning are indicated in italic. Uppercase indicates nucleic acids encoding antibody variable region sequences. Nucleic acids encoding CDRs are underlined.

DETAILED DESCRIPTION OF THE INVENTION

Figure 1:
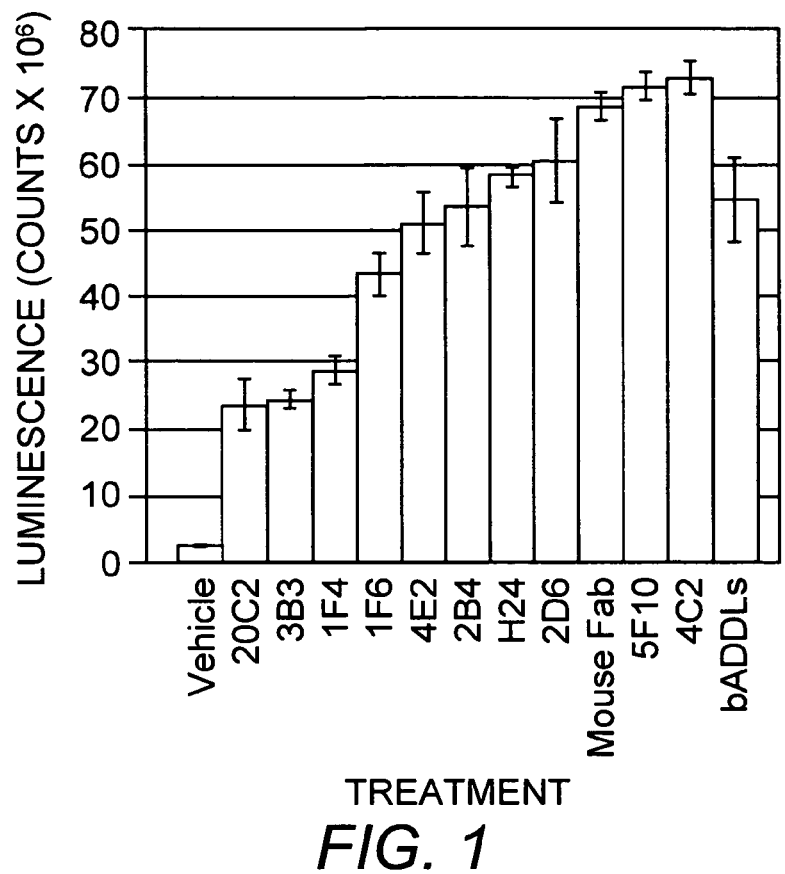
FIG. 1 shows the results from an alkaline phosphatase assay, wherein anti-ADDL antibodies differentially block neurons.

Monoclonal antibodies, which differentially recognize multi-dimensional conformations of Aβ-derived diffusible ligands (i.e., ADDLs), have now been generated. Advantageously, the instant monoclonal antibodies can distinguish between Alzheimer's Disease and control human brain extracts, and identify endogenous oligomers in Alzheimer's Disease brain slices and in cultured hippocampal cells. Further, the instant antibodies neutralize endogenous and synthetic ADDLs in solution. So-called "synthetic" ADDLs are produced in vitro by mixing purified amyloid β1-42 under conditions that generate ADDLs. See U.S. Pat. No. 6,218,506. Particular antibodies disclosed herein exhibit a high degree of selectivity for 3-24mers, with minimal detection of monomer Aβ peptides. Further, recognition of ADDLs by selected antibodies of the invention is not blocked by short peptides that encompass the linear sequence of Aβ1-42 or Aβ1-40. However, binding is blocked by Aβ1-28, indicating an epitope based on a conformationally unique structure also found in Aβ1-28. Delineation of epitopes of the instant antibodies indicated that these antibodies recognize similar core linear sequences with similar affinity and specificity characteristics as measured by ELISA. Moreover, the instant antibodies differentially block the ability of ADDL-containing preparations to bind primary cultures of rat hippocampal neurons and immortalized neuroblastoma cell lines, and also block ADDL assembly. This finding demonstrates that these antibodies possess a differential ability to recognize a multi-dimensional conformation of ADDLs despite similar linear sequence recognition and affinities. Since ADDLs are known to associate with a subset of neurons and disrupt normal neuronal function, one use of this current invention is the development and/or identification of antibodies that prevent the binding of ADDLs to neurons. Such antibodies would be useful in the treatment of ADDL related diseases including Alzheimer's Disease. A refinement of this use would be to specifically use humanized and/or affinity-matured versions of these antibodies for the prevention of ADDL binding to neurons and assembly of ADDLs.

Accordingly, the present invention is an isolated antibody that differentially recognizes one or more multi-dimensional conformations of ADDLs. An antibody of the instant invention is said to be isolated when it is present in the substantial absence of other biological macromolecules of the same type. Thus, an "isolated antibody" refers to an antibody which is substantially free of other antibodies; however, the molecule may include some additional agents or moieties which do not deleteriously affect the basic characteristics of the antibody (e.g., binding specificity, neutralizing activity, etc.).

Antibodies which are capable of specifically binding one or more multi-dimensional conformations of ADDLs, bind particular ADDLs derived from the oligomerization of Aβ1-42, but do not cross-react with other Aβ peptides, namely Aβ1-12, Aβ1-28, Aβ1-40, and Aβ12-28 as determined by western blot analyses as disclosed herein; and preferentially bind ADDLs in solution (see, e.g., Example 21). Specific binding between two entities generally refers to an affinity of at least $10^6$, $10^7$, $10^8$, $10^9$, or $10^{10}$ $M^{-1}$. Affinities greater than $10^8$ $M^{-1}$ are desired to achieve specific binding.

In particular embodiments, an antibody that is capable of specifically binding a multi-dimensional conformation of one or more ADDLs is also raised against (i.e., an animal is immunized with) multi-dimensional conformations of ADDLs. In other embodiments, an antibody that is capable of specifically binding a multi-dimensional conformation of one or more ADDLs is raised against a low n-mer-forming peptide such as Aβ1-42[Nle35-Dpro37].

The term "epitope" refers to a site on an antigen to which B and/or T cells respond or a site on a molecule against which an antibody will be produced and/or to which an antibody will bind. For example, an epitope can be recognized by an antibody defining the epitope.

A linear epitope is an epitope wherein an amino acid primary sequence comprises the epitope recognized. A linear epitope typically includes at least 3, and more usually, at least 5, for example, about 8 to about 10 amino acids in a unique sequence.

A conformational epitope, in contrast to a linear epitope, is an epitope wherein the primary sequence of the amino acids comprising the epitope is not the sole defining component of the epitope recognized (e.g., an epitope wherein the primary sequence of amino acids is not necessarily recognized by the antibody defining the epitope). Typically a conformational epitope encompasses an increased number of amino acids relative to a linear epitope. With regard to recognition of conformational epitopes, the antibody recognizes a three-dimensional structure of the peptide or protein. For example, when a protein molecule folds to form a three-dimensional structure, certain amino acids and/or the polypeptide backbone forming the conformational epitope become juxtaposed enabling the antibody to recognize the epitope. Methods of determining conformation of epitopes include but are not limited to, for example, x-ray crystallography, two-dimensional nuclear magnetic resonance spectroscopy and site-directed spin labeling and electron paramagnetic resonance spectroscopy. See, for example, Epitope Mapping Protocols in Methods in Molecular Biology (1996) Vol. 66, Morris (Ed.).

Aβ-derived diffusible ligands or ADDLs refer to soluble oligomers of amyloid β1-42 which are desirably composed of aggregates of less than eight or nine amyloid β1-42 peptides and are found associated with Alzheimer's Disease. This is in contrast to high molecular weight aggregation intermediates, which form stings of micelles leading to fibril formation.

As exemplified herein, the instant antibody binds or recognizes at least one multi-dimensional conformation of an ADDL (see, e.g., FIG. 3). In particular embodiments, the instant antibody binds at least two, at least three, or at least four multi-dimensional conformations of an ADDL. Multi-dimensional conformations of ADDLs are intended to encompass dimers, trimers, tetramers pentamers, hexamers, heptamers, octamers, nonamers, decamers, etc as defined by analysis via SDS-PAGE. Because trimer, tetramer, etc. designations can vary with the assay method employed (see, e.g., Bitan, et al. (2005) *Amyloid* 12:88-95) the definition of trimer, tetramer, and the like, as used herein, is according to SDS-PAGE analysis. To illustrate the differentially binding capabilities of the instant antibodies, it has been found that certain antibodies will recognize one multi-dimensional conformation, for example, tetramers of ADDLs (e.g., antibody 2D6 or 4E2), while other antibodies recognize several multi-dimensional conformations, for example, trimers and tetramers of ADDLs (e.g., antibody 2A10, 2B4, 5F10, or 20C2). As such, the antibodies of the instant invention have oligomer-specific characteristics. In particular embodiments, a multi-dimensional conformation of an ADDL is associated with a specific polypeptide structure which results in a conformational epitope that is recognized by an antibody of the present invention. In other embodiments, an antibody of the invention specifically binds a multi-dimensional conformation ADDL having a size range of approximately a trimer or tetramer, which have molecular weights in excess of >50 kDa.

In certain embodiments, in addition to binding to a multi-dimensional conformation, the instant antibody binds to a selected linear epitope of amyloid β1-42. A linear epitope of an ADDLs is intended as a four, five, six or more amino acid residue peptide located in the N-terminal 10, 11, 12, 15 or 20 amino acid residues of amyloid β1-42. In particular embodiments, an antibody of the invention specifically binds to a linear epitope within residues 1-10, 1-8, 3-10, or 3-8 of amyloid β1-42. Exemplary linear epitopes of amyloid β1-42 include, but are not limited to, amino acid residues EFRHDS (SEQ ID NO:177); DAEFRHDS (SEQ ID NO:178), and EFRHDSGY (SEQ ID NO:179).

While antibodies of the instant invention may have similar linear epitopes, such linear epitopes are not wholly indicative of the binding characteristics of the instant antibodies (i.e., ability to block ADDL binding to neurons, prevent tau phosphorylation and inhibit ADDL assembly) because, as is well known to the skilled artisan, the linear epitope may only correspond to a portion of the antigen's epitope (see, e.g., Breitling and Dübel (1999) In: Recombinant Antibodies, John Wiley & Sons, Inc., NY, pg. 115). For example, 20C2 was found to bind assemblies of charge-inverted, truncated Aβ7-42 peptide, which lack the linear epitope for 20C2 (i.e., amino acid residues 3-8) and contain a very different sequence corresponding to residues 7-16 of Aβ. Therefore 20C2 binds to conformational epitopes that depend upon elements from within residues 17-42 of Aβ, but only when in a multidimensional conformation. The antibodies of the instant invention can be distinguished from those of the art as being capable of differentially recognizing multi-dimensional ADDLs and accordingly differentially blocking ADDL binding to neurons, differentially preventing tau phosphorylation and differentially inhibiting ADDL assembly.

An antibody, as used in accordance with the instant invention includes, but is not be limited to, polyclonal or monoclonal antibodies, and chimeric, human (e.g. isolated from B cells), humanized, neutralizing, bispecific or single chain antibodies thereof. In one embodiment, an antibody of the instant invention is monoclonal. For the production of antibodies, various hosts including goats, rabbits, chickens, rats, mice, humans, and others, can be immunized by injection with synthetic or natural ADDLs. Methods for producing antibodies are well-known in the art. See, e.g., Kohler and Milstein ((1975) Nature 256:495-497) and Harlow and Lane (Antibodies: A Laboratory Manual (Cold Spring Harbor Laboratory, New York (1988)).

Depending on the host species, various adjuvants can be used to increase the immunological response. Adjuvants used in accordance with the instant invention desirably augment the intrinsic response to ADDLs without causing conformational changes in the immunogen that affect the qualitative form of the response. Particularly suitable adjuvants include 3 De-O-acylated monophosphoryl lipid A (MPL™; RIBI ImmunoChem Research Inc., Hamilton, Mont.; see GB 2220211) and oil-in-water emulsions, such as squalene or peanut oil, optionally in combination with immune stimulants, such as monophosphoryl lipid A (see Stoute, et al. (1997) N. Engl. J. Med. 336:86-91), muramyl peptides (e.g., N-acetylmuramyl-L-threonyl-D-isoglutamine (thr-MDP), N-acetyl-normuramyl-L-alanyl-D-isoglutamine (nor-MDP), N-acetylmuramyl-L-alanyl-D-isoglutaminyl-L-alanine-2-(1'-2'dipalmitoyl-sn-glycero-3-hydroxyphosphoryloxy)-ethylamine (E-PE), N-acetylglucsaminyl-N-acetylmuramyl-L-Al-D-isoglu-L-Ala-dipalmitoxy propylamide (DTP-DPP)), or other bacterial cell wall components. Specific examples of oil-in-water emulsions include MF59 (WO 90/14837), containing 5% Squalene, 0.5% TWEEN™ 80, and 0.5% SPAN 85 (optionally containing various amounts of MTP-PE) formulated into submicron particles using a microfluidizer such as Model 110Y microfluidizer (Microfluidics, Newton, Mass.); SAF containing 10% Squalene, 0.4% TWEEN™ 80, 5% PLURONIC®-blocked polymer L121, and thr-MDP, either microfluidized into a submicron emulsion or vortexed to generate a larger particle size emulsion; and RIBI™ adjuvant system (RAS) (Ribi ImmunoChem, Hamilton, Mont.) containing 2% squalene, 0.2% TWEEN™ 80, and one or more bacterial cell wall components such as monophosphoryllipid A, trehalose dimycolate (TDM), and cell wall skeleton (CWS).

Another class of adjuvants is saponin adjuvants, such as STIMULON™ (QS-21, Aquila, Framingham, Mass.) or particles generated therefrom such as ISCOMs (immunostimulating complexes) and ISCOMATRIX® (CSL Ltd., Parkville, Australia). Other suitable adjuvants include Complete Freund's Adjuvant (CFA), Incomplete Freund's Adjuvant (IFA), mineral gels such as aluminum hydroxide, and surface-active substances such as lysolecithin, PLURONIC® polyols, polyanions, peptides, CpG (WO 98/40100), keyhole limpet hemocyanin, dinitrophenol, and cytokines such as interleukins (IL-1, IL-2, and IL-12), macrophage colony stimulating factor (M-CSF), and tumor necrosis factor (TNF). Among adjuvants used in humans, BCG (bacilli Calmette-Guerin) and *Corynebacterium parvum* are particularly suitable.

An antibody to a multi-dimensional conformation ADDL is generated by immunizing an animal with ADDLs. Generally, ADDLs can be generated synthetically or by recombinant fragment expression and purification. Synthetic ADDLs can be prepared as disclosed herein or in accordance with the methods disclosed in U.S. Pat. No. 6,218,506 or in co-pending applications U.S. Ser. Nos. 60/695,528 and 60/695,526. Further, ADDLs can be fused with another protein such as keyhole limpet hemocyanin to generate an antibody against the chimeric molecule. The ADDLs can be conformationally constrained to form an epitope useful as described herein and furthermore can be associated with a surface for example, physically attached or chemically bonded to a surface in such a manner so as to allow for the production of a conformation which is recognized by the antibodies of the present invention.

Monoclonal antibodies to multi-dimensional conformations of ADDLs can be prepared using any technique which provides for the production of antibody molecules by continuous cell lines in culture. These include, but are not limited to, the hybridoma technique, the human B-cell hybridoma technique, and the EBV-hybridoma technique (Kohler, et al. (1975) Nature 256:495-497; Kozbor, et al. (1985) J. Immunol. Methods 81:31-42; Cote, et al. (1983) Proc. Natl. Acad. Sci. 80:2026-2030; Cole, et al. (1984) Mol. Cell Biol. 62:109-120). Exemplary monoclonal antibodies include murine antibodies designated 2A10, 4C2, 2D6, 4E2, 20C2, 2B4, 5F10, 2H4, 2E12, 1F6, 1F4, 3B3, 5G12, 6B7, 6B11, 11B4, 11B5, 14A11, 15G6, 17G4, 20C2, 3B7, 1E3, 1A9, 1G3, 1A7 and 1E5.

In addition, humanized and chimeric antibodies can be produced by splicing of mouse antibody genes to human antibody genes to obtain a molecule with appropriate antigen specificity and biological activity (see Morrison, et al. (1984) Proc. Natl. Acad. Sci. 81, 6851-6855; Neuberger, et al. (1984) Nature 312:604-608; Takeda, et al. (1985) Nature 314:452-454; Queen, et al. (1989) Proc. Natl. Acad. Sci. USA 86:10029-10033; WO 90/07861). For example, a mouse antibody is expressed as the Fv or Fab fragment in a phage selection vector. The gene for the light chain (and in a parallel experiment, the gene for the heavy chain) is exchanged for a library of human antibody genes. Phage antibodies, which still bind the antigen, are then identified. This method, commonly known as chain shuffling, provided humanized antibodies that should bind the same epitope as the mouse antibody from which it descends (Jespers, et al. (1994) *Biotechnology NY* 12:899-903). As an alternative, chain shuffling can be performed at the protein level (see, Figini, et al. (1994) *J. Mol. Biol.* 239:68-78).

Human antibodies can also be obtained using phage-display methods. See, e.g., WO 91/17271 and WO 92/01047. In these methods, libraries of phage are produced in which members display different antibodies on their outer surfaces. Antibodies are usually displayed as Fv or Fab fragments. Phage displaying antibodies with a desired specificity are selected by affinity enrichment to ADDLs. Human antibodies against ADDLs can also be produced from non-human transgenic mammals having transgenes encoding at least a segment of the human immunoglobulin locus and an inactivated endogenous immunoglobulin locus. See, e.g., WO 93/12227 and WO 91/10741, each incorporated herein by reference. Human antibodies can be selected by competitive binding experiments, or otherwise, to have the same epitope specificity as a particular mouse antibody. Such antibodies are particularly likely to share the useful functional properties of the mouse antibodies. Human polyclonal antibodies can also be provided in the form of serum from humans immunized with an immunogenic agent. Optionally, such polyclonal antibodies can be concentrated by affinity purification using ADDLs as an affinity reagent.

Humanized antibodies can also be produced by veneering or resurfacing of murine antibodies. Veneering involves replacing only the surface fixed region amino acids in the mouse heavy and light variable regions with those of a homologous human antibody sequence. Replacing mouse surface amino acids with human residues in the same position from a homologous human sequence has been shown to reduce the immunogenicity of the mouse antibody while preserving its ligand binding. The replacement of exterior residues generally has little, or no, effect on the interior domains, or on the interdomain contacts. (See, e.g., U.S. Pat. No. 6,797,492).

Human or humanized antibodies can be designed to have IgG, IgD, IgA, IgM or IgE constant regions, and any isotype, including IgG1, IgG2, IgG3 and IgG4. In particular embodiments, an antibody of the invention is IgG or IgM, or a combination thereof. A particular combination embraces a constant region formed by selective incorporation of human IgG4 sequences into a standard human IgG2 constant region. An exemplary mutant IgG2 Fc is IgG2m4, set forth herein as SEQ ID NO:254. Antibodies can be expressed as tetramers containing two light and two heavy chains, as separate heavy chains and light chains or as single chain antibodies in which heavy and light chain variable domains are linked through a spacer. Techniques for the production of single chain antibodies are well-known in the art.

Exemplary humanized antibodies produced by CDR grafting and veneering are disclosed herein for antibodies designated 4E2, 26D6, 20C2, 3B3, 2H4, and 1F6. Amino acid sequences for IgG1 and IgG2M4 heavy chain variable regions, as well as kappa light chain variable regions for humanized 4E2, 26D6, 20C2, 3B3, 2H4, and 1F6 generated by CDR grafting and veneering are presented in FIGS. 11A to 11Y and set forth herein as SEQ ID NOs:152 to 176.

Diabodies are also contemplated. A diabody refers to an engineered antibody construct prepared by isolating the binding domains (both heavy and light chain) of a binding antibody, and supplying a linking moiety which joins or operably links the heavy and light chains on the same polypeptide chain thereby preserving the binding function (see, Holliger et al. (1993) *Proc. Natl. Acad. Sci. USA* 90:6444; Poljak (1994) *Structure* 2:1121-1123). This forms, in essence, a radically abbreviated antibody, having only the variable domain necessary for binding the antigen. By using a linker that is too short to allow pairing between the two domains on the same chain, the domains are forced to pair with the complementary domains of another chain and create two antigen-binding sites. These dimeric antibody fragments, or diabodies, are bivalent and bispecific. The skilled artisan will appreciate that any method to generate diabodies can be used. Suitable methods are described by Holliger, et al. (1993) supra, Poljak (1994) supra, Zhu, et al. (1996) *Biotechnology* 14:192-196, and U.S. Pat. No. 6,492,123, incorporated herein by reference.

Fragments of an isolated antibody of the invention are also expressly encompassed by the instant invention. Fragments are intended to include Fab fragments, F(ab')$_2$ fragments, F(ab') fragments, bispecific scFv fragments, Fd fragments and fragments produced by a Fab expression library, as well as peptide aptamers. For example, F(ab')$_2$ fragments are produced by pepsin digestion of the antibody molecule of the invention, whereas Fab fragments are generated by reducing the disulfide bridges of the F(ab')$_2$ fragments. Alternatively, Fab expression libraries can be constructed to allow rapid and easy identification of monoclonal Fab fragments with the desired specificity (see Huse, et al. (1989) *Science* 254:1275-1281). In particular embodiments, antibody fragments of the present invention are fragments of neutralizing antibodies which retain the variable region binding site thereof. Exemplary are F(ab')$_2$ fragments, F(ab') fragments, and Fab fragments. See generally Immunology: Basic Processes (1985) $2^{nd}$ edition, J. Bellanti (Ed.) pp. 95-97.

Peptide aptamers which differentially recognize multi-dimensional conformations of ADDLs can be rationally designed or screened for in a library of aptamers (e.g., provided by Aptanomics S A, Lyon, France). In general, peptide aptamers are synthetic recognition molecules whose design is based on the structure of antibodies. Peptide aptamers consist of a variable peptide loop attached at both ends to a protein scaffold. This double structural constraint greatly increases the binding affinity of the peptide aptamer to levels comparable to that of an antibody (nanomolar range).

Exemplary nucleic acid sequences encoding heavy and light chain variable regions for use in producing antibody and antibody fragments of the instant invention are disclosed herein in FIGS. 6 and 10 (i.e., SEQ ID NOs:1-24 and SEQ ID NOs:132-151). As will be appreciated by the skilled artisan, the heavy chain variable regions disclosed herein can be used in combination with any one of the light chain variable regions disclosed herein to generate antibodies with modified affinities, dissociate constants, epitopes and the like. For example, combining the light chain variable region of 2H4 (encoded by SEQ ID NO:12) with the heavy chain variable region of 2A10 (encoded by SEQ ID NO:13) may provide for recognition of a larger linear epitope.

Exemplary heavy and light chain CDRs for use in producing an antibody or antibody fragment of the instant invention are disclosed in FIGS. 7A-7F and have amino acid sequences set forth in SEQ ID NOs:25, 26, and 28 (heavy chain CDR1); SEQ ID NOs: 29, 30, 31, 33, 34, 35, and 36 (heavy chain CDR2); SEQ ID NOs:38, 39, 40, 41, 43, 44, 45, 46, 47 and 48 (heavy chain CDR3); SEQ ID NOs:49, 50, 51 and 53 (light chain CDR1); SEQ ID NOs:54, 55, 56, and 58 (light chain CDR2); and SEQ ID NOs:59, 60, 61, 62, 63, 64, and 66 (light chain CDR3). Particular embodiments of the heavy and light chains of the antibody or antibody fragments of the instant invention are as follows. A heavy chain CDR1 having an amino acid sequence of Ser-Phe-Gly-Met-His (SEQ ID NO:28) or Thr-Ser-Gly-Met-Gly-Val-Xaa (SEQ ID NO:27), wherein Xaa is an amino acid with no side chain or a small side chain (e.g., Ser, Gly, or Ala). A heavy chain CDR2 having an amino acid sequence of His-Ile-Xaa$_1$-Trp-Asp-Asp-Asp-Lys-Xaa$_2$-Tyr-Asn-Pro-Ser-Leu-Lys-Ser (SEQ ID NO:32), wherein Xaa$_1$ is an amino acid with an aromatic side chain group (e.g., Phe, Tyr or Trp) and Xaa$_2$ is Ser, Arg or Tyr; or a heavy chain CDR2 having an amino acid sequence of Tyr-Ile-Xaa$_1$-Xaa$_2$-Xaa$_3$-Ser-Xaa$_4$-Thr-Ile-Tyr-Tyr-Ala-Asp-Thr-Val-Lys-Arg (SEQ ID NO:37), wherein Xaa$_1$ and Xaa$_2$ are amino acids with a polar side chain group (e.g., Arg, Ser, Gly, Thr, Cys, Tyr, Asn, Gln, Lys, or His); Xaa$_3$ is Gly or Val; and Xaa$_4$ is an amino acid with a polar and uncharged side group (e.g., Gly, Ser, Thr, Cys, Tyr, Asn, or Gln). A heavy chain CDR3 having an amino acid sequence of Arg-Ser-Ile-Xaa$_1$-Xaa$_2$-Xaa$_3$-Xaa$_4$-Pro-Glu-Asp-Tyr-Phe-Xaa$_5$-Tyr (SEQ ID NO:42), wherein Xaa$_1$ is an amino acid with a polar and uncharged side group (e.g., Gly, Ser, Thr, Cys, Tyr, Asn, or Gln); Xaa$_2$ is an amino acid with hyroxyl side chain group (e.g., Ser or Thr); Xaa$_3$ and Xaa$_4$ are amino acids with an aliphatic side chain group (e.g., Ala, Val, Leu, Ile, or Pro); and Xaa$_5$ is Asp or Ala. A light chain CDR1 having an amino acid sequence of Arg-Ser-Ser-Gln-Ser-Xaa$_1$-Xaa$_2$-His-Ser-Asn-Gly-Asn-Thr-Tyr-Leu-Xaa$_3$ (SEQ ID NO:52), wherein Xaa$_1$ and Xaa$_2$ are amino acids with an aliphatic side chain group (e.g., Ala, Val, Leu, Ile, or Pro) and Xaa$_3$ is an amino acid with a charged side chain group (e.g., Asp, Glu, Arg, His, or Lys). A light chain CDR2 having an amino acid sequence of Lys-Xaa$_1$-Ser-Asn-Arg-Phe-Xaa$_2$ (SEQ ID NO:57), wherein Xaa$_1$ is an amino acid with an aliphatic side chain group (e.g., Ala, Val, Leu, Ile, or Pro) and Xaa$_2$ is Ser or Phe. A light chain CDR3 having an amino acid sequence of Xaa$_1$-Gln-Xaa$_2$-Xaa$_3$-Xaa$_4$-Val-Pro-Xaa$_5$-Thr (SEQ ID NO:65), wherein Xaa$_1$ is Ser or Phe; Xaa$_2$ is an amino acid with no side chain (e.g., gly) or hyroxyl side chain group (e.g., Ser or Thr); Xaa$_3$ is an amino acid with a hyroxyl side chain group (e.g., Ser or Thr); Xaa$_4$ is His, Tyr or Leu; and Xaa$_5$ is an amino acid with an aliphatic side chain group (e.g., Ala, Val, Leu, Ile, or Pro). As will be appreciated by the skilled artisan, one or more of the CDRs within the heavy and light chain variable regions of an antibody can be replaced with one or more CDRs from another antibody to generate a wholly new antibody or antibody fragment. For example, replacing CDR3 of the heavy chain of 5F10 with the CDR3 of the heavy chain from 4E2 (SEQ ID NO:41) may enhance that ability of 5F10 to block binding of ADDLs to neuronal cells.

Antibodies with particular characteristics are contemplated. In one embodiment, an antibody which binds the 3-8 amino acid epitope of Aβ1-42 has a heavy chain CDR1 amino acid sequence of Thr-Ser-Gly-Met-Gly-Val-Xaa (SEQ ID NO:27), wherein Xaa is an amino acid with no side chain or a small side chain (e.g., Ser, Gly, or Ala); or a heavy chain CDR2 amino acid sequence of His-Ile-Xaa$_1$-Trp-Asp-Asp-Asp-Lys-Xaa$_2$-Tyr-Asn-Pro-Ser-Leu-Lys-Ser (SEQ ID NO:32), wherein Xaa$_1$ is an amino acid with an aromatic side chain group (e.g., Phe, Tyr or Trp) and Xaa$_2$ is Ser, Arg or Tyr. In another embodiment, an antibody with a moderate affinity for large (>50 kDa) ADDL aggregates over small (<30 kDa) aggregates (i.e. SEC Peak 1 and Peak 2, respectively), has a heavy chain CDR3 amino acid sequence of Arg-Ser-Ile-Xaa$_1$-Xaa$_2$-Xaa$_3$-Xaa$_4$-Pro-Glu-Asp-Tyr-Phe-Xaa$_5$-Tyr (SEQ ID NO:42), wherein Xaa$_1$ is an amino acid with a polar and uncharged side group (e.g., Gly, Ser, Thr, Cys, Tyr, Asn, or Gln), Xaa$_2$ is an amino acid with hyroxyl side chain group (e.g., Ser or Thr), Xaa$_3$ and Xaa$_4$ are amino acids with an aliphatic side chain group (e.g., Ala, Val, Leu, Ile, or Pro), and Xaa$_5$ is Asp or Ala.

Antibodies or antibody fragments of the present invention can have additional moieties attached thereto. For example, a microsphere or microparticle can be attached to the antibody or antibody fragment, as described in U.S. Pat. No. 4,493,825, the disclosure of which is incorporated herein by reference.

Moreover, antibody or antibody fragments of the invention can be mutated and selected for increased antigen affinity, neutralizing activity (i.e., the ability to block binding of ADDLs to neuronal cells or the ability to block ADDL assembly), or a modified dissociation constant. Mutator strains of *E. coli* (Low, et al. (1996) *J. Mol. Biol.* 260:359-368), chain shuffling (Figini, et al. (1994) supra), and PCR mutagenesis are established methods for mutating nucleic acid molecules encoding antibodies. By way of illustration, increased affinity can be selected for by contacting a large number of phage antibodies with a low amount of biotinylated antigen so that the antibodies compete for binding. In this case, the number of antigen molecules should exceed the number of phage antibodies, but the concentration of antigen should be somewhat below the dissociation constant. Thus, predominantly mutated phage antibodies with increased affinity bind to the biotinylated antigen, while the larger part of the weaker affinity phage antibodies remains unbound. Streptavidin can then assist in the enrichment of the higher affinity, mutated phage antibodies from the mixture (Schier, et al. (1996) *J. Mol. Biol.* 255:28-43). Exemplary affinity-maturated light chain CDR$^3$ amino acid sequences are disclosed herein (see Tables 11 and 12), with particular embodiments embracing a light chain CDR3 amino acid sequence of Xaa$_1$-Gln-Xaa$_2$-Thr-Arg-Val-Pro-Leu-Thr (SEQ ID NO: 318), wherein Xaa$_1$ is Phe or Leu, and Xaa$_2$ is Ala or Thr.

For some therapeutic applications it may be desirable to reduce the dissociation of the antibody from the antigen. To achieve this, the phage antibodies are bound to biotinylated antigen and an excess of unbiotinylated antigen is added. After a period of time, predominantly the phage antibodies with the lower dissociation constant can be harvested with streptavidin (Hawkins, et al. (1992) *J. Mol. Biol.* 226:889-96).

Various immunoassays including those disclosed herein can be used for screening to identify antibodies, or fragments thereof, having the desired specificity for multi-dimensional conformations of ADDLs. Numerous protocols for competitive binding (e.g, ELISA), latex agglutination assays, immunoradiometric assays, kinetics (e.g., BIACORE™ analysis) using either polyclonal or monoclonal antibodies, or fragments thereof, are well-known in the art. Such immunoassays typically involve the measurement of complex formation between a specific antibody and its cognate antigen. A two-site, monoclonal-based immunoassay utilizing monoclonal antibodies reactive to two non-interfering epitopes is suitable, but a competitive binding assay can also be employed. Such assays can also be used in the detection of multi-dimensional conformations of ADDLs in a sample.

An antibody or antibody fragment can also be subjected to other biological activity assays, e.g., displacement of ADDL binding to neurons or cultured hippocampal cells or blockade of ADDL assembly, in order to evaluate neutralizing or pharmacological activity and potential efficacy as a prophylactic or therapeutic agent. Such assays are described herein and are well-known in the art.

Antibodies and fragments of antibodies can be produced and maintained as hybridomas or alternatively recombinantly produced in any well-established expression system including, but not limited to, *E. coli*, yeast (e.g., *Saccharomyces* spp. and *Pichia* spp.), baculovirus, mammalian cells (e.g., myeloma, CHO, COS), plants, or transgenic animals (Breitling and Dübel (1999) In: Recombinant Antibodies, John Wiley & Sons, Inc., NY, pp. 119-132). Exemplary nucleic acid sequences of IgG1 and IgG2m4 heavy chain variable regions, as well as kappa light chain variable regions for humanized 4E2, 26D6, 20C2, 3B3, 2H4, and 1F6 generated by CDR grafting and veneering are presented in FIGS. 10A to 10T and set forth herein as SEQ ID NOs:132 to 151. For antibodies and fragments of antibodies can be isolated using any appropriate methods including, but not limited to, affinity chromatography, immunoglobulins-binding molecules (e.g., proteins A, L, G or H), tags operatively linked to the antibody or antibody fragment (e.g., His-tag, FLAG®-tag, Strep tag, c-myc tag) and the like. See, Breitling and Dübel (1999) supra.

Antibodies and antibody fragments of the instant invention have a variety of uses including, diagnosis of diseases associated with accumulation of ADDLs, blocking or inhibiting binding of ADDLs to neuronal cells, blocking ADDL assembly, prophylactically or therapeutically treating a disease associated with ADDLs, identifying therapeutic agents that prevent binding of ADDLs to neurons, and preventing the phosphorylation of tau protein at Ser202/Thr205.

Antibody and antibody fragments of the instant invention are also useful in a method for blocking or inhibiting binding of ADDLs to neuronal cells. This method of the invention is carried out by contacting a neuron, in vitro or in vivo, with an antibody or antibody fragment of the present invention so that binding of ADDLs to the neuron is blocked. In particular embodiments, an antibody or antibody fragment of the instant invention achieves at least a 15%, 20%, 30%, 40%, 50%, 60%, 70%, 80%, 90%, 95%, or 97% decrease in the binding of ADDLs as compared to binding of ADDLs in the absence of the antibody or antibody fragment. The degree to which an antibody can block the binding of ADDLs to a neuron can be determined in accordance with the methods disclosed herein, i.e., immunocytochemistry or cell-based alkaline phosphatase assay or any other suitable assay. Antibodies particularly useful for decreasing binding of ADDLs to neuronal cells include the exemplary 20C2, 3B3, 1F4, 1F6, 4E2, 2B4, 2D6, and 2H4 monoclonal antibodies.

Antibody and antibody fragments of the instant invention are further useful in a method for blocking or inhibiting assembly of ADDLs. This method involves contacting a sample containing amyloid β 1-42 peptides with an antibody or antibody fragment of the instant invention so that ADDL assembly is inhibited. The degree to which an antibody can block the assembly of ADDLs can be determined in accordance with the methods disclosed herein, i.e., FRET or fluorescence polarization or any other suitable assay. Antibodies particularly useful for blocking the assembly of ADDLs include the exemplary 1F4, 20C2, 4C2, 1F6, 2B4, 5F10, 2A10, and 2D6 antibodies.

Antibodies disclosed herein are also useful in methods for preventing the phosphorylation of tau protein at Ser202/Thr205. This method involves contacting a sample containing tau protein with an antibody or antibody fragment of the instant invention so that binding of ADDLs to neurons is blocked thereby preventing phosphorylation of tau protein. The degree to which an antibody can prevent the phosphorylation of tau protein at Ser202/Thr205 can be determined in accordance with the methods disclosed herein or any other suitable assay.

Blocking or decreasing binding of ADDLs to neurons, inhibiting assembly of ADDLs, and preventing the phosphorylation of tau protein at Ser202/Thr205 all find application in methods of prophylactically or therapeutically treating a disease associated with the accumulation of ADDLs. Accordingly, the present invention also embraces the use of an antibody or antibody fragment of the instant invention to prevent or treat a disease associated with the accumulation of ADDLs (e.g. Alzheimer's or similar memory-related disorders). Patients amenable to treatment include individuals at risk of disease but not exhibiting symptoms, as well as patients presently exhibiting symptoms. In the case of Alzheimer's Disease, virtually anyone is at risk of suffering from Alzheimer's Disease if he or she lives long enough. Therefore, the antibody or antibody fragments of the present invention can be administered prophylactically to the general population without the need for any assessment of the risk of the subject patient. The present methods are especially useful for individuals who have a known genetic risk of Alzheimer's Disease. Such individuals include those having relatives who have been diagnosed with the disease, and those whose risk is determined by analysis of genetic or biochemical markers. Genetic markers of risk for Alzheimer's Disease include mutations in the APP gene, particularly mutations at position 717 and positions 670 and 671 referred to as the Hardy and Swedish mutations respectively. Other markers of risk are mutations in the presenilin genes, PS1 and PS2, and ApoE4, family history of Alzheimer's Disease, hypercholesterolemia or atherosclerosis. Individuals presently suffering from Alzheimer's Disease can be recognized from characteristic dementia, as well as the presence of risk factors described above. In addition, a number of diagnostic tests are available for identifying individuals who have Alzheimer's Disease. These include measurement of CSF tau and Aβ1-42 levels. Individuals suffering from Alzheimer's Disease can also be diagnosed by ADRDA criteria or the method disclosed herein.

In asymptomatic patients, treatment can begin at any age (e.g., 10, 20, 30 years of age). Usually, however, it is not necessary to begin treatment until a patient reaches 40, 50, 60 or 70 years of age. Treatment typically entails multiple dosages over a period of time. Treatment can be monitored by assaying for the presence of ADDLs over time.

In therapeutic applications, a pharmaceutical composition or medicament containing an antibody or antibody fragment of the invention is administered to a patient suspected of, or already suffering from such a disease associated with the accumulation of ADDLs in an amount sufficient to cure, or at least partially arrest, the symptoms of the disease (biochemical, histologic and/or behavioral), including its complications and intermediate pathological phenotypes in development of the disease. In prophylactic applications, a pharmaceutical composition or medicament containing an antibody or antibody fragment of the invention is administered to a patient susceptible to, or otherwise at risk of, a disease associated with the accumulation of ADDLs in an amount sufficient to achieve passive immunity in the patient thereby eliminating or reducing the risk, lessening the severity, or delaying the outset of the disease, including biochemical, histologic and/or behavioral symptoms of the disease, its complications and intermediate pathological phenotypes presenting during development of the disease. In some methods, administration of agent reduces or eliminates myocognitive impairment in patients that have not yet developed characteristic Alzheimer's pathology. In particular embodiments, an effective amount of an antibody or antibody fragment of the invention is an amount which achieves at least a 15%, 20%, 30%, 40%, 50%, 60%, 70%, 80%, 90%, 95%, or 97% decrease in the binding of ADDLs to neurons in the patient as compared to binding of ADDLs in the absence of treatment. As such, impairment of long-term potentiation/memory formation is decreased.

Effective doses of the compositions of the present invention, for the treatment of the above described conditions vary depending upon many different factors, including means of administration, physiological state of the patient, whether the patient is human or an animal, other medications administered, and whether treatment is prophylactic or therapeutic. Usually, the patient is a human but nonhuman mammals such as dogs or transgenic mammals can also be treated.

Treatment dosages are generally titrated to optimize safety and efficacy. For passive immunization with an antibody or antibody fragment, dosage ranges from about 0.0001 to 100 mg/kg, and more usually 0.01 to 5 mg/kg, of the host body weight are suitable. For example, dosages can be 1 mg/kg body weight or 10 mg/kg body weight or within the range of 1-10 mg/kg. An exemplary treatment regime entails administration once per every two weeks or once a month or once every 3 to 6 months. In some methods, two or more antibodies of the invention with different binding specificities are administered simultaneously, in which case the dosage of each antibody administered falls within the ranges indicated. Antibodies are usually administered on multiple occasions, wherein intervals between single dosages can be weekly, monthly or yearly. Intervals can also be irregular as indicated by measuring blood levels of antibody to ADDLs in the patient. In some methods, dosage is adjusted to achieve a plasma antibody concentration of 1-1000 µg/mL and in some methods 25-300 µg/mL. Alternatively, the antibody or antibody fragment can be administered as a sustained-release formulation, in which case less frequent administration is required. Dosage and frequency vary depending on the half-life of the antibody in the patient. In general, human and humanized antibodies have longer half-lives than chimeric antibodies and nonhuman antibodies. As indicated above, dosage and frequency of administration can vary depending on whether the treatment is prophylactic or therapeutic. In prophylactic applications, a relatively low dosage is administered at relatively infrequent intervals over a long period of time. Some patients continue to receive treatment for the rest of their lives. In therapeutic applications, a relatively high dosage at relatively short intervals is sometimes required until progression of the disease is reduced or terminated, and preferably until the patient shows partial or complete amelioration of symptoms of disease. Thereafter, the patient can be administered a prophylactic regime.

Antibody and antibody fragments of the instant invention can be administered as a component of a pharmaceutical composition or medicament. Pharmaceutical compositions or medicaments generally contain the active therapeutic agent and a variety of other pharmaceutically acceptable components. See Remington: The Science and Practice of Pharmacy, Alfonso R. Gennaro, editor, 20th ed. Lippincott Williams & Wilkins: Philadelphia, Pa., 2000. The preferred form depends on the intended mode of administration and therapeutic application. Pharmaceutical compositions can contain, depending on the formulation desired, pharmaceutically-acceptable, non-toxic carriers or diluents, which are defined as vehicles commonly used to formulate pharmaceutical compositions for animal or human administration. Diluents are selected so as not to affect the biological activity of the combination. Examples of such diluents are distilled water, physiological phosphate-buffered saline, Ringer's solutions, dextrose solution, and Hank's solution.

Pharmaceutical compositions can also contain large, slowly metabolized macromolecules such as proteins, polysaccharides such as chitosan, polylactic acids, polyglycolic acids and copolymers (such as latex-functionalized SEPHAROSE™, agarose, cellulose, and the like), polymeric amino acids, amino acid copolymers, and lipid aggregates (such as oil droplets or liposomes).

Administration of a pharmaceutical composition or medicament of the invention can be carried out via a variety of routes including, but not limited to, oral, topical, pulmonary, rectal, subcutaneous, intradermal, intranasal, intracranial, intramuscular, intraocular, or intra-articular injection, and the like. The most typical route of administration is intravenous followed by subcutaneous, although other routes can be equally effective. Intramuscular injection can also be performed in the arm or leg muscles. In some methods, agents are injected directly into a particular tissue where deposits have accumulated, for example, intracranial injection. In some embodiments, an antibody or antibody fragment is injected directly into the cranium. In other embodiments, antibody or antibody fragment is administered as a sustained-release composition or device, such as a MEDIPAD™ device.

For parenteral administration, antibody or antibody fragments of the invention can be administered as injectable dosages of a solution or suspension of the substance in a physiologically acceptable diluent with a pharmaceutical carrier that can be a sterile liquid such as water, oils, saline, glycerol, or ethanol. Additionally, auxiliary substances, such as wetting or emulsifying agents, surfactants, pH buffering substances and the like can be present in compositions. Other components of pharmaceutical compositions are those of petroleum, animal, vegetable, or synthetic origin, for example, peanut oil, soybean oil, and mineral oil. In general, glycols such as propylene glycol or polyethylene glycol are suitable liquid carriers, particularly for injectable solutions. Antibodies can be administered in the form of a depot injection or implant preparation which can be formulated in such a manner as to permit a sustained-release of the active ingredient An exemplary composition contains an antibody at 5 mg/mL, formulated in aqueous buffer composed of 50 mM L-histidine, 150 mM NaCl, adjusted to pH 6.0 with HCl.

Typically, compositions are prepared as injectables, either as liquid solutions or suspensions; solid forms suitable for solution in, or suspension in, liquid vehicles prior to injection can also be prepared. The preparation also can be emulsified or encapsulated in liposomes or micro particles such as polylactide, polyglycolide, or copolymer for enhanced delivery.

For suppositories, binders and carriers include, for example, polyalkylene glycols or triglycerides; such suppositories can be formed from mixtures containing the active ingredient in the range of 0.5% to 10%, or more desirably 1%-2%.

Oral formulations include excipients, such as pharmaceutical grades of mannitol, lactose, starch, magnesium stearate, sodium saccharine, cellulose, and magnesium carbonate. These compositions take the form of solutions, suspensions, tablets, pills, capsules, sustained-release formulations or powders and contain 10%-95% of active ingredient, or more suitably 25%-70%.

Topical application can result in transdermal or intradermal delivery. Topical administration can be facilitated by co-administration of the agent with cholera toxin or detoxified derivatives or subunits thereof or other similar bacterial toxins (see Glenn, et al. (1998) *Nature* 391:851). Co-administration can be achieved by using the components as a mixture or as linked molecules obtained by chemical crosslinking or expression as a fusion protein.

Alternatively, transdermal delivery can be achieved using a skin path or using transferosomes (Paul, et al. (1995) *Eur. J. Immunol.* 25:3521-24; Cevc, et al. (1998) *Biochem. Biophys. Acta* 1368:201-15).

An antibody or antibody fragment of the invention can optionally be administered in combination with other agents that are at least partly effective in treatment of amyloidogenic disease.

Antibody and antibody fragments of the instant invention also find application in the identification of therapeutic agents that prevent the binding of ADDLs to neurons (e.g. a hippocampal cell) thereby preventing downstream events attributed to ADDLs. Such an assay is carried out by contacting a neuron with ADDLs in the presence of an agent and using an antibody of antibody fragment of the invention to determine binding of the ADDLs to the neuron in the presence of the agent. As will be appreciated by the skilled artisan, an agent that blocks binding of ADDLs to a neuron will decrease the amount of ADDLs bound to the neuron as compared to a neuron which has not been contacted with the agent; an amount which is detectable in an immunoassay employing an antibody or antibody fragment of the instant invention. Suitable immunoassays for detecting neuronal-bound ADDLs are disclosed herein.

Agents which can be screened using the method provided herein encompass numerous chemical classes, although typically they are organic molecules, preferably small organic compounds having a molecular weight of more than 100 and less than about 2,500 daltons. Agents encompass functional groups necessary for structural interaction with proteins, particularly hydrogen bonding, and typically include at least an amine, carbonyl, hydroxyl or carboxyl group, preferably at least two of the functional chemical groups. The agents often contain cyclical carbon or heterocyclic structures and/or aromatic or polyaromatic structures substituted with one or more of the above functional groups. Agents can also be found among biomolecules including peptides, antibodies, saccharides, fatty acids, steroids, purines, pyrimidines, derivatives, structural analogs or combinations thereof. Agents are obtained from a wide variety of sources including libraries of natural or synthetic compounds.

A variety of other reagents such as salts and neutral proteins can be included in the screening assays. Also, reagents that otherwise improve the efficiency of the assay, such as protease inhibitors, nuclease inhibitors, anti-microbial agents, and the like can be used. The mixture of components can be added in any order that provides for the requisite binding.

Agents identified by the screening assay of the present invention will be beneficial for the treatment of amyloidogenic diseases and/or tauopathies. In addition, it is contemplated that the experimental systems used to exemplify these concepts represent research tools for the evaluation, identification and screening of novel drug targets associated with amyloid beta induction of tau phosphorylation.

The present invention also provides methods for detecting ADDLs and diagnosing a disease associated with accumulation of ADDLs using an antibody or antibody fragment of the instant invention. A disease associated with accumulation of ADDLs is intended to include any disease wherein the accumulation of ADDLs results in physiological impairment of long-term potentiation/memory formation. Diseases of this type include, but are not limited to, Alzheimer's Disease and similar memory-related disorders.

In accordance with these methods, a sample from a patient is contacted with an antibody or antibody fragment of the invention and binding of the antibody or antibody fragment to the sample is indicative of the presence of ADDLs in the sample. As used in the context of the present invention, a sample is intended to mean any bodily fluid or tissue which is amenable to analysis using immunoassays. Suitable samples which can be analyzed in accordance with the methods of the invention include, but are not limited to, biopsy samples and fluid samples of the brain from a patient (e.g., a mammal such as a human). For in vitro purposes (e.g., in assays monitoring oligomer formation), a sample can be a neuronal cell line or tissue sample. For diagnostic purposes, it is contemplated that the sample can be from an individual suspected of having a disease associated with accumulation of ADDLs or from an individual at risk of having a disease associated with accumulation of ADDLs, e.g., an individual with a family history which predisposes the individual to a disease associated with accumulation of ADDLs.

Detection of binding of the antibody or antibody fragment to ADDLs in the sample can be carried out using any standard immunoassay (e.g., as disclosed herein), or alternatively when the antibody fragment is, e.g., a peptide aptamer, binding can be directly detected by, for example, a detectable marker protein (e.g., β-galactosidase, GFP or luciferase) fused to the aptamer. Subsequently, the presence or absence of the ADDL-antibody complex is correlated with the presence or absence, respectively, of ADDLs in the sample and therefore the presence or absence, respectively, of a disease associated with accumulation of ADDLs. It is contemplated that one or more antibodies or antibody fragments of the present invention can be used in conjunction with current non-invasive immuno-based imaging techniques to greatly enhance detection and early diagnosis of a disease associated with accumulation of ADDLs.

To facilitate diagnosis the present invention also pertains to a kit for containing an antibody or antibody fragment of the instant invention. The kit includes a container holding one or more antibody or antibody fragments which recognizes multi-dimensional conformation of ADDLs and instructions for using the antibody for the purpose of binding to ADDLs to form an antibody-antigen complex and detecting the formation of the antibody-antigen complex such that the presence or absence of the antibody-antigen complex correlates with presence or absence of ADDLs in the sample. Examples of containers include multiwell plates which allow simultaneous detection of ADDLs in multiple samples.

The invention is described in greater detail by the following non-limiting examples.

Example 1

General Materials and Methods

ADDL Preparation. ADDLs in F12 medium (Biosource, Camarillo, Calif.) were prepared from Aβ1-42 in accordance with established methods (Lambert, et al. (2001) supra). Briefly, Aβ1-42 peptide (American Peptide Co., Sunnyvale, Calif. or California Peptide Research, Inc., Napa, Calif.) was weighed and placed in a glass vial capable of holding a sufficient quantity of HFIP (1,1,1,3,3,3-hexafluoro-2-propanol) to achieve a peptide concentration of 10 mg/mL. HFIP was added to the dry peptide, the vial was capped and gently swirl to mix, and the peptide/HFIP solution was stored at room temperature for at least one hour. Aliquots (50 or 100 µL, 0.5 or 1.0 mg, respectively) of peptide solution was dispensed into a series of 1.5 mL conical centrifuge tubes. The tubes were placed in a speedvac overnight to remove the HFIP. Tubes containing the dried peptide film were capped and stored at −70° C. in a sealed container with dessicant.

Prior to use, the Aβ1-42 peptide film was removed from −70° C. storage and allowed to warm to room temperature. Fresh DMSO (44 μL/mg of peptide film; 5 mM) was added and the peptide/DMSO mixture was incubated on a vortex mixer at the lowest possible speed for ten minutes. F12 media (2 mL/mg peptide) was dispensed into each tube of DMSO/peptide and the tube was capped and mixed by inversion. The 100 μM preparation was stored at 2-8° C. for eighteen to twenty four hours. The samples were centrifuged at 14,000×g for ten minutes at 2-8° C. The supernatant was transferred to a fresh tube and stored at 2-8° C. until used.

Biotinylated ADDL preparations (bADDLs) were prepared in the same manner as described above for ADDL preparations using 100% N-terminal biotinylated amyloid beta peptide (American Peptide Company, Sunnyvale, Calif.).

ADDL Fibril Preparation. To room temperature ADDL peptide film was added 2 mL of 10 mM hydrochloric acid per mg peptide. The solution was mixed on a vortex mixer at the lowest possible speed for five to ten minutes and the resulting preparation was stored at 37° C. for eighteen to twenty four hours before use.

Monomer Preparation. HFIP dry down preparations of amyloid beta (1-40) peptide (Aβ1-40) were prepared as outlined for Aβ(1-42) peptide. The peptide film was dissolved in 2 mL of 25 mM borate buffer (pH 8.5) per mg of peptide, divided into aliquots, and frozen at −70° C. until used.

Human Fibril Preparation. Samples obtained from frozen human cortex were homogenized in 20× cold F12 medium with protease inhibitors (COMPLETE®, Roche Diagnostics Corporation, Indianapolis, Ind.) for 1 minute. The sample was then centrifuged at 10,000×g for 1 hour at 4° C. After washing twice with F12, the pellet was resuspended in 2% SDS/F12 and incubated on ice for 30 minutes. The sample was subsequently centrifuged at 220,000×g for 1 hour at 4° C. The pellet was resuspended in cold F12 and sonicated for 1 minute in 15-second bursts. Protein was determined using COOMASSIE PLUS™ kit (Pierce Biotechnology, Rockford, Ill.).

Immunization. The resulting soluble Aβ oligomers, referred to herein as "synthetic" ADDLs, were mixed 1:1 with complete Freund's adjuvant (first and second vaccination) or incomplete Freund's adjuvant (all subsequent vaccinations) and injected subcutaneously (first two vaccinations) or intraperitoneally into three mice in a total volume of ~1 mL/mouse. Each injection consisted of purified ADDLs equivalent to 194±25 μg total protein. Mice were injected approximately every three weeks. After six injections, one mouse died and its spleen was frozen. The spleen from the mouse with the highest titer serum was then fused with SP2/0 myeloma cells in the presence of polyethylene glycol and plated out into six 96-well plates. The cells were cultured at 37° C. with 5% $CO_2$ for ten days in 200 μL of HAT selection medium, which is composed of ISCOV medium supplemented with 10% fetal bovine serum (FBS), 1 μg/mL HYBRIMAX® (azaserine-hypoxanthine; Sigma-Aldrich, St. Louis, Mo.), and 30% conditioned media collected from SP2/0 cell culture. The cultures were fed once with ISCOV medium supplemented with 10% FBS on day 10, and the culture supernatants were removed on day 14 to screen for positive wells in ELISA. The positive cultures were further cloned by limiting dilutions with probability of 0.3 cells per well. The positive clones were confirmed in ELISA and further expanded.

Screening of supernates involved five assays: a dot blot and western immunoblot (Lambert, et al. (2001) supra), a native immunoblot using synthetic ADDLs, and a dot blot and western blot using endogenous fibrils obtained from human tissue. These assays tested the binding of antibodies to ADDLs (the dot blot) and identified the oligomer(s) that had the greatest affinity (western). All antibodies were tested in the dot blot using 5 pmole ADDLs (576 supernates in the first fusion and 1920 supernates in the second). Those supernatants that tested positive were then screened further using western blot at 10-20 pmole ADDLs. The screen was repeated to identify low positives or false positives. Ten wells supernatants expanded for the first mouse and forty-five wells were expanded for the second mouse. The expanded cells were then frozen or subcloned.

Monoclonal antibody-containing ascites were produced in female balb/c mice using standard protocols (Current Protocol of Molecular Biology). Briefly, mice were primed by intraperitoneal injection of 0.5 mL of pristane. One week after the priming, mice were injected intraperitoneally with approximately $5 \times 10^6$ hybridoma cells in 1 mL phosphate-buffered saline (PBS). Ascites were collected ten to fourteen days later. IgG purification was carried out by using BIO-RAD® AFFI-GEL® Protein A MAPS® II kit, according to manufacturer's protocol. For each run, 3 mL ascites were desalted by passage through a desalting column and elution in 4 mL binding buffer. The sample was then applied to the Protein A column. After washing with 40 mL binding buffer, the column was eluted with elution buffer and the 5 mL fractions were collected. Samples were neutralized by addition of 60 μL of 10 N NaOH. To exchange the buffer to PBS, the samples were applied to a second desalting column and eluted with PBS.

Control Antibodies. Polyclonal antibodies M71/2 and M90/1 were obtained from Bethyl Laboratories, Inc. (Montgomery, Tex.). Anti-Aβ monoclonal antibodies 6E10 (raised against residues 1-17) and 4G8 (raised against residues 17-24) were obtained from Signet Labs (Dedham, Mass.). Monoclonal antibody WO-2 is known in the art for its ability to recognize both 1-40 and 1-42 via western blot analysis (Ida, et al. (1996) J. Biol. Chem. 271: 22908-22914. Monoclonal antibody BAM-10 (raised against Aβ1-40) was obtained from ABCAM® (Cambridge, Mass.). Monoclonal antibody 26D6 is well-known in the art for its ability to recognize amino acids 1-12 of Aβ sequence (Lu, et al. (2000) Nat. Med. 6:397-404).

Immunoblot Analysis. Sodium dodecyl sulfate polyacrylamide gel electrophoresis (SDS-PAGE) was performed using established methods (Lambert, et al. (2001) supra), except that 10-20% Tris-Tricine gels (BIO-RAD®, Hercules, Calif.) were used and the separation was performed at 120 V. Gels were transferred according to standard methods and secondary antibody was routinely used at a 1:40,000 dilution.

For initial screening, 2.7 μg ADDLs, equivalent to ~16-20 pmol/lane, were separated on two-dimensional (2D) 4-20% gels. Electrophoresis and transfer were as above. Using the tracking dye as a guide, the nitrocellulose was placed into a Surf-blot apparatus (Idea Scientific, Minneapolis, Minn.) and 200 μL of hybridoma supernate mixed with blocking buffer, composed of 5% nonfat dry milk in tris-buffered saline with TWEEN™ 20 (TBS-T; Lambert et al. (2001) supra), was added to each of 20-21 wells. After incubation at room temperature for 1.5 hour with rocking, the supernatants were removed and the wells were washed with 200 μL blocking buffer. The membrane was then removed from the Surf-blot apparatus and washed 3×15 minutes in TBS-T. The secondary antibody (anti-mouse, IgG conjugated-HRP, 1:40,000;

Molecular Probes, Eugene, Oreg.) was then incubated with the membrane for 1 hour at room temperature. After washing (3×15 minutes), the oligomers were visualized with half-strength SUPERSIGNAL® (Pierce, Rockland, Ill.). The western immunoblot using human fibrils was performed in the same manner using approximately 64 µg of human fibrillar tissue in each 2D SDS-PAGE immunoblot.

Native polyacrylamide gel electrophoresis was performed according established methods (Chromy, et al. (2003) *Biochemistry* 42:12749-12760) except that the separation was performed at 120 V.

Western Blot. Separated proteins were transferred to nitrocellulose. Blots were blocked with 5% non-fat dry milk or 1% bovine serum albumin (BSA) in TBS-T (TBS with 0.1% TWEEN™ 20) overnight, incubated with primary antibody (ies) for 1.5 hours, washed, and incubated the horseradish peroxidase (HRP)-conjugated secondary antibody (Amersham Biosciences Corp., Piscataway, N.J.) for 1 hour. After final washing, proteins were visualized with a West Femto chemiluminescence kit (Pierce Biotechnology, Rockford, Ill.) and a KODAK® Image Station 440 CF or with film (HYPERFILM™, Amersham Biosciences Corp., Piscataway, N.J.).

Hippocampal Cultures. Cultures were prepared from E18 embryos according to standard methods (Brewer (1997) *J. Neurosci. Methods* 71:143-155; Stevens, et al. (1996) *J. Neurosci. Res.* 46:445-455). Viable cells were counted and plated on coverslips coated with polylysine (200 µg/mL) at densities from $1.5 \times 10^4 - 10^6$ cells/cm$^2$. The medium was changed by removing half of the medium and replacing it with supplemented NEUROBASAL™ media.

Primary Neurons. Primary hippocampal cultures were prepared from frozen, dissociated neonatal rat hippocampal cells (Cambrex, Corp., East Rutherford, N.J.) that were thawed and plated in 96-well COSTAR® plates at a concentration of 20,000 cells per well. The cells were maintained in NEUROBASAL™ media without L-glutamine (GIBCO-BRL™, Gaithersburg, Md.) and supplemented with B27 (GIBCO-BRL™, Gaithersburg, Md.) for a period of two weeks and then used for binding studies.

B103 Cells. The B103 neuroblastoma cell line (Schubert and Behl (1993) *Brain Res.* 629:275-82) was grown in DMEM without phenol red (GIBCO-BRL™, Gaithersburg, Md.), in the presence of 10% FBS (Hyclone, Logan, Utah) and 1% Pen-Strep (GIBCO-BRL™, Gaithersburg, Md.). Exponentially growing B103 cells were dissociated and plated in 96-well CORNING® plates at a concentration of 5,000 cells/well. Twenty-four hours after plating, the cells were used to assess ADDL and bADDL binding as well as characterize commercial and novel anti-ADDL monoclonal antibodies.

Dot Blot Analysis. Dot blots were performed according to Lambert, et al. ((2001) supra) applying either ADDLs (5 pmole/dot) or fibrils to the nitrocellulose. For later dot blots, ADDLs were applied to dry nitrocellulose in duplicate at various pmolar concentrations in 0.5 µL using a template derived from the Surf-blot apparatus. Samples were then dried for 15 minutes, blocked with blocking buffer for 1 hour, and incubated for 1.5 hour with antibody plus or minus peptide, which had been pre-incubated for at least 1 hour at room temperature. The solution was removed from the Surf-blot apparatus, the wells were washed with blocking buffer, and the membrane was removed from the apparatus. The nitrocellulose was washed, treated with secondary antibody, and visualized as indicated above.

Immunocytochemistry. Immunocytochemistry was performed according to established methods (Lambert, et al. (2001) supra), except the secondary antibodies were conjugated to ALEXAFLUOR® 588 (Molecular Probes, Eugene, Oreg.). Antibodies and ADDLs were preincubated for 1 hour at room temperature, at a molar ratio of 1:4 antibody:ADDL before application to the 21-day hippocampal cell culture. For endogenous ADDLs, human brain protein (prepared as in Lambert, et al. (2001) supra) was incubated with cells for 1 hour before the cells were washed, fixed, and visualized as above.

Lightly fixed frozen sections (4% paraformaldehyde at 4° C. for 30 hours and cryoprotected in 40 µm sucrose) from Alzheimer's Disease and control hippocampus were incubated with antibody (1:1000 in phosphate-buffered saline (PBS)) overnight at 4° C. After removal of antibody, sections were washed 3 times with PBS and incubated with secondary antibody at room temperature. Binding was then visualized with DAB (SIGMA™, St. Louis, Mo.). Sections were then counterstained with hematoxylin, mounted, and imaged on a NIKON® ECLIPSE® E600 light microscope with a SPOT™ INSIGHT™ digital video camera (v. 3.2).

Quantitative Immunocytochemistry. Cultured hippcampal cells were incubated with 500 nM ADDLs for 1 hour at 37° C. ADDLs were removed by washing and cells were fixed with 3.7% formaldehyde. Cells were incubated with 0.1% TRI-TON™ X-100 in PBS-NGS (PBS with 10% normal goat serum) for 30 minutes, washed once, and incubated with the desired primary antibody(ies) (diluted in PBS-NGS) overnight at 4° C. Samples were washed and incubated with the appropriate secondary antibody(ies), e.g., ALEXAFLUOR® 488 or 594 anti-mouse and anti-rabbit IgGs (Molecular Probes, Inc., Eugene, Oreg.), for 2 hours at 37° C. Coverslips were washed and mounted in PROLONG® anti-fade mounting medium (Molecular Probes, Inc., Eugene, Oreg.) and imaged using a LEICA® TCS SP2 confocal Scanner DMRXE7 microscope.

ELISA. Polyclonal anti-ADDLs IgG (M90/1; Bethyl Laboratories, Inc., Montgomery, Tex.) was plated at 0.25 mg/well on IMMULON™ 3 REMOVAWELL™ strips (Dynatech Labs, Chantilly, Va.) for 2 hours at room temperature and the wells blocked with 2% BSA in TBS. Samples diluted with 1% BSA in F12 were added to the wells, allowed to bind for 2 hours at 4° C., and washed 3× with BSA/TBS at room temperature. Monoclonal antibodies diluted in BSA/TBS were incubated for 90 minutes at room temperature and detected with a VECTASTAIN® ABC kit to mouse IgG. The HRP label was visualized with BIO-RAD® peroxidase substrate and read at 405 nm on a Dynex MRX-TC microplate reader.

Example 2

Development and Characterization of Anti-ADDL Antibodies

Three mice were inoculated with ADDLs (194±25 µg protein/injection) every three weeks for a total of six inoculations. Hybridomas made from the fusion of these mice spleens with SP2 cells were grown in 96-well plates. Supernates from these wells were screened in dot blots with synthetic ADDLs to identify positive clones, which were compared with dot blots of endogenous fibrils to identify differences. Hybridomas that bound only synthetic ADDLs and not endogenous fibrils were sought. To further refine what the products of the hybridomas bound to and under what conditions binding occurred, three western blots of each positive clone were performed: SDS-PAGE of ADDLs, native gels of ADDLs, and SDS-PAGE with endogenous fibrils.

Approximately 40 clones were selected for further examination. Each clone was tested for recognition of soluble Alzheimer's Disease brain extract, for identification of ADDLs bound to cultured hippocampal cells, and for the ability to block ADDL binding under various conditions. Selected antibodies were collected from culture medium and further purified using Protein G SEPHAROSE™.

Each time a set of hybridomas was screened via dot blot, approximately ~30% yielded positive supernates. Of these, only one or two hybridomas bound synthetic ADDLs and not endogenous fibrils. Approximately 2% of the original number of clones bound synthetic ADDLs and not monomer at low ADDL concentrations, as determined by western blot analysis. Clone 3B7, which bound synthetic ADDLs and not fibrils on western blots, was kept for further analysis.

One to two clones were identified that bound higher molecular weight material (12-24 mer) better than trimer/tetramer oligomers. Two to three clones were identified which could bind to native ADDLs under native conditions, but failed to bind ADDLs in the presence of SDS.

The results of this analysis indicated that ADDLs are good antigens in mice and monoclonal antibodies can be developed that bind to synthetic ADDLs with much greater affinity than to monomers.

Example 3

Immunohistochemical Analysis of Endogenous and Synthetic ADDLs Bound to Cultured Hippocampal Cells Cultured hippocampal cells were also analyzed to determine whether monoclonal antibodies that distinguish between Alzheimer's Disease and control brain extracts could identify ADDLs (either endogenous or synthetic) bound to cultured cells. Hippocampal cultures were prepared according to established protocols and allowed to grow for 3-4 weeks. Synthetic ADDLs were prepared according to standard protocols (e.g., U.S. Pat. No. 6,218,506). Endogenous ADDLs were extracted from Alzheimer's Disease brain according to Gong, et al. ((2003) supra). ADDLs (100 nM in F12, or 2 mg total protein in F12) were incubated with the cells for 1 hour and then washed and fixed according to standard methods. Following washing, the cells were incubated with 20C2, 3B7, M94, 2A10, 4E2, 2D6, 4C2, 2B4, 5F10, or 5G12 monoclonal antibody and subsequently with anti-mouse secondary conjugated to ALEXAFLUOR® 488. Images were taken on a NIKON® DIAPHOT™ epifluorescent microscope with COOLSNAP™ HQ camera and analyzed using METAMORPH™ software (Universal Imaging, Downingtown, Pa.).

Both endogenous and synthetic ADDLs exhibited the standard hot spot pattern in cultured cells when visualized by 20C2. Thus, monoclonal antibody 20C2 identifies both synthetic and endogenous ADDLs bound to cultured hippocampal cells. As 3B7 did not bind to fibrils, higher molecular weight oligomers, and monomers, hot spot binding of ADDLs by 3B7 was attributed to oligomeric ADDLs. The other antibodies appeared to recognize a variety of epitopes on ADDLs bound to cells, ranging from hot spots on processes (M94, 2A10) to cell body specific attachment (4E2) and other states in between (2D6, 4C2, 2B4, 5F10, 5G12).

Example 4

Inhibition of ADDL Binding to Neurons Using Murine Anti-ADDL Antibodies

To determine whether monoclonal antibodies that distinguish between Alzheimer's Disease and control brain extracts could also block binding of ADDLs to cultured cells, cultured hippocampal cells were preincubated with 20C2 antibody and ADDL binding was determined by immunocytochemistry. Hippocampal cultures were prepared according to established methods and allowed to grow for 3-4 weeks. Synthetic ADDLs were prepared according to standard protocols (e.g., see U.S. Pat. No. 6,218,506 and the like). Endogenous ADDLs were extracted from Alzheimer's Disease brain according to Gong, et al. ((2003) supra). ADDLs (100 nM in F12, or 2 mg total protein in F12) were preincubated with 20C2 antibody for 1 hour and subsequently added to cells for 1 hour at 37° C. Cells were washed, fixed, and incubated with anti-mouse secondary conjugated to ALEXAFLUOR® 488.

Both endogenous and synthetic ADDL binding to cultured cells was blocked by preincubation with 20C2. Vehicle and no-secondary antibody control images were black.

Example 5

Detection of ADDL Binding to Neurons Using Biotinylated ADDLs

The binding of ADDLs or bADDLs (biotinylated ADDLs) to neurons was detected using standard immunofluorescence procedures. Primary hippocampal neurons (cultured for fourteen days) or B103 cells (plated for twenty-four hours) were incubated with 5-25 µm ADDLs or bADDLs for one hour at 37° C. and the cells were subsequently washed three to four times with warm culture medium to remove unbound ADDLs or bADDLs. The cells were then fixed for ten minutes at room temperature with 4% paraformaldehyde prepared from 16% paraformaldehyde (Electron Microscopy Sciences, Fort Washington, Pa.) diluted in PBS. Subsequently, the solution was removed and fresh fixative added for an additional ten minutes at room temperature. The cells were permeabilized (4% paraformaldehyde solution with 0.1% TRITON™-X 100; SIGMA, St. Louis, Mo.) for ten minutes, washed six times with PBS and incubated for one hour at 37° C. with blocking buffer (PBS with 10% BSA; Sigma, St. Louis, Mo.). At this point, the protocols for the detection of bound ADDLs and bADDLs diverge. To detect ADDL binding, the cells were incubated overnight at 37° C. with 4G8 (diluted 1:1,000 in PBS containing 1% BSA; Signet Labs, Dedham, Mass.), 6E10 (1:1,000; Signet Labs, Dedham, Mass.), or one of the anti-ADDL monoclonal antibodies disclosed herein (diluted 1:1,000). In addition, a polyclonal antiserum raised against tau (1:1,000; Sigma, St. Louis, Mo.) was used to visualize the cell processes. The next day, the cells were washed three times with PBS, incubated for one hour at room temperature with an ALEXA® 594-labeled anti-mouse secondary (diluted 1:500 in PBS with 1% BSA; Molecular Probes, Eugene, Oreg.) and an ALEXA® 488-labeled anti-rabbit secondary (diluted 1:1,000; Molecular Probes, Eugene, Oreg.), washed three times in PBS and the binding observed using a microscope with fluorescence capabilities. For the detection of bADDL binding, the cells were incubated overnight with the tau antibody. Subsequently, the cells were washed three times with PBS, incubated for one hour at room temperature with an ALEXA® 488-labeled anti-rabbit secondary (as above) and an ALEXA® 594-labeled streptavidin, 1:500 dilution (Molecular Probes, Eugene, Oreg.), washed 5-6 times in PBS and the binding visualized with a fluorescence microscope. If the staining of the cell nuclei was desired, the nuclei were labeled with DAPI (1:1000) according to standard protocols.

For immunocytochemical analysis of ADDLs using an ADDL-specific monoclonal antibody, cells were washed, fixed, permeabilized and blocked after incubation with ADDLs. To detect the bound bADDLs with monoclonal antibodies, the cells were incubated overnight with 4G8, 6E10 or one of the instant anti-ADDL monoclonal antibodies and immunoreactivity was subsequently detected with an ALEXA® 488-labeled anti-mouse secondary antibody. The bound bADDLs were visualized with an ALEXA® 594-labeled streptavidin and the nuclei stained with DAPI. After staining, the colocalization of bADDL binding and ADDL immunoreactivity was detected with a fluorescence microscope.

Specific immunoreactivity with primary hippocampal cells incubated with ADDLs was seen with each of the monoclonal antibodies evaluated (i.e., 20C2, 2H4, 2B4, and 2A10). The bound ADDLs appeared as punctate staining along the neuronal processes and cell soma. This pattern was only seen on a subset of neurons, a pattern that is consistent with previous reports describing ADDL binding to primary neurons using both commercial and non-commercial antibodies. The pattern of staining and the results of a number of control studies demonstrated the specificity of these antibodies.

The use of bADDLs offered a simplified method to detect bound ADDLs and evaluate the blockade of ADDL binding with the monoclonal antibodies. When bADDLs were added to primary hippocampal cells and the binding evaluated with a fluorescent-labeled streptavidin, specific binding was seen along the neuronal processes of a subset of cells in culture. If the cells were then fixed, processed for immunocytochemistry and an anti-ADDL antibody used to visualize binding, a similar pattern of staining was observed. Furthermore, the superimposition of these staining patterns revealed a perfect overlap of the antibody staining and bound bADDLs, thus demonstrating that bADDLs and ADDLs are functionally equivalent and the use of bADDLs in binding assays.

Example 6

Detecting and Measuring Murine anti-ADDL Monoclonal Antibody Differential Displacement of bADDL Binding to Neurons The ability of antibodies to block the binding of ADDLs or bADDLs to neuronal cultures (primary neurons or B103 cells) was characterized using the immunocytochemical methods described herein with a few modifications. Monoclonal antibodies were mixed with 1-10 µm bADDLs at a molar ratio of 1:1, 1:5 or 1:10 (antibody:bADDLs) and incubated in a siliconized microcentrifuge tube for one hour at 37° C. on a slow rotator (Miltenyi Biotec, Auburn, Calif.). Subsequently, the antibody/bADDL mixture was added to cells and allowed to further incubate for one hour at 37° C. After incubation, the cells were washed, fixed, permeabilized, blocked and incubated overnight with a polyclonal antiserum raised against tau to visualize the cell processes. The next day, the cells were washed, incubated with an ALEXA® 488-labeled anti-rabbit secondary antibody and an ALEXA® 594-labeled streptavidin and the cells were stained with DAPI to allow detection of nuclei. Once stained, the degree of binding was assessed visually with a fluorescence microscope.

To quantitatively assess the degree of bADDL binding and the ability of anti-ADDL antibodies to abate this interaction, a cell-based alkaline phosphatase assay was developed. Monoclonal antibodies or PBS were mixed at a 1:1 (B103 cells) or 1:5 (primary neurons) molar ratio with 2.5-10 µm (final concentration) of bADDLs and incubated for one hour at 37° C. on a slow rotator. After preincubation, the antibody/bADDL preparations were added to the B103 or primary neuron cultures and incubated for an additional one hour at 37° C. At the end of the incubation period, the bADDLs/antibody mixture was removed and the plates washed six times with media. The cells were fixed in 4% paraformaldehyde for ten minutes at room temperature, the solution removed, fresh fixative added and the cells fixed for an additional ten minutes. The cells were permeabilized with 4% paraformaldehyde containing 0.1% TRITON™ X-100 (2 times, each for ten minutes at room temperature), washed six times in PBS and treated with 10% BSA in PBS for one hour at 37° C. Alkaline phosphatase-conjugated streptavidin (1:1, 500 in 1% BSA; Molecular Probes, Eugene, Oreg.) was added to the cells for one hour at room temperature. The cells were rinsed six times with PBS, the alkaline phosphatase substrate (CDP-STAR® with SAPPHIRE-II™; Applied Biosystems, Foster City, Calif.) added to the cells and incubated for thirty minutes prior to determining the luminescence on a LJL Luminometer (Analyst AD; LJL BioSystems, Sunnyvale, Calif.).

When the binding of bADDLs to the neurons was evaluated, an antibody-dependant pattern of staining was observed. Some of the antibodies investigated markedly reduced the binding of bADDLs, while others were less effective. Unexpectedly, a third group of antibodies appeared to enhance the binding of bADDLs to neurons. While the results of these studies were qualitative and not quantitative in nature, they indicated that the antibodies differentially blocked bADDL binding to neurons. Quantitative assessment demonstrated a similar trend (FIG. 1). That is, some antibodies abated the binding of bADDLs to neurons, some were weak or had little effect and a few enhanced the binding (i.e., 5F10 and 4C2). Moreover, a mouse Fab was unable to block the binding of bADDLs, further demonstrating the specificity of the monoclonal antibodies in this assay.

Figure 2:
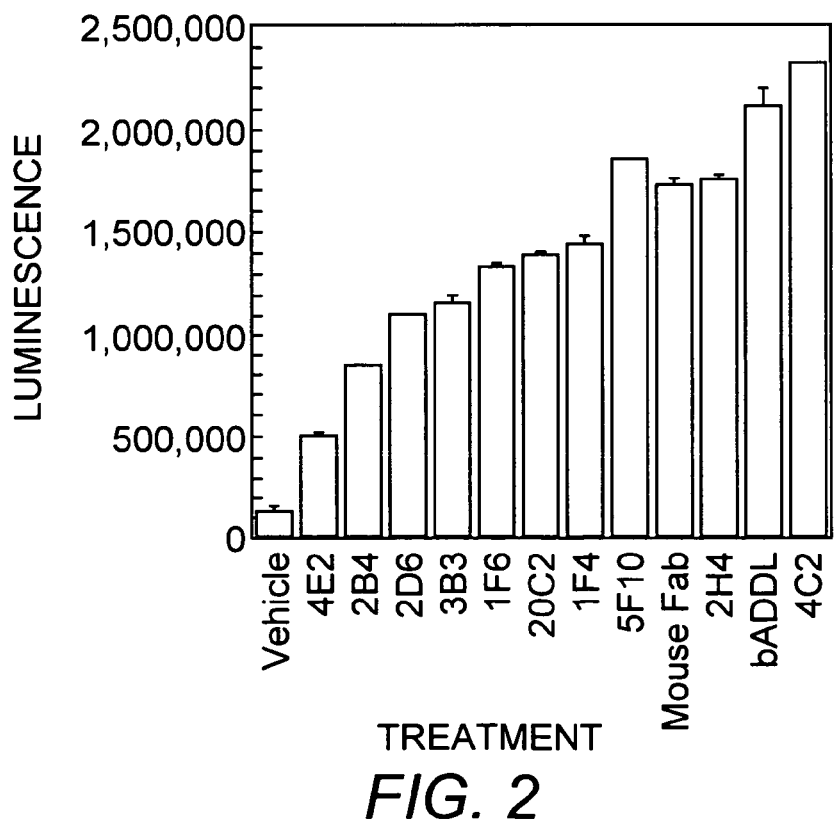
FIG. 2 shows a summary of bADDL binding when B103 cells are pre-incubated with anti-ADDL antibodies.

Analysis of bADDL binding and blockade with monoclonal antibodies in the neuroblastoma cell line B103 demonstrated specific bADDL binding to B103 cells, but not to an ovarian cell line (CHO). Moreover, the binding was dramatically attenuated when bADDLs were pre-incubated with an anti-ADDL monoclonal antibody prior to the addition to B103 cells. Quantitative assessment of the blockade of bADDL binding to B103 cells with monoclonal antibodies indicated that the monoclonal antibodies were not equal in their ability to block bADDL binding to cells (FIG. 2). As seen with the primary hippocampal cells, some antibodies were quite good at blocking binding, while others were less effective. Furthermore, the antibody 4C2 also enhanced the ability of bADDLs to bind to B103 cells in culture.

To show that bADDLs also bind to regions of the hippocampus that are involved in learning and memory, a series of binding studies were conducted using rat hippocampal slice cultures. Binding studies showed that neurons in the CA1-3 and dentate gyrus regions of the hippocampus were capable of binding bADDLs, while neurons in other regions did not. When the bADDLs were pre-incubated with an anti-ADDL monoclonal antibody, the degree of bADDL binding was attenuated in a dose-dependant manner. These results showed that monoclonal antibodies can also abate the binding of bADDLs to a subset of hippocampal neurons, neurons that a critical for learning and memory.

Example 7

Binding of Anti-ADDL Antibodies to Endogenous ADDLs from Alzheimer's and Control Brain To further characterize the monoclonal antibodies disclosed herein, it was determined whether the monoclonal antibodies could identify ADDLs from soluble extracts of human Alzheimer's Disease brain (endogenous ADDLs) and distinguish that from extracts of control brain. Synthetic ADDLs and human brain extracts prepared in F12 were diluted in F12 and spotted (1 pmole ADDLs; 0.5 µg brain extract) in duplicate onto dry HYBOND™ ECL™ nitrocellulose. Brain tissue, with corresponding CERAD grades (Consortium to Establish a Registry for Alzheimer's Disease) and Braak stages, was obtained from NU Brain Bank Core. The blot was allowed to dry 20 minutes and then incubated in 3% $H_2O_2$ in TBS (20 mM Tris-HCl, pH 7.5, 0.8% NaCl) for 20 minutes at room temperature. The blot was cut into strips and blocked with 5% milk in TBS-T (0.1% TWEEN™-20 in TBS) for 1 hour at room temperature. Rabbit polyclonal antibody M71/2 (1:2500, 0.4 µg; Bethyl Laboratories, Inc., Montgomery, Tex.); monoclonal antibody 6E10 (1:500, 3 µg; Signet Labs, Dedham, Mass.); and monoclonal antibodies 20C2 (1.52 mg/mL, 5 µg), 11B5 (2.54 mg/ml, 5 µg), 2B4 (1.71 mg/mL, 5 µg), and 2A10 (1.93 mg/mL, 7.5 µg) as disclosed herein (FIG. 3) were diluted in 1.5 mL of milk/TBS-T and incubated for 1 hour at room temperature. The blots were washed 3×10 minutes with TBS-T. The blots were incubated with horseradish peroxidase (HRP)-linked secondary antibody (1:40,000 in milk/TBS-T; Amersham Life Science, Inc., Arlington Heights, Ill.) for 1 hour at room temperature. The blots were washed 3×10 minutes with TBS-T, rinsed 3 times with $dH_2O$, developed with SUPERSIGNAL™ substrate (1:1 dilution with $ddH_2O$; Pierce, Rockland, Ill.) and exposed to HYPERFILM™ ECL™ (Amersham Life Science, Inc., Arlington Heights, Ill.).

All antibodies tested identified synthetic ADDLs with robust binding, except 2A10, which had weaker binding, even though it was tested at higher protein concentration. Polyclonal antibody M71/2 and monoclonal antibodies 20C2 and 11B5 bound strongly to both Alzheimer's Disease samples, but showed only very faint binding, similar to background in control brain. In contrast, monoclonal antibodies 6E10, 2B4, and 2A10 showed weak binding to Alzheimer's Disease brain.

The results of this analysis indicated that two of the monoclonal antibodies tested could distinguish between Alzheimer's Disease and control brain, wherein binding to endogenous oligomers was with a high degree of specificity. In addition, these data indicate that detection can be accomplished in early stages of Alzheimer's Disease.

Example 8

Immunohistochemical Analysis of Alzheimer's Disease and Control Brain Slices

Immunohistochemical analysis using the monoclonal antibodies disclosed herein was carried out to determine whether ADDLs can be visualized in brain slices using monoclonal antibodies that distinguish between Alzheimer's Disease and control brain extracts, and to demonstrate the nature of ADDL labeling (e.g., diffuse, perineuronal, plaque-like, etc.) and its distribution in human tissue. Sections (40 µm) of fixed Alzheimer's Disease and control brain were prepared in accordance with standard methods. The slices were labeled with several monoclonal and one polyclonal antibody and subsequently counterstained with hematoxylin to identify cell nuclei. Images were obtained using a NIKON® ECLIPSE® E600 light microscope with a SPOT™ INSIGHT™ digital video camera (v. 3.2).

Immunohistochemical analysis indicated that ADDL staining was manifest in Alzheimer's Disease brain in the hippocampus, entorhinal cortex, and middle frontal gyrus. In a severe Alzheimer's Disease case, there was abundant light ADDLs staining in what appeared predominantly as a plaque-type distribution. Some light ADDL staining was observed as peri-neuronal in one Alzheimer's Disease case. In contrast, there is no staining using either antibody in any regions of control samples, not even a rare neuron surrounded by dot-like immunostaining.

These data indicate that polyclonal and monoclonal antibodies can be used to identify ADDLs in fixed human tissue, wherein labeling is varied, consisting of plaque-like regions, vascular regions, and peri-neuronal labeling of individual cells and some clusters. Further, labeling of ADDLs in Alzheimer's Disease, but not control, brain was observed in at least three brain regions: hippocampus, entorhinal cortex, and middle frontal gyrus.

Example 9

Immunostaining of Aβ1-40 Monomer-Like Control

Aβ1-40 oligomerizes slowly in DMSO/F12 compared to ADDLs. Thus, it was determined whether Aβ1-40 could serve as a monomer-like control. ADDLs were subjected to size exclusion chromatography (SEC) on a SUPERDEX® 75 column (ADDL063), which resolved into two peaks. Aβ1-40 was prepared in DMSO/F12 (45.5 mM), frozen and thawed. Samples were diluted with F12 and mixed ~2:1 with Tricine sample buffer (BIO-RAD®, Waltham, Mass.). SDS-PAGE was carried out on 10-20% Tris-Tricine gels (BIO-RAD®, Waltham, Mass.) with Tris/Tricine/SDS buffer (BIO-RAD®, Waltham, Mass.) at 120V at room temperature for 80 minutes. The gel was silver stained (60 pmoles Aβ1-40 or ADDLs; 40 pmoles Peaks 1 or 2) with SILVERXPRESS™ (INVITROGEN™, Carlsbad, Calif.). Alternatively, the gels (20 pmoles Aβ1-40 or ADDLs; 30 pmoles Peaks 1 or 2) were electroblotted onto HYBOND™ ECL™ nitrocellulose using 25 mM Tris-192 mM glycine, 20% v/v methanol, pH 8.3, 0.02% SDS at 100V for 1 hour at 8° C. The blots were blocked with 5% milk in TBS-T (0.1% TWEEN™-20 in 20 mM Tris-HCl, pH 7.5, 0.8% NaCl) overnight at 8° C. Monoclonal antibody 6E10 (1:2000; Signet Labs, Dedham, Mass.), monoclonal antibody 20C2 (1.52 mg/mL, 1:2000; FIG. 3), or polyclonal antibody M71/2 (1:4000, Bethyl Laboratories, Inc., Montgomery, Tex.) was diluted in milk/TBS-T and incubated with the blots for 90 minutes at room temperature. The blots were washed 3×10 minutes with TBS-T and subsequently incubated with HRP-conjugated secondary antibody (1:40,000 in TBS-T; Amersham Life Science, Inc., Arlington Heights, Ill.) for 1 hour at room temperature. After three washes with TBS-T, 10 minutes per wash, the blots were rinsed 3× with $dH_2O$, developed with SUPERSIGNAL® West Femto Maximum Sensitivity substrate (1:1 dilution with $ddH_2O$; Pierce, Rockland, Ill.) and exposed to HYPERFILM™ ECL™ (Amersham Life Science, Inc., Arlington Heights, Ill.).

Silver stain analysis showed Aβ1-40 as a heavy monomer band. In contrast, ADDLs and Peak 1 showed monomer, trimer and tetramer, although there was less tetramer. Silver stain analysis of Peak 2 showed heavy monomer with a lighter trimer and very light tetramer band.

Immunostaining of Aβ1-40 with 6E10 showed only a light monomer band. Immunostaining of ADDLs and Peak 1 with 6E10 showed monomer, trimer, tetramer and 12-24mer. Peak 2 showed heavy monomer staining with 6E10 and some light trimer and tetramer with no 12-24mer. There was no monomer staining of Aβ1-40 with 20C2 or M71/2. While both 20C2 and M71/2 showed minimal or no monomer staining of ADDLs and Peak 1, these samples had trimer, tetramer, and 12-24mer staining with 20C2 and M71/2. Peak 2 immunostaining with 20C2 and M71/2 showed light monomer, trimer and tetramer with no 12-24mer observed. Aβ1-40 immunostained lighter with 6E10 than did the ADDL monomer, despite heavier silver staining.

These results indicated that, in contrast to the 6E10 antibody which shows good recognition of monomer, gels transferred with 0.02% SDS in the transfer buffer showed minimal monomer detection with the oligomer-specific antibodies. Immunostaining of SEC fractions showed Peak 2 composed mostly of monomer with small amounts of trimer and tetramer and no 12-24mer, while Peak 1 has monomer, trimer, tetramer and the 12-24mers.

To further characterize the monoclonal antibodies with respect to binding to Peak 1 and Peak 2, a sandwich ELISA was developed using polyclonal antibody M90 to ADDLs as the capture antibody. SEC peak 1 and peak 2 fractions referred to herein are the two major peaks of ADDLs that were fractionated on a SEPHADEX™ 75 column to distinguish between potentially bioactive and inactive oligomers. Non-denaturing gel electrophoresis confirmed the separation into large (>50 kDa) and small (<30 kDa) aggregates that were stable at 37° C. These peaks were used separately as the detection substance for clone supernates. Binding was visualized with a VECTASTAIN® kit. Differences between recognition of the two peaks was observed for all antibodies. For example, compare the ratio of peak 1 to peak 2 for antibodies 2B4 and 20C2 (FIG. 3). Only one antibody reflects the control antibody (6E10) preference for peak 2.

Example 10

Detection of ADDL Formation from Aβ1-42

Polyclonal antibodies have been used in dot-blots to show time-dependent ADDL formation from Aβ1-42. Thus, it was demonstrated that monoclonal 20C2 antibody, which preferentially binds to oligomers, could also show increased signal with time as ADDLs form from Aβ1-42. Aβ1-42, ~750 pmoles HFIP film, was dissolved in 1.5 mL DMSO (0.5 mM) and 2 μL aliquots diluted to a final volume of 100 μL with F12 (10 nM) and incubated on ice. Two μL (20 fmol) of reaction mixture was spotted on dry HYBOND™ ECL™ nitrocellulose (Amersham Life Science, Inc., Arlington Heights, Ill.) at specified time points. The nitrocellulose was blocked with 5% non-fat dry milk in TBS-T (20 mM Tris-HCl, pH 7.5, 0.8% NaCl, 0.1% TWEEN™-20) for 1 hour at room temperature. Polyclonal antibody M90/1 (Bethyl. Laboratories, Inc., Montgomery, Tex.) or monoclonal antibody 20C2 (1.52 mg/mL) was diluted 1:2000 in milk/TBS-T and incubated with the blot for 90 minutes at room temperature followed by washing 3×10 minutes with TBS-T. HRP-conjugated secondary antibodies (Amersham Life Science, Inc., Arlington Heights, Ill.) were diluted 1:40,000 in milk/TBS-T and the blot incubated for 60 minutes at room temperature followed by washing as above. After a brief rinse with $dH_2O$, the blot was incubated for 60 seconds with SUPERSIGNAL® West Femto Maximum Sensitivity substrate (diluted 1:1 with $ddH_2O$; Pierce, Rockland, Ill.) and exposed to HYPERFILM™ ECL™ (Amersham Life Science, Inc., Arlington Heights, Ill.). Dot blots were scanned and intensity of spots was determined with ADOBE® PHOTOSHOP®.

Both antibodies detected time-dependent ADDL formation from Aβ1-42, wherein the results for 20C2 showed better signal and consistency. Neither antibody could detect Aβ1-40 at a concentration equivalent to ADDLs. These data further demonstrate the oligomer-specificity of this antibody, since monomers are present all the time and oligomers form with time. In addition, both M90/1 and 20C2 showed minimal recognition of Aβ1-40 monomers even at a 100-fold higher concentration than ADDLs.

Example 11

Competition Dot Blot Assays

To determine whether the monoclonal antibodies disclosed herein could bind monomers, a competition dot blot assay was performed with synthetic ADDLs, 20C2, and Aβ1-40. ADDLs were applied to dry nitrocellulose at 10 pmol/0.5 μL. While the nitrocellulose was being blocked in 5% NDM/TBS-T for one hour, ADDLs and fresh Aβ1-40 at various concentrations were incubated with 200 μL each of 20C2 (1.5 μg/mL final concentration) in 5% NDM/TBS-T for 1 hour. These solutions were then applied to the nitrocellulose using the SURF-BLOT apparatus and incubated at room temperature for 1.5 hours with rocking. The blot was subsequently visualized with anti-mouse IgG-HRP and chemiluminescence. Quantitation was performed using the KODAK® IMAGESTATION® 440 and EXCEL®.

Results of this analysis indicated that synthetic ADDLs in solution could effectively and specifically block 20C2 binding to ADDLs immobilized on nitrocellulose with a half maximal inhibition observed at <50 nM for ADDLs. In contrast, Aβ1-40 in solution did not block binding of 20C2 to immobilized ADDLs.

To determine which portions constitute the binding epitope of the Aβ1-42 molecule, a competition dot blot assay was performed with ADDLs, 20C2, and peptides. ADDLs were spotted on nitrocellulose at four concentrations (1, 0.5, 0.25, and 0.125 pmole) each in 0.5 μL. While the nitrocellulose was being blocked in 5% NDM/TBS-T for two hours, the peptides at 50, 100 and 200 pmol were added to 200 μL of 20C2 (1.52 μg/mL final concentration=1.9 pmol, in 5% NDM/TBS-T) and rocked at room temperature. The solutions were subsequently incubated with the nitrocellulose using the SURF-BLOT apparatus for 1.5 hours at room temperature. Binding was visualized with anti-mouse IgG-HRP using chemiluminescence.

The results of this analysis indicated that binding to ADDLs was blocked by the ADDLs themselves and by Aβ1-28, but no other combination of peptides. Thus, the binding epitope required some conformation that Aβ1-28 could attain, but that was not available on Aβ1-12 and Aβ12-28 or their combination. Alternatively, Aβ1-28 forms a dimer that blocks binding of ADDLs by steric hindrance.

To determine whether Aβ1-28 aggregates (similar to Aβ1-42) or folds such that it blocks the binding epitope for 20C2, SDS-PAGE gels were silver stained and western blot analysis was performed. ADDLs and Aβ1-28 (60 pmol in each of two lanes used for silver stain and 20 pmol otherwise) were separated using a 10-20% Tris-Tricine SDS-PAGE. The 60 pmol lanes were excised and stained with SILVERXPRESS™ (INVITROGEN™, Carlsbad, Calif.); alternatively, the gels (20 pmoles ADDLs and Aβ1-28) were electroblotted onto HYBOND™ ECL™ nitrocellulose using 25 mM Tris-192 mM glycine, 20% v/v methanol, pH 8.3, 0.02% SDS at 100V for 1 hour at 8° C. The blots were blocked with 5% milk in TBS-T (0.1% TWEEN™-20 in 20 mM Tris-HCl, pH 7.5, 0.8% NaCl). Samples were incubated with 20C2 (1:1000, 1.52 mg/mL) or 20C2+Aβ1-28 (2 nmol, preincubated for 2 hour) for 1.5 hour at room temperature in the above blocking buffer. Binding was visualized with anti-mouse IgG-HRP (1:40,000 in TBS-T) and chemiluminescence.

Silver staining showed monomer, trimer and tetramer in the ADDL lane, whereas the Aβ1-28 lane had one species, which ran at about a dimer. ADDLs, but not Aβ1-28, were visualized by 20C2 and binding to all ADDL species by 20C2 was blocked by Aβ1-28. Moreover, while the 20C2 binding epitope is blocked by Aβ1-28, 20C2 does not recognize the Aβ1-28 peptide in a western blot.

Example 12

Isotype Analysis of Anti-ADDL Antibodies

To further characterize the monoclonal antibodies disclosed herein, isotype analysis was performed using the SIGMA IMMUNOTYPE™ Kit with the Mouse Monoclonal Antibody Isotyping Reagents, following the manufacturer's directions (Sigma-Aldrich Co., St. Louis, Mo.). Results of this analysis are presented in FIG. 3.

Example 13

Core Linear Epitope Mapping of Anti-ADDL Antibodies

Specific interaction of the anti-ADDL monoclonal antibodies with amyloid beta peptide was detected in standard ELISA assays. Briefly, synthetic peptides, or ADDL or fibril in some cases, were used as antigen to coat on NUNC™ MAXISORB™ plate at concentration of 4 μg/mL (about 800 to 1200 nM). Unless specified, the peptides were coated in 5 mM sodium bicarbonate buffer, pH 9.6, overnight at 4° C. After blocking the plates with PBS containing 0.05% TWEEN™ 20 and 3% (w/v) nonfat dry milk for one hour, the monoclonal antibody was titrated in blocking buffer at a determined concentration and the plates were incubated for one hour at ambient temperature with gentle rocking. After washing, HRP-conjugated goat anti-mouse IgG (H+L), diluted in blocking buffer, was added to the plates. The calorimetric substrate, TMB, was added to the plates after extensive washes to remove unbound HRP-conjugate. The absorbance was measured at wavelength of 450 nm on a plate reader.

To map the core linear epitope for the anti-ADDL monoclonal antibodies, a set of overlapping, ten amino acid peptides was synthesized to cover Aβ1-42 (Table 1). Three peptides of fourteen amino acids, with reversed amino acid sequence of Aβ1-42 were also synthesized as nonspecific control peptides.

TABLE 1

| N- | C- | Peptide Sequence | Mol. Wt. | SEQ ID NO: |
|---|---|---|---|---|
| 1 | 42 | DAEFRHDSGYEVHHQKLVFFAEDVGSNKGAIIGLMVGGVVIA | | 180 |
| 1 | 7 | DAEFRHD | 929.8 | 181 |
| 1 | 8 | DAEFRHDS | 975.4 | 178 |
| 1 | 9 | DAEFRHDSG | 10352.5 | 182 |
| 1 | 10 | DAEFRHDSGY | 1195.4 | 183 |
| 2 | 11 | AEFRHDSGYE | 1209.3 | 184 |
| 3 | 12 | EFRHDSGYEV | 1237.4 | 185 |
| 4 | 13 | FRHDSGYEVH | 1245.2 | 186 |
| 5 | 14 | RHDSGYEVHH | 1235.7 | 187 |
| 6 | 15 | HDSGYEVHHQ | 1207.4 | 188 |
| 7 | 16 | DSGYEVHHQK | 1198.5 | 189 |
| 8 | 17 | SGYEVHHQKL | 1196.8 | 190 |
| 9 | 18 | GYEVHHQKLV | 1208.3 | 191 |
| 10 | 19 | YEVHHQKLVF | 1298.6 | 192 |
| 11 | 20 | EVHHQKLVFF | 1282.9 | 193 |
| 12 | 21 | VHHQKLVFFA | 1224.4 | 194 |
| 13 | 22 | HHQKLVFFAE | 1254.5 | 195 |
| 14 | 23 | HQKLVFFAED | 1232.5 | 196 |
| 15 | 24 | QKLVFFAEDV | 1177.3 | 197 |

TABLE 1-continued

| N- | C- | Peptide Sequence | Mol. Wt. | SEQ ID NO: |
|---|---|---|---|---|
| 16 | 25 | KLVFFAEDVG | 1123.8 | 198 |
| 17 | 26 | LVFFAEDVGS | 1082.3 | 199 |
| 18 | 27 | VFFAEDVGSN | 1083.0 | 200 |
| 19 | 28 | FFAEDVGSNK | 1112.2 | 201 |
| 20 | 29 | FAEDVGSNKG | 1022.6 | 202 |
| 21 | 30 | AEDVGSNKGA | 946.5 | 203 |
| 22 | 31 | EDVGSNKGAI | 988.1 | 204 |
| 23 | 32 | DVGSNKGAII | 972.2 | 205 |
| 24 | 33 | VGSNKGAIIG | 914.4 | 206 |
| 25 | 34 | GSNKGAIIGL | 928.5 | 207 |
| 26 | 35 | SNKGAIIGLM | 1002.2 | 208 |
| 27 | 36 | NKGAIIGLMV | 1014.7 | 209 |
| 28 | 37 | KGAIIGLMVG | 957.4 | 210 |
| 29 | 38 | GAIIGLMVGG | 886.3 | 211 |
| 30 | 39 | AIIGLMVGGV | 928.3 | 212 |
| 31 | 40 | IIGLMVGGVV | 956.5 | 213 |
| 32 | 41 | IGLMVGGVVI | 956.4 | 214 |
| 33 | 42 | GLMVGGVVIA | 914.2 | 215 |
| 14 | 1 | HHVEYGSDHRFEAD | 1923.8 | 216 |
| 28 | 15 | KNSGVDEAFFVLKQ | 1806.9 | 217 |
| 42 | 29 | AIVVGGVMLGIIAGKK | 1751.5 | 218 |

All peptides were dissolved in DMSO at about 400 to 500 µM (1 mg/mL) and stored in multiple aliquots at −20° C. The peptides were used in an ELISA assay for determination of the core epitope of the anti-ADDL monoclonal antibodies. Each monoclonal antibody was tested at four concentrations (3, 1, 0.3 and 0.1 µg/mL) against either an N-terminal peptide set (from residues 1 to 25) or a C-terminal peptide set (from residues 17 to 42), with control peptides. The core linear epitopes for the panel of monoclonal antibodies are listed in Table 2. Several commercial monoclonal antibodies (6E10, BAM-10, 4G8 and WO-2) were included in the experiment to validate the assay format, and the results confirmed their core linear epitopes as reported in published literature.

TABLE 2

| Antibody | Core Epitope* | Epitope Sequence within Aβ1-42 | SEQ ID NO: |
|---|---|---|---|
| | | DAEFRHDSGYEVHHQKLVFFAEDVGSNKGAIIGLMVGGVVIA | 180 |
| 6E10 | 5-11 | RHDSGYE | 219 |
| BAM-10 | 3-8 | EFRHDS | 220 |
| 4G8 | xx-21 | EVHHQKLVFFA | 221 |
| WO-2 | 3-8 | EFRHDS | 220 |
| 26D6 | 3-8 | EFRHDS | 220 |
| 2A10[a] | 3-8 | EFRHDS | 220 |
| 2B4[b] | 3-8 | EFRHDS | 220 |

TABLE 2-continued

| Antibody | Core Epitope* | Epitope Sequence within Aβ1-42 | SEQ ID NO: |
|---|---|---|---|
| 4C2[a] | 3-8 | EFRHDS | 220 |
| 4E2[a] | 3-8 | EFRHDS | 220 |
| 2H4[c] | 1-8 | DAEFRHDS | 178 |
| 20C2[a] | 3-8 | EFRHDS | 220 |
| 2D6[a] | 3-8 | EFRHDS | 220 |
| 5F10[c] | 3-8 | EFRHDS | 220 |
| 1F4[a] | nd | | |
| 1F6[a] | nd | | |
| 2E12[a] | 3-10 | EFRHDSGY | 222 |
| 3B3[a] | nd | | |

*Position within Aβ1-42. [a]IgG1, [b]IgG2b, [c]IgG2a. nd, not determined.

Nine out of twelve ADDL-specific monoclonal antibodies evaluated were mapped to the N-terminal region of Aβ1-42, and seven of these mapped to amino acid residues 3 to 8. Two monoclonal antibodies, 2H4 and 2E12, prefer slightly bigger epitopes. Three monoclonal antibodies, 1F4, 1F6 and 3B3, failed to bind the overlapping peptide set, even at high concentration of 3 μg/mL, but their epitopes were estimated to be located at the N-terminus of Aβ1-42, as they could bind to Aβ1-20 peptide, which was used as a positive control in the experiments.

Example 14

Affinity and Specificity of Mouse Anti-ADDL Antibodies

A solution-based binding assay was developed to determine the specificity and affinity of anti-ADDL antibodies to different amyloid beta peptide preparations (ADDL, fibril, Aβ1-40, Aβ1-20). A quantitative ELISA was established that was capable of capturing the linear range of dose-response of monoclonal antibodies against ADDL coated on NUNC™ plates. Based on this information, a fixed concentration of monoclonal antibody was selected that could give consistent OD signals in ELISA just above assay noise (OD 450 nm reading around 0.2 to 0.5). IgG at this fixed concentration was then incubated with different amyloid beta peptide substrates (ADDL, fibril, Aβ1-40, Aβ1-20) in 20 point titrations in solution at room temperature overnight to reach equilibrium. The quantity of free IgG within the mixture was determined the next day in a quantitative ELISA with a one hour incubation on regular ELISA plates. The fraction of bound IgG was calculated and the correlations of bound IgG to titration of free ligand (substrates) were used to derive $K_D$, using the GraFit program (Erithacus Software, Surrey, UK). Thus, the substrate preference for each antibody to different amyloid beta peptide preparations was presented as the intrinsic affinity values ($K_D$).

There were several advantages of using this assay format. First, the interaction of the antibody and substrate was in solution phase, thus, there was no constraint from any solid surface such as in regular ELISA assay or BIACORE™ experiment, where potential influence of solid surface from ELISA plates or sensor chip on monoclonal antibody and substrate interaction has to be taken into consideration for interpretation of data. Second, the interactions were allowed to reach equilibrium. Therefore, the interaction of IgG and substrate occurred at limiting concentrations of both components with no concerns for precipitation of IgG or additional amyloid beta peptide oligomerization due to high experimental concentration. Third, the assay readout was independent of antigen in the solution; thus, any heterology of amyloid beta in different peptide preparations (e.g., ADDL or fibril) would not interfere with data interpretation and mathematical modeling. The assay sensitivity was limited to ELISA assay detection limits which allowed this assay to evaluate monoclonal antibodies with $K_D$ values in the nanomolar range. Alternative substrates such fluorescent reagents are contemplated to improve the sensitivity range. It is believed that the immune complex was minimally disrupted during the one hour incubation to capture the free IgG in quantitative ELISA.

The quantities of free IgG were determined by a standard curve and plotted against titrations of different substrate. The quantities of bound IgG with different substrates were plotted and the information was used in GraFit for curve fitting with appropriate mathematic models. The summary of $K_D$, expressed in nM ranges, for the panel of monoclonal antibodies disclosed herein is presented in Table 3.

TABLE 3

| Antibody* | ADDL | | Fibril | | Aβ1-40 | | Aβ1-20 | |
|---|---|---|---|---|---|---|---|---|
| | $K_D$ | SE | $K_D$ | SE | $K_D$ | SE | $K_D$ | SE |
| 20C2 | 0.92 | 0.09 | 3.62 | 0.4 | 30.48 | 5.05 | 71.3 | 24.4 |
| 2A10 | 2.29 | 0.25 | 6.72 | 7 | 14.69 | 2.64 | 5 | 1 |
| 2B4 | 2.09 | 0.24 | 10.5 | 0.9 | 27.57 | 4.88 | 22.4 | 2.43 |
| 2D6 | 5.05 | 0.52 | 0 | 9 | 25.66 | 5.84 | 0 | 0.26 |
| 5F10 | 11.9 | 1.63 | 14.4 | 1.2 | 23.54 | 6.21 | 1.63 | 7.07 |
| 4E2 | 0 | 0.42 | 1 | 6 | 20.24 | 2.07 | 30.1 | 4.39 |
| 4C2 | 4.26 | 1.03 | 28.9 | 2.4 | 21.89 | 4.14 | 7 | 3.23 |

TABLE 3-continued

| Antibody | ADDL | | Fibril | | Aβ1-40 | | Aβ1-20 | |
|---|---|---|---|---|---|---|---|---|
| * | K_D | SE | K_D | SE | K_D | SE | K_D | SE |
| 1F4 | 8.08 | 0.84 | 5 | 0 | IC | IC | *6.10* | *3.23* |
| 1F6 | 9.24 | N/T | 9.40 | 5.7 | N/T | N/T | 28.4 | IC |
| 3B3 | N/T | 0.74 | 19.1 | *8* | *104.6* | *21.8* | 0 | N/T |
| 2E12 | 10.0 | IC | 7 | 1.6 | *8* | *6* | 28.4 | IC |
| WO-2 | 2 | 0.04 | 12.5 | 0 | IC | IC | 0 | IC |
| | IC | 2 | 2 | 3.6 | 6.15 | 0.62 | IC | *3.53* |
| | 0.57 | | N/T | 9 | | | N/T | |
| | | | 7.21 | 1.6 | | | IC | |
| | | | IC | 6 | | | IC | |
| | | | 1.15 | N/T | | | *19.2* | |
| | | | | 0.5 | | | 6 | |
| | | | | 9 | | | | |
| | | | | IC | | | | |
| | | | | 0.1 | | | | |
| | | | | 2 | | | | |

*All antibodies were IgG.
Values listed in italic are high SE and poor fitting.
IC inconclusive data
N/T not tested.

Example 15

Detecting and Measuring Tau Phosphorylation

Hyperphosporylated Tau (pTau) is a hallmark of Alzheimer's5 Disease, although little is known about the events that cause this hyperphosphorylation. Without wishing to be bound by any theory, it is believed that ADDLs may play a role in this phosphorylation event. To investigate this, neuronal cultures (primary neurons and B103 cells) were grown as described above, 1 µm bADDLs or vehicle was added to the media and the cultures were maintained for an additional one, six or twenty four hours. At the end of each incubation, the cells were washed, fixed, permeabilized, blocked and incubated overnight with a monoclonal antiserum raised against pTau (AT8, 1:500; Pierce, Rockland, Ill.). The next day, the cells were washed, incubated with an ALEXA® 488-labeled anti-mouse secondary antibody and an ALEXA® 594-labeled streptavidin and the cells were stained with DAPI to allow detection of nuclei. The cells were then assessed using a fluorescence microscope, with the degree of pTau staining and correlation with bADDL binding being noted at each time-point.

The results of this analysis indicated that bADDL binding to B103 cells increased the level of pTau in the cellular processes, when compared with vehicle-treated cells. A similar change was also noted in primary hippocampal cells. When cells were exposed to bADDLs for six hours, an increase in pTau staining was observed in a subpopulation of cells, cells that also bound bADDL. A time-course study with B103 cells further investigated the modulation of pTau by bADDLs. The addition of bADDLs resulted in a marginal increase in pTau at one hour. However, pTau staining was dramatically increased six hours after the addition of bADDLs and remained elevated up to 24 hours later. Thus, these data indicate that ADDL binding to neurons can initiate a cascade of intracellular events that results in the hyperphosphorylation of tau, the accumulation of neurofibrillary tangles and eventual cell death. To this end, one skilled in the art can appreciate that blocking the binding of ADDLs to neurons, would in turn prevent such downstream events and be beneficial for the treatment of amyloidogenic diseases and/or tauopathies. Moreover, a better understanding of the signaling events that are triggered by ADDL binding and result in pTau production may also elucidate additional pathways that are suitable targets for the development of novel therapeutics.

Example 16

Aβ Peptide/ADDL-Antibody Interaction and Assembly Inhibition

Changes in ADDL assembly kinetics and oligomeric size, in the presence of selected monoclonal antibodies disclosed herein were observed by fluorescence resonance energy transfer (FRET) and fluorescence polarization (FP) using a 1:4 mixture of fluorescein-labeled Aβ1-42 monomers to native peptide monomers. The auto-quenching of flourescein emission upon monomer incorporation into ADDLs results in a three- to five-fold reduction of fluorescence intensity over the short hour timescale due to FRET. In addition, the increase in size when monomers assemble into oligomeric ADDL species results in a two-fold FP increase. The FRET and FP kinetic progress curves of ADDL assembly, in the presence of various novel and commercial anti-ADDL and anti-Aβ peptide antibodies, showed differences in the ability of the antibodies to inhibit ADDL assembly and/or bind peptide oligomers (FIG. 4).

Assays were performed in 384-well CORNING® Non-Binding Surface black, opaque microtiter plates. The assay buffer was composed of 50 mM MOPS-Tris (pH 8.0) with 100 mM MgCl$_2$. The assay volume, containing 0.2 µM FITC-Aβ1-42 and 0.8 µM Aβ1-42, was 50 µL and the assay temperature was 37° C. ADDL assembly was monitored with a Tecan GENios Pro plate reader, exciting at a wavelength of 485 nm and detecting emission at a wavelength of 515 nm. Kinetic traces were collected by recording fluorescence intensity and polarization readings every five minutes over a six-hour time course. Negative control reactions, which did not appreciably assemble into ADDLs during this time, lacked MgCl$_2$ but contained all other buffer and peptide components. Positive control reactions contained all buffer components in the absence of added monoclonal antibody reagents. To test for ADDL binding and assembly inhibition, antibodies were incubated with the peptide mixture at eight concentrations from 500 nM decreasing to 5 nM.

This assay was useful for classifying different profiles of ADDL binding behavior and ADDL assembly inhibition. The binding and neutralization of larger ADDL species, through interaction with ADDL-specific and/or conformational epitopes, serves as a viable therapeutic strategy. In addition, the inhibition of oligomerization into large ADDLs by binding an ADDL-specific and/or conformational epitope present in transient, intermediate ADDL assembly species (non-monomer) provides an alternative strategy for anti-ADDL therapy. The FP progress curves, which demonstrated striking differences between antibodies, denotes such intermediate or stable species binding. Correlating the FP/FRET behavior of monoclonal antibodies with other functional, cellular and in vivo effects allows for the selection of desired immunotherapy modes of action.

Figure 4:
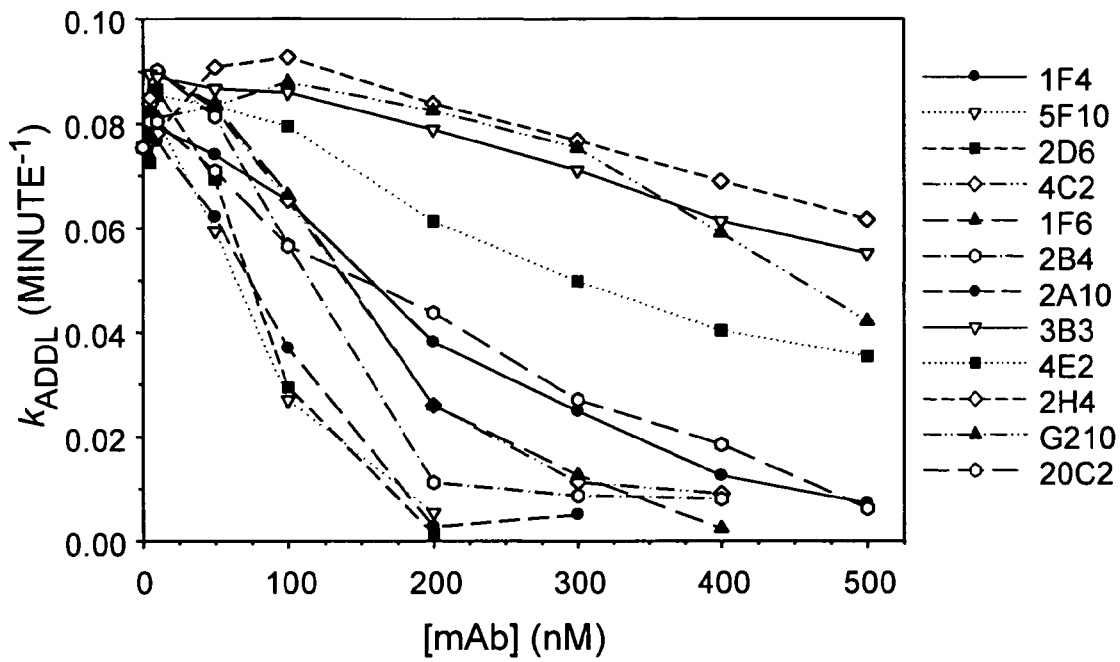
FIG. 4 shows a summary of ADDL assembly inhibition of the antibodies disclosed herein.
Figure 5:
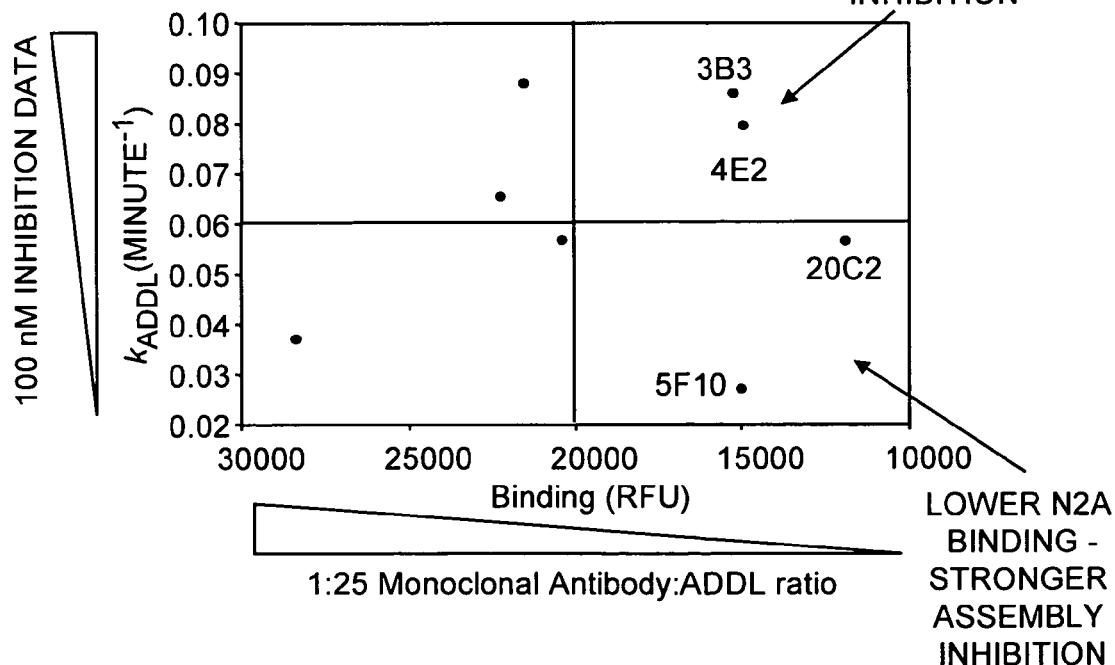
FIG. 5 shows an N2A binding:$k_{ADDL}$ correlation plot.

The results of the analyses disclosed herein indicates that 1F6, 2A10, 5F10, 2D6, and 2B4 exhibit potent assembly inhibition, whereas 20C2, 1F4, and 4C2 exhibit intermediate assembly inhibition and 2H4, 3B3 and 4E2 show weak assembly inhibition (FIG. 4). As summarized in Table 4 and illustrated in FIG. 5, 20C2, 4E2, 3B3 and 5F10 show a variety of biochemical behaviors.

TABLE 4

|  | Potent Assembly Inhibition by FP/FRET | Weak or no Assembly Inhibition by FT/FRET |
| --- | --- | --- |
| FP laddering at 30 minutes | 20C2 | 4E2 |
| Low or no FP laddering at 30 minutes | 5F10, 1A9 | 3B3 |

Further, antibody 1A9, one of five purified antibodies (i.e., 1A9, 1E3, 1G3, 1A7, and 1E5) generated against a low n-mer-forming peptide Aβ1-42[Nle35-Dpro37], segregates with 5F10 in terms of its assembly inhibition and FP behavior.

Example 17

Isolation of Mouse Antibody Variable Region Sequences

The cDNAs coding for the variable domains of the mouse antibody were cloned and sequenced following a polymerase chain reaction (PCR) using specially designed primers that hybridize to the 5'-ends of the mouse constant regions and to the murine leader sequences upstream of the V regions. This ensured that the mouse variable region sequences obtained were complete and accurate. In short, mRNA was extracted from mouse hybridoma cell lines using the QIAGEN® OLI-GOTEX® Direct mRNA Mini Kit and subsequently converted to cDNA using a first-strand cDNA synthesis kit. The cDNA was then used as template in PCR reactions to obtain the antibody variable region sequences.

To obtain the light chain variable region sequence, eleven independent PCR reactions were set up using each of the eleven light chain 5' PCR primers (MKV-1 to MKV-11) and the 3' PCR primer MKC-1 (Table 5).

TABLE 5

| 5' Primer | Sequence | SEQ ID NO: |
| --- | --- | --- |
| MKV-1 | GAT CTC TAG ATG AAG ATT GCC TGT TAG CTG TTG GGT GCT G | 223 |
| MKV-2 | GAT CTC TAG ATG GAG WCA GAC ACA CTC CTC YTA TGG GTG | 224 |
| MKV-3 | GAT CTC TAG ATG AGT GTG CTC ACT CAG GTC CTG GSG TTG | 225 |
| MKV-4 | GAT CTC TAG ATG AGG RCC CCT GCT CAG WTT YTT GGM WTC TTG | 226 |
| MKV-5 | GAT CTC TAG ATG GAT TTW CAG GTG CAG ATT WTC AGC TTC | 227 |
| MKV-6 | GAT CTC TAG ATG AGG TKC YYT GYT SAY CTY CTC TGR GG | 228 |
| MKV-7 | GAT CTC TAG ATG GGC WTC AAA GAT GGA GTC ACA KWY YCW GG | 229 |
| MKV-8 | GAT CTC TAG ATG TGG CGG YCT KTT TYC MMT TTT TCA ATG | 230 |
| MKV-9 | GAT CTC TAG ATG GTR TCC WCA SCT CAG TTC CTT G | 231 |
| MKV-10 | GAT CTC TAG ATG TAT ATA TGT TTG TTG TCT ATT TCT | 232 |
| MKV-11 | GAT CTC TAG ATG GAA GCC CCA GCT CAG CTT CTC TTC C | 333 |

| 3' Primer | Sequence | SEQ ID NO: |
| --- | --- | --- |
| MKC-1 | GAT CGA GCT CAC TGG ATG GTG GGA ACA TGG | 234 |

Moreover, 20C2 was found to bind to assemblies of charge-inverted, truncated Aβ7-42 peptide assemblies as determined by SEC/ICC, indicating a lack of conventional linear epitope binding to the Aβ7-42 charge-inverted peptide, which has a very different sequence corresponding to residues 7-16 of Aβ, i.e., Aβ(7-42) [Orn$_7$Orn$_{11}$D$_{13}$D$_{14}$E$_{16}$Nle$_{35}$]. Therefore, 20C2 binds to conformational epitopes that depend upon elements from within residues 17-42 of Aβ, but only when assembled.

Underlined and italic sequences denote XbaI and SacI restriction sites, respectively. W=A or T, M=A or C, K=G or T, Y=C or T, and R=A or G.

To obtain the heavy chain variable region sequences twelve independent PCR reactions were set up using each of the twelve heavy chain 5' PCR primers (MHV-1 to MHV-12) and the appropriate isotype specific 3' primer (MHCG-1, MHCG-2A, MHCG-2B, MHCG-3) (Table 6).

TABLE 6

| 5' Primer | Sequence | SEQ ID NO: |
|---|---|---|
| MHV-1 | GAT CTC TAG ATG AAA TGC AGC TGG GGC ATS TTC TTC | 235 |
| MHV-2 | GAT CTC TAG ATG GGA TGG AGC TRT ATC ATS YTC TT | 236 |
| MHV-3 | GAT CTC TAG ATG AAG WTG TGG TTA AAC TGG GTT TTT | 237 |
| MHV-4 | GAT CTC TAG ATG RAC TTT GGG YTC AGC TTG RTT T | 238 |
| MHV-5 | GAT CTC TAG ATG GGA CTC CAG GCT TCA ATT TAG TTT TCC TT | 239 |
| MHV-6 | GAT CTC TAG ATG GCT TGT CYT TRG SGC TRC TCT TCT GC | 240 |
| MHV-7 | GAT CTC TAG ATG GRA TGG AGC KGG RGT CTT TMT CTT | 241 |
| MHV-8 | GAT CTC TAG ATG AGA GTG CTG ATT CTT TTG TG | 242 |
| MHV-9 | GAT CTC TAG ATG GMT TGG GTG TGG AMC TTG CTT ATT CCT G | 243 |
| MHV-10 | GAT CTC TAG ATG GGC AGA CTT ACC ATT CTC ATT CCT G | 244 |
| MHV-11 | GAT CTC TAG ATG GAT TTT GGG CTG ATT TTT TTT ATT G | 245 |
| MHV-12 | GAT CTC TAG ATG ATG GTG TTA AGT CTT CTG TAC CTG | 246 |

| 3' Primer | Sequence | SEQ ID NO: |
|---|---|---|
| MHCG-1 | GCATC GAG CTC CAG TGG ATA GAC AGA TGG GGG | 247 |
| MHCG-2A | GCATC GAG CTC CAG TGG ATA GAC CGA TGG GGG | 248 |
| MHCG-2B | GCATC GAG CTC CAG TGG ATG AGC TGA TGG GGG | 249 |
| MHCG-3 | GCATC GAG CTC CAA GGG ATA GAC AGA TGG GGG | 250 |

Underlined and italic sequences denote XbaI and SacI restriction sites, respectively. W = A or T, M = A or C, K = G or T, Y = C or T, and R = A or G.

Each of the light chain PCR reactions contained 46 µL INVITROGEN™ PLATINUM® PCR Super Mix, 1.0 µL of one of the 100 µM 5' primers (MKV-1 to MKV-11), 1.0 µL of the 100 µM 3' primer (MKC-1), and 2.0 µL of hybridoma cDNA. Similar PCR reactions were employed to clone the mouse heavy chain 20 variable region sequences. Reactions were placed in a DNA thermal cycler and, after an initial denaturation step at 97° C. for 2.0 minutes, subjected to 30 cycles of: 95° C. for 30 seconds, 55° C. for 45 seconds, and 72° C. for 90 seconds. Following the last cycle, a final extension step at 72° C. for 10 minutes was employed. To determine which PCR reactions yielded product, 5 µL aliquots from each reaction were separated on 1.5% (w/v) agarose/1× TAE buffer gels, containing 0.5 µg/mL ethidium bromide. PCR products from reactions that produced fragments of the expected size (420 to 500 bp) were then gel purified, digested with XbaI and SacI and ligated into the XbaI and SacI sites in the multicloning region of plasmid pNEB193 (New England Biolabs, Beverly, Mass.). Alternatively, PCR products were ligated directly into plasmid pCR®2.1 using the INVITROGEN™, TA CLONING® kit. Ligation products were then transformed into XL-1 cells and aliquots of the transformed E. coli were plated onto LB agar plates containing 50 µg/mL ampicillin and overlaid with 40 µL of X-Gal stock (50 mg/mL) and 40 µL IPTG (100 mM) solution for blue/white selection. Plates were incubated overnight at 37° C. and potential clones were identified as white colonies. DNA from at least 24 independent clones for each PCR product were sequenced on both strands using universal forward and reverse primers for pNEB193 and pCR®2.1. The resulting sequences were then assembled into a contig to generate a consensus sequence for each antibody light and heavy chain variable region. Using this approach the sequences were determined for the light and heavy antibody variable regions of hybridoma's 20C2, 5F10, 2D6, 2B4, 4E2, 2H4, 2A10, 3B3, 1F6, 1F4, 2E12 and 4C2 (FIGS. 6A-6X).

The six complementarity-determining regions (CDRs), which form the structure complementary to the antigen, are underlined in FIGS. 6A-6X. Upon analysis of the CDRs and corresponding antigen epitopes (Table 2), sequence similarities were observed. Antibodies sharing the 3-8 amino acid epitope of Aβ1-42 (i.e., 2A10, 4C2, 2D6, 4E2, 20C2, 2B4, and 5F10) shared highly homologous CDR1 (FIG. 7A) and CDR2 (FIG. 7B) sequences of the heavy chain. Antibody 2H4, which was found to recognize the 1-8 amino acid epitope of Aβ1-42, appeared to have unique CDR3 (FIG. 7C) sequences of the heavy chain and unique CDR1 (FIG. 7D), CDR2 (FIG. 7E), and CDR3 (FIG. 7F) sequences of the light chain. Similarly, antibody 2E12, which was found to recognize the 3-10 amino acid epitope of Aβ1-42, had unique CDR3 sequences of the heavy chain (FIG. 7C). Further, antibodies 2A10, 2B4, 4C2 and 4E2, having similar affinities for SEC Peak 1 and Peak 2 ADDLs (see FIG. 3), shared highly homologous CDR3 sequences of the heavy chain (FIG. 7C). Moreover, amino acid substitutions in CDR3 of the heavy chain of antibody 4E2 appeared to enhance blockage of binding of ADDLs to neuronal cells, as 4E2 is more effective than antibody 2D6 at blocking ADDL binding to neurons and the sequences of the heavy and light chains of 4E2 and 2D6 were identical except for three amino acid residues of CDR3 of the heavy chain; Ser vs. Asn, Thr vs. Ser, and Ile vs. Val for 2D6 and 4E2, respectively (FIG. 7C).

Example 18

Humanization of Mouse Anti-ADDL Antibody Variable Region Sequences

Mouse antibody heavy and light variable domains nucleic acids obtained from mouse hybridoma cell lines 20C2, 26D6, 4E2, 3B3, 2H4 and 1F6 were humanized using a CDR grafting approach and in the case of 20C2 and 26D6 a veneering strategy. It will be appreciated by those skilled in the art that humanization of mouse antibody sequences can maximize the therapeutic potential of an antibody by improving its serum half-life and Fc effector functions thereby reducing the anti-globulin response.

Humanization by CDR grafting was carried out by selecting the human light and heavy chain variable regions from the NCBI protein database with the highest homology to the mouse variable domains. The mouse variable region sequences were compared to all human variable region sequences in the database using the protein-protein Basic Local Alignment Search Tool (BLAST). Subsequently, mouse CDRs were joined to the human framework regions and the preliminary amino acid sequence was analyzed. All differences between the mouse and human sequences in the framework regions were evaluated particularly if they were part of the canonical sequences for loop structure or were residues located at the VL/VH interface (O'Brien and Jones (2001) In: Antibody Engineering, Kontermann and Dubel (Eds.), Springer Laboratory Manuals). Framework regions were also scanned for unusual or rare amino acids in comparison to the consensus sequences for the human subgroup and for potential glycosylation sites. Wherein amino acid sequence differences existed between the mouse and human framework region sequences that were not found to be involved in canonical sequences, or located at the VL/VH interface, the human residue was selected at that position. Wherein a difference in a key residue existed, two versions of the variable region sequence were generated for evaluation. The CDR grafting strategy made the minimum number of changes to the human framework region so that good antigen binding was achieved while maintaining human framework regions that closely matched the sequence from a natural human antibody. The design of humanized amino acid sequences using CDR grafting is shown in FIG. 8.

Humanized sequences for 20C2 and 26D6 were also designed using a veneering strategy (See, e.g., U.S. Pat. No. 6,797,492). Humanization was carried out by selecting the human light and heavy chain variable regions from the NCBI protein database with the highest homology to the mouse variable domains, as well as to the closest human antibody germline family or families (see, Kabat, eta 1. (1991) Sequences of proteins of immunological interest, 5*th* ed., U.S. Dept. Health and Human Services, NIH, Washington DC). The mouse variable region sequences were compared to all human variable region sequences in the database using protein-protein BLAST. The murine variable sequences and their closest human homologues were modeled to the closest crystallized human antibody as determined by computer modeling as practiced in the art. From the model of the murine VH and VL sequences, a surface area map was constructed, which dictated the solvent accessibility of the amino acids in the mouse heavy and light variable regions. To confirm the modeling, these exposed residues were compared position-by-position with known surface accessible residues (see, e.g., Padlan (1994) *Mol. Immunol.* 31(3):169-217). A score was assigned for each residue in the sequence designating it as exposed, mostly exposed, partly buried, mostly buried and buried according to established methods (see, U.S. Pat. No. 6,797,492). Mouse framework residues that scored as exposed or mostly exposed and differed from the homologous human sequence were changed to the human residue at that position. The designed veneered sequences retained the mouse CDRs, residues neighboring the CDRs, residues known be involved in canonical sequences, residues located at the VL/VH interface, and residues at the N-terminal sequences of the mouse heavy and light chain. The N-terminal sequences are known to be contiguous with the CDR surface and are potentially involved in ligand binding. Likewise, care was taken to limit changes in Pro, Gly, or charged residues. Once the veneered sequences were finalized they were remodeled to look for are any potential obvious structural issues. In some instances, more then one veneered sequence was generated for analysis. The design of humanized amino acid sequences using the veneering approach is shown in FIG. 9.

Once the humanized amino acid sequences were selected the sequences were reverse-translated to obtain the corresponding DNA sequence. The DNA sequences were codon-optimized using art-established methods (Lathe (1985) *J. Mol. Biol.* 183(1):1-12) and designed with flanking restriction enzyme sites for cloning into human antibody expression vectors. The DNA sequences synthesized are presented in FIGS. 10A-10T. For the 20C2 humanized antibodies designed by CDR grafting and veneering, both human IgG1/kappa and IgG2m4/kappa versions were constructed, wherein IgG2m4 represents selective incorporation of human IgG4 sequences into a standard human IgG2 constant region. IgG1/kappa and IgG2m4/kappa versions were also made for the 26D6 CDR grafted antibody. For all other antibodies only the IgG1/kappa versions were made. The complete amino acid sequence of the resulting antibodies is shown in FIGS. 11A-11Y.

Antibodies were expressed by co-transient transfection of separate light and heavy chain expression plasmids into 293 EBNA cells. In cases where more then one humanized heavy or light chain sequence was designed for a given antibody, all combinations of heavy and light chains were combined to generate the corresponding antibodies. Antibodies were purified from culture supernatant 7-10 days post-transfection using protein A columns and used in subsequent analysis.

Example 19

Generation of IgG2m4 Antibodies

IgG2m4 antibody derivatives were prepared to decrease Fc receptor engagement, C1q binding, unwanted cytotoxicity or immunocomplex formation while maintaining both the long half-life and pharmacokinetic properties of a typical human antibody. The basic antibody format of IgG2m4 is that of IgG2, which has been shown to possess a superior half-life in experimental models (Zuckier, et al. (1994) *Cancer Suppl.* 73:794-799). The structure of IgG2 was modified to eliminate C1q binding, through selective incorporation of IgG4 sequences, while maintaining the typical low level of FcγR binding (Canfield and Morrison (1991) *J. Exp. Med.* 173: 1483-1491). This was achieved by using cross-over points wherein sequences of IgG2 and IgG4 were identical, thereby producing an antibody containing natural Fc sequences rather than any artificial mutational sequences.

The IgG2m4 form of the human antibody constant region was formed by selective incorporation of human IgG4 sequences into a standard human IgG2 constant region, as shown in FIG. 12. Conceptually, IgG2m4 resulted from a pair of chain-swaps within the CH2 domain as shown in FIG. 12. Four single mutations were made corresponding to sequences from IgG4. The Fc residues mutated in IgG2 included His268Gln, Val309Leu, Ala330Ser, and Pro331Ser, which minimized the potential for neoepitopes. The specific IgG4 amino acid residues placed into the IgG2 constant region are shown in Table 7, along with other alternatives from the basic structure.

TABLE 7

| Residue (Kabat numbering) | Residue in IgG2 | Residue in IgG4 | Residue in IgG2m4 | Alternative residue in IgG2m4 | Comment |
|---|---|---|---|---|---|
| 189 | Pro or Thr* | Pro | Thr | Pro | Key polymorphism of IgG2; Pro residue present in IGHG*01 allotype and Thr residue present in IGHG2*02 allotype[a,b]. |
| 268 | His | Gln | Gln | — | Change in the B/C loop known to be involved in FcγRII binding[c]. |
| 309 | Val | Leu or Val | Leu | Val | FcRn binding domain |
| 330 | Ala | Ser | Ser | — | Key residue for C1q binding[d]; also potentially involved in binding FcγRII and FcγRIII[e]. |
| 331 | Pro | Ser | Ser | — | Key residue for C1q binding[d,f] and FcγRI binding[g]; also potentially involved in binding FcγRII and FcγRIII[e]. |
| 397 | Met or Val* | Val | Met | Val | Val residue present in IGHG*01 allotype and Met residue present in IGHG2*02 allotype[a]. |

*Positions marked with an asterisk are subject to allelic variations.
[a]Hougs, et al. (2001) Immunogenetics 52(3-4): 242-8.
[b]WO 97/11971.
[c]Medgyesi, et al. (2004) Eur. J. Immunol. 34: 1127-1135.
[d]Tao, et al. (1991) J. Exp. Med. 173: 1025-1028.
[e]Armour et al. (1999) Eur. J. Immunol. 29: 2613.
[f]Xu, et al. (1994) J. Biol. Chem. 269: 3469-3474.
[g]Canfield and Morrison (1991) J. Exp. Med. 173: 1483.

Example 20

Binding Affinity of Humanized Anti-ADDL Antibodies

To evaluate ADDL binding affinity of the humanized antibodies, titration ELISAs were conducted as disclosed herein. Streptavidin-coated, 96-well microtiter plates (Sigma, St. Louis, Mo.) were coated with 10% biotinylated ADDL antigen (1 μM). A series of 2-fold dilutions of purified antibody, starting at 500 ng/mL was added to the ADDL captured plates and the plates were incubated for 2 hours at 25° C. After washing five times with PBS solution using a plate washer (Bio-Tek, Winooski, Va.), polyclonal goat anti-human kappa light chain antibody (Biomeda, Foster City, Calif.) was added at a 1/2000 dilution in 3% non-fat milk blocker and incubated at room temperature for 1 hour. A rabbit anti-goat IgG (H+L) HRP-conjugated (Bethyl Laboratories, Inc., Montgomery, Tex.) detection antibody was then added at a 1/2000 dilution in blocking solution and incubated for 1 hour at room temperature. After washing with PBS, HRP substrate, 3,3',5'5'-tetramethylbenzidine (ready-to-use TMB; Sigma, St. Louis, Mo.) was added and the reaction was stopped after 10 minutes with 0.5 N $H_2SO_4$. Absorbance at wavelength of 450 nm was read in a plate reader (model VICTOR V; Perkin Elmer, Boston, Mass.) and data were processed using EXCEL® work sheet. Assay variations between plates were estimated within 20%.

Different groups of humanized antibodies were compared in different experiments. A comparison of IgG1 antibodies 20C2A, 20C2B, 3B3, 4E2, 1F6 and 2H4 humanized by CDR grafting indicated that all antibodies could bind to ADDLs, wherein binding with 1F6 was weaker than the majority and 20C2A was the strongest. The four different humanized versions of 20C2 IgG1 antibodies (two CDR grafted versions and two veneered versions) were also compared and found to exhibit very similar ADDL binding curves with all binding slightly better then a chimeric 20C2 antibody. The seven different humanized versions of 26D6 IgG1 (one CDR grafted versions and six veneered versions) were also compared. All were found to have ADDL binding curves similar to the chimeric form of 26D6. The IgG1 and IgG2m4 antibodies for the two 20C2 versions humanized by CDR grafting were also analyzed and found to have comparable binding curves as did the IgG1 and IgG2m4 isotypes of 26D6 humanized by CDR grafting.

Example 21

Inhibition of ADDL Binding to Neurons Using Humanized Anti-ADDL Antibodies

The humanized anti-ADDL antibodies were further evaluated for their ability to block ADDL binding to primary hippocampal neurons using the methods disclosed herein. The relevant antibodies, or PBS as a control, were mixed at a 1:1 (B103 neuroblastoma cells) or 1:5 (primary hippocampal neurons) molar ratio with 2.5-10 μm (final concentration) of bADDLs and incubated for one hour at 37° C. on a slow rotator. After the preincubation, the antibody/bADDL preparations were added to the B103 or primary neuron cultures and incubated for an additional hour at 37° C. At the end of the incubation period, the bADDLs/antibody mixture was removed and the plates washed six times with media. The cells were then fixed in 4% paraformaldehyde for ten minutes at room temperature, the solution removed, fresh fixative added, and the cells fixed for an additional ten minutes. The cells were permeabilized with 4% paraformaldehyde containing 0.1% TRITON™ X-100 (2 times, each for ten minutes at room temperature), washed six times in PBS and then treated with 10% BSA in PBS for one hour at 37° C. Alkaline phosphatase-conjugated streptavidin (1:1,500 in 1% BSA; Molecular Probes, Eugene, Oreg.) was then added to the cells for one hour at room temperature. The cells were rinsed six times with PBS, the alkaline phosphatase substrate (CDP-STAR® with SAPPHIRE-II™; Applied Biosystems, Foster City, Calif.) added to the cells and incubated for thirty minutes prior to determining the luminescence on a LJL Luminometer (Analyst AD; LJL Biosystems, Sunnyvale, Calif.). As with the murine antibodies, the humanized versions of 26D6, 20C2, 4E2, 3B3, 2H4 and 1F6 were capable of inhibiting the binding of ADDL preparations to B103 neuroblastoma cells and to primary neurons.

Example 22

Affinity Maturation of a Humanized Anti-ADDL Antibody

Nucleic acid molecules encoding humanized 20C2 version A variable heavy chain only, light chain only, or heavy chain and light chain together were cloned in the Fab phage-display vector pFab3d. Nucleic acid sequence analysis confirmed sequence and orientation in pFab3d. The annotated 20C2 Fab sequences in pFab3d are presented in FIG. 13 and set forth herein as SEQ ID NO:255 for the heavy chain and SEQ ID NO:256 for the light chain. The three constructs were used in the 20C2 maturation program using art-established phage-displayed Fab library methods.

Briefly, two libraries were designed to mutate the nine wild-type amino acids of CDR3 of the light (kappa) chain of 20C2 (i.e., Phe-Gln-Gly-Ser-Leu-Val-Pro-Leu-Thr; SEQ ID NO:60). These libraries were designated LC3-1 and LC3-2 representing light chain CDR3 sequences of Xaa-Xaa-Xaa-Xaa-Xaa-Val-Pro-Leu-Thr (SEQ ID NO:257) and Phe-Gln-Gly-Ser-Xaa-Xaa-Xaa-Xaa-Xaa (SEQ ID NO:258), respectively. Biotinylated reverse primers, 20C2LC3-1 (SEQ ID NO:259) and 20C2LC3-2 (SEQ ID NO:260), were used in combination with forward primer 20C2LC3F (SEQ ID NO:261) to generate the LC3-1 and LC3-2 libraries (see FIG. 14). Primers were purified by polyacrylamide gel electrophoresis, whereas the vector DNA was purified by gel electrophoresis and electroelution. The two light chain libraries were designed to be randomly mutated. The final diversities of the three 10G5H6 $LC_3$ libraries were $4.76 \times 10^8$ and $7.45 \times 10^8$, respectively (Table 8). Sequence analysis of approximately 100 clones from the libraries showed 100% diversity of mutant clones at the designed amino acid positions.

TABLE 8

| | 20C2 Library | |
| --- | --- | --- |
| Characteristic | LC3-1 | LC3-2 |
| Vector | pFab3d20C2HS | pFab3d20C2HS |
| Number of Transformants | $4.76 \times 10^8$ | $7.45 \times 10^8$ |
| Library Diversity | $4.76 \times 10^8 \times 0.89 = 4.24\ 10^8$ | $7.45 \times 10^8 \times 0.90 = 6.71\ 10^8$ |
| Primary Library Volume | 2 mL | 2 mL |
| Primary Library Titer | $2.13 \times 10^{11}$ | $*9.3 \times 10^{10}$ |

*Higher titers are achieved by concentration or phage rescue.

Soluble panning of the two 20C2 light chain libraries against high molecular weight bADDL was completed. Briefly, four rounds of panning were carried out using biotinylated high molecular weight ADDL (bADDL). The first three rounds were carried out using approximately 1.5 μM antigen concentration (input=$1 \times 10^{10}$ to $1 \times 10^{11}$). Upon completion of the third round, the outputs of the two libraries were combined and divided into three groups for analysis with 10 nM, 100 nM and approximately 1.5 μM antigen to increase panning stringency. As such, a total of 58 output plates were tested in phage ELISA assays, i.e., two plates per library in the first round (a total of four plates), six plates per library in the second round (a total of 12 plates), eight plates for LC3-1 and 10 plates for LC3-2 libraries in the third round (a total of 18 plates) and eight plates for each antigen concentration in the fourth round (a total of 24 plates).

Panning resulted in 1000 hits, 436 of which were sequenced (Table 9).

TABLE 9

| Round | Antigen | Input | Output | % Recovery | ELISA Screen* | Sequenced |
| --- | --- | --- | --- | --- | --- | --- |
| $1^a$ | 1.6 μM | $2.13 \times 10^{10}$ | $7.3 \times 10^4$ | $3.42 \times 10^{-6}$ | 0% (0/176) | 0 |
| $2^a$ | 2.0 μM | $1.55 \times 10^{11}$ | $1.88 \times 10^5$ | $1.21 \times 10^{-6}$ | 1.5% (8/528) | 8 |
| $3^a$ | 1.1 μM | $1.80 \times 10^{10}$ | $7.8 \times 10^4$ | $4.3 \times 10^{-6}$ | 5.8% (41/704) | 41 |
| $1^b$ | 1.6 μM | $9.30 \times 10^9$ | $5.7 \times 10^4$ | $6.13 \times 10^{-6}$ | 2.3% (7/176) | 4 |
| $2^b$ | 2.0 μM | $1.23 \times 10^{11}$ | $1.07 \times 10^5$ | $8.7 \times 10^{-7}$ | 4.5% (24/528) | 24 |
| $3^b$ | 1.1 μM | $1.37 \times 10^{10}$ | $3.32 \times 10^5$ | $2.42 \times 10^{-5}$ | 15% (134/880) | 134 |
| $4^c$ | 1.1 μM | $3.0 \times 10^{11}$ | $1.37 \times 10^5$ | $4.6 \times 10^{-7}$ | 39% (274/704) | — |

TABLE 9-continued

| Round | Antigen | Input | Output | % Recovery | ELISA Screen* | Sequenced |
|---|---|---|---|---|---|---|
| 4[c] | 100 nM | $3.0 \times 10^{11}$ | $3.88 \times 10^5$ | $1.29 \times 10^{-6}$ | 41% (290/704) | — |
| 4[c] | 10 nM | $3.0 \times 10^{11}$ | $1.6 \times 10^5$ | $5.3 \times 10^{-7}$ | 32% (225/704) | 225 |
| | | | | Total | 1000/5104 | 436 |

[a]20C2 LC3-1 versus high molecular weight 10% bADDL.
[b]20C2 LC3-2 versus high molecular weight 10% bADDL.
[c]20C2 LC3-1 + 20C2 LC3-2 versus high molecular weight 10% bADDL.
*Hits per total number of colonies.

Sequence and frequency of highly enriched clones are presented in Table 10.

TABLE 10

| Clone Designation | CDR3 | SEQ ID NO: | Round 2 | Round 3 | Round 4 | Total |
|---|---|---|---|---|---|---|
| Hu20C2LC | FQGSLVPLT | 60 | 6 | 15 | 14 | 35 |
| SJ-p1-31 | ADTTHVPLT | 262 | | 1 | 2 | 3 |
| SJ-p1-14 | AHSTFVPLT | 263 | 1 | 1 | 2 | 4 |
| 4P2-12-E3 | AQASFVPLT | 264 | | | 2 | 2 |
| SJ-p1-38 | AQATKVPLT | 265 | | 1 | 1 | 2 |
| 4P3-59 | AQSSKVPLT | 266 | | | 2 | 2 |
| SJ-p2-14 | AQSTLVPLT | 267 | | 1 | 2 | 3 |
| 4P3-11 | FAASSVPLT | 268 | | | 2 | 2 |
| 4P3-1 | FESTYVPLT | 269 | | | 2 | 2 |
| SJ-p2-10 | FESSRVPLT | 270 | | 1 | 1 | 2 |
| SJ-p2-11 | FNATWVPLT | 271 | | 2 | | 2 |
| SJ-p2-60 | FQASRVPLT | 272 | | 1 | 5 | 6 |
| SJ-p1-18 | FQATRVPLT | 273 | | 1 | 5 | 6 |
| SJ-p3-51 | FQGSFIGLS | 274 | 1 | | 1 | 2 |
| SJ-p3-16 | FQGSFIPGT | 275 | | 2 | 3 | 5 |
| SJ-p8-8F | FQGSFLPPS | 276 | | 1 | 1 | 2 |
| SJ-p3-26 | FQGSFLPQL | 277 | 1 | 2 | | 3 |
| SJ-p3-15 | FQGSLFPPV | 278 | 1 | 2 | | 3 |
| SJ-p2-70 | FQGSLFSPS | 279 | 1 | 5 | | 6 |
| SJ-p3-24 | FQGSRIPIS | 280 | | 1 | 1 | 2 |
| SJ-p3-33 | FQGSRLPVS | 281 | | 2 | 3 | 5 |
| SJ-p3-14 | FQGSRVPLV | 282 | | 2 | 1 | 3 |
| SJ-p2-1F | FQSSFVPLT | 283 | | 6 | 8 | 14 |
| 4P1-22 | FQSSRVPLT | 284 | | | 15 | 15 |
| SJ-p2-44 | GQTTLVPLT | 285 | | 1 | 3 | 4 |
| SJ-p1-56 | RESTLVPLT | 286 | | 2 | 1 | 3 |
| 4P1-40 | HQSSKVPLT | 287 | | | 4 | 4 |

TABLE 10-continued

| Clone Designation | CDR3 | SEQ ID NO: | Round 2 | Round 3 | Round 4 | Total |
|---|---|---|---|---|---|---|
| SJ-p2-20 | IQTSLVPLT | 288 | | 2 | | 2 |
| SJ-p1-41 | IQAALVPLT | 289 | | 1 | 1 | 2 |
| SJ-p2-13 | LQSSFVPLT | 290 | 1 | 4 | | 5 |
| 4P1-26 | LETSRVPLT | 291 | | | 3 | 3 |
| SJ-p1-33 | LASSHVPLT | 292 | | 2 | 1 | 3 |
| SJ-p2-27 | LNSTTVPLT | 293 | | 2 | 4 | 6 |
| SJ-p2-62 | LQSKSVPLT | 294 | | 2 | | 2 |
| 4P2-26-E5 | LQSVRVPLT | 295 | | | 3 | 3 |
| 4P1-32 | LQSSLVPLT | 296 | | | 5 | 5 |
| SJ-p2-37 | LQTGRVPLT | 297 | | 2 | 2 | 4 |
| SJ-p2-64 | LQTSFVPLT | 298 | | 3 | | 3 |
| 4P1-20 | LQTSNVPLT | 299 | | | 5 | 5 |
| SJ-p2-39 | LQTTRVPLT | 300 | | 2 | 6 | 8 |
| SJ-p2-52 | LSSTFVPLT | 301 | | 3 | 1 | 4 |
| SJ-p2-6L | LSSTHVPLT | 302 | | 2 | 1 | 3 |
| 4P1-77 | LTSSAVPLT | 303 | | | 2 | 2 |
| SJ-p1-59 | LVSSLVPLT | 304 | | 2 | | 2 |
| SJ-p2-23 | METANVPLT | 305 | | 2 | | 2 |
| SJ-p1-9M | MQSSFVPLT | 306 | | 1 | 3 | 4 |
| SJ-p2-28 | MQSSLVPLT | 307 | | 1 | 2 | 3 |
| SJ-p1-21 | MQTSKVPLT | 308 | | 1 | 1 | 2 |
| 4P1-17 | SQARMVPLT | 309 | | | 3 | 3 |
| SJ-p2-66 | SQASRVPLT | 310 | | 1 | 2 | 3 |
| SJ-p1-49 | TQSTQVPLT | 311 | | 2 | 1 | 3 |
| SJ-p2-24 | VGATFVPLT | 312 | | 1 | 1 | 2 |
| 4P1-41 | VQSSAVPLT | 313 | | | 2 | 2 |
| SJ-p2-51 | VQTSLVPLT | 314 | | 12 | 31 | 43 |
| 4P1-64 | VQTSVVPLT | 315 | | | 3 | 3 |
| SJ-p2-55 | VQTTAVPLT | 316 | | 2 | | 2 |
| SJ-p1-25 | LQTARVPLT | 317 | | 1 | 3 | 4 |

Fab fragments from the 10 top clones based on enrichment frequency were prepared and a total of 15 clones were converted into IgG1 humanized A version and two clones, 20C2-6 and 20C2-8, were converted to IgG1 humanized B version. KD values for these clones were measured by BIACORE™ using biotin-Aβ1-20 (Table 11) and bADDL (Table 12) as antigens. Dramatic improvements in affinity were observed as compared to parental humanized 20C2A and 20C2B, as well as mouse 20C2 antibodies. In particular, low nanomolar to sub-picomolar KDs were achieved with a light chain CDR3 of the sequence Xaa$_1$-Gln-Xaa$_2$-Thr-Arg-Val-Pro-Leu-Thr (SEQ ID NO:318), wherein Xaa$_1$ is Phe or Leu and Xaa$_2$ is Ala or Thr. Moreover, a comparison between KD values obtained with BIACORE™ using biotin-Aβ1-20 and bADDL further demonstrates that anti-ADDL antibodies such as 20C2 preferentially bind multi-dimensional conformations of ADDLs over monomeric Aβ peptides.

TABLE 11

| Name | Clone | LC-CDR3 | SEQ ID NO: | KD (Biotin-Aβ1-20) | | |
|---|---|---|---|---|---|---|
| | | | | Fab | IgG1#1 | IgG1#2 |
| 20C2-1A | SJ-p2-60 | FQASRVPLT | 272 | 91 nM | 1.2 nM | — |
| 20C2-2A | SJ-p1-18 | FQATRVPLT | 273 | 28 nM | 686 pM | 2 nM |
| 20C2-3A | SJ-p3-16 | FQGSFIPGT | 275 | — | 1.7 nM | — |
| 20C2-5A | SJ-p2-1F | FQSSFVPLT | 283 | 41 nM | 912 pM | 1.5 nM |
| 20C2-6A | 4P1-22 | FQSSRVPLT | 284 | 18 nM | 544 pM | 714 pM |
| 20C2-6B | 4P1-22 | FQSSRVPLT | 284 | — | 53 pM | — |
| 20C2-7A | SJ-p2-27 | LNSTTVPLT | 293 | 128 nM | — | — |
| 20C2-8A | SJ-p2-39 | LQTTRVPLT | 300 | 14 nM | 140 pM | 376 pM |
| 20C2-8B | SJ-p2-39 | LQTTRVPLT | 300 | — | 46 pM | 64 pM |
| 20C2-9A | SJ-p2-51 | VQTSLVPLT | 314 | 36 nM | 241 pM | 420 pM |
| 20C2-10A | SJ-p3-33 | FQGSRLPVS | 281 | — | 84 nM | — |
| 20C2-11A | SJ-p3-6 | FQGSLLPLS | 319 | — | — | — |
| 20C2-12A | 4P1-32 | LQSSLVPLT | 296 | 617 nM | 1.5 nM | — |
| 20C2-13A | 4p1-20 | LQTSNVPLT | 299 | 94 nM | 3 nM | — |
| 20C2-18A | SJ-p1-9M | MQSSFVPLT | 306 | 126 nM | 1.8 nM | — |
| 20C2-20A | SJ-p3-15 | FQGSLFPPV | 278 | | 21 nM | |
| 20C2-22A | SJ-p2-66 | SQASRVPLT | 310 | | 2.3 nM | |
| 20C2-23A | 4P1-40 | HQSSKVPLT | 287 | | 649 pM | 1.5 nM |
| 20C2-24A | SJ-p2-44 | GQTTLVPLT | 285 | | 1.9 nM | |
| 20C2A | | FQGSLVPLT | 60 | | 27 nM | |
| 20C2B | | FQGSLVPLT | 60 | | 5.4 nM | |
| Mouse-20C2 | | FQGSLVPLT | 60 | 83 nM | 3.4 nM | |

TABLE 12

| Name | Clone | LC-CDR3 | SEQ ID NO: | KD (bADDL) | | |
|---|---|---|---|---|---|---|
| | | | | Fab | IgG1#1 | IgG1#2 |
| 20C2-1A | SJ-p2-60 | FQASRVPLT | 272 | 85 nM | 75 pM | — |
| 20C2-2A | SJ-p1-18 | FQATRVPLT | 273 | 28 nM | 15 pM | 0.3 pM |
| 20C2-3A | SJ-p3-16 | FQGSFIPGT | 275 | — | 3.7 nM | — |
| 20C2-5A | SJ-p2-1F | FQSSFVPLT | 283 | 41 nM | 317 pM | 68 pM |
| 20C2-6A | 4P1-22 | FQSSRVPLT | 284 | 42 nM | 4.3 pM | 24 pM |
| 20C2-6B | 4P1-22 | FQSSRVPLT | 284 | — | 53 pM | — |
| 20C2-7A | SJ-p2-27 | LNSTTVPLT | 293 | 435 nM | — | — |
| 20C2-8A | SJ-p2-39 | LQTTRVPLT | 300 | 13 nM | 3 pM | 0.7 pM |
| 20C2-8B | SJ-p2-39 | LQTTRVPLT | 300 | — | 13 pM | 0.8 pM |
| 20C2-9A | SJ-p2-51 | VQTSLVPLT | 314 | 40 nM | — | 2 pM |
| 20C2-1GA | SJ-p3-33 | FQGSRLPVS | 281 | — | 7.7 nM | |

TABLE 12-continued

| Name | Clone | LC-CDR3 | SEQ ID NO: | KD (bADDL) Fab | IgG1#1 | IgG1#2 |
|---|---|---|---|---|---|---|
| 20C2-11A | SJ-p3-6 | FQGSLLPLS | 319 | — | — | — |
| 20C2-12A | 4P1-32 | LQSSLVPLT | 296 | 238 nM | 15 pM | — |
| 20C2-13A | 4p1-20 | LQTSNVPLT | 299 | 567 nM | 764 pM | |
| 20C2-18A | SJ-p1-9M | MQSSFVPLT | 306 | 85 nM | 149 pM | |
| 20C2-20A | SJ-p3-15 | FQGSLFPPV | 278 | | 6.9 nM | |
| 20C2-22A | SJ-p2-66 | SQASRVPLT | 310 | | 198 pM | |
| 20C2-23A | 4P1-40 | HQSSKVPLT | 287 | | 85 pM | 66 pM |
| 20C2-24A | SJ-p2-44 | GQTTLVPLT | 285 | | 114 pM | |
| 20C2A | | FQGSLVPLT | 60 | | | |
| 20C2B | | FQGSLVPLT | 60 | | | |
| Mouse-20C2 | | FQGSLVPLT | 60 | 62 nM | 4.1 nM | |

What is claimed is:

1. An isolated antibody, or antigen binding fragment thereof, capable of differentially recognizing a multi-dimensional conformation of one or more Aβ-derived diffusible ligands, wherein
   (a) the light chain variable region of the antibody or antigen binding fragment comprises,
      ((i) a CDR1 of SEQ ID NO: 50,
      (ii) a CDR2 of SEQ ID NO: 54, and
      (iii) a CDR3 of SEQ ID NO: 300; and
   (b) the heavy chain variable region of the antibody or antigen binding fragment comprises,
      (i) a CDR1 of SEQ ID NO: 25,
      (ii) a CDR2 of SEQ ID NO: 30, and
      (iii) a CDR3 of SEQ ID NO:43.

2. A kit for detecting Aβ-derived diffusible ligands comprising the isolated antibody, or antigen binding fragment thereof, of claim 1.

3. The isolated antibody of claim 1, wherein said antibody is a monoclonal antibody.

4. The isolated antibody of claim 3, wherein said antibody is humanized.

5. The isolated antibody of claim 4, wherein said antibody is affinity matured.

6. A method for attenuating binding of Aβ-derived diffusible ligands to a neuron comprising contacting the neuron with the antibody of claim 1 so that binding of Aβ-derived diffusible ligands to the neuron is attenuated.

7. A method for inhibiting assembly of Aβ-derived diffusible ligands comprising contacting a sample containing amyloid β1-42 peptides with the antibody of claim 1 thereby inhibiting assembly of Aβ-derived diffusible ligands.

8. A method for inhibiting the phosphorylation of tau protein at Ser202/Thr205 comprising contacting a sample containing a tau protein with the antibody of claim 1 thereby inhibiting the phosphorylation of tau protein at Ser202/Thr205.

9. A method for identifying a putative therapeutic agent that attenuates the binding of Aβ-derived diffusible ligands to neurons comprising
   (a) contacting a composition comprising a neuron with Aβ-derived diffusible ligands in the presence of an agent;
   (b) contacting the composition with an antibody of claim 1; and
   (c) detecting the amount of antibody bound in the presence of the agent;
   wherein a decrease in the amount of antibody bound in the presence of the agent as compared to the amount of antibody bound in the absence of the agent indicates that the agent is a putative therapeutic agent for attenuating binding of Aβ-derived diffusible ligands to neurons.

10. A method for detecting Aβ-derived diffusible ligands in a sample comprising contacting a sample with the antibody of claim 1 and determining the presence of a complex comprising the Aβ-derived diffusible ligands and the antibody.

11. A method for diagnosing a disease associated with Aβ-derived diffusible ligands comprising contacting a sample with the antibody of claim 1 and determining the presence of a complex comprising Aβ-derived diffusible ligands and the antibody wherein the complex is diagnostic of a disease associated with Aβ-derived diffusible ligands.

12. A pharmaceutical composition comprising the isolated antibody, or antigen binding fragment of claim 1 in admixture with a pharmaceutically acceptable carrier.

13. A method for attenuating symptoms of a disease associated with Aβ-derived diffusible ligands comprising administering an effective amount of the pharmaceutical composition of claim 12.

14. An isolated monoclonal antibody capable of differentially recognizing a multi-dimensional conformation of one or more Aβ-derived diffusible ligands, wherein said antibody comprises heavy and light chain variable regions comprising SEQ ID NO:71 and SEQ ID NO:323, respectively.

* * * * *

UNITED STATES PATENT AND TRADEMARK OFFICE
CERTIFICATE OF CORRECTION

PATENT NO. : 7,780,963 B2
APPLICATION NO. : 11/256332
DATED : August 24, 2010
INVENTOR(S) : Acton et al.

It is certified that error appears in the above-identified patent and that said Letters Patent is hereby corrected as shown below:

At column 1, line 11, please delete "This invention was made in the course of research sponsored, in part, by the National Institutes of Health (Grant Nos. NIH RO1-AG18877 and NIH RO1-AG22547). The U.S. Government may have certain rights in this invention."

At column 1, line 11, please insert --This invention was made with government support under Grant Numbers R01AG18877 and R01AG22547 awarded by the National Institutes of Health and Grant Number EEC-0118025 awarded by the National Science Foundation (NSEC). The government has certain rights in the invention.--

Signed and Sealed this

Ninth Day of November, 2010

David J. Kappos
*Director of the United States Patent and Trademark Office*